(12) United States Patent
Masuyama et al.

(10) Patent No.: US 8,530,137 B2
(45) Date of Patent: *Sep. 10, 2013

(54) PHOTORESIST COMPOSITION

(75) Inventors: Tatsuro Masuyama, Toyonaka (JP); Satoshi Yamaguchi, Kawachinagano (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 212 days.

This patent is subject to a terminal disclaimer.

(21) Appl. No.: 13/025,876

(22) Filed: Feb. 11, 2011

(65) Prior Publication Data

US 2011/0200935 A1 Aug. 18, 2011

(30) Foreign Application Priority Data

Feb. 16, 2010 (JP) .................. 2010-031081

(51) Int. Cl.
*G03F 7/004* (2006.01)
*G03F 7/20* (2006.01)
*G03F 7/30* (2006.01)
*G03F 7/38* (2006.01)

(52) U.S. Cl.
USPC ........ 430/270.1; 430/919; 430/921; 430/326; 430/330; 430/311; 546/248; 546/227; 546/153; 546/164; 546/165; 546/172; 548/542; 562/37

(58) Field of Classification Search
None
See application file for complete search history.

(56) References Cited

U.S. PATENT DOCUMENTS 5,998,099 A 12/1999 Houlihan et al.
2008/0166660 A1 7/2008 Takata et al.

FOREIGN PATENT DOCUMENTS

JP 2002-131917 A 5/2002

OTHER PUBLICATIONS

Houlihan et al ("Study of Base Additives for Use in a Single Layer 193 nm Resist Based Upon Poly(norbornene/maleicanhydride/ acrylic acid/tert-butyl Acrylate)", Proceedings of SPIE, vol. 4345, p. 67-77 (2001)).*

* cited by examiner

*Primary Examiner* — Sin J. Lee
(74) *Attorney, Agent, or Firm* — Birch, Stewart, Kolasch & Birch, LLP

(57) ABSTRACT

The present invention provides a photoresist composition having a sulfonium salt comprising an anion represented by the formula (IA):

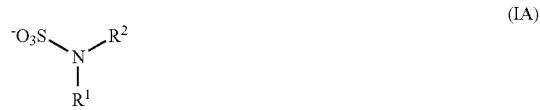

wherein $R^1$ and $R^2$ independently represent a hydrogen atom, a C1-C12 aliphatic hydrocarbon group, a C3-C20 saturated cyclic hydrocarbon group, a C6-C20 aromatic hydrocarbon group or a C7-C21 aralkyl group, and the aliphatic hydrocarbon group, the saturated cyclic hydrocarbon group, the aromatic hydrocarbon group and the aralkyl group can have one or more substituents selected from the group consisting of a hydroxyl group, a cyano group, a fluorine atom, a trifluoromethyl group and a nitro group, and one or more —$CH_2$— in the aliphatic hydrocarbon group can be replaced by —O— or —CO—, or $R^1$ and $R^2$ are bonded each other to form a C4-C20 nitrogen-containing ring together with the nitrogen atom to which they are bonded, an acrylic resin having an acid-labile group and being insoluble or poorly soluble in an aqueous alkali solution but becoming soluble in an aqueous alkali solution by the action of an acid, and an acid generator.

5 Claims, No Drawings

PHOTORESIST COMPOSITION

This nonprovisional application claims priority under 35 U.S.C. §119(a) on Patent Application No. 2010-031081 filed in JAPAN on Feb. 16, 2010, the entire contents of which are hereby incorporated by reference.

FIELD OF THE INVENTION

The present invention relates to a photoresist composition.

BACKGROUND OF THE INVENTION

A photoresist composition is used for semiconductor microfabrication employing a lithography process.

US 2008/0166660 A1 discloses a photoresist composition comprising a resin having a structural unit derived from 2-ethyl-2-adamantyl methacrylate, a structural unit derived from 3-hydroxy-1-adamantyl methacrylate, a structural unit derived from 2-(5-oxo-4-oxatricyclo[4.2.1.0$^{3,7}$]nonan-2-yloxy)-2-oxoethyl methacrylate and a structural unit derived from α-methacryloyloxy-γ-butyrolactone, an acid generator comprising triphenylsulfonium 4-oxoadamantan-1-yloxy-carbonyl(difluoro)methanesulfonate, quencher comprising 2,6-diisopropylaniline, and solvents.

U.S. Pat. No. 5,998,099 A discloses bis(tert-butylphenyl) iodonium cyclamate as an additive for a photoresist composition and a photoresist composition comprising bis(tert-butylphenyl)iodonium cyclamate.

SUMMARY OF THE INVENTION

The present invention is to provide a photoresist composition.

The present invention relates to the followings:

<1> A photoresist composition comprising a sulfonium salt having an anion represented by the formula (IA):

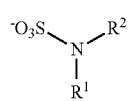

wherein $R^1$ and $R^2$ independently represent a hydrogen atom, a C1-C12 aliphatic hydrocarbon group, a C3-C20 saturated cyclic hydrocarbon group, a C6-C20 aromatic hydrocarbon group or a C7-C21 aralkyl group, and the aliphatic hydrocarbon group, the saturated cyclic hydrocarbon group, the aromatic hydrocarbon group and the aralkyl group can have one or more substituents selected from the group consisting of a hydroxyl group, a cyano group, a fluorine atom, a trifluoromethyl group and a nitro group, and one or more —CH$_2$— in the aliphatic hydrocarbon group can be replaced by —O— or —CO—, or $R^1$ and $R^2$ are bonded each other to form a C4-C20 nitrogen-containing ring together with the nitrogen atom to which they are bonded, an acrylic resin having an acid-labile group and being insoluble or poorly soluble in an aqueous alkali solution but becoming soluble in an aqueous alkali solution by the action of an acid, and an acid generator;

<2> The photoresist composition <1>, wherein the sulfonium salt having an anion represented by the formula (IA) has a cation represented by the formula (IB):

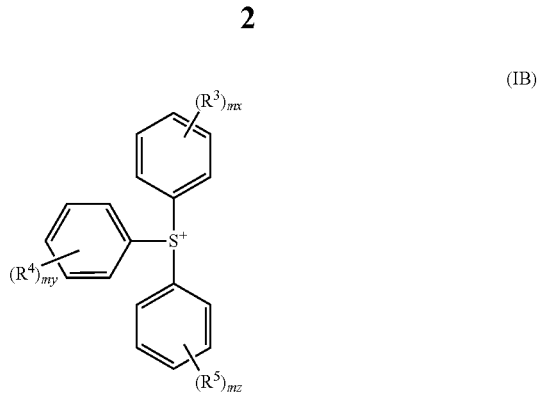

wherein $R^3$, $R^4$ and $R^5$ are independently in each occurrence a hydroxyl group, a halogen atom, a C1-C12 alkoxy group, a C1-C30 aliphatic hydrocarbon group, a C3-C36 saturated cyclic hydrocarbon group or a C6-C18 aromatic hydrocarbon group, and one or more hydrogen atoms in the aliphatic hydrocarbon group can be replaced by a hydroxyl group, a C1-C12 alkoxy group or a C6-C18 aromatic hydrocarbon group, one or more hydrogen atoms of the saturated cyclic hydrocarbon group can be replaced by a halogen atom, a C2-C4 acyl group or a glycidyloxy group, one or more hydrogen atoms of the aromatic hydrocarbon group can be replaced by a halogen atom, a hydroxyl group, a C1-C36 aliphatic hydrocarbon group, a C3-C36 saturated cyclic hydrocarbon group or a C1-C12 alkoxy group, and mx, my and mz independently represent an integer of 0 to 5;

<3> The photoresist composition according to <1> or <2>, wherein $R^1$ and $R^2$ independently represent a C1-C12 aliphatic hydrocarbon group, a C3-C20 saturated cyclic hydrocarbon group, a C6-C20 aromatic hydrocarbon group or a C7-C21 aralkyl group, and the aliphatic hydrocarbon group, the saturated cyclic hydrocarbon group, the aromatic hydrocarbon group and the aralkyl group can have one or more substituents selected from the group consisting of a hydroxyl group, a cyano group, a fluorine atom, a trifluoromethyl group and a nitro group, and one or more —CH$_2$— in the aliphatic hydrocarbon group can be replaced by —O— or —CO—, or $R^1$ and $R^2$ are bonded each other to form a C4-C20 nitrogen-containing ring together with the nitrogen atom to which they are bonded;

<4> The photoresist composition according to <1> or <2>, wherein $R^1$ represents a C1-C12 aliphatic hydrocarbon group, a C3-C20 saturated cyclic hydrocarbon group, a C6-C20 aromatic hydrocarbon group or a C7-C21 aralkyl group, and the aliphatic hydrocarbon group, the saturated cyclic hydrocarbon group, the aromatic hydrocarbon group and the aralkyl group can have one or more substituents selected from the group consisting of a hydroxyl group, a cyano group, a fluorine atom, a trifluoromethyl group and a nitro group, and one or more —CH$_2$— in the aliphatic hydrocarbon group can be replaced by —O— or —CO—, $R^2$ represents a C7-C20 saturated cyclic hydrocarbon group, a C6-C20 aromatic hydrocarbon group or a C7-C21 aralkyl group, and the aliphatic hydrocarbon group, the saturated cyclic hydrocarbon group, the aromatic hydrocarbon group and the aralkyl group can have one or more substituents selected from the group consisting of a hydroxyl group, a cyano group, a fluorine atom, a trifluoromethyl group and a nitro group, and one or more —CH$_2$— in the aliphatic hydrocarbon group can be replaced by —O— or —CO—, or R¹ and R² are bonded each other to form a C4-C20 nitrogen-containing ring together with the nitrogen atom to which they are bonded;

<5> A process for producing a photoresist pattern comprising the following steps (1) to (5):

(1) a step of applying the photoresist composition according to any one of <1> to <4> on a substrate, (2) a step of forming a photoresist film by conducting drying, (3) a step of exposing the photoresist film to radiation, (4) a step of baking the exposed photoresist film, and (5) a step of developing the baked photoresist film with an alkaline developer, thereby forming a photoresist pattern;

<6> A salt represented by the formula (I):

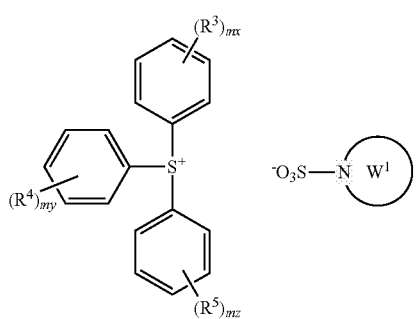

(I)

wherein $R^3$, $R^4$ and $R^5$ are independently in each occurrence a hydroxyl group, a halogen atom, a C1-C12 alkoxy group, a C1-C30 aliphatic hydrocarbon group, a C3-C36 saturated cyclic hydrocarbon group or a C6-C18 aromatic hydrocarbon group, and one or more hydrogen atoms in the aliphatic hydrocarbon group can be replaced by a hydroxyl group, a C1-C12 alkoxy group or a C6-C18 aromatic hydrocarbon group, one or more hydrogen atoms of the saturated cyclic hydrocarbon group can be replaced by a halogen atom, a C2-C4 acyl group or a glycidyloxy group, one or more hydrogen atoms of the aromatic hydrocarbon group can be replaced by a halogen atom, a hydroxyl group, a C1-C36 aliphatic hydrocarbon group, a C3-C36 saturated cyclic hydrocarbon group or a C1-C12 alkoxy group, mx, my and mz independently represent an integer of 0 to 5, and $W^1$ represents a nitrogen-containing heteroring which can have one or more substituents.

DESCRIPTION OF PREFERRED EMBODIMENTS

The photoresist composition of the present invention comprises the following three components:

a sulfonium salt having an anion represented by the formula (IA):

(IA)

wherein R¹ and R² independently represent a hydrogen atom, a C1-C12 aliphatic hydrocarbon group, a C3-C20 saturated cyclic hydrocarbon group, a C6-C20 aromatic hydrocarbon group or a C7-C21 aralkyl group, and the aliphatic hydrocarbon group, the saturated cyclic hydrocarbon group, the aromatic hydrocarbon group and the aralkyl group can have one or more substituents selected from the group consisting of a hydroxyl group, a cyano group, a fluorine atom, a trifluoromethyl group and a nitro group, and one or more —CH₂— in the aliphatic hydrocarbon group can be replaced by —O— or —CO—, or R¹ and R² are bonded each other to form a C4-C20 nitrogen-containing ring together with the nitrogen atom to which they are bonded (hereinafter, the sulfonium salt having the anion represented by the formula (IA) is simply referred to as SALT (IA) and the anion represented by the formula (IA) is simply referred to as ANION (IA)), an acrylic resin having an acid-labile group and being insoluble or poorly soluble in an aqueous alkali solution but becoming soluble in an aqueous alkali solution by the action of an acid (hereinafter, simply referred to as RESIN (A)), and an acid generator.

First, SALT (IA) will be illustrated.

SALT (IA) is a salt consisting of a cation having a positive electric charge on trivalent sulfur atom and ANION (IA).

In the formula (IA), it is preferred that R¹ and R² independently represent a C1-C12 aliphatic hydrocarbon group, a C3-C20 saturated cyclic hydrocarbon group, a C6-C20 aromatic hydrocarbon group or a C7-C21 aralkyl group, and the aliphatic hydrocarbon group, the saturated cyclic hydrocarbon group, the aromatic hydrocarbon group and the aralkyl group can have one or more substituents selected from the group consisting of a hydroxyl group, a cyano group, a fluorine atom, a trifluoromethyl group and a nitro group, and one or more —CH₂— in the aliphatic hydrocarbon group can be replaced by —O— or —CO—, or R¹ and R² are bonded each other to form a C4-C20 nitrogen-containing ring together with the nitrogen atom to which they are bonded.

It is more preferred that R' represents a C1-C12 aliphatic hydrocarbon group, a C3-C20 saturated cyclic hydrocarbon group, a C6-C20 aromatic hydrocarbon group or a C7-C21 aralkyl group, and the aliphatic hydrocarbon group, the saturated cyclic hydrocarbon group, the aromatic hydrocarbon group and the aralkyl group can have one or more substituents selected from the group consisting of a hydroxyl group, a cyano group, a fluorine atom, a trifluoromethyl group and a nitro group, and one or more —CH₂— in the aliphatic hydrocarbon group can be replaced by —O— or —CO—, and $R^2$ represents a C7-C20 saturated cyclic hydrocarbon group, a C6-C20 aromatic hydrocarbon group or a C7-C21 aralkyl group, and the aliphatic hydrocarbon group, the saturated cyclic hydrocarbon group, the aromatic hydrocarbon group and the aralkyl group can have one or more substituents selected from the group consisting of a hydroxyl group, a cyano group, a fluorine atom, a trifluoromethyl group and a nitro group, and one or more —CH₂— in the aliphatic hydrocarbon group can be replaced by —O— or —CO—, or R¹ and R² are bonded each other to form a C4-C20 nitrogen-containing ring together with the nitrogen atom to which they are bonded.

Examples of the C1-C12 aliphatic hydrocarbon group include a C1-C12 alkyl group such as a methyl group (IR-1), an ethyl group (IR-2), a propyl group (IR-3), an isopropyl group (IR-4), a butyl group (IR-5), a sec-butyl group (IR-6), a tert-butyl group (IR-7), a pentyl group (IR-8), a hexyl group (IR-9), a heptyl group (IR-10), an octyl group (IR-11), a 2-ethylhexyl group (IR-12), a nonyl group (IR-13), a decyl group (IR-14), an undecyl group (IR-15) and a dodecyl group (IR-16).

Examples of the C3-C20 saturated cyclic hydrocarbon group include a C3-C20 cycloalkyl group such as a cyclopropyl group (IR-21), a cyclobutyl group (IR-22), a cycloheptyl group (IR-23), a cyclohexyl group (IR-24), a cycloheptyl group (IR-25), a cyclooctyl group (IR-26), a cyclononyl group (IR-27) and a cyclodecyl group (IR-28), and a C7-C20 polycyclic saturated hydrocarbon group such as a 1-norbornyl group (IR-29), a 1-adamantyl group (IR-30), a 2-adamantyl group (IR-31), a 2-isobornyl group (IR-32), a 2-norbornyl group (IR-39) and the following.

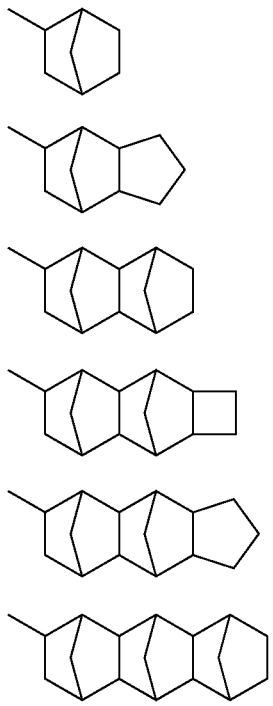

(IR-33)
(IR-34)
(IR-35)
(IR-36)
(IR-37)
(IR-38)

Examples of the C6-C20 aromatic hydrocarbon group include a phenyl group (IR-51), a 1-naphthyl group (IR-52), a 1-anthryl group (IR-53), a p-methylphenyl group (IR-54), a p-tert-butylphenyl group (IR-55), a p-adamantylphenyl group (IR-56), a 2-naphthyl group (IR-57), a 2-anthryl group (IR-58) and a 9-anthryl group (IR-59).

Examples of the C7-C21 aralkyl group include a benzyl group (IR-61).

Examples of the aliphatic hydrocarbon group having one or more hydroxyl groups include the following.

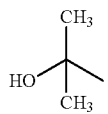

(IR-91)
(IR-92)
(IR-93)
(IR-94)
(IR-95)
(IR-96)

Examples of the aliphatic hydrocarbon group having one or more cyano groups include the following.

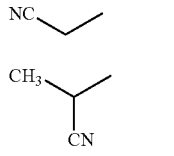

(IR-101)
(IR-102)
(IR-103)
(IR-104)
(IR-105)
(IR-106)

Examples of the aliphatic hydrocarbon group having one or more fluorine atoms include the following.

—CF$_2$—CF$_3$ (IR-111)

—CF$_2$—CF$_2$—CF$_3$ (IR-112)

—CF$_2$—CF$_2$—CF$_2$—CF$_3$ (IR-113)

—CF$_2$H (IR-114)

—CF$_2$—CF$_2$H (IR-115)

—CF$_2$—CF$_2$—CF$_2$H (IR-116)

CF$_2$—CF$_2$—CF$_2$—CF$_2$H (IR-117)

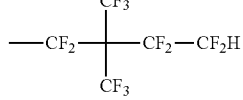

(IR-118)

Examples of the aliphatic hydrocarbon group having one or more nitro groups include the following.

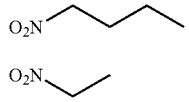

(IR-121)
(IR-122)

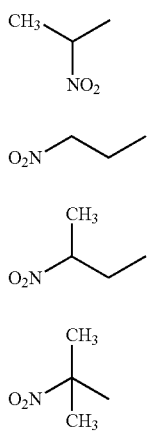

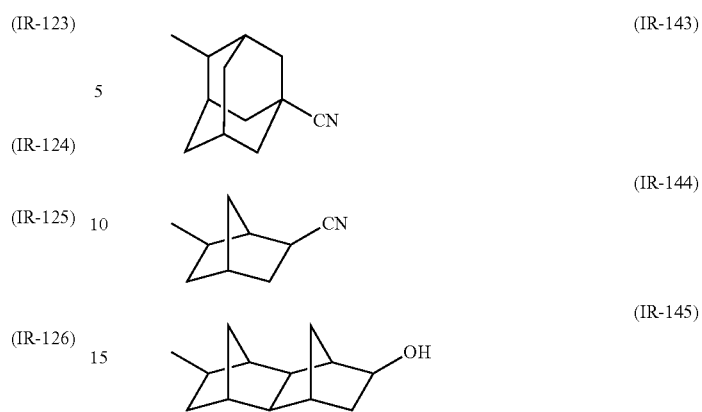

Examples of the saturated cyclic hydrocarbon group having one or more hydroxyl groups include the following.

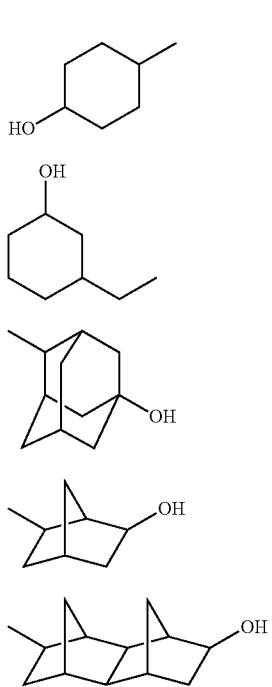

Examples of the saturated cyclic hydrocarbon group having one or more fluorine atoms include the following.

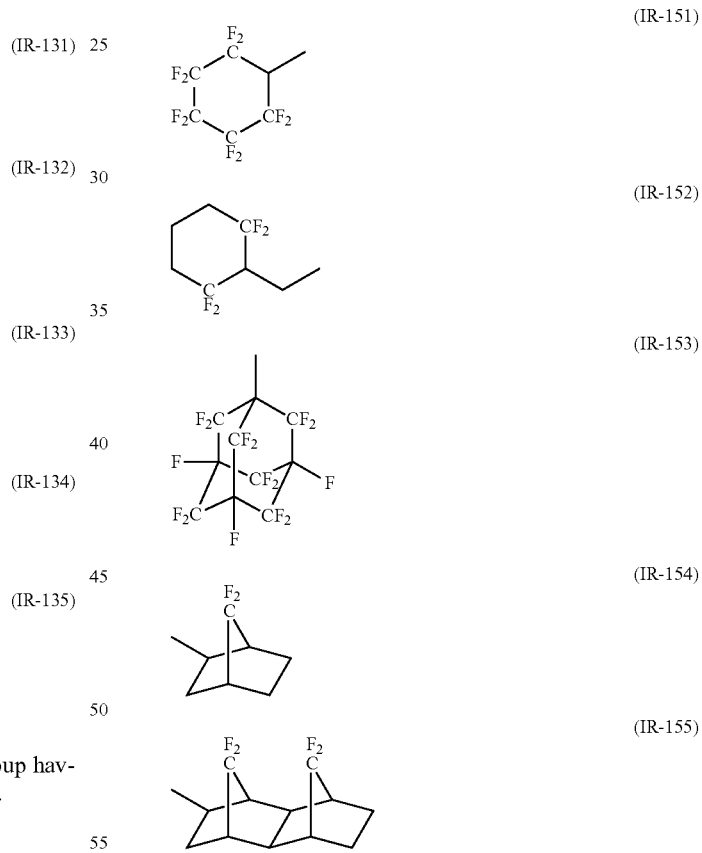

Examples of the saturated cyclic hydrocarbon group having one or more cyano groups include the following.

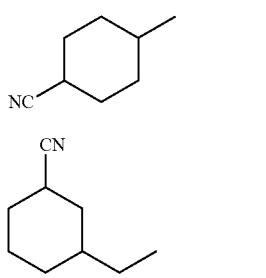

Examples of the saturated cyclic hydrocarbon group having one or more nitro groups include the following.

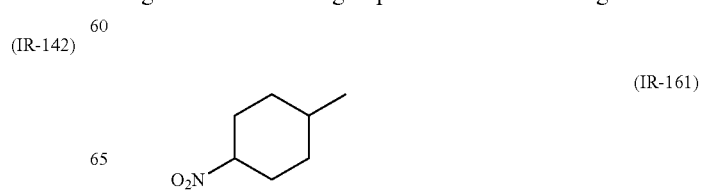

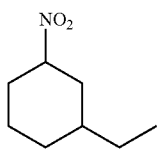
(IR-162)
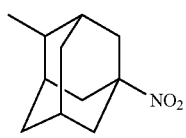
(IR-163)
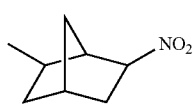
(IR-164)
(IR-165)
Examples of the aromatic hydrocarbon group having one or more hydroxyl groups include the following.
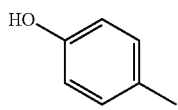
(IR-171)
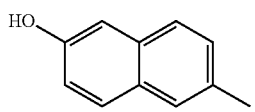
(IR-172)
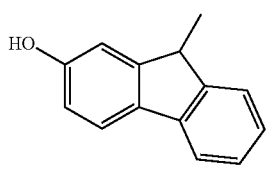
(IR-173)
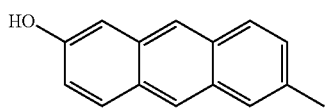
(IR-174)
Examples of the aromatic hydrocarbon group having one or more cyano groups include the following.
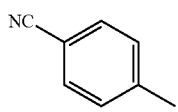
(IR-181)
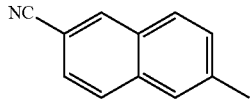
(IR-182)
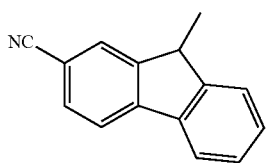
(IR-183)
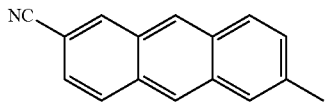
(IR-184)
Examples of the aromatic hydrocarbon group having one or more fluorine atoms include the following.
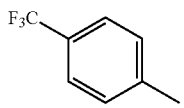
(IR-191)
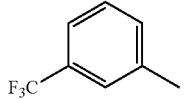
(IR-192)
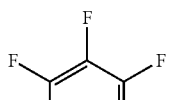
(IR-193)
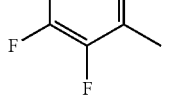
(IR-194)
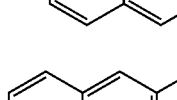
(IR-195)
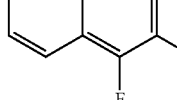
(IR-196)
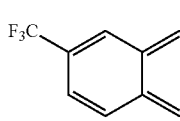
(IR-197)
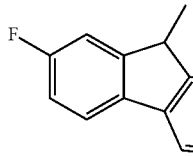
(IR-198)

-continued

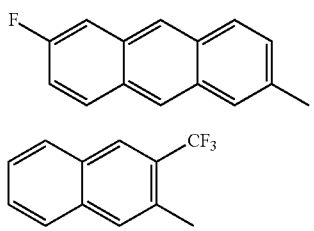
(IR-199)

(IR-200)

Examples of the aromatic hydrocarbon group having one or more nitro groups include the following.

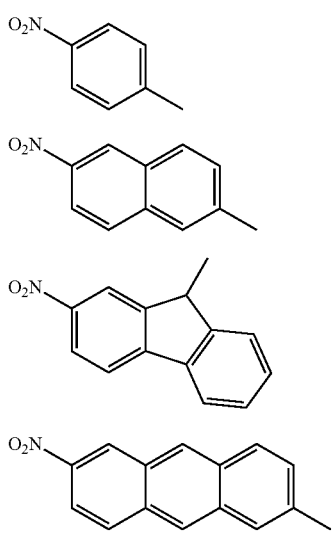
(IR-211)

(IR-212)

(IR-213)

(IR-214)

Examples of the aralkyl group having one or more hydroxyl groups include the following.

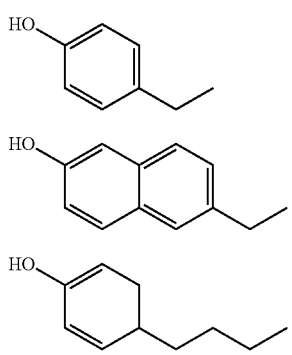
(IR-221)

(IR-222)

(IR-223)

Examples of the aralkyl group having one or more cyano groups include the following.

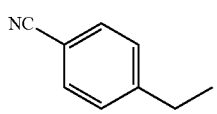
(IR-231)

-continued

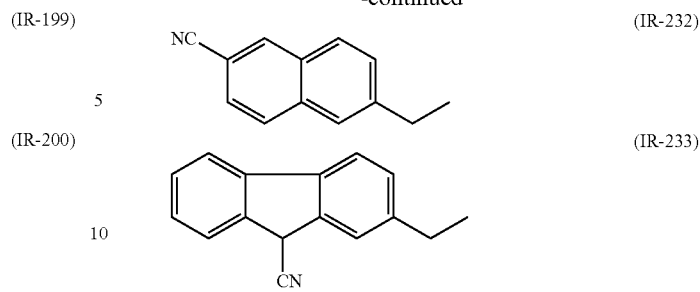
(IR-232)

(IR-233)

Examples of the aralkyl group having one or more fluorine atoms include the following.

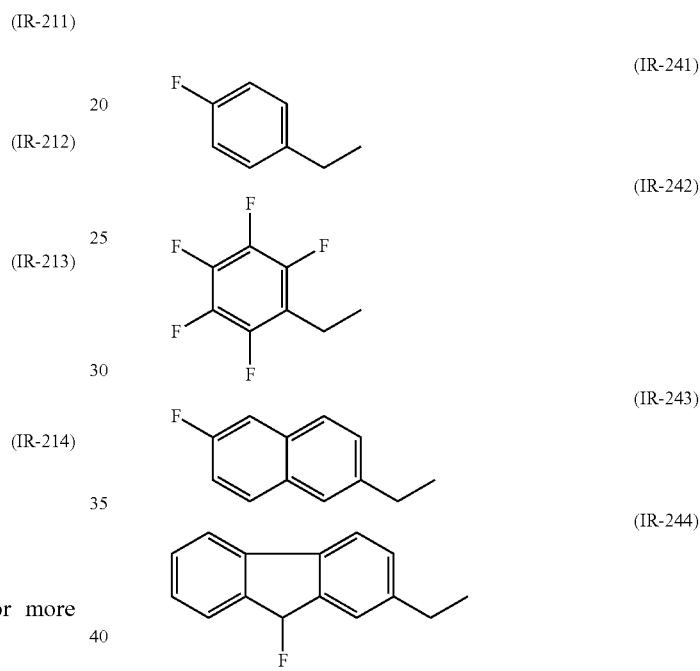
(IR-241)

(IR-242)

(IR-243)

(IR-244)

Examples of the aralkyl group having one or more nitro groups include the following.

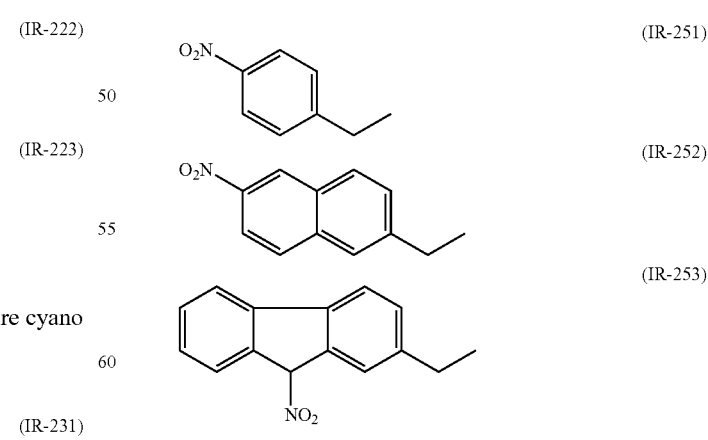
(IR-251)

(IR-252)

(IR-253)

Examples of the aliphatic hydrocarbon group in which one or more —$CH_2$— are replaced by —O— or —CO— include the following.

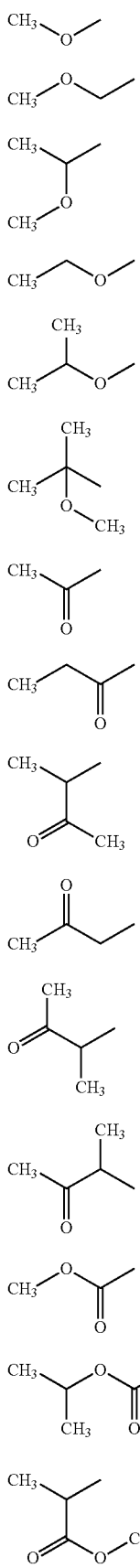
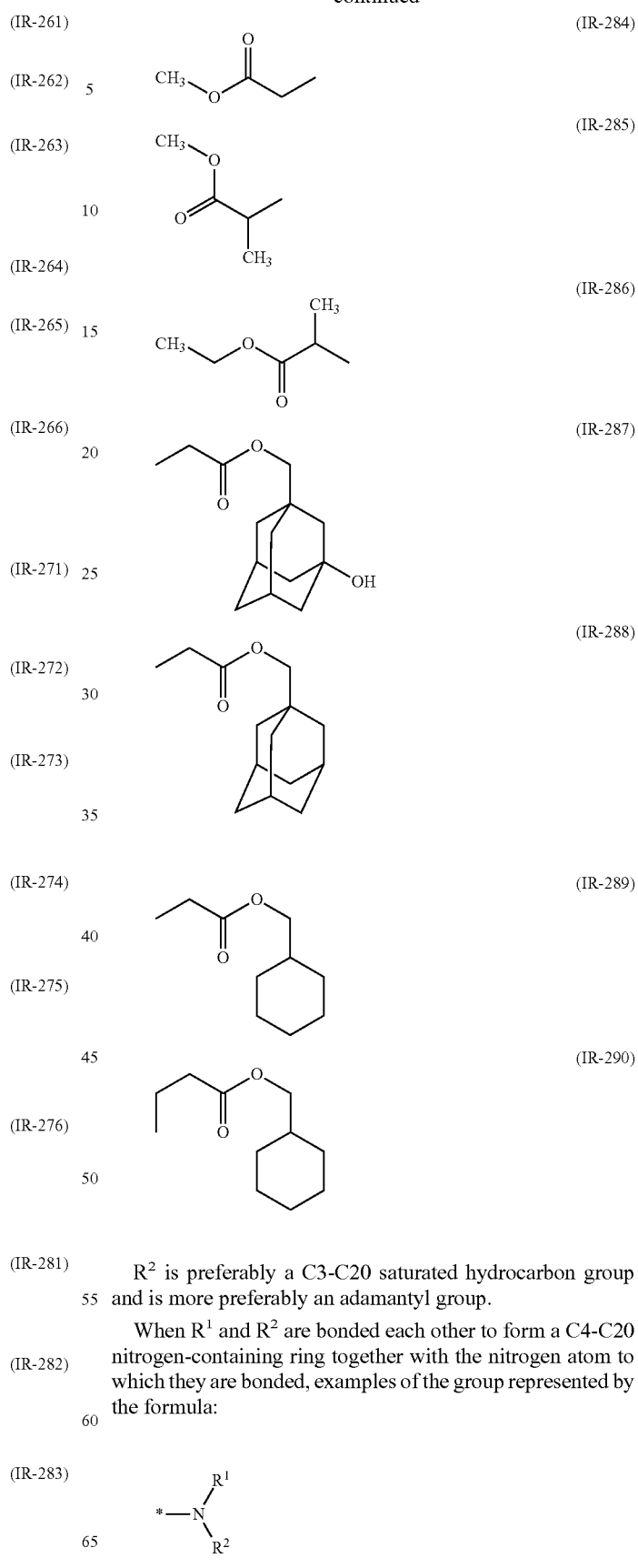
R² is preferably a C3-C20 saturated hydrocarbon group and is more preferably an adamantyl group.
When R¹ and R² are bonded each other to form a C4-C20 nitrogen-containing ring together with the nitrogen atom to which they are bonded, examples of the group represented by the formula:

wherein * represents a binding position to —SO$_3^-$ include the following.
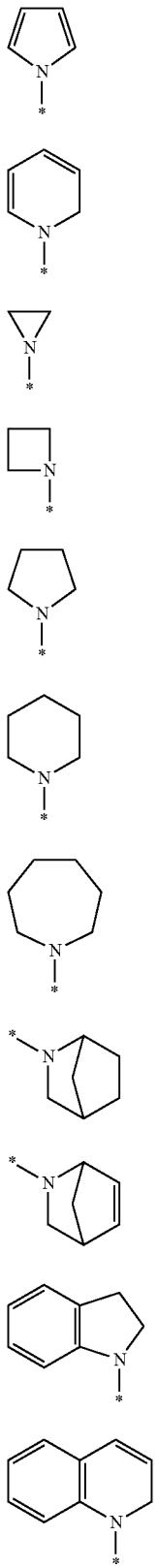
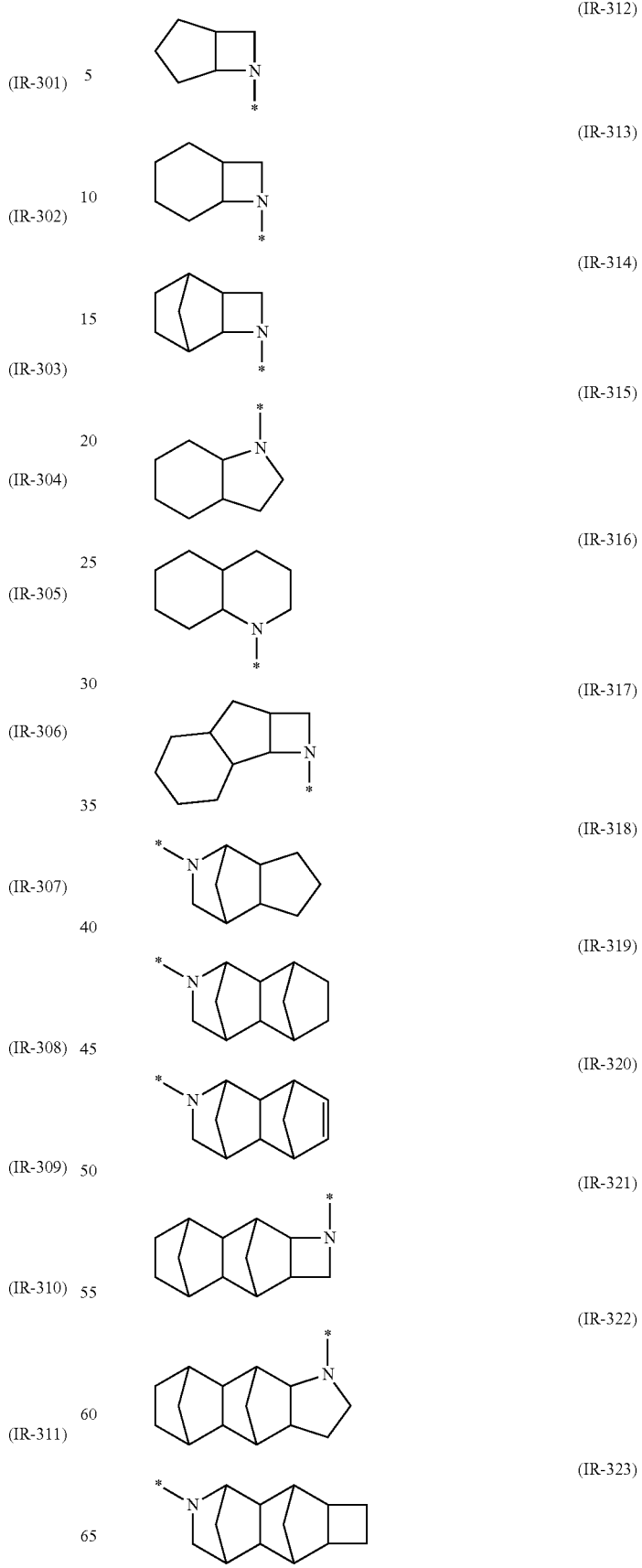

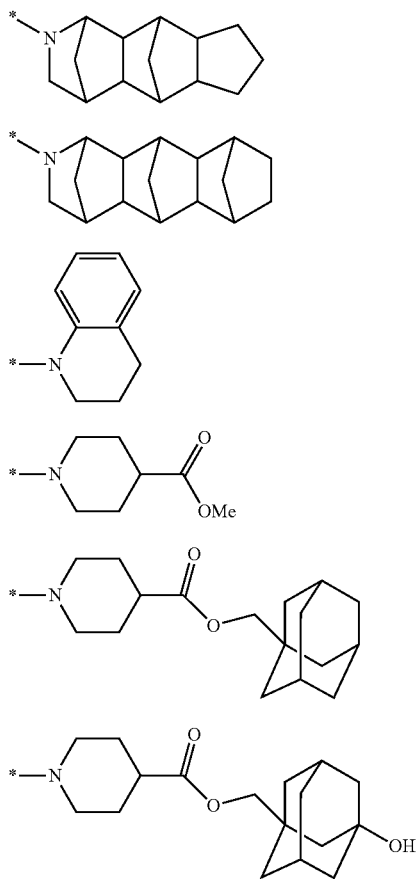

Examples of the cation of SALT (IA) include cations represented by the formulae (IB) and (IC):

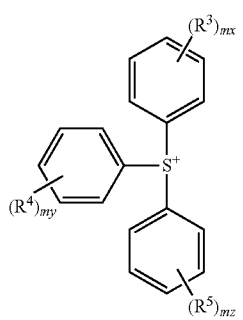

(IB)

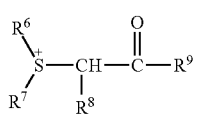

(IC)

wherein $R^3$, $R^4$ and $R^5$ are independently in each occurrence a hydroxyl group, a halogen atom, a C1-C12 alkoxy group, a C1-C30 aliphatic hydrocarbon group, a C3-C36 saturated cyclic hydrocarbon group or a C6-C18 aromatic hydrocarbon group, and one or more hydrogen atoms in the aliphatic hydrocarbon group can be replaced by a hydroxyl group, a C1-C12 alkoxy group or a C6-C18 aromatic hydrocarbon group, one or more hydrogen atoms of the saturated cyclic hydrocarbon group can be replaced by a halogen atom, a C2-C4 acyl group or a glycidyloxy group, one or more hydrogen atoms of the aromatic hydrocarbon group can be replaced by a halogen atom, a hydroxyl group, a C1-C36 aliphatic hydrocarbon group, a C3-C36 saturated cyclic hydrocarbon group or a C1-C12 alkoxy group, and mx, my and mz independently represent an integer of 0 to 5, $R^6$ and $R^7$ independently represent a C1-C36 aliphatic hydrocarbon group or a C3-C36 saturated cyclic hydrocarbon group, or $R^6$ and $R^7$ are bonded to form a C2-C11 divalent acyclic hydrocarbon group which forms a ring together with the adjacent $S^+$, and one or more —$CH_2$— in the divalent acyclic hydrocarbon group may be replaced by —CO—, —O— or —S—, $R^8$ represents a hydrogen atom, a C1-C36 aliphatic hydrocarbon group, a C3-C36 saturated cyclic hydrocarbon group or a C6-C18 aromatic hydrocarbon group, $R^9$ represents a C1-C12 aliphatic hydrocarbon group, a C3-C18 saturated cyclic hydrocarbon group or a C6-C18 aromatic hydrocarbon group and the aromatic hydrocarbon group can have one or more substituents selected from the group consisting of a C1-C12 aliphatic hydrocarbon group, a C1-C12 alkoxy group, a C3-C18 saturated cyclic hydrocarbon group and an C2-C13 acyloxy group, or $R^8$ and $R^9$ are bonded each other to form a C1-C10 divalent acyclic hydrocarbon group which forms a 2-oxocycloalkyl group together with the adjacent —CHCO—, and one or more —$CH_2$— in the divalent acyclic hydrocarbon group may be replaced by —CO—, —O— or —S—.

The aliphatic hydrocarbon group has preferably 1 to 12 carbon atoms. The saturated cyclic hydrocarbon group represented has preferably 3 to 18 carbon atoms and more preferably 4 to 12 carbon atoms. Examples of the aliphatic hydrocarbon group and the aromatic hydrocarbon group include the same as described above. Preferable examples of the aliphatic hydrocarbon group include a methyl group, an ethyl group, a propyl group, an isopropyl group, a butyl group, a sec-butyl group, a tert-butyl group, a pentyl group, a hexyl group, an octyl group and a 2-ethylhexyl group. Preferable examples of the saturated cyclic hydrocarbon group include a cyclopropyl group, a cyclobutyl group, a cyclopentyl group, a cyclohexyl group, a cycloheptyl group, a cyclodecyl group, a 2-alkyl-a-adamantyl group, a 1-(1-adamantyl)-1-alkyl group and an isobornyl group. Preferable examples of the aromatic group include a phenyl group, a 4-methylphenyl group, a 4-ethylphenyl group, a 4-tert-butylphenyl group, a 4-cyclohexylphenyl group, a 4-methoxyphenyl group, a biphenyl group and a naphthyl group. Examples of the aliphatic hydrocarbon group having an aromatic hydrocarbon group include a benzyl group. Examples of the alkoxy group include a methoxy group, an ethoxy group, a propoxy group, an isopropoxy group, a butoxy group, a sec-butoxy group, a tert-butoxy group, a pentyloxy group, a hexyloxy group, a heptyloxy group, an octyloxy group, a 2-ethylhexyloxy group, a nonyloxy group, a decyloxy group, an undecyloxy group and a dodecyloxy group.

Examples of the C3-C12 divalent acyclic hydrocarbon group formed by bonding $R^6$ and $R^7$ include a trimethylene group, a tetramethylene group and a pentamethylene group. Examples of the ring group formed together with the adjacent $S^+$ and the divalent acyclic hydrocarbon group include a thiolan-1-ium ring (tetrahydrothiophenium ring), a thian-1-ium ring and a 1,4-oxathian-4-ium ring. A C3-C7 divalent a cyclic hydrocarbon group is preferable.

Examples of the C1-C10 divalent acyclic hydrocarbon group formed by bonding $R^8$ and $R^9$ include a methylene group, an ethylene group, a trimethylene group, a tetramethylene group and a pentamethylene group and examples of the ring group include the followings.
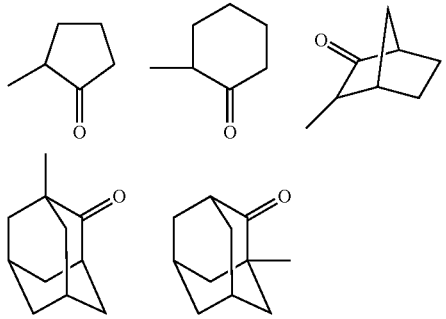
Examples of the cation represented by the formula (IB) include the cations represented by the formulae (IB-1) to (IB-21).
(IB-1)
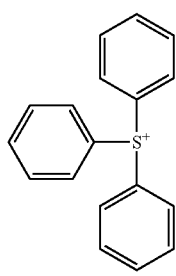
(IB-2)
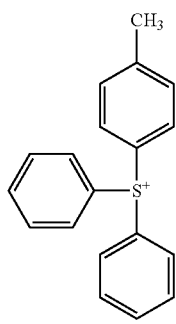
(IB-3)
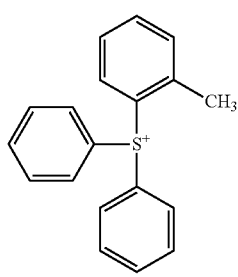
(IB-4)
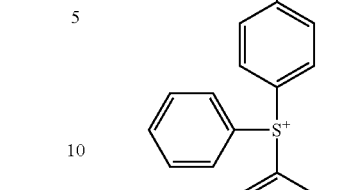
(IB-5)
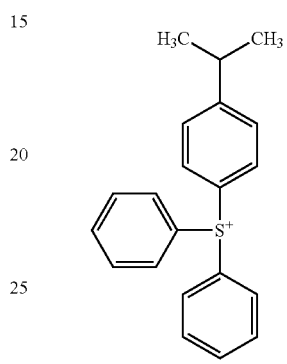
(IB-6)
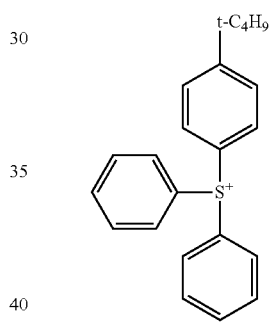
(IB-7)
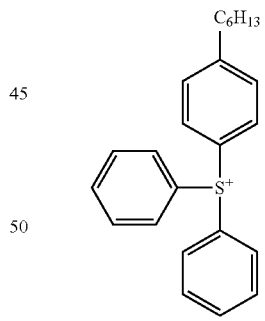
(IB-8)
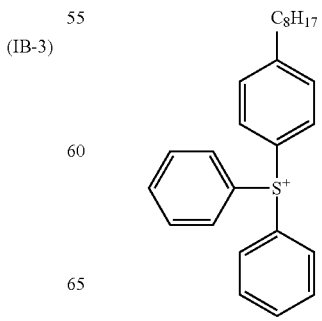

(IB-9)
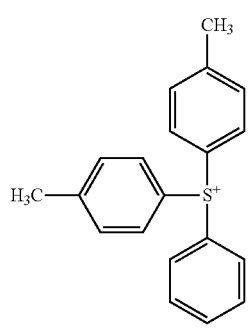
(IB-10)
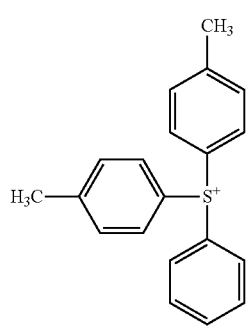
(IB-11)
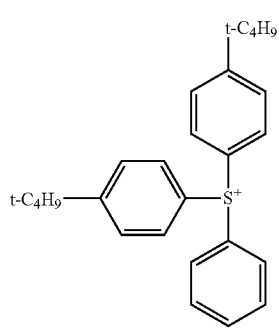
(IB-12)
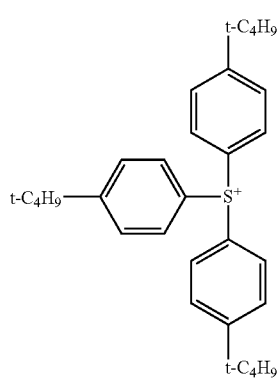
(IB-13)
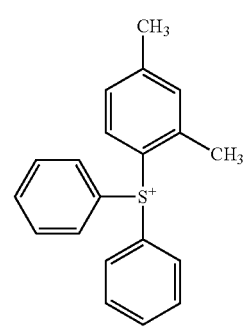
(IB-14)
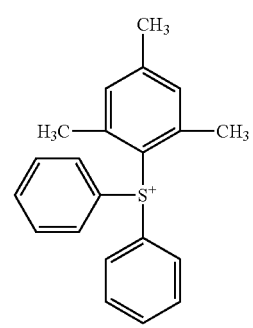
(IB-15)
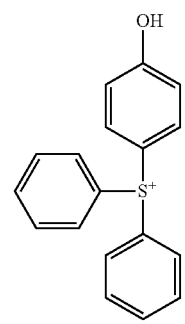
(IB-16)
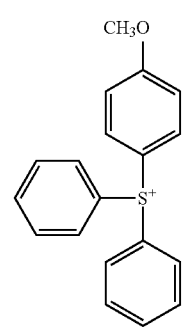
(IB-17)

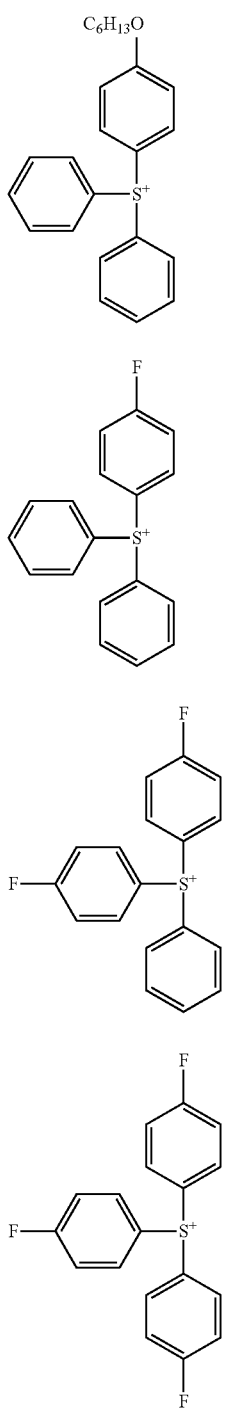
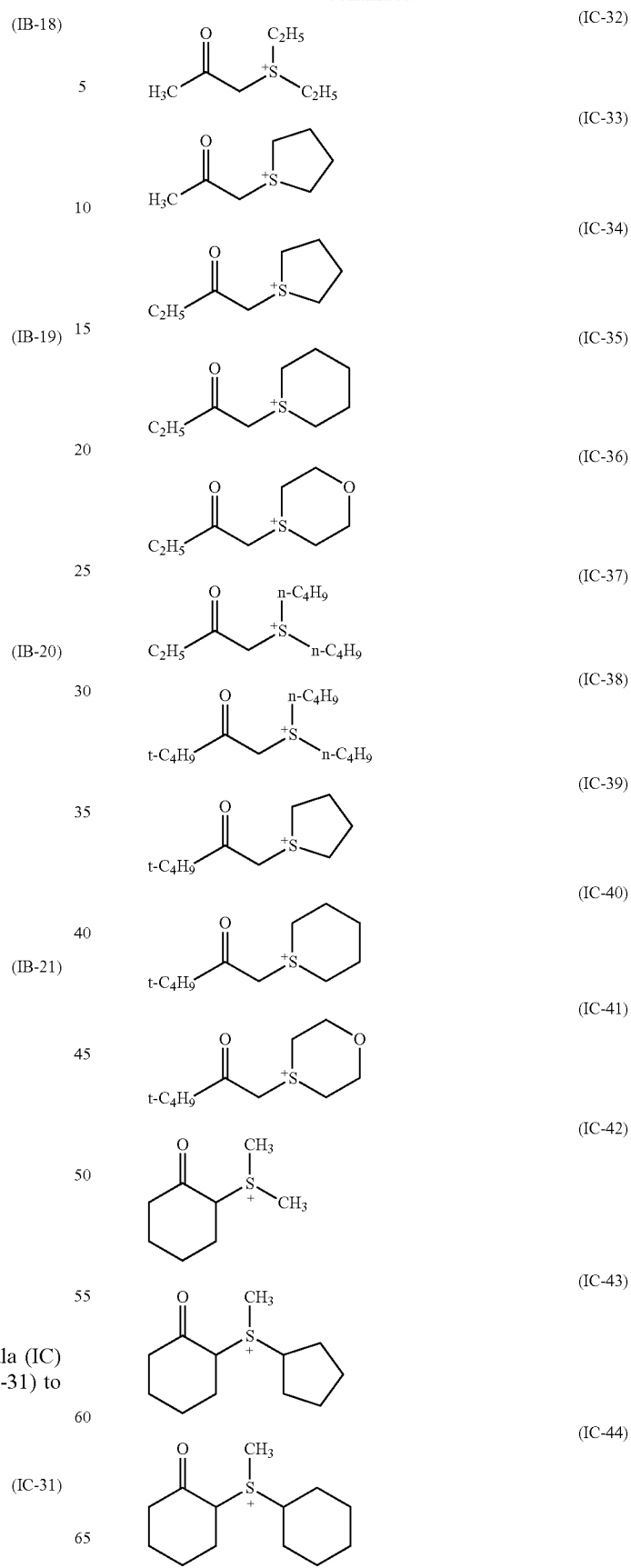
Examples of the cation represented by the formula (IC) include the cations represented by the formulae (IC-31) to (IC-72).
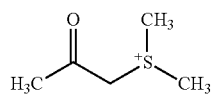

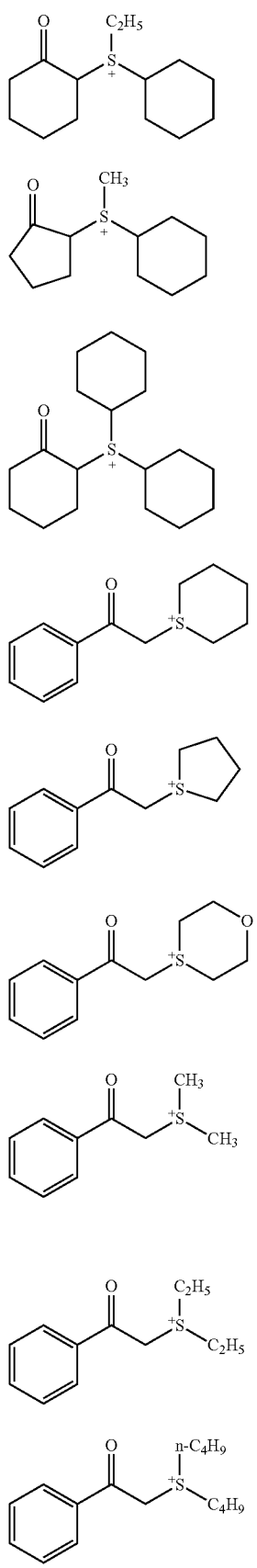
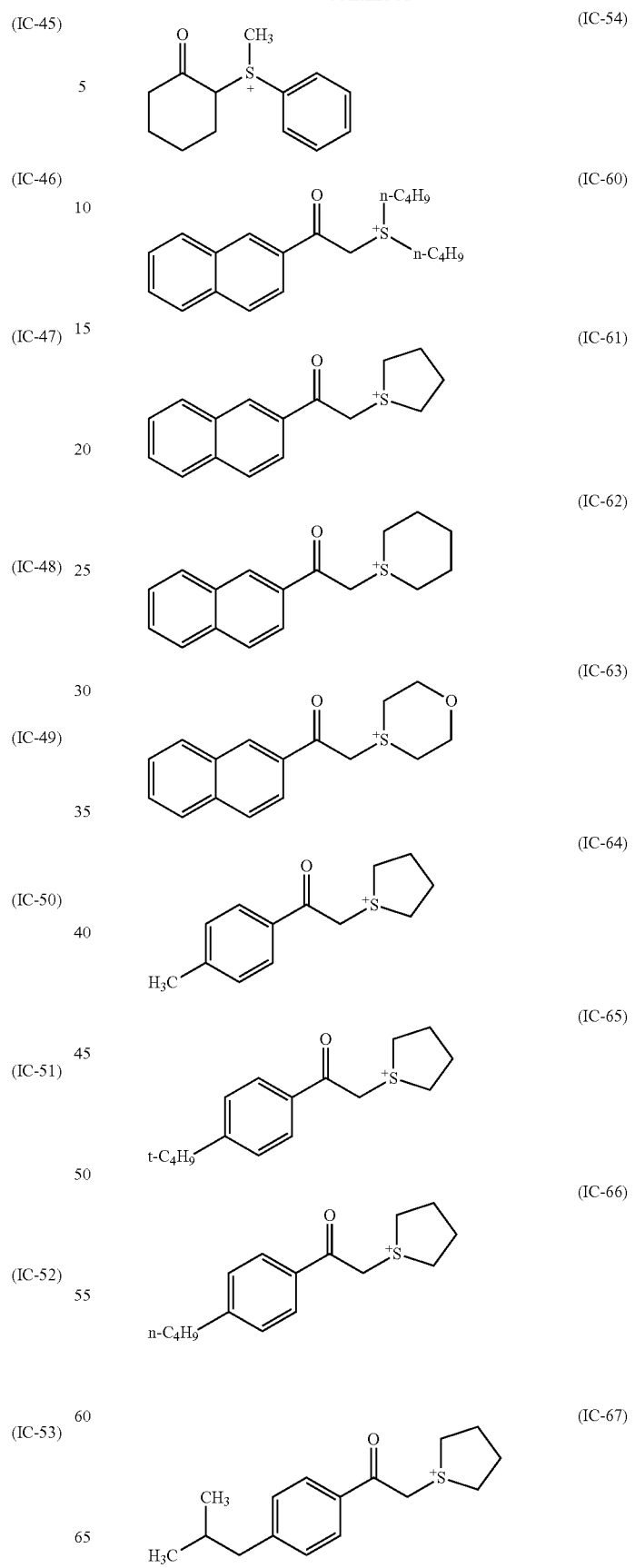

-continued (IC-68)
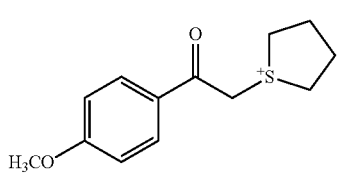

(IC-69)
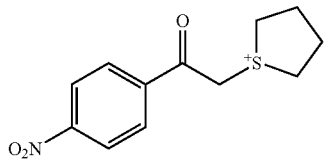

(IC-70)
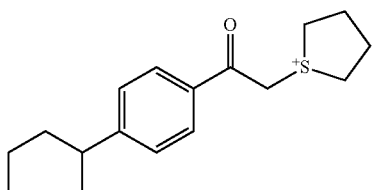

(IC-71)
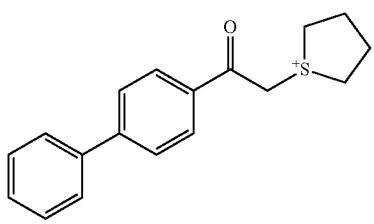

(IC-72)
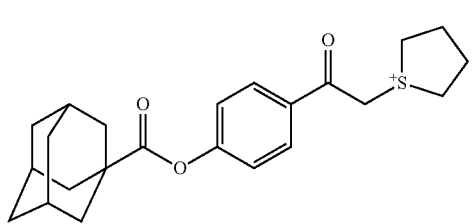

SALT (IA) is preferable a salt represented by the formula (I):

(I)
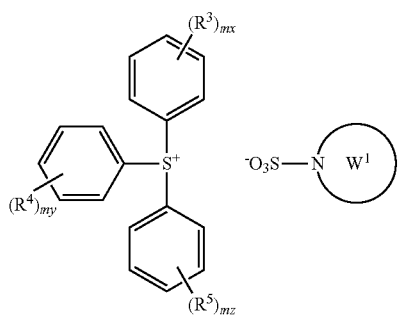

wherein $R^3$, $R^4$, $R^5$, mx, my and mz are the same as defined above and $W^1$ represents a nitrogen-containing heteroring which can have one or more substituents.

Examples of the nitrogen-containing heteroring which can have one or more substituents include the above-mentioned groups represented by the formulae (IR-301) to (IR-329).

Examples of SALT (IA) are shown in the following Tables. For example, SALT (I-1) consists of the cation represented by the formula (IB-1) and ANION (IA) wherein $R^1$ is a hydrogen atom and $R^2$ is the group represented by the formula (IR-1) and is represented by the following formula:

(I-1)
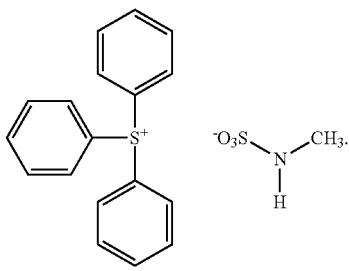

For example, SALT (I-409) consists of the cation represented by the formula (IB-10) and ANION (IA) wherein $R^1$ and $R^2$ are bonded each other to form the group represented by the formula (IR-316) together with the nitrogen atom to which they are bonded, and is represented by the following formula:

(I-409)
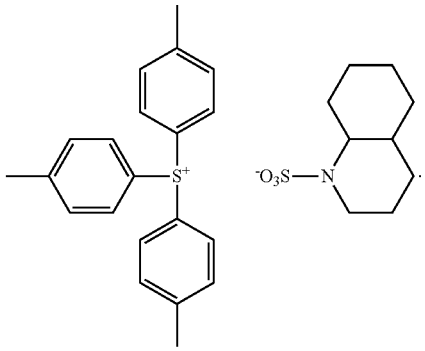

TABLE 1

| SALT (IA) | ANION (IA) | | cation |
|---|---|---|---|
| | $R^1$ | $R^2$ | |
| I-1 | H | IR-1 | IB-1 |
| I-2 | H | IR-2 | IB-1 |
| I-3 | H | IR-3 | IB-1 |
| I-4 | H | IR-4 | IB-1 |
| I-5 | H | IR-5 | IB-1 |
| I-6 | H | IR-6 | IB-1 |
| I-7 | H | IR-7 | IB-1 |
| I-8 | H | IR-8 | IB-1 |
| I-9 | H | IR-9 | IB-1 |
| I-10 | H | IR-10 | IB-1 |
| I-11 | H | IR-11 | IB-1 |
| I-12 | H | IR-12 | IB-1 |
| I-13 | H | IR-13 | IB-1 |
| I-14 | H | IR-14 | IB-1 |
| I-15 | H | IR-15 | IB-1 |
| I-16 | H | IR-16 | IB-1 |
| I-17 | H | IR-21 | IB-1 |
| I-18 | H | IR-22 | IB-1 |
| I-19 | H | IR-23 | IB-1 |
| I-20 | H | IR-24 | IB-1 |
| I-21 | H | IR-25 | IB-1 |
| I-22 | H | IR-26 | IB-1 |
| I-23 | H | IR-27 | IB-1 |

TABLE 1-continued

| SALT (IA) | ANION (IA) R¹ | R² | cation |
|---|---|---|---|
| I-24 | H | IR-28 | IB-1 |
| I-25 | H | IR-29 | IB-1 |

TABLE 2

| SALT (IA) | ANION (IA) R¹ | R² | cation |
|---|---|---|---|
| I-26 | H | IR-30 | IB-1 |
| I-27 | H | IR-31 | IB-1 |
| I-28 | H | IR-32 | IB-1 |
| I-29 | H | IR-33 | IB-1 |
| I-30 | H | IR-34 | IB-1 |
| I-31 | H | IR-35 | IB-1 |
| I-32 | H | IR-36 | IB-1 |
| I-33 | H | IR-37 | IB-1 |
| I-34 | H | IR-38 | IB-1 |
| I-35 | H | IR-51 | IB-1 |
| I-36 | H | IR-52 | IB-1 |
| I-37 | H | IR-53 | IB-1 |
| I-38 | H | IR-54 | IB-1 |
| I-39 | H | IR-55 | IB-1 |
| I-40 | H | IR-56 | IB-1 |
| I-41 | H | IR-61 | IB-1 |
| I-42 | H | IR-91 | IB-1 |
| I-43 | H | IR-92 | IB-1 |
| I-44 | H | IR-93 | IB-1 |
| I-45 | H | IR-94 | IB-1 |
| I-46 | H | IR-95 | IB-1 |
| I-47 | H | IR-96 | IB-1 |
| I-48 | H | IR-101 | IB-1 |
| I-49 | H | IR-102 | IB-1 |
| I-50 | H | IR-103 | IB-1 |

TABLE 3

| SALT (IA) | ANION (IA) R¹ | R² | cation |
|---|---|---|---|
| I-51 | H | IR-104 | IB-1 |
| I-52 | H | IR-105 | IB-1 |
| I-53 | H | IR-106 | IB-1 |
| I-54 | H | IR-111 | IB-1 |
| I-55 | H | IR-112 | IB-1 |
| I-56 | H | IR-113 | IB-1 |
| I-57 | H | IR-114 | IB-1 |
| I-58 | H | IR-115 | IB-1 |
| I-59 | H | IR-116 | IB-1 |
| I-60 | H | IR-117 | IB-1 |
| I-61 | H | IR-118 | IB-1 |
| I-62 | H | IR-121 | IB-1 |
| I-63 | H | IR-122 | IB-1 |
| I-64 | H | IR-123 | IB-1 |
| I-65 | H | IR-124 | IB-1 |
| I-66 | H | IR-125 | IB-1 |
| I-67 | H | IR-126 | IB-1 |
| I-68 | H | IR-131 | IB-1 |
| I-69 | H | IR-132 | IB-1 |
| I-70 | H | IR-133 | IB-1 |
| I-71 | H | IR-134 | IB-1 |
| I-72 | H | IR-135 | IB-1 |
| I-73 | H | IR-141 | IB-1 |
| I-74 | H | IR-142 | IB-1 |
| I-75 | H | IR-143 | IB-1 |

TABLE 4

| SALT (IA) | ANION (IA) R¹ | R² | cation |
|---|---|---|---|
| I-76 | H | IR-144 | IB-1 |
| I-77 | H | IR-145 | IB-1 |
| I-78 | H | IR-151 | IB-1 |
| I-79 | H | IR-152 | IB-1 |
| I-80 | H | IR-153 | IB-1 |
| I-81 | H | IR-154 | IB-1 |
| I-82 | H | IR-155 | IB-1 |
| I-83 | H | IR-161 | IB-1 |
| I-84 | H | IR-162 | IB-1 |
| I-85 | H | IR-163 | IB-1 |
| I-86 | H | IR-164 | IB-1 |
| I-87 | H | IR-165 | IB-1 |
| I-88 | H | IR-171 | IB-1 |
| I-89 | H | IR-172 | IB-1 |
| I-90 | H | IR-173 | IB-1 |
| I-91 | H | IR-174 | IB-1 |
| I-92 | H | IR-181 | IB-1 |
| I-93 | H | IR-182 | IB-1 |
| I-94 | H | IR-183 | IB-1 |
| I-95 | H | IR-184 | IB-1 |
| I-96 | H | IR-191 | IB-1 |
| I-97 | H | IR-192 | IB-1 |
| I-98 | H | IR-193 | IB-1 |
| I-99 | H | IR-194 | IB-1 |
| I-100 | H | IR-195 | IB-1 |

TABLE 5

| SALT (IA) | ANION (IA) R¹ | R² | cation |
|---|---|---|---|
| I-101 | H | IR-196 | IB-1 |
| I-102 | H | IR-197 | IB-1 |
| I-103 | H | IR-198 | IB-1 |
| I-104 | H | IR-199 | IB-1 |
| I-105 | H | IR-200 | IB-1 |
| I-106 | H | IR-211 | IB-1 |
| I-107 | H | IR-212 | IB-1 |
| I-108 | H | IR-213 | IB-1 |
| I-109 | H | IR-214 | IB-1 |
| I-110 | H | IR-221 | IB-1 |
| I-111 | H | IR-231 | IB-1 |
| I-112 | H | IR-241 | IB-1 |
| I-113 | H | IR-251 | IB-1 |
| I-114 | H | IR-261 | IB-1 |
| I-115 | H | IR-262 | IB-1 |
| I-116 | H | IR-263 | IB-1 |
| I-117 | H | IR-264 | IB-1 |
| I-118 | H | IR-265 | IB-1 |
| I-119 | H | IR-266 | IB-1 |
| I-120 | H | IR-271 | IB-1 |
| I-121 | H | IR-272 | IB-1 |
| I-122 | H | IR-273 | IB-1 |
| I-123 | H | IR-274 | IB-1 |
| I-124 | H | IR-275 | IB-1 |
| I-125 | H | IR-276 | IB-1 |

TABLE 6

| SALT (IA) | ANION (IA) R¹ | R² | cation |
|---|---|---|---|
| I-126 | H | IR-281 | IB-1 |
| I-127 | H | IR-282 | IB-1 |
| I-128 | H | IR-283 | IB-1 |
| I-129 | H | IR-284 | IB-1 |
| I-130 | H | IR-285 | IB-1 |
| I-131 | H | IR-286 | IB-1 |
| I-132 | IR-1 | IR-1 | IB-1 |

TABLE 6-continued

| SALT (IA) | ANION (IA) R¹ | R² | cation |
|---|---|---|---|
| I-133 | IR-2 | IR-2 | IB-1 |
| I-134 | IR-3 | IR-3 | IB-1 |
| I-135 | IR-4 | IR-4 | IB-1 |
| I-136 | IR-5 | IR-5 | IB-1 |
| I-137 | IR-6 | IR-6 | IB-1 |
| I-138 | IR-7 | IR-7 | IB-1 |
| I-139 | IR-8 | IR-8 | IB-1 |
| I-140 | IR-9 | IR-9 | IB-1 |
| I-141 | IR-10 | IR-10 | IB-1 |
| I-142 | IR-11 | IR-11 | IB-1 |
| I-143 | IR-12 | IR-12 | IB-1 |
| I-144 | IR-13 | IR-13 | IB-1 |
| I-145 | IR-14 | IR-14 | IB-1 |
| I-146 | IR-15 | IR-15 | IB-1 |
| I-147 | IR-16 | IR-16 | IB-1 |
| I-148 | IR-21 | IR-21 | IB-1 |
| I-149 | IR-22 | IR-22 | IB-1 |
| I-150 | IR-23 | IR-23 | IB-1 |

TABLE 7

| SALT (IA) | ANION (IA) R¹ | R² | cation |
|---|---|---|---|
| I-151 | IR-24 | IR-24 | IB-1 |
| I-152 | IR-25 | IR-25 | IB-1 |
| I-153 | IR-26 | IR-26 | IB-1 |
| I-154 | IR-27 | IR-27 | IB-1 |
| I-155 | IR-28 | IR-28 | IB-1 |
| I-156 | IR-29 | IR-29 | IB-1 |
| I-157 | IR-30 | IR-30 | IB-1 |
| I-158 | IR-31 | IR-31 | IB-1 |
| I-159 | IR-32 | IR-32 | IB-1 |
| I-160 | IR-33 | IR-33 | IB-1 |
| I-161 | IR-34 | IR-34 | IB-1 |
| I-162 | IR-35 | IR-35 | IB-1 |
| I-163 | IR-36 | IR-36 | IB-1 |
| I-164 | IR-37 | IR-37 | IB-1 |
| I-165 | IR-38 | IR-38 | IB-1 |
| I-166 | H | IR-287 | IB-1 |
| I-167 | H | IR-288 | IB-1 |
| I-168 | H | IR-289 | IB-1 |
| I-169 | H | IR-290 | IB-1 |
| I-170 | IR-271 | IR-23 | IB-1 |
| I-171 | IR-271 | IR-24 | IB-1 |
| I-172 | IR-271 | IR-30 | IB-1 |

TABLE 8

| SALT (IA) | ANION (IA) Group formed by bonding R¹ and R² each other together with the nitrogen atom to which they are bonded | cation |
|---|---|---|
| I-201 | IR-301 | IB-1 |
| I-202 | IR-302 | IB-1 |
| I-203 | IR-303 | IB-1 |
| I-204 | IR-304 | IB-1 |
| I-205 | IR-305 | IB-1 |
| I-206 | IR-306 | IB-1 |
| I-207 | IR-307 | IB-1 |
| I-208 | IR-308 | IB-1 |
| I-209 | IR-309 | IB-1 |
| I-210 | IR-310 | IB-1 |
| I-211 | IR-311 | IB-1 |
| I-212 | IR-312 | IB-1 |
| I-213 | IR-313 | IB-1 |
| I-214 | IR-314 | IB-1 |
| I-215 | IR-315 | IB-1 |
| I-216 | IR-316 | IB-1 |

TABLE 8-continued

| SALT (IA) | ANION (IA) Group formed by bonding R¹ and R² each other together with the nitrogen atom to which they are bonded | cation |
|---|---|---|
| I-217 | IR-317 | IB-1 |
| I-218 | IR-318 | IB-1 |
| I-219 | IR-319 | IB-1 |
| I-220 | IR-320 | IB-1 |
| I-221 | IR-321 | IB-1 |
| I-222 | IR-322 | IB-1 |
| I-223 | IR-323 | IB-1 |
| I-224 | IR-324 | IB-1 |
| I-225 | IR-325 | IB-1 |
| I-226 | IR-326 | IB-1 |
| I-227 | IR-327 | IB-1 |
| I-228 | IR-328 | IB-1 |
| I-229 | IR-329 | IB-1 |

TABLE 9

| SALT (IA) | ANION (IA) R¹ | R² | cation |
|---|---|---|---|
| I-301 | H | IR-6 | IB-10 |
| I-302 | H | IR-6 | IB-12 |
| I-303 | H | IR-6 | IB-21 |
| I-304 | H | IR-6 | IC-49 |
| I-305 | H | IR-23 | IB-10 |
| I-306 | H | IR-23 | IB-12 |
| I-307 | H | IR-23 | IB-21 |
| I-308 | H | IR-23 | IC-49 |
| I-309 | H | IR-24 | IB-10 |
| I-310 | H | IR-24 | IB-12 |
| I-311 | H | IR-24 | IB-21 |
| I-312 | H | IR-24 | IC-49 |
| I-313 | H | IR-30 | IB-10 |
| I-314 | H | IR-30 | IB-12 |
| I-315 | H | IR-30 | IB-21 |
| I-316 | H | IR-30 | IC-49 |
| I-317 | H | IR-33 | IB-10 |
| I-318 | H | IR-33 | IB-12 |
| I-319 | H | IR-33 | IB-21 |
| I-320 | H | IR-33 | IC-49 |
| I-321 | H | IR-35 | IB-10 |
| I-322 | H | IR-35 | IB-12 |
| I-323 | H | IR-35 | IB-21 |
| I-324 | H | IR-35 | IC-49 |
| I-325 | H | IR-113 | IB-10 |

TABLE 10

| SALT (IA) | ANION (IA) R¹ | R² | cation |
|---|---|---|---|
| I-326 | H | IR-113 | IB-12 |
| I-327 | H | IR-113 | IB-21 |
| I-328 | H | IR-113 | IC-49 |
| I-329 | H | IR-131 | IB-10 |
| I-330 | H | IR-131 | IB-12 |
| I-331 | H | IR-131 | IB-21 |
| I-332 | H | IR-131 | IC-49 |
| I-333 | H | IR-151 | IB-10 |
| I-334 | H | IR-151 | IB-12 |
| I-335 | H | IR-151 | IB-21 |
| I-336 | H | IR-151 | IC-49 |
| I-337 | H | IR-172 | IB-10 |
| I-338 | H | IR-172 | IB-12 |
| I-339 | H | IR-172 | IB-21 |
| I-340 | H | IR-172 | IC-49 |
| I-341 | H | IR-194 | IB-10 |
| I-342 | H | IR-194 | IB-12 |
| I-343 | H | IR-194 | IB-21 |

TABLE 10-continued

| SALT (IA) | ANION (IA) R¹ | R² | cation |
|---|---|---|---|
| I-344 | H | IR-194 | IC-49 |
| I-345 | IR-23 | IR-23 | IB-10 |
| I-346 | IR-23 | IR-23 | IB-12 |
| I-347 | IR-23 | IR-23 | IB-21 |
| I-348 | IR-23 | IR-23 | IC-49 |
| I-349 | IR-24 | IR-24 | IB-10 |
| I-350 | IR-24 | IR-24 | IB-12 |

TABLE 11

| SALT (IA) | ANION (IA) R¹ | R² | cation |
|---|---|---|---|
| I-351 | IR-24 | IR-24 | IB-21 |
| I-352 | IR-24 | IR-24 | IC-49 |
| I-353 | H | IR-287 | IB-6 |
| I-354 | H | IR-287 | IB-10 |
| I-355 | H | IR-287 | IC-49 |
| I-356 | H | IR-288 | IB-6 |
| I-357 | H | IR-288 | IB-10 |
| I-358 | H | IR-288 | IC-49 |
| I-359 | H | IR-289 | IB-6 |
| I-360 | H | IR-289 | IB-10 |
| I-361 | H | IR-289 | IC-49 |
| I-362 | H | IR-290 | IB-6 |
| I-363 | H | IR-290 | IB-10 |
| I-364 | H | IR-290 | IC-49 |
| I-365 | H | IR-193 | IB-6 |
| I-366 | H | IR-193 | IB-10 |
| I-367 | H | IR-193 | IC-49 |
| I-368 | IR-271 | IR-23 | IB-10 |
| I-369 | IR-271 | IR-24 | IB-10 |
| I-370 | IR-271 | IR-30 | IB-10 |

TABLE 12

| SALT (IA) | ANION (IA) Group formed by bonding R¹ and R² each other together with the nitrogen atom to which they are bonded | cation |
|---|---|---|
| I-401 | IR-306 | IB-10 |
| I-402 | IR-306 | IB-12 |
| I-403 | IR-306 | IB-21 |
| I-404 | IR-306 | IC-49 |
| I-405 | IR-314 | IB-10 |
| I-406 | IR-314 | IB-12 |
| I-407 | IR-314 | IB-21 |
| I-408 | IR-314 | IC-49 |
| I-409 | IR-316 | IB-10 |
| I-410 | IR-316 | IB-12 |
| I-411 | IR-316 | IB-21 |
| I-412 | IR-316 | IC-49 |
| I-413 | IR-305 | IB-6 |
| I-414 | IR-305 | IB-10 |
| I-415 | IR-305 | IC-49 |
| I-416 | IR-326 | IB-6 |
| I-417 | IR-326 | IB-10 |
| I-418 | IR-326 | IC-49 |
| I-419 | IR-327 | IB-6 |
| I-420 | IR-327 | IB-10 |
| I-421 | IR-327 | IC-49 |
| I-422 | IR-328 | IB-6 |
| I-423 | IR-328 | IB-10 |
| I-424 | IR-328 | IC-49 |
| I-425 | IR-329 | IB-6 |
| I-426 | IR-329 | IB-10 |
| I-427 | IR-329 | IC-49 |

Among them, preferred are SALT (I-26), SALT (I-29), SALT (I-98), SALT (I-150), SALT (I-151), SALT (I-166), SALT (I-205), SALT (I-206), SALT (I-214), SALT (I-216), SALT (I-226), SALT (I-227), SALT (I-313), SALT (I-317), SALT (I-321), SALT (I-337), SALT (I-341), SALT (I-349), SALT (I-354), SALT (I-366), SALT (I-401), SALT (I-405), SALT (I-409) and SALT (I-410), SALT (I-414), SALT (I-417) and SALT (I-420), and more preferred are SALT (I-151), SALT (I-205), SALT (I-216), SALT (I-309), SALT (I-313), SALT (I-349), SALT (I-354), SALT (I-366), SALT (I-401), SALT (I-409), SALT (I-414), SALT (I-417) and SALT (I-420), and especially preferred are SALT (I-205), SALT (I-216), SALT (I-313), SALT (I-349), SALT (I-354), SALT (I-366), SALT (I-401), SALT (I-409), SALT (I-414), SALT (I-417) and SALT (I-420).

The process for producing SALT (IA) wherein the cation is the cation represented by the formula (IB) is illustrated below.

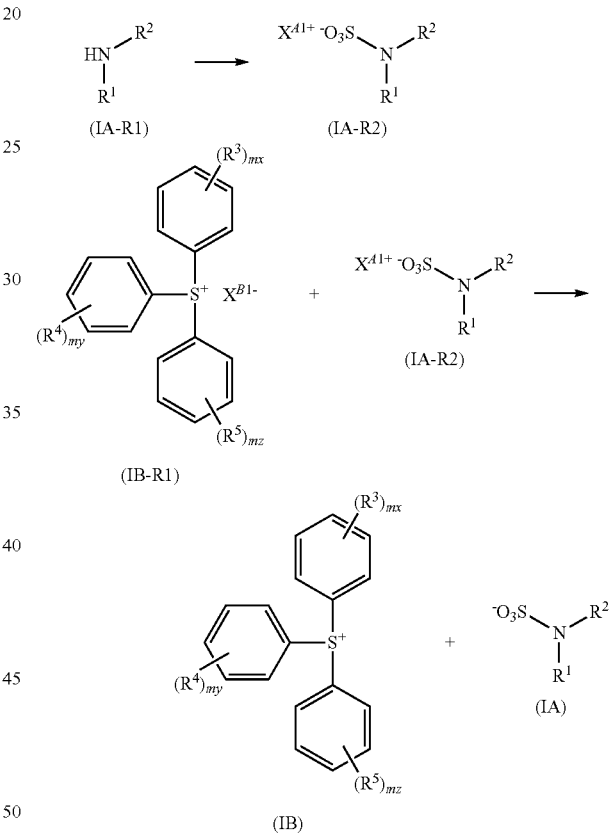

wherein $R^1$, $R^2$, $R^3$, $R^4$, $R^5$, mx, my and mz are the same as defined above, $X^{A1+}$ represents an ammonium cation and $X^{B1-}$ represents an alkylsulfate ion, a sulfate ion, a carboxylate anion, an alkoxy anion, a hydroxyl anion or a halogen anion selected from the group consisting of Cl⁻, Br⁻ and I⁻.

A salt represented by the formula (IA-R²) can be produced by reacting an amine represented by the formula (IA-R1) with a sulfur-containing compound in a solvent such as chloroform, dichloroethane, dichloromethane, acetonitrile, N,N-dimethylformamide and tetrahydrofuran in the presence of a base such as triethylamine, 1,8-diazabicyclo[5.4.0]-7-undecene (DBU), dimethylaminopyridine and pyridine. Examples of the sulfur-containing compound include chlorosulfuric acid, sulfur trioxide and a salt of sulfuric acid such as triethylammonium sulfate . SALT (IA) wherein the cation is the cation represented by the formula (IB) can be produced by reacting the salt represented by the formula (IA-R2) with a salt represented by the formula (IB-R1) in a solvent such as chloroform, dichloroethane, dichloromethane, acetonitrile, N,N-dimethylformamide and tetrahydrofuran.

The content of SALT (IA) in the photoresist composition is usually 0.01 to 1.5 parts by weight relative to 10 parts of RESIN (A) and preferably 0.05 to 0.5 parts by weight.

Next, RESIN (A) will be illustrated.

RESIN (A) is an acrylic resin having an acid-labile group and being insoluble or poorly soluble in an aqueous alkali solution but becoming soluble in an aqueous alkali solution by the action of an acid.

In this specification, "an acid-labile group" means a group capable of being eliminated by the action of an acid. In this specification, "acrylic resin" means a resin obtained by polymerizing an acrylic acid, methacrylic acid and/or its derivative.

Examples of the acid-labile group include a group represented by the formula (1a):

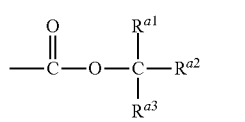

(1a)

wherein $R^{a1}$, $R^{a2}$ and $R^{a3}$ independently each represent an aliphatic hydrocarbon group or a saturated cyclic hydrocarbon group, or $R^{a1}$ and $R^{a2}$ are bonded each other to form a ring.

Examples of the aliphatic hydrocarbon group include a C1-C8 alkyl group such as a methyl group, an ethyl group, a propyl group, an isopropyl group, a butyl group, a pentyl group, a hexyl group, a heptyl group and an octyl group. The saturated cyclic hydrocarbon group may be monocyclic or polycyclic, and examples thereof include a monocyclic saturated hydrocarbon group such as a C3-C20 cycloalkyl group (e.g. a cyclopentyl group, a cyclohexyl group, a methylcyclohexyl group, a dimethylcyclohexyl group, a cycloheptyl group and a cyclooctyl group) and a polycyclic saturated hydrocarbon group such as a decahydronaphthyl group, an adamantyl group, a norbornyl group, a methylnorbornyl group, and the followings:

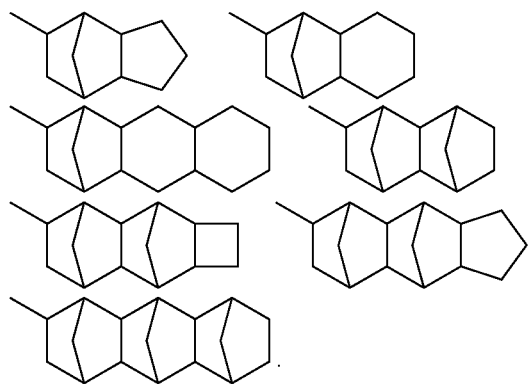

The saturated cyclic hydrocarbon group preferably has 3 to 20 carbon atoms and more preferably has 3 to 12 carbon atoms.

Examples of the ring formed by bonding $R^{a1}$ and $R^{a2}$ each other include the following groups and the ring preferably has 3 to 12 carbon atoms.

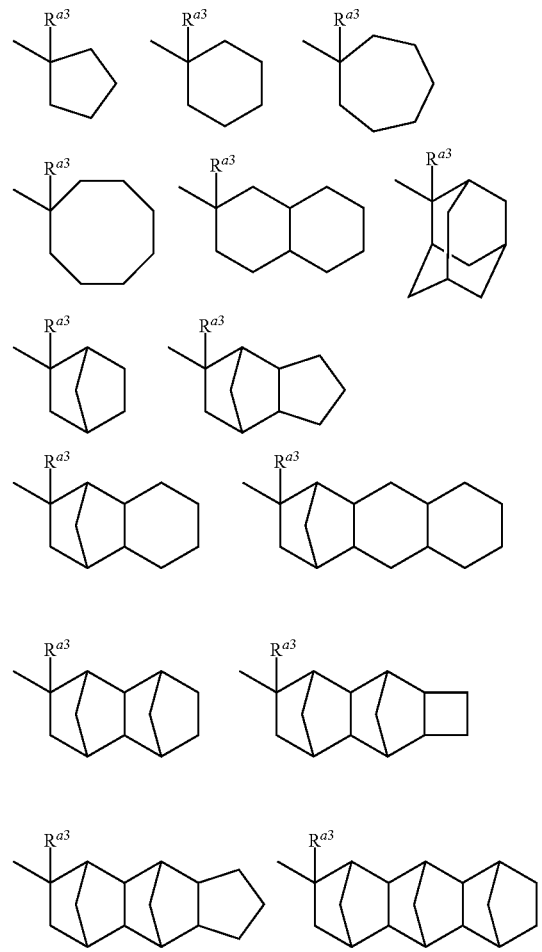

wherein $R^{a1}$ is the same as defined above.

The group represented by the formula (1a) wherein $R^{a1}$, $R^{a2}$ and $R^{a3}$ independently each represent a C1-C8 alkyl group such as a tert-butyl group, the group represented by the formula (1a) wherein $R^{a1}$ and $R^{a2}$ are bonded each other to form an adamantyl ring and $R^{a3}$ is a C1-C8 alkyl group such as a 2-alkyl-2-adamantyl group, and the group represented by the formula (1a) wherein $R^{a1}$ and $R^{a2}$ are C1-C8 alkyl groups and $R^{a3}$ is an adamantyl group such as a 1-(1-adamantyl)-1-alkylalkoxycarbonyl group are preferable.

An Acrylic monomer having a bulky acid-labile group such as a C5-C20 saturated cyclic hydrocarbon group in its side chain is preferable since a photoresist composition having excellent resolution tends to be obtained.

The structural unit having an acid-labile group is derived from a acrylic monomer having an acid-labile group in its side chain, and an acrylate monomer having an acid-labile group in its side chain or a methacrylate monomer having an acid-labile group in its side chain is preferable.

Preferable examples of the acrylic monomer having an acid-labile group include monomers represented by the formulae (a1-1) and (a1-2):

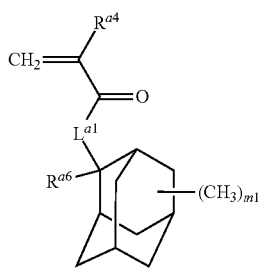

(a1-1)

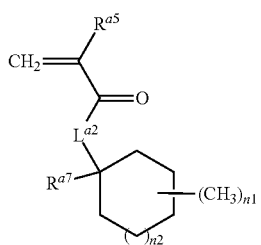

(a1-2)

wherein $R^{a4}$ and $R^{a5}$ independently represent a hydrogen atom or a methyl group, $R^{a6}$ and $R^{a7}$ independently represents a C1-C8 aliphatic hydrocarbon group or a C3-C10 saturated cyclic hydrocarbon group, $L^{a1}$ and $L^{a2}$ independently represent *-O— or *-O—$(CH_2)_{k1}$—CO—O— in which * represents a binding position to —CO—, and k1 represents an integer of 1 to 7, m1 represents an integer of 0 to 14 and n1 represents an integer of 0 to 10.

The aliphatic hydrocarbon group preferably has 1 to 6 carbon atoms, and the saturated cyclic hydrocarbon group preferably has 3 to 8 carbon atoms and more preferably 3 to 6 carbon atoms.

Examples of the aliphatic hydrocarbon group include a C1-C8 alkyl group such as a methyl group, an ethyl group, a propyl group, an isopropyl group, a butyl group, a tert-butyl group, a 2,2-dimethylethyl group, a 1-methylpropyl group, a 2,2-dimethylpropyl group, a 1-ethylpropyl group, a 1-methylbutyl group, a 2-methylbutyl group, a 3-methylbutyl group, a 1-propylbutyl group, a pentyl group, a 1-methylpentyl group, a hexyl group, a 1,4-dimethylhexyl group, a heptyl group, a 1-methylheptyl group and an octyl group. Examples of the saturated cyclic hydrocarbon group include a cyclohexyl group, a methylcyclohexyl group, a dimethylcyclohexyl group, a cycloheptyl group, a methylcycloheptyl group, a norbornyl group and a methylnorbornyl group.

$L^{a1}$ is preferably *-O— or *-O—$(CH_2)_{f1}$—CO—O— in which * represents a binding position to —CO—, and f1 represents an integer of 1 to 4, and is more preferably *-O— or *-O—$CH_2$—CO—O—, and is especially preferably *-O—.

$L^{a2}$ is preferably *-O— or *-O—$(CH_2)$ in which * represents a binding position to —CO—, and f1 represents an integer of 1 to 4, and is more preferably *-O— or *-O—$CH_2$—CO—O—, and is especially preferably *-O—.

In the formula (a1-1), m1 is preferably an integer of 0 to 3, and is more preferably 0 or 1. In the formula (a1-2), n1 is preferably an integer of 0 to 3, and is more preferably 0 or 1.

Examples of the monomer represented by the formula (a1-1) include the following.

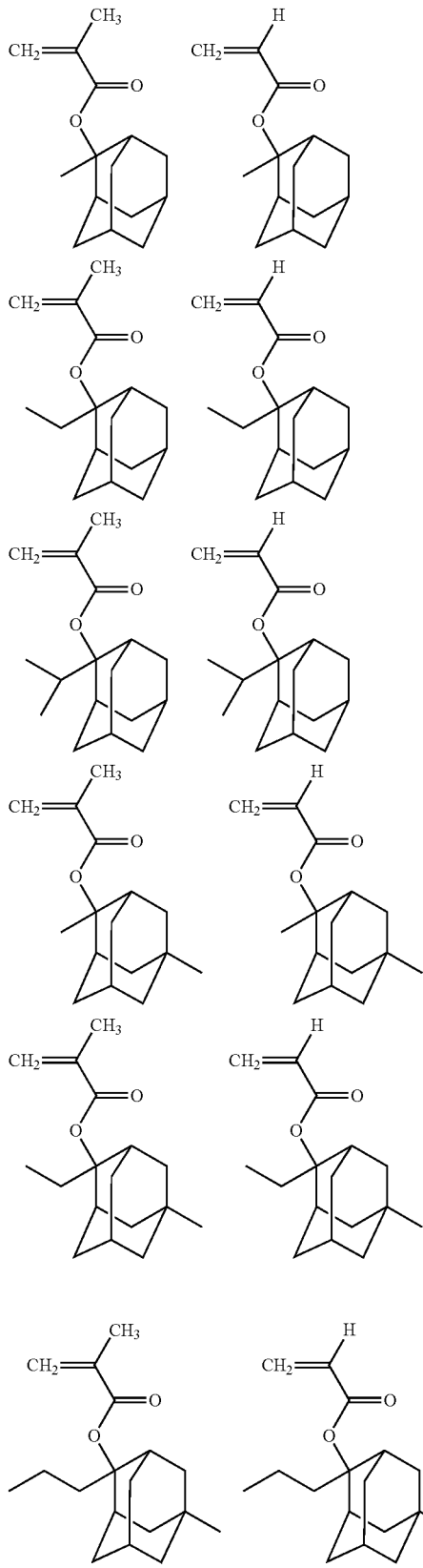

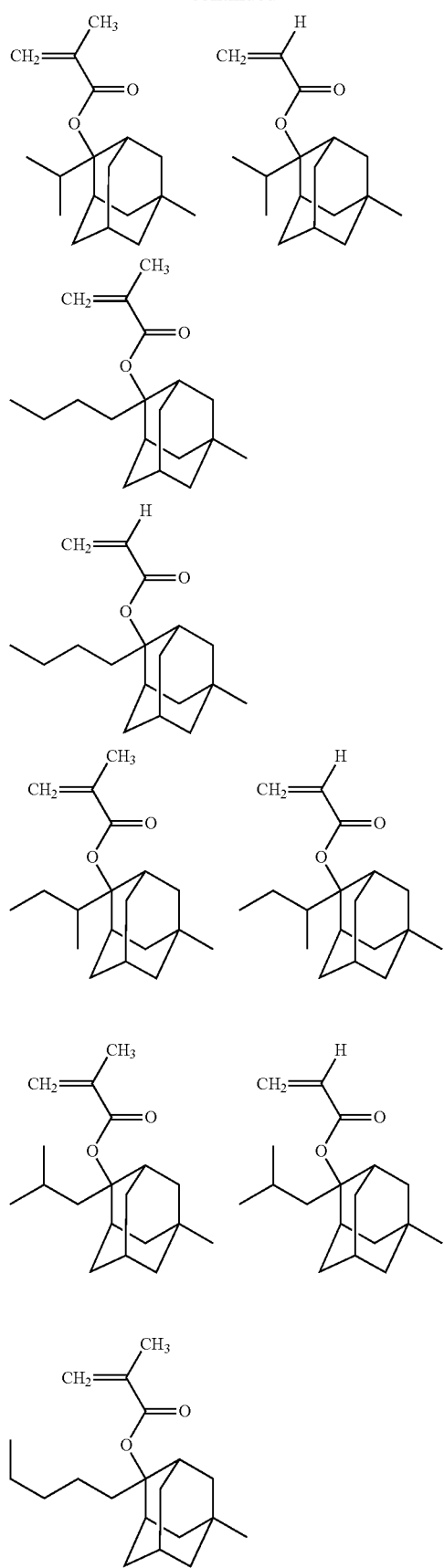
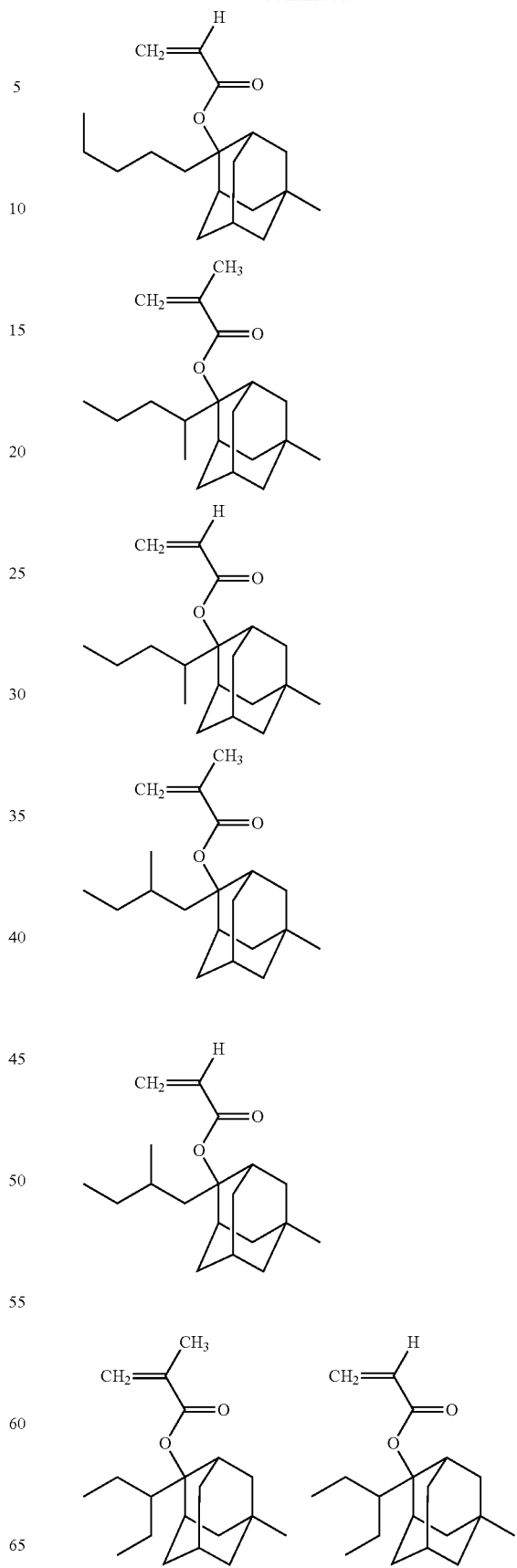

-continued
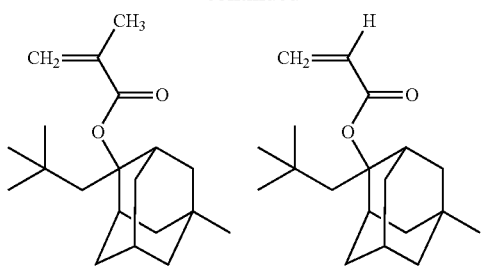
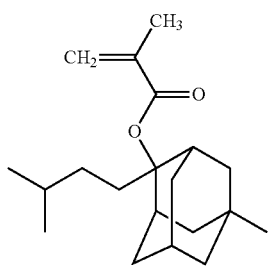
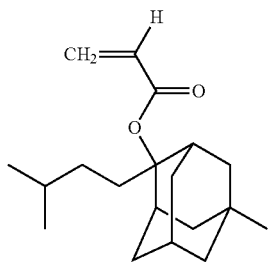
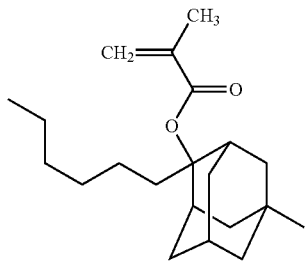
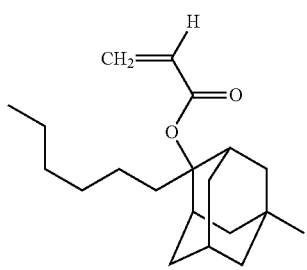
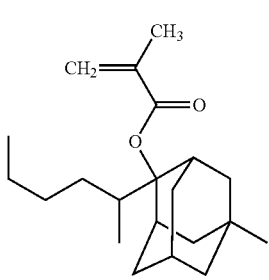
-continued
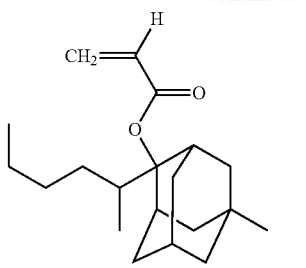
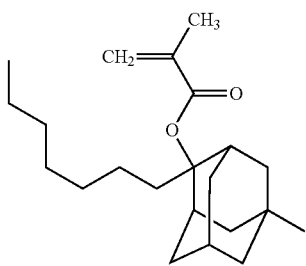
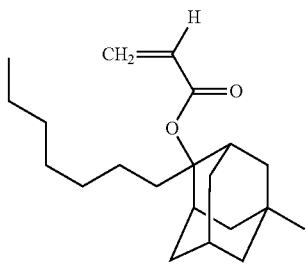
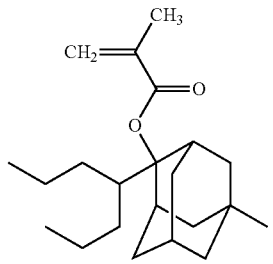
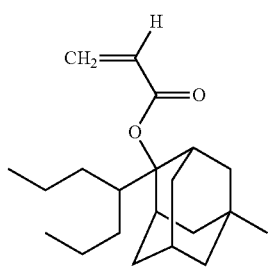
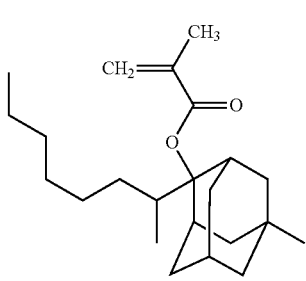

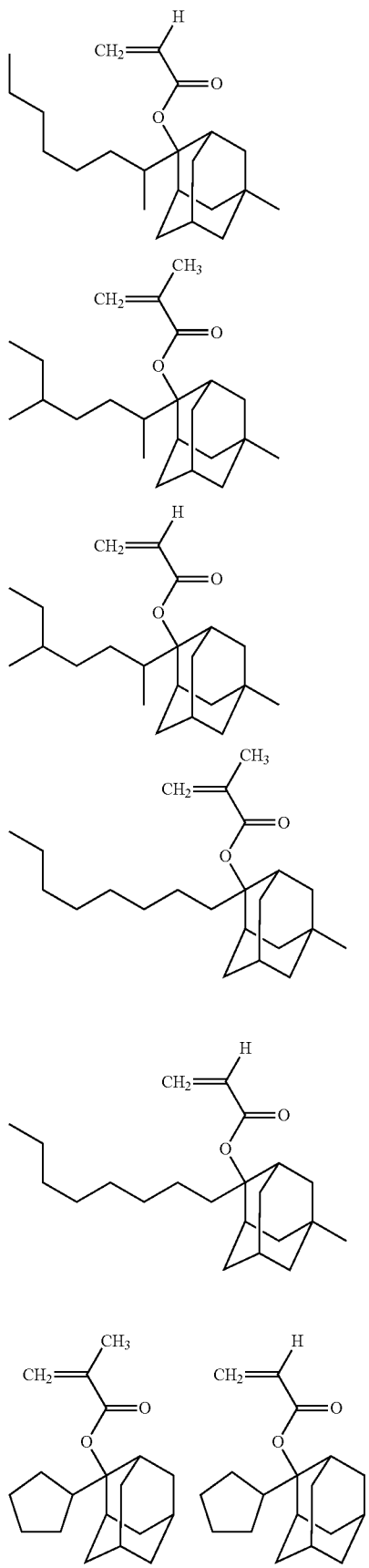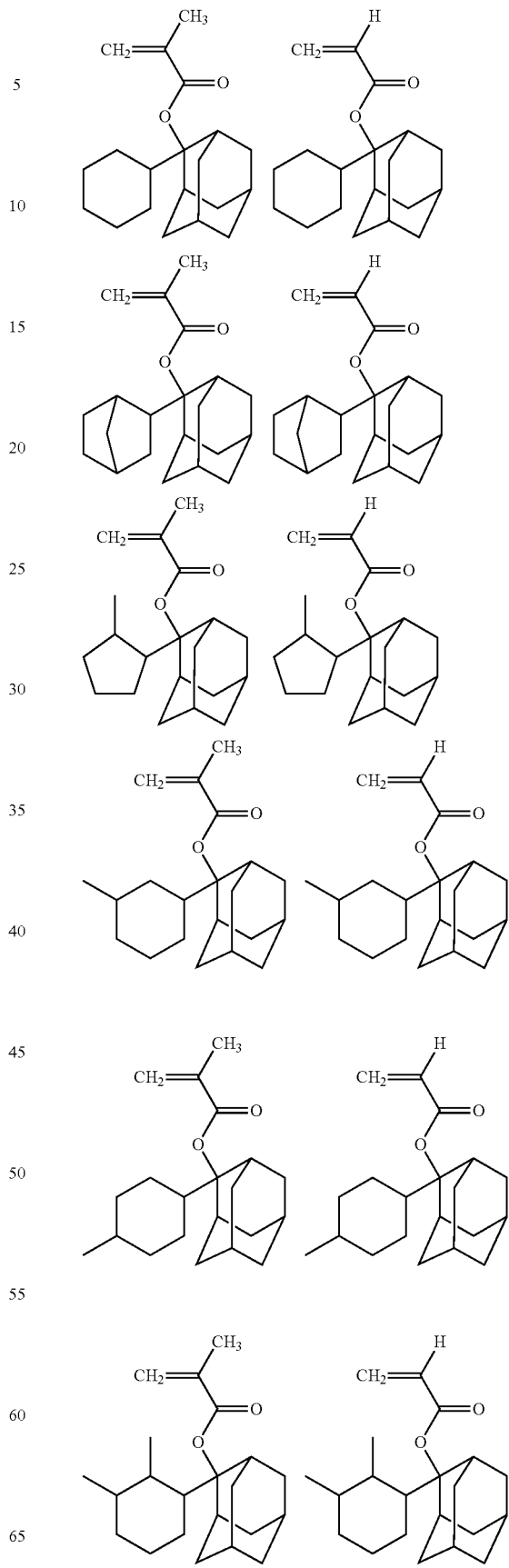

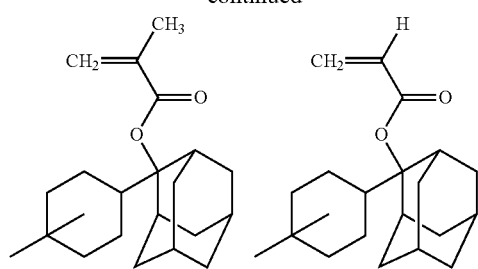
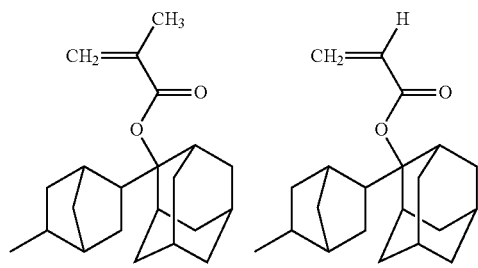
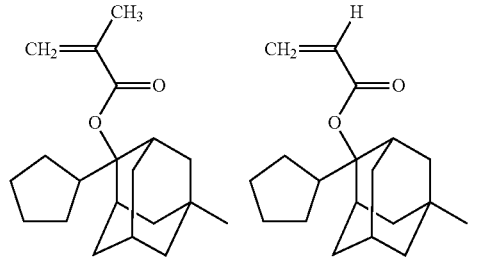
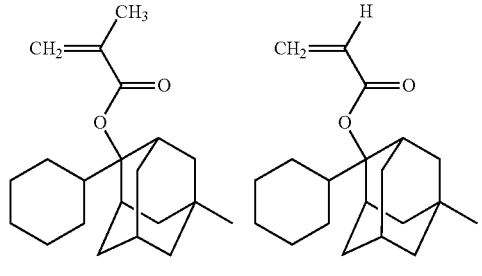
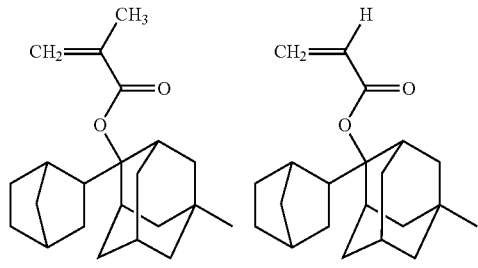
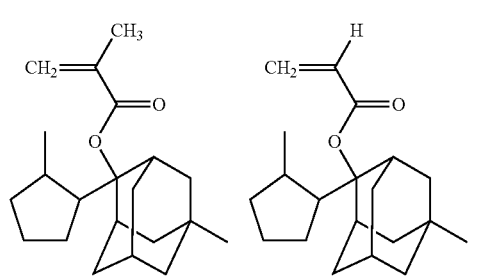
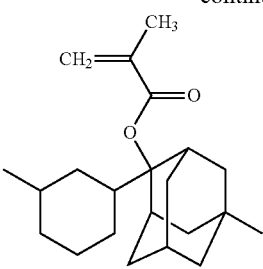
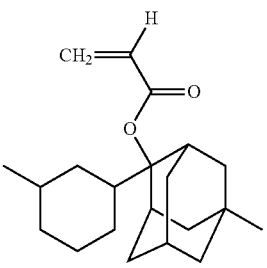
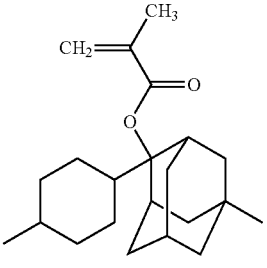
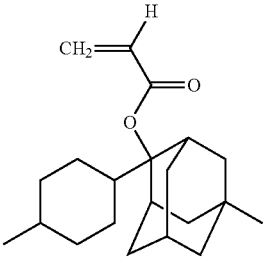
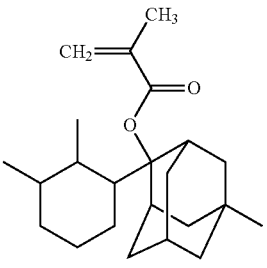
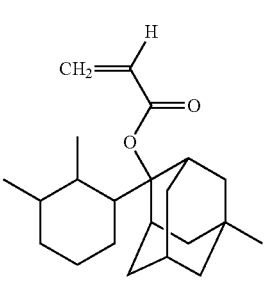

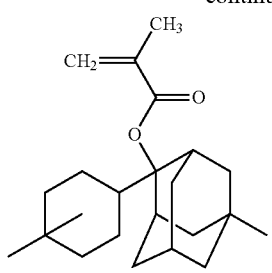
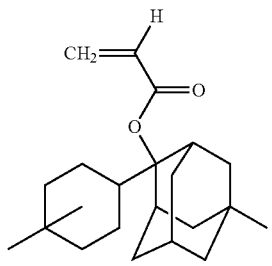
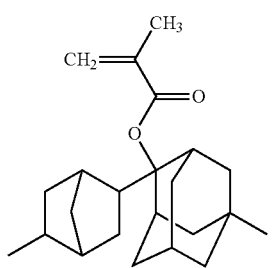
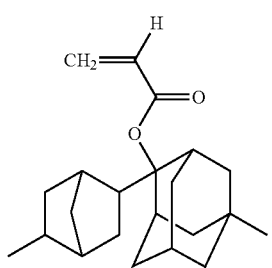
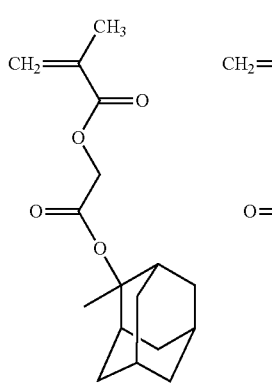
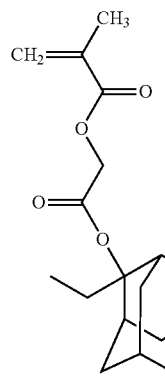
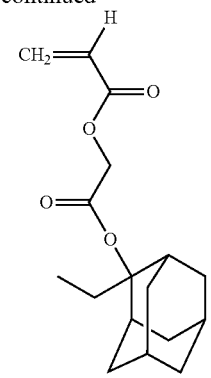
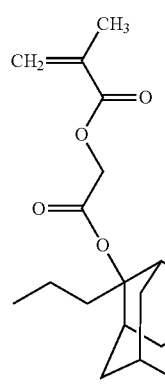
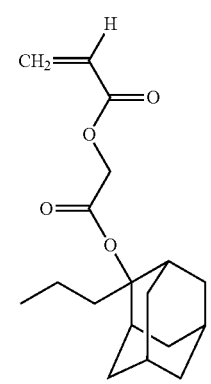
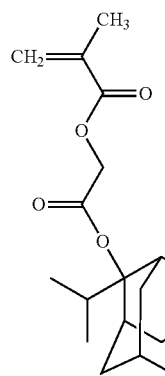
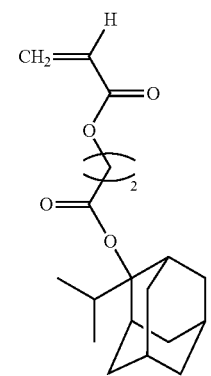
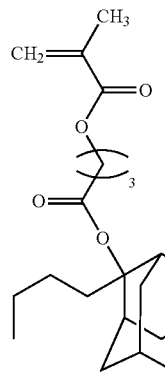
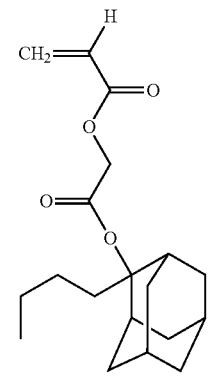

-continued
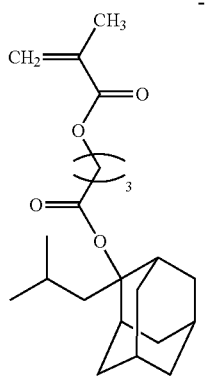 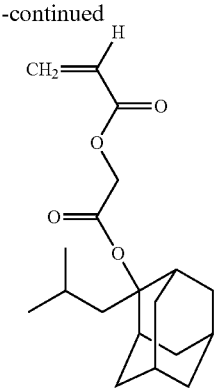 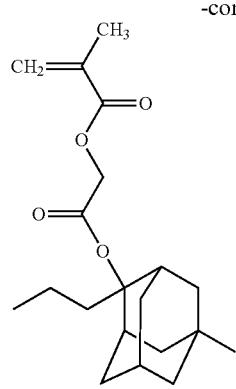 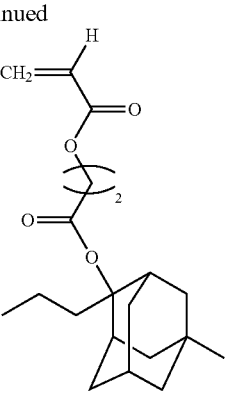
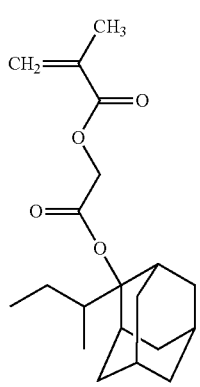 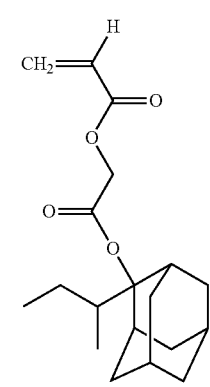 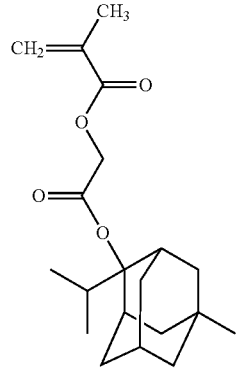 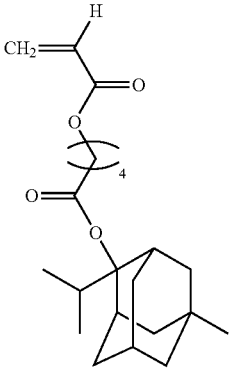
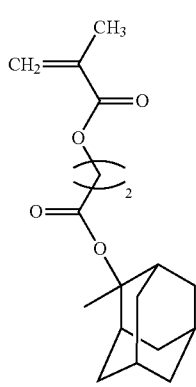 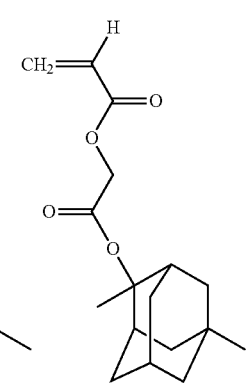 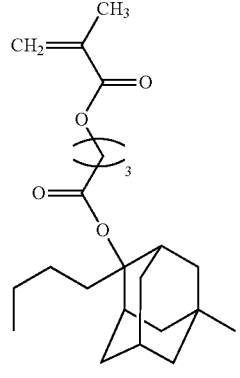 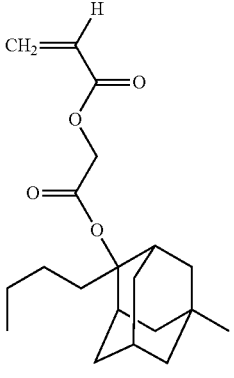
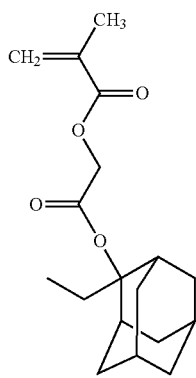 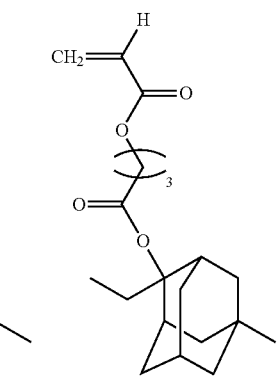 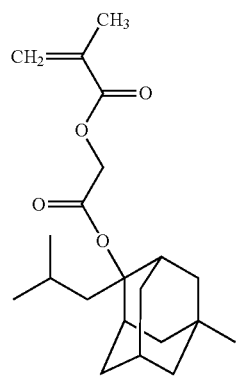 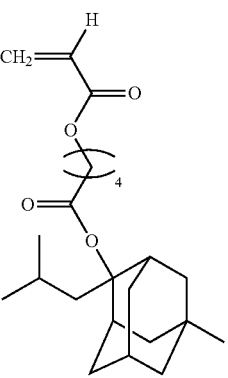

51
-continued
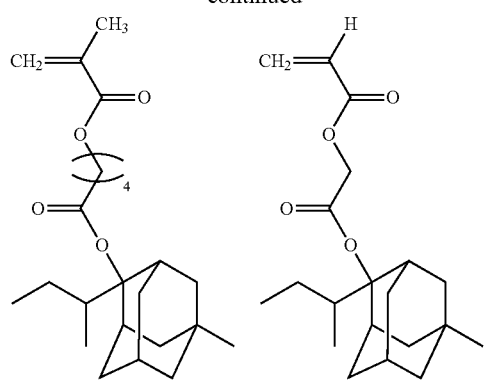
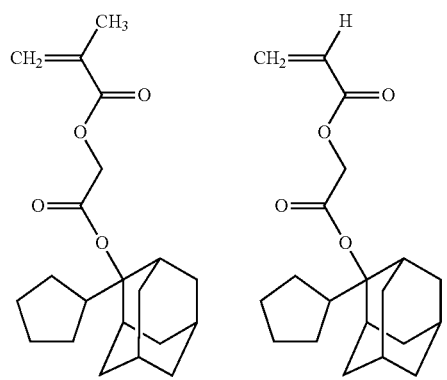
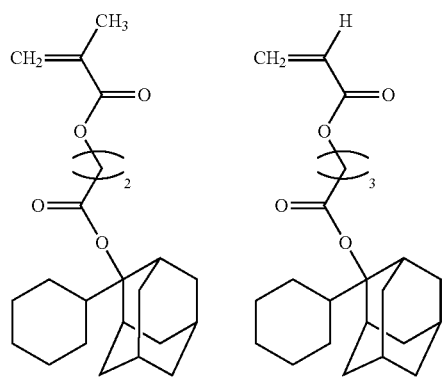
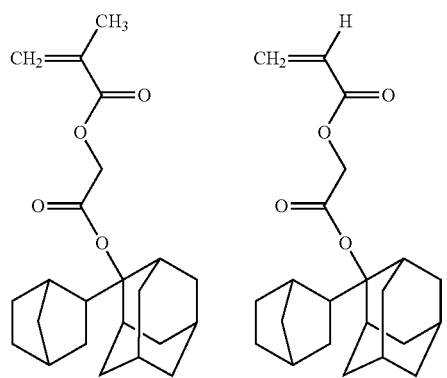
52
-continued
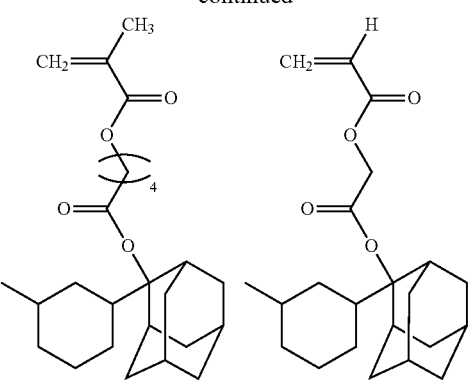
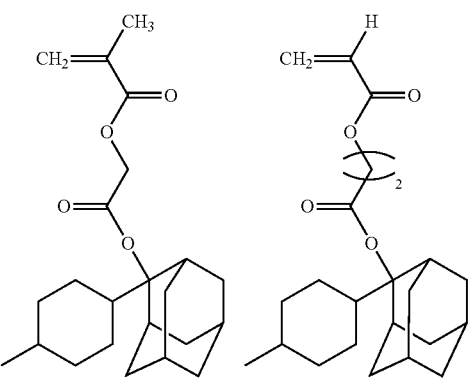
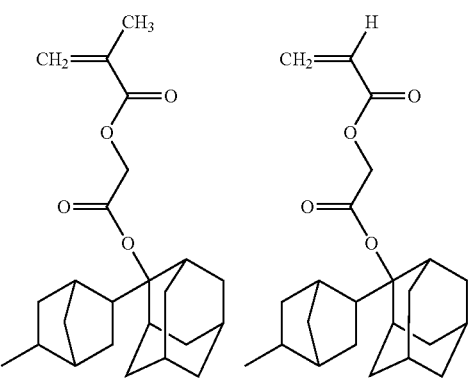
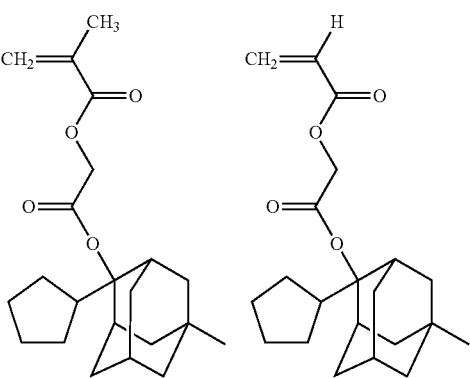

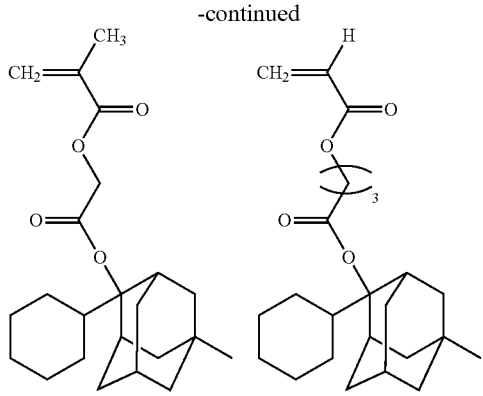
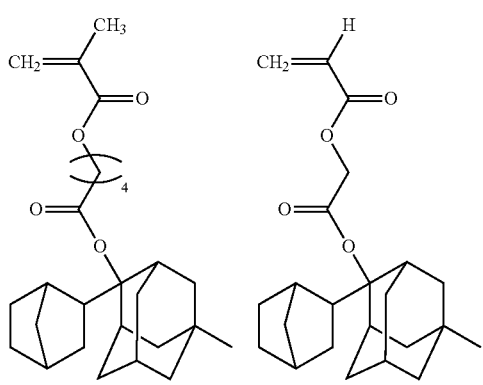
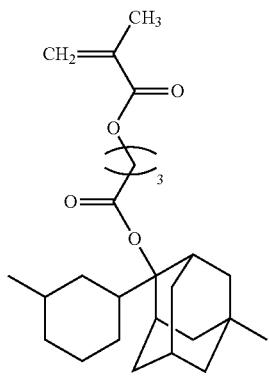
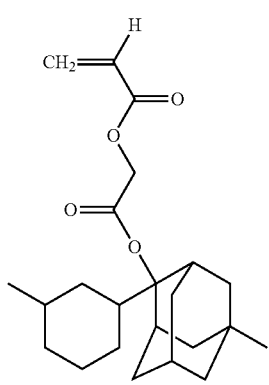
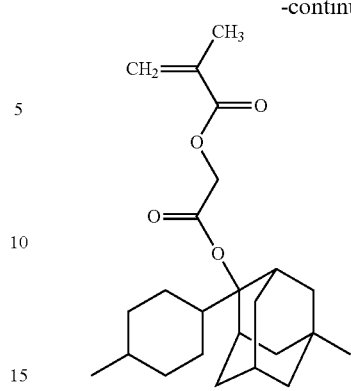
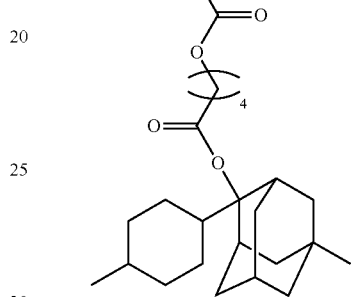
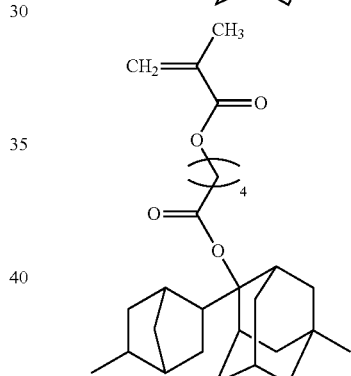
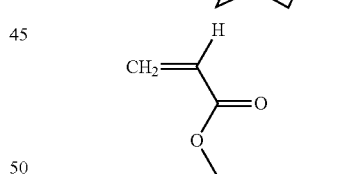
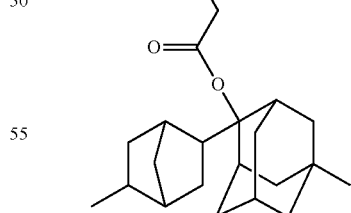
Among them, preferred are 2-methyl-2-adamantyl acrylate, 2-methyl-2-adamantyl methacrylate, 2-ethyl-2-adamantyl acrylate, 2-ethyl-2-adamantyl methacrylate, 2-isopropyl-2-adamantyl acrylate and 2-isopropyl-2-adamantyl methacrylate, and more preferred are 2-methyl-2-adamantyl methacrylate, 2-ethyl-2-adamantyl methacrylate, and 2-isopropyl-2-adamantyl methacrylate.

Examples of the monomer represented by the formula (a1-2) include the followings.

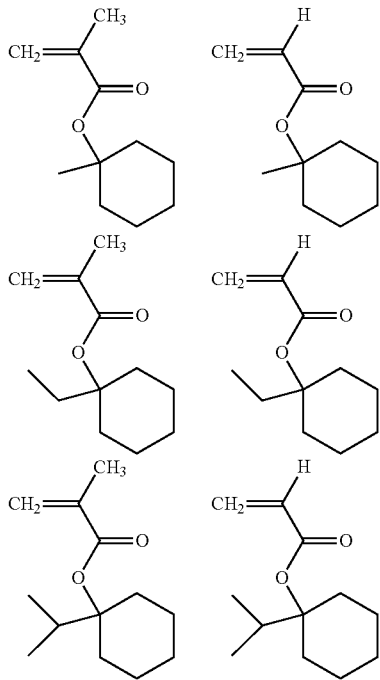

Among them, preferred are 1-ethyl-1-cyclohexyl acrylate and 1-ethyl-1-cyclohexyl methacrylate, and more preferred is 1-ethyl-1-cyclohexyl methacrylate.

The content of the structural unit derived from an acrylic monomer having an acid-labile group in RESIN (A) is usually 10 to 95% by mole, preferably 15 to 90% by mole and more preferably 20 to 85% by mole based on 100% by mole of all the structural units of RESIN (A).

RESIN (A) can contain one or more structural units having an acid-labile group other than the structural unit derived from an acrylic monomer having an acid-labile group in its side chain and examples of the monomer giving other structural unit having an acid-labile group include a monomer represented by the formula (a1-3):

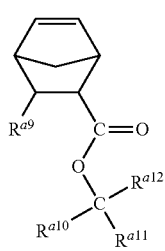

(a1-3)

wherein $R^{a9}$ represents a hydrogen atom, a C1-C3 aliphatic hydrocarbon group which can have one or more substituents, a carboxyl group, a cyano group or a —COOR$^{a13}$ group in which $R^{a13}$ represents a C1-C8 aliphatic hydrocarbon group or a C3-C8 saturated cyclic hydrocarbon group, and the C1-C8 aliphatic hydrocarbon group and the C3-C8 saturated cyclic hydrocarbon group can have one or more hydroxyl groups, and one or more —CH$_2$— in the C1-C8 aliphatic hydrocarbon group and the C3-C8 saturated cyclic hydrocarbon group can be replaced by —O— or —CO—, $R^{a10}$, $R^{a11}$ and $R^{a12}$ independently represent a C1-C12 aliphatic hydrocarbon group or a C3-C12 saturated cyclic hydrocarbon group, or $R^{a10}$ and $R^{a11}$ are bonded each other to form a ring together with the carbon atom to which $R^{a10}$ and $R^{a11}$ are bonded, and the C1-C12 aliphatic hydrocarbon group and the C3-C12 saturated cyclic hydrocarbon group can have one or more hydroxyl groups, and one or more —CH$_2$— in the C1-C12 aliphatic hydrocarbon group and the C3-C12 saturated cyclic hydrocarbon group can be replaced by —O— or —CO—.

Examples of the substituent include a hydroxyl group. Examples of the C1-C3 aliphatic hydrocarbon group which can have one or more substituents include a methyl group, an ethyl group, a propyl group, a hydroxymethyl group and a 2-hydroxyethyl group. Examples of $R^{a13}$ include a methyl group, an ethyl group, a propyl group, a 2-oxo-oxolan-3-yl group and a 2-oxo-oxolan-4-yl group. Examples of $R^{a10}$, $R^{a11}$ and $R^{a12}$ include a methyl group, an ethyl group, a cyclohexyl group, a methylcyclohexyl group, a hydroxycyclohexyl group, an oxocyclohexyl group and an adamantyl group, and examples of the ring formed by bonding $R^{a10}$ and $R^{a11}$ each other together with the carbon atom to which $R^{a10}$ and $R^{a11}$ are bonded include a cyclohexane ring and an adamantane ring.

Examples of the monomer represented by the formula (a1-3) include tert-butyl 5-norbornene-2-carboxylate, 1-cyclohexyl-1-methylethyl 5-norbornene-2-carboxylate, 1-methylcyclohexyl 5-norbornene-2-carboxylate, 2-methyl-2-adamantyl 5-norbornene-2-carboxylate, 2-ethyl-2-adamantyl 5-norbornene-2-carboxylate, 1-(4-methylcyclohexyl)-1-methylethyl 5-norbornene-2-carboxylate, 1-(4-hydroxylcyclohexyl)-1-methylethyl 5-norbornene-2-carboxylate, 1-methyl-1-(4-oxocyclohexyl) ethyl 5-norbornene-2-carboxylate and 1-(1-adamantyl)-1-methylethyl 5-norbornene-2-carboxylate.

When RESIN (A) has a structural unit derived from the monomer represented by the formula (a1-3), the photoresist composition having excellent resolution and higher dry-etching resistance tends to be obtained.

When RESIN (A) contains the structural unit derived form the monomer represented by the formula (a1-3), the content of the structural unit derived from the monomer represented by the formula (a1-3) is usually 10 to 95% by mole and preferably 15 to 90% by mole and more preferably 20 to 85% by mole based on total molar of all the structural units of RESIN (A).

Other examples of the monomer giving other structural unit having an acid-labile group include a monomer represented by the formula (a1-4):

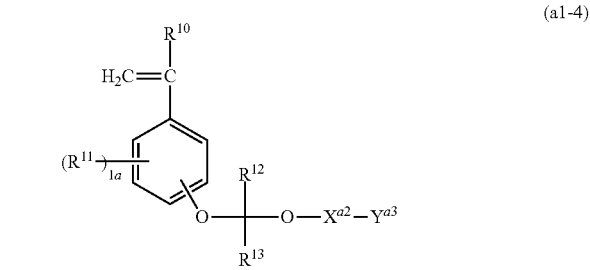

(a1-4)

wherein $R^{10}$ represents a hydrogen atom, a halogen atom, a C1-C6 alkyl group or a C1-C6 halogenated alkyl group, $R^{11}$ is independently in each occurrence a halogen atom, a hydroxyl group, a C1-C6 alkyl group, a C1-C6 alkoxy group, a C2-C4 acyl group, a C2-C4 acyloxy group, an acryloyl group or a methacryloyl group, la represents an integer of 0 to 4, $R^{12}$ and $R^{13}$ each independently represent a hydrogen atom or a C1-C12 hydrocarbon group, $X^{a2}$ represents a single bond or a C1-C17 divalent saturated hydrocarbon group in which one or more —CH$_2$— can be replaced by —O—, —CO—, —S—, —SO$_2$— or —N(R$^c$)— wherein $R^c$ represents a hydrogen atom or a C1-C6 alkyl group, and $Y^{a3}$ represents a C1-C12 aliphatic hydrocarbon group, a C3-C18 saturated cyclic hydrocarbon group or a C6-C18 aromatic hydrocarbon group, and the C1-C12 aliphatic hydrocarbon group, the C2-C18 saturated cyclic hydrocarbon group and the C6-C18 aromatic hydrocarbon group can have one or more substituents.

Examples of the halogen atom include a fluorine atom.

Examples of the C1-C6 alkyl group include a methyl group, an ethyl group, a propyl group, an isopropyl group, a butyl group, an isobutyl group, a sec-butyl group, a tert-butyl group, a pentyl group and a hexyl group, and a C1-C4 alkyl group is preferable and a C1-C2 alkyl group is more preferable and a methyl group is especially preferable.

Examples of the C1-C6 halogenated alkyl group include a trifluoromethyl group, a pentafluoroethyl group, a heptafluoropropyl group, a heptafluoroisopropyl group, a nonafluorobutyl group, a nonafluoro-sec-butyl group, a nonafluoro-tert-butyl group, a perfluoropentyl group and a perfluorohexyl group.

Examples of the C1-C6 alkoxy group include a methoxy group, an ethoxy group, a propoxy group, an isopropoxy group, a butoxy group, an isobutoxy group, a sec-butoxy group, a tert-butoxy group, a pentyloxy group and a hexyloxy group, and a C1-C4 alkoxy group is preferable and a C1-C2 alkoxy group is more preferable and a methoxy group is especially preferable.

Examples of the C2-C4 acyl group include an acetyl group, a propionyl group and a butyryl group, and examples of the C2-C4 acyloxy group include an acetyloxy group, a propionyloxy group and a butyryloxy group.

Examples of the C1-C12 hydrocarbon group include a C1-C12 aliphatic hydrocarbon group such as a methyl group, an ethyl group, a propyl group, an isopropyl group, a butyl group, an isobutyl group, a sec-butyl group, a tert-butyl group, a pentyl group, a hexyl group, a heptyl group, an octyl group, a 2-ethylhexyl group, a nonyl group, a decyl group, an undecyl group and a dodecyl group, and a C3-C12 saturated cyclic hydrocarbon group such as a cyclohexyl group, an adamantyl group, a 2-alkyl-2-adamantyl group, a 1-(1-adamantyl)-1-alkyl group and an isobornyl group.

Examples of the C1-C17 divalent saturated hydrocarbon group include a C1-C17 alkanediyl group such as a methylene group, an ethylene group, a propane-1,3-diyl group, a butane-1,4-diyl group, a pentane-1,5-diyl group, a hexane-1,6-diyl group, a heptane-1,7-diyl group, an octane-1,8-diyl group, a nonane-1,9-diyl group, a decane-1,10-diyl group, a undecane-1,1'-diyl group, a dodecane-1,12-diyl group, a tridecane-1,13-diyl group, a tetradecane-1,14-diyl group, a pentadecane-1,15-diyl group, a hexadecane-1,16-diyl group and a heptadecane-1,17-diyl group.

Examples of the C1-C12 aliphatic hydrocarbon group include a methyl group, an ethyl group, a propyl group, anisopropyl group, a butyl group, an isobutyl group, a sec-butyl group, a tert-butyl group, a pentyl group, a hexyl group, a heptyl group, an octyl group, a 2-ethylhexyl group, a nonyl group, a decyl group, an undecyl group and a dodecyl group. Examples of the C3-C18 saturated cyclic hydrocarbon group include a cyclopropyl group, a cyclobutyl group, a cyclopentyl group, a cyclohexyl group, a cycloheptyl group, a cyclooctyl group, a cyclononyl group, a cyclodecyl group, a norbornyl group, a 1-adamantyl group, a 2-adamantyl group, an isobornyl group and the following groups:

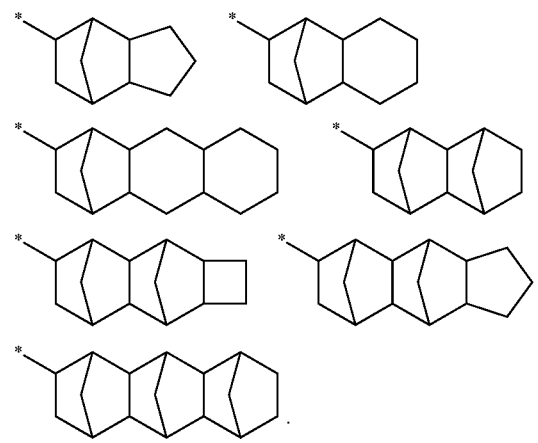

Examples of the C6-C18 aromatic hydrocarbon group include a phenyl group, a naphthyl group, an anthryl group, a p-methylphenyl group, a p-tert-butylphenyl group and a p-adamantylphenyl group.

Examples of the monomer represented by the formula (a1-4) include the followings.

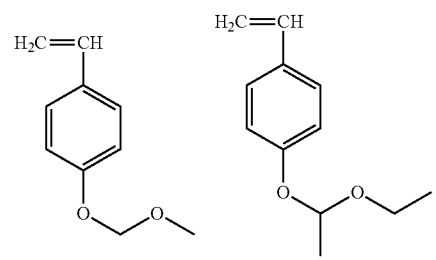

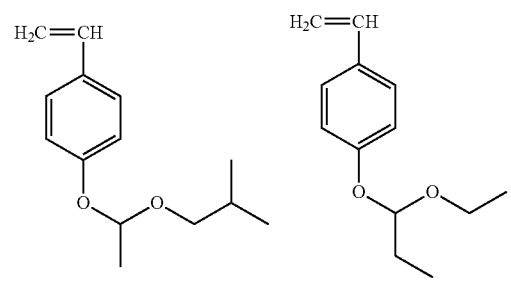

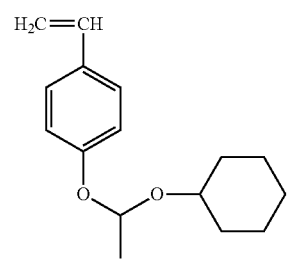

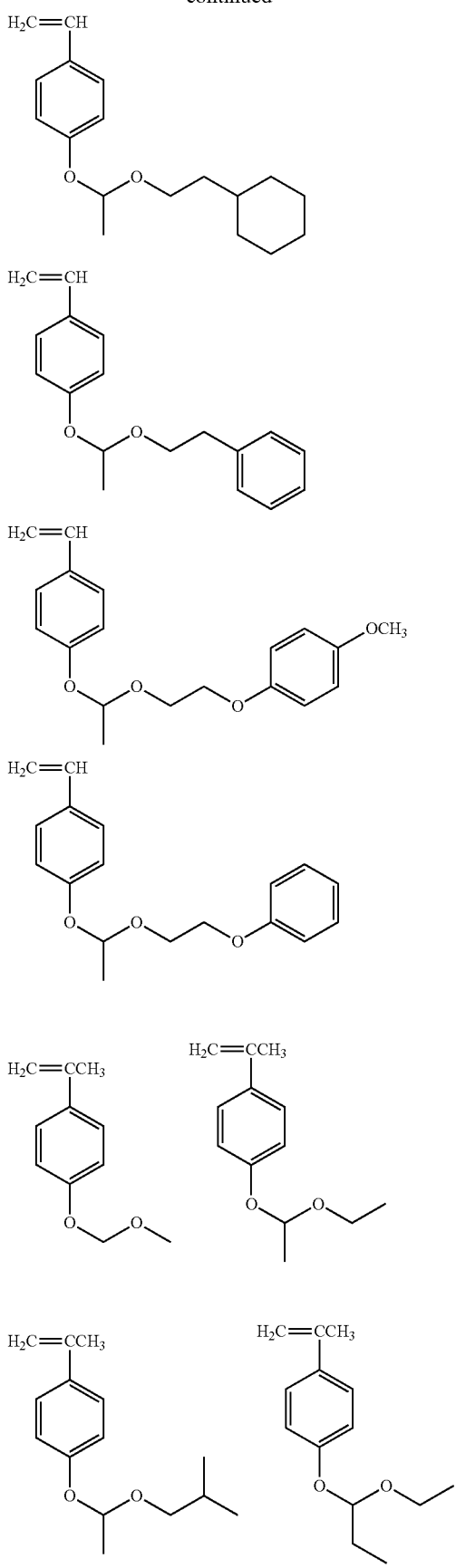

-continued
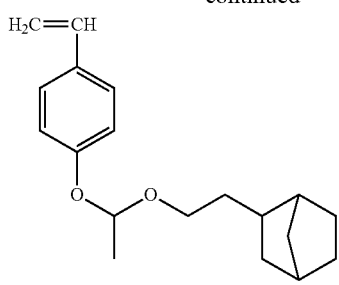
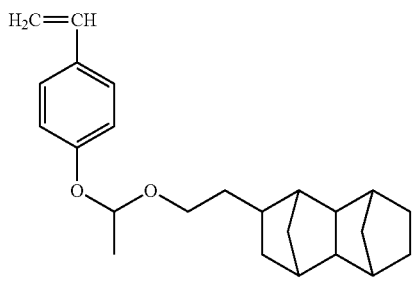
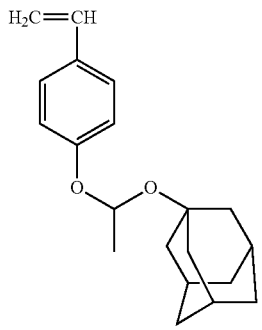
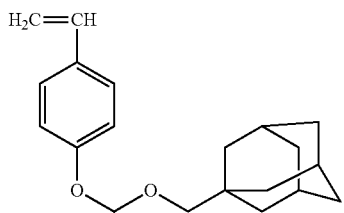
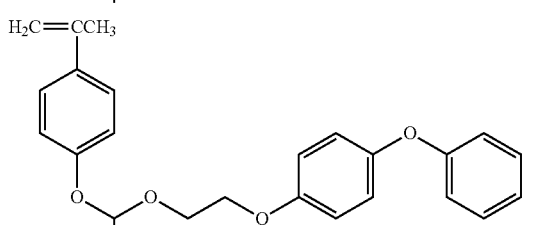
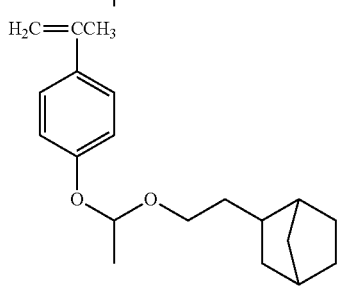
-continued
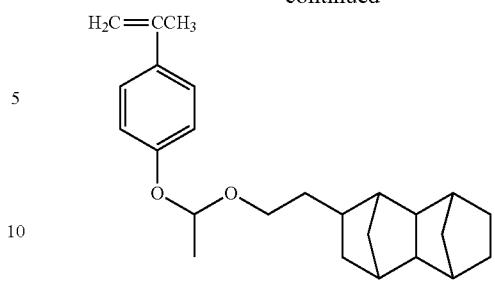
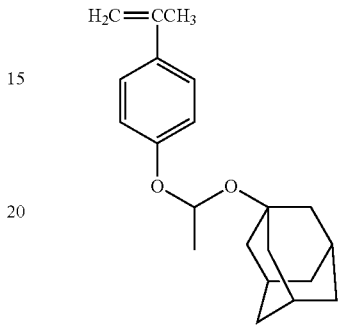
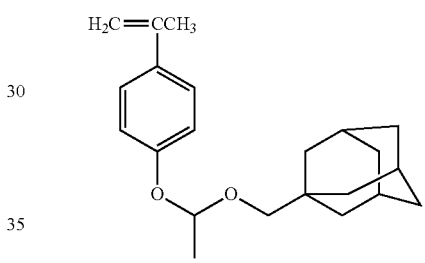
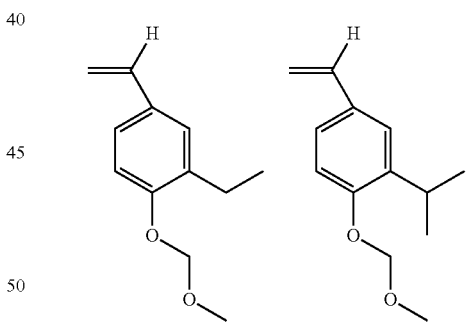
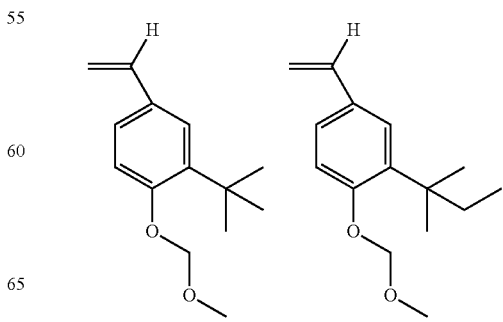

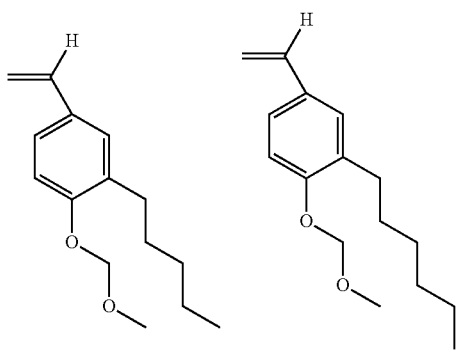
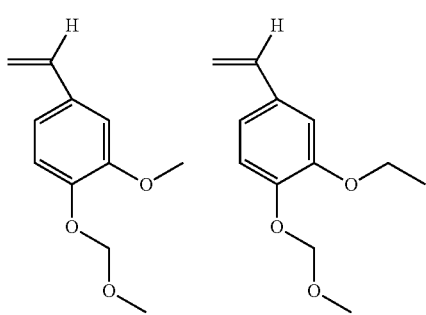
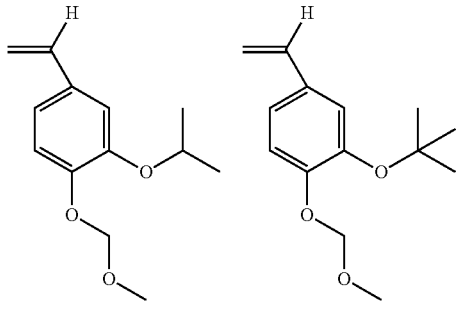
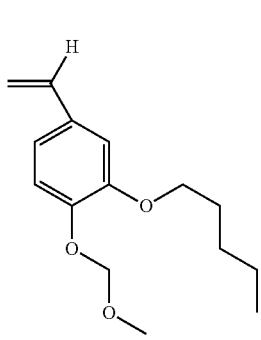
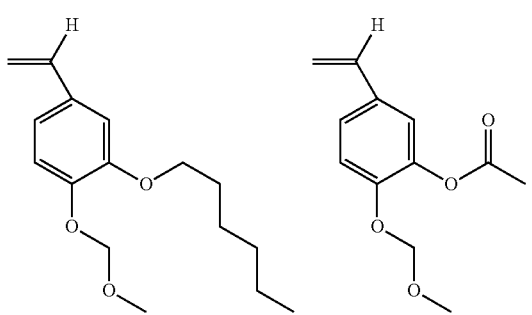
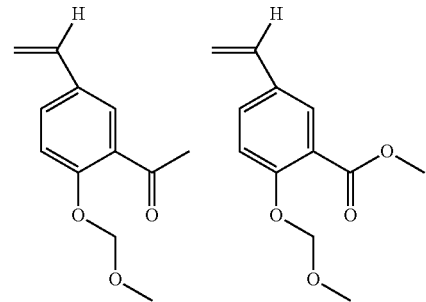
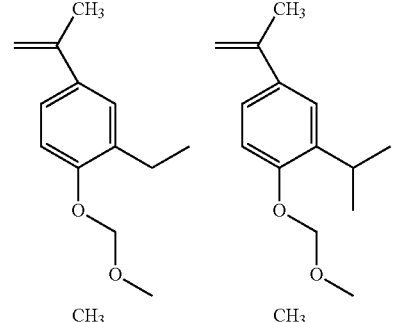
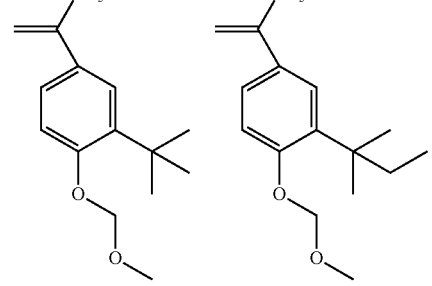
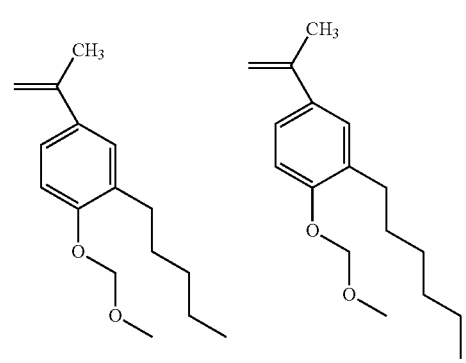
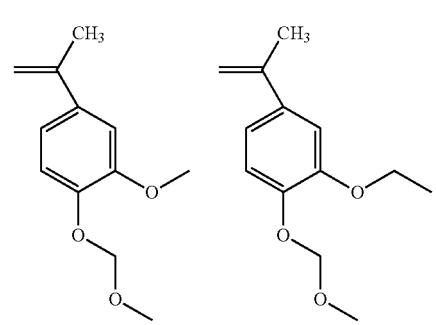

-continued

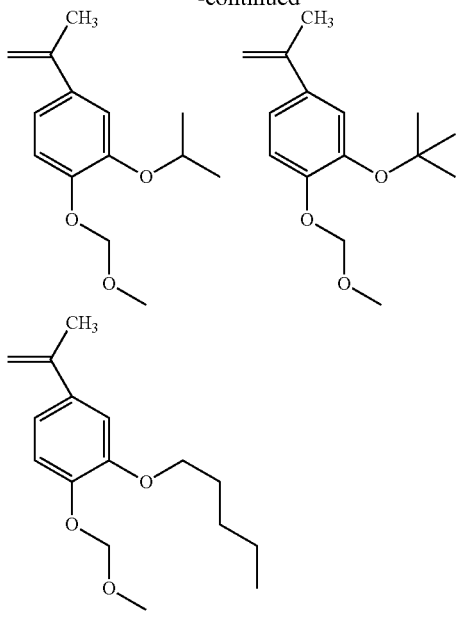
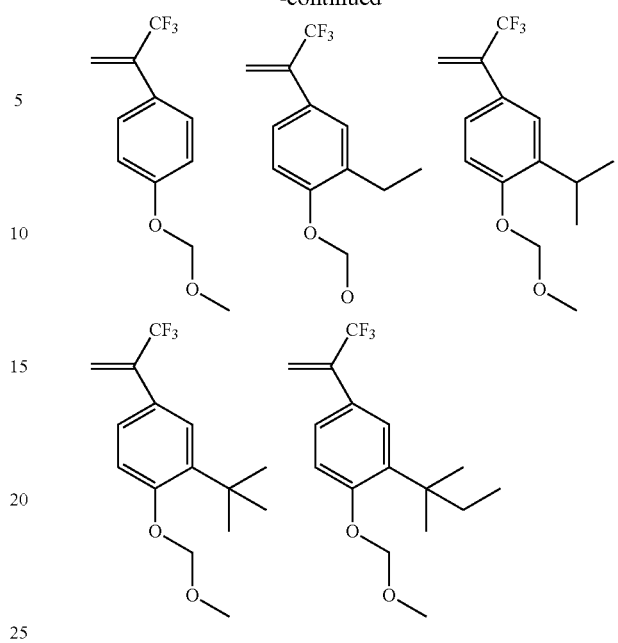
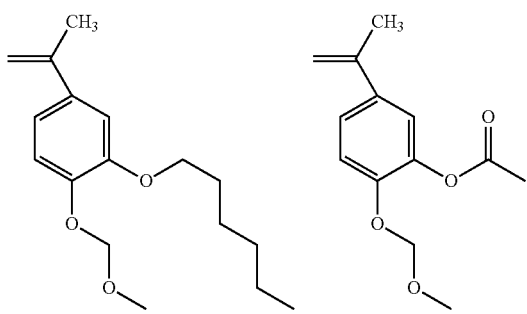
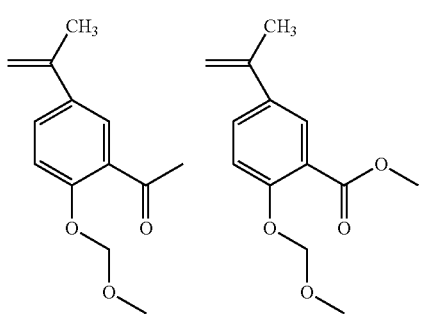
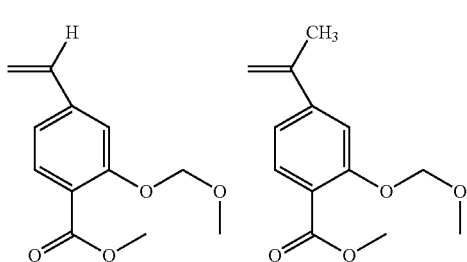

When RESIN (A) contains the structural unit derived form the monomer represented by the formula (a1-4), the content of the structural unit derived from the monomer represented by the formula (a1-4) is usually 10 to 95% by mole and preferably 15 to 90% by mole and more preferably 20 to 85% by mole based on total molar of all the structural units of RESIN (A).

RESIN (A) can have two or more kinds of structural units derived from the acrylic monomers having an acid-labile group.

RESIN (A) preferably contains the structural unit derived from the acrylic monomer having an acid-labile group and a structural unit derived from a monomer having no acid-labile group. RESIN (A) can have two or more kinds of structural units derived from the monomers having no acid-labile group. When RESIN (A) contains the structural unit derived from the acrylic monomer having an acid-labile group and the structural unit derived from the monomer having no acid-labile group, the content of the structural unit derived from the acrylic monomer having an acid-labile group is usually 10 to 80% by mole and preferably 20 to 60% by mole based on total molar of all the structural units of RESIN (A). The content of the structural unit derived from an acrylic monomer having an adamantyl group, especially the acrylic monomer represented by the formula (a1-1) in the structural unit derived from the acrylic monomers having an acid-labile group is preferably 15% by mole or more from the viewpoint of dry-etching resistance of the photoresist composition.

The monomer having no acid-labile group preferably contains one or more hydroxyl groups or a lactone ring. When RESIN (A) contains the structural unit derived from the monomer having no acid-labile group and having one or more hydroxyl groups or a lactone ring, a photoresist composition having good resolution and adhesiveness of photoresist to a substrate tends to be obtained.

Examples of the monomer having no acid-labile group and having one or more hydroxyl groups include a monomer represented by the formula (a2-0):

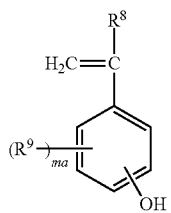

(a2-0)

wherein $R^8$ represents a hydrogen atom, a halogen atom, a C1-C6 alkyl group or a C1-C6 halogenated alkyl group, $R^9$ is independently in each occurrence a halogen atom, a hydroxyl group, a C1-C6 alkyl group, a C1-C6 alkoxy group, a C2-C4 acyl group, a C2-C4 acyloxy group, an acryloyl group or a methacryloyl group, ma represents an integer of 0 to 4, and a monomer represented by the formula (a2-1):

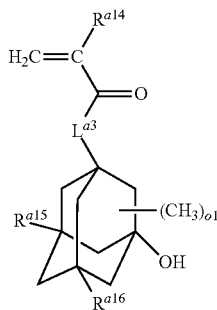

(a2-1)

wherein $R^{a14}$ represents a hydrogen atom or a methyl group, $R^{a15}$ and $R^{a16}$ each independently represent a hydrogen atom, a methyl group or a hydroxyl group, $L^{a3}$ represents *-O— or *-O—$(CH_2)_{k2}$—CO—O— in which * represents a binding position to —CO—, and k2 represents an integer of 1 to 7, and of represents an integer of 0 to 10. wherein $R^{16}$ represents a hydrogen atom or a methyl group, $R^{17}$ and $R^{18}$ independently represent a hydrogen atom, a methyl group or a hydroxyl group, $M^2$ represents *-O— or *-O—$(CH_2)_{k2}$—CO—O— in which * represents a binding position to —CO—, and k2 represents an integer of 1 to 7, and c represents an integer of 0 to 10.

When KrF excimer laser (wavelength: 248 nm) lithography system, or a high energy laser such as electron beam and extreme ultraviolet is used as an exposure system, RESIN (A) containing the structural unit derived from the monomer represented by the formula (a2-0) is preferable, and when ArF excimer laser (wavelength: 193 nm) is used as an exposure system, RESIN (A) containing the structural unit derived from the monomer represented by the formula (a2-1) is preferable.

In the formula (a2-0), examples of the halogen atom include a fluorine atom, examples of the C1-C6 alkyl group include a methyl group, an ethyl group, a propyl group, an isopropyl group, a butyl group, an isobutyl group, a sec-butyl group, a tert-butyl group, a pentyl group and a hexyl group, and a C1-C4 alkyl group is preferable and a C1-C2 alkyl group is more preferable and a methyl group is especially preferable. Examples of the C1-C6 halogenated alkyl group include a trifluoromethyl group, a pentafluoroethyl group, a heptafluoropropyl group, a heptafluoroisopropyl group, a nonafluorobutyl group, a nonafluoro-sec-butyl group, a nonafluoro-tert-butyl group, a perfluoropentyl group and a perfluorohexyl group. Examples of the C1-C6 alkoxy group include a methoxy group, an ethoxy group, a propoxy group, an isopropoxy group, a butoxy group, an isobutoxy group, a sec-butoxy group, a tert-butoxy group, a pentyloxy group and a hexyloxy group, and a C1-C4 alkoxy group is preferable and a C1-C2 alkoxy group is more preferable and a methoxy group is especially preferable. Examples of the C2-C4 acyl group include an acetyl group, a propionyl group and a butyryl group, and examples of the C2-C4 acyloxy group include an acetyloxy group, a propionyloxy group and a butyryloxy group. In the formula (a2-0), ma is preferably 0, 1 or 2, and is more preferably 0 or 1, and especially preferably 0.

RESIN (A) containing the structural unit derived from the monomer represented by the formula (a2-0) and the structural unit derived from the monomer having an acid generator can be produced, for example, by polymerizing a monomer having an acid-labile group and a monomer obtained by protecting a hydroxyl group of the monomer represented by the formula (a2-0) with an acetyl group followed by conducting deacetylation of the obtained polymer with a base.

Examples of the monomer represented by the formula (a2-0) include the followings.

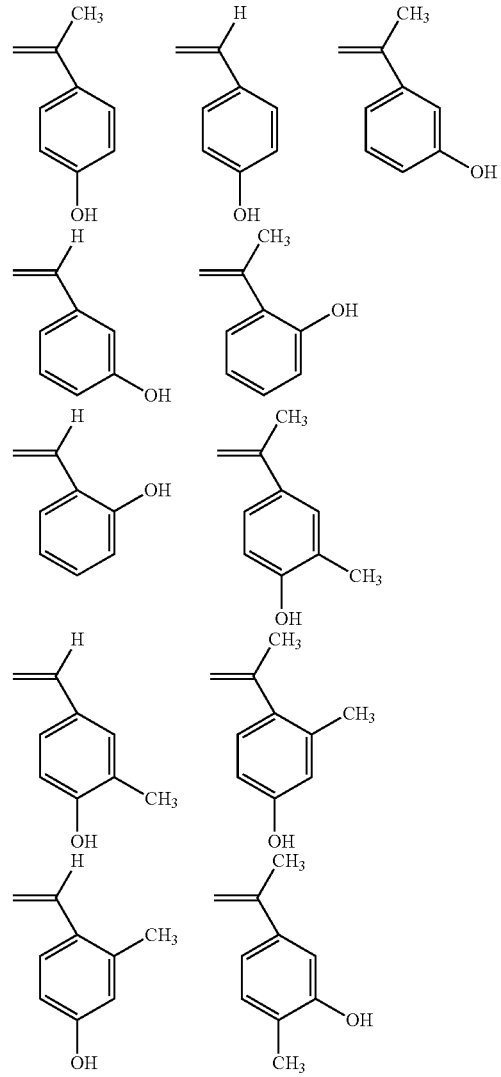

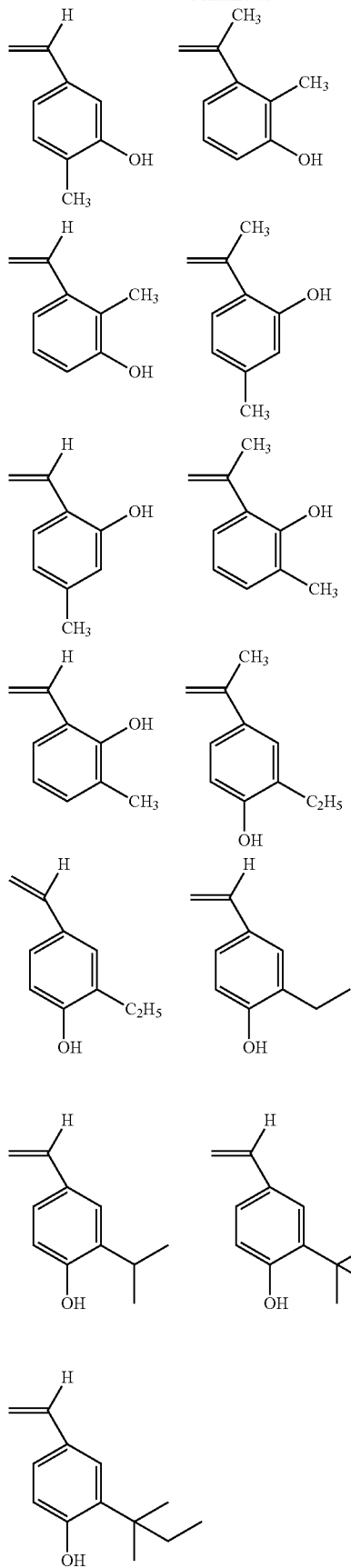
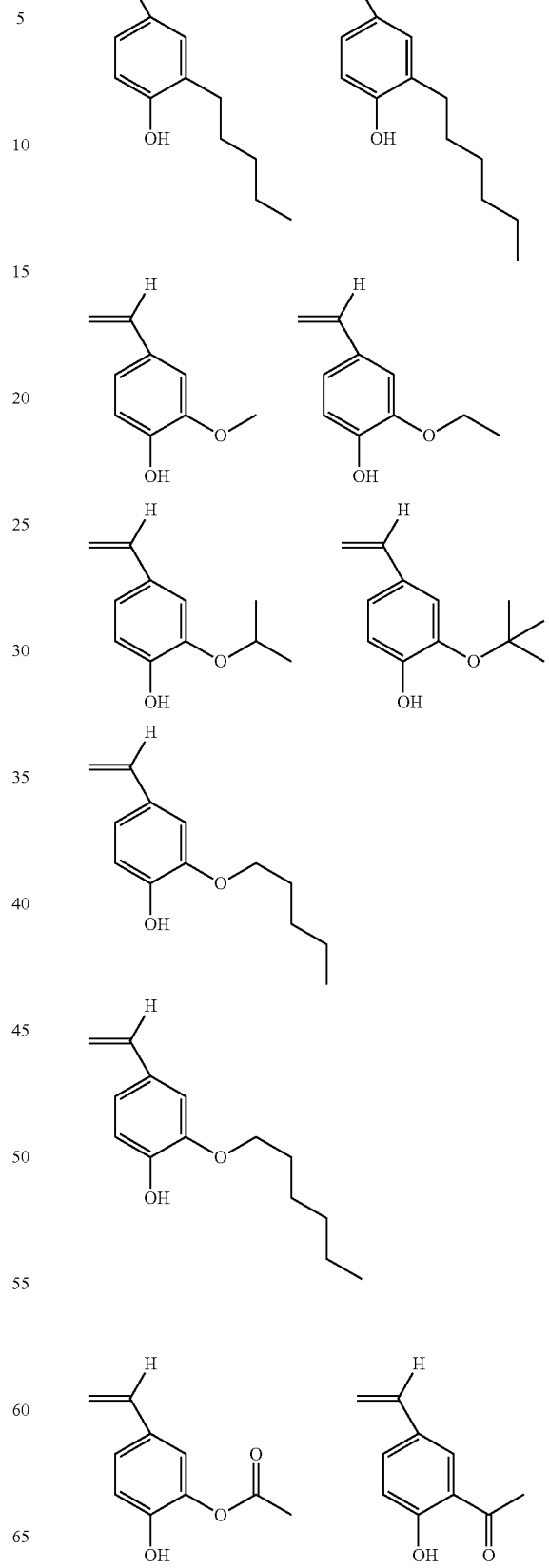

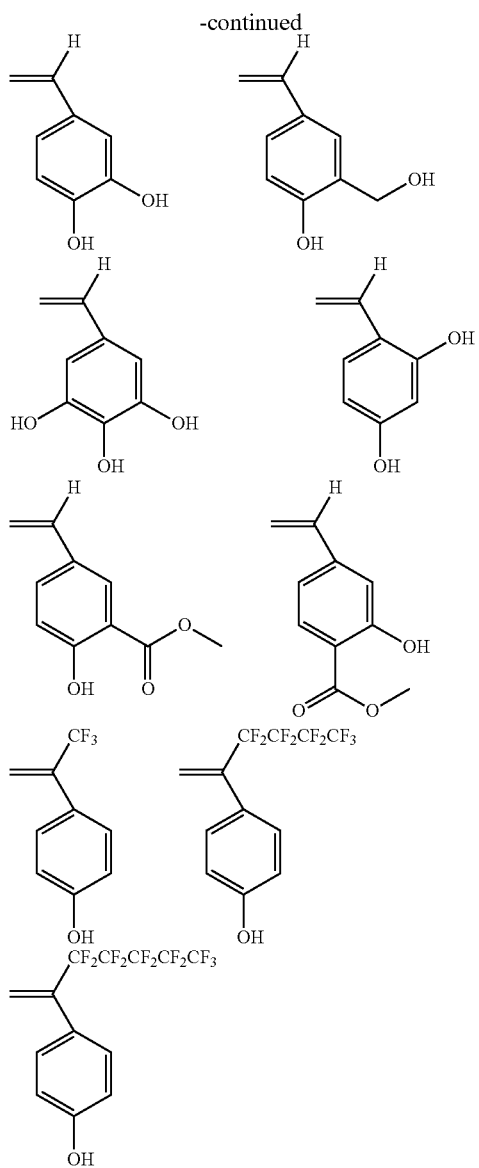

Among them, preferred are 4-hydroxystyrene and 4-hydroxy-α-methylstyrene.

When RESIN (A) contains the structural unit derived from the monomer represented by the formula (a2-0), the content of the structural unit derived from the monomer represented by the formula (a2-0) is usually 5 to 90% by mole and preferably 10 to 85% by mole and more preferably 15 to 80% by mole based on total molar of all the structural units of RESIN (A).

In the formula (a2-1), $R^{a14}$ is preferably a methyl group, $R^{a15}$ is preferably a hydrogen atom, $R^{a16}$ is preferably a hydrogen atom or a hydroxyl group, $L^{a3}$ is preferably *-O— or *-O—$(CH_2)_{f2}$—CO—O— in which * represents a binding position to —CO—, and f2 represents an integer of 1 to 4, and is more preferably *-O—, and of is preferably 0, 1, 2 or 3 and is more preferably 0 or 1.

Examples of the monomer represented by the formula (a2-1) include the followings, and 3-hydroxy-1-adamantyl acrylate, 3-hydroxy-1-adamantyl methacrylate, 3,5-dihydroxy-1-adamantyl acrylate, 3,5-dihydroxy-1-adamantyl methacrylate, 1-(3,5-dihydroxy-1-adamantyloxycarbonyl) methyl acrylate and 1-(3,5-dihydroxy-1-adamantyloxycarbonyl)methyl methacrylate are preferable, and 3-hydroxy-1-adamantyl methacrylate and 3,5-dihydroxy-1-adamantyl methacrylate are more preferable.

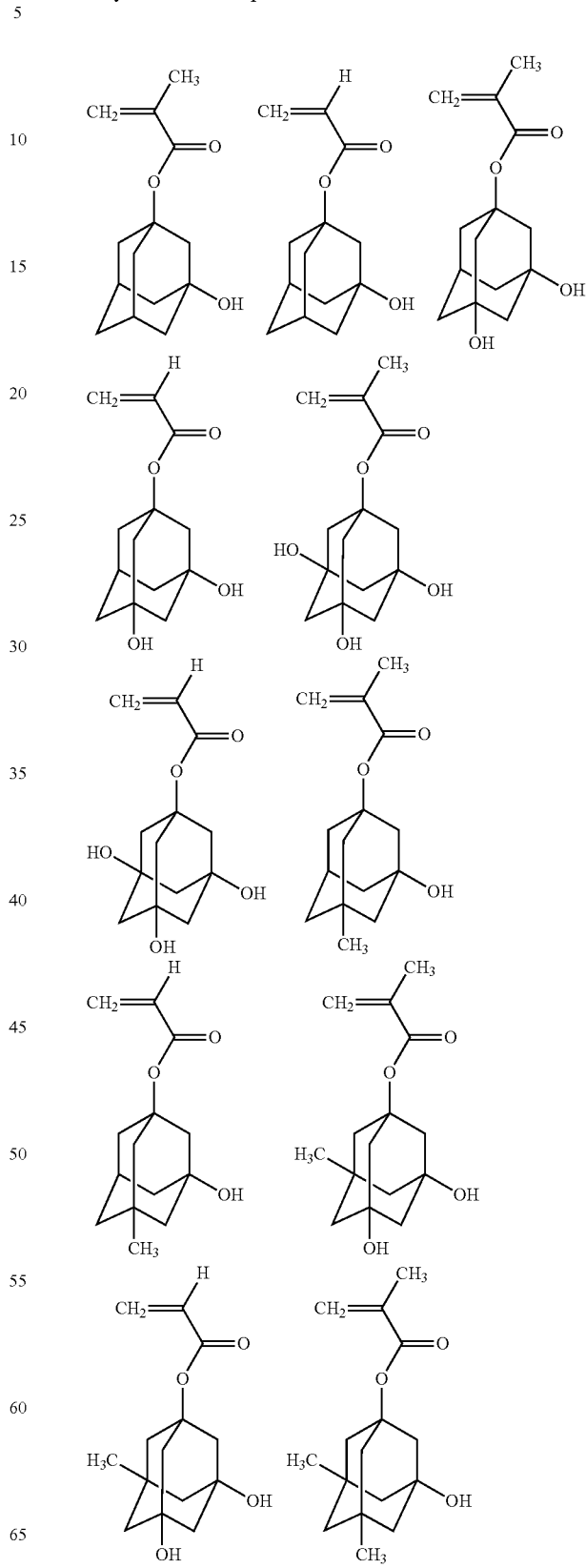

73
-continued
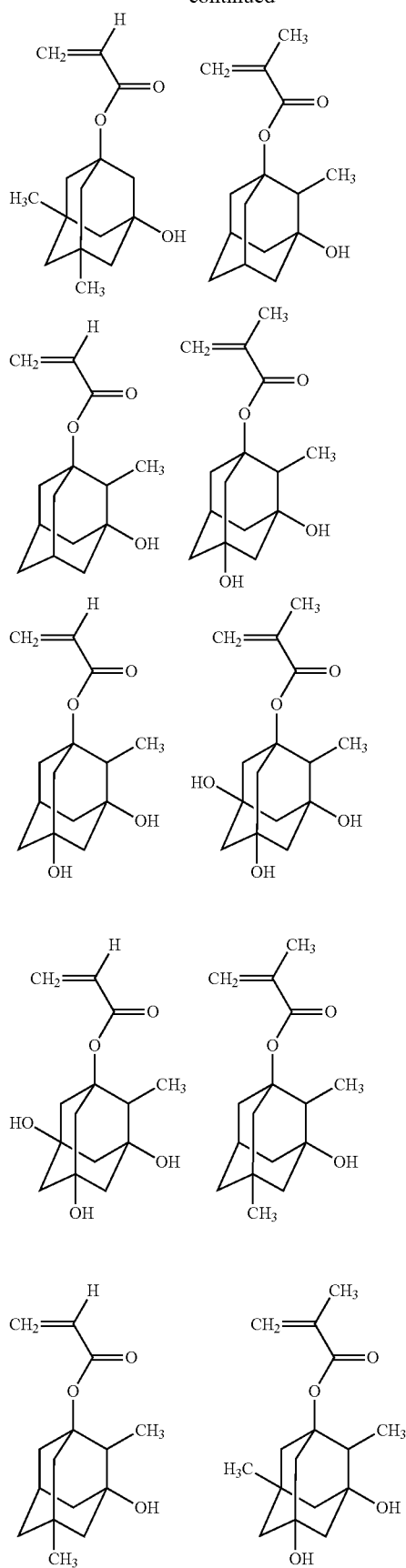
74
-continued
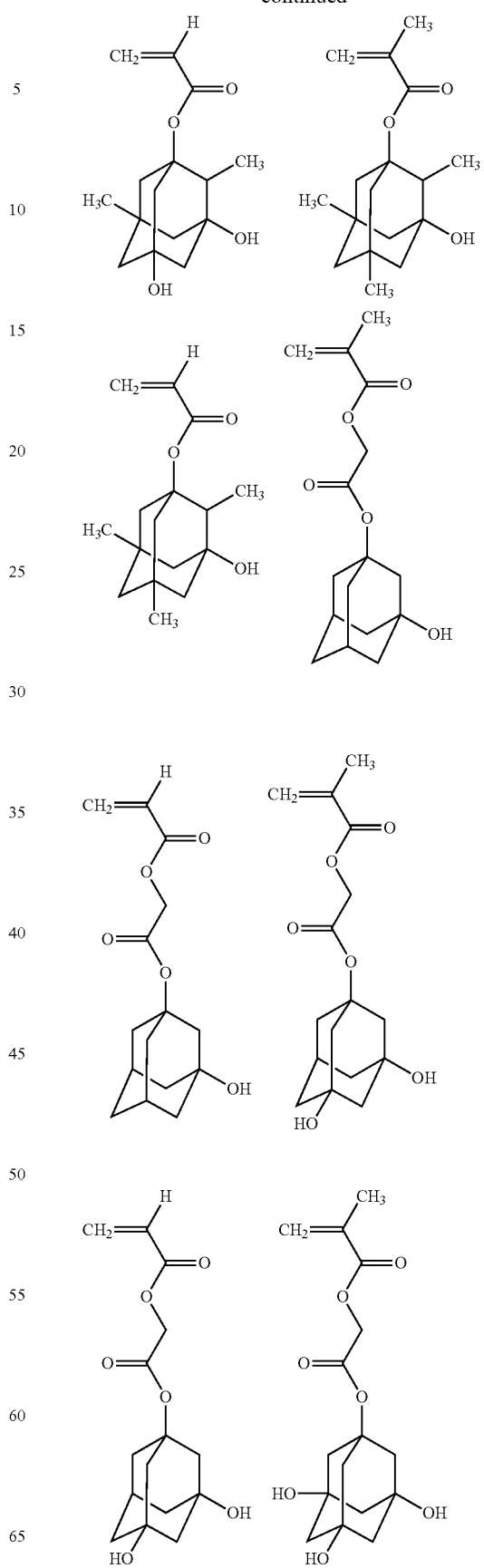

-continued

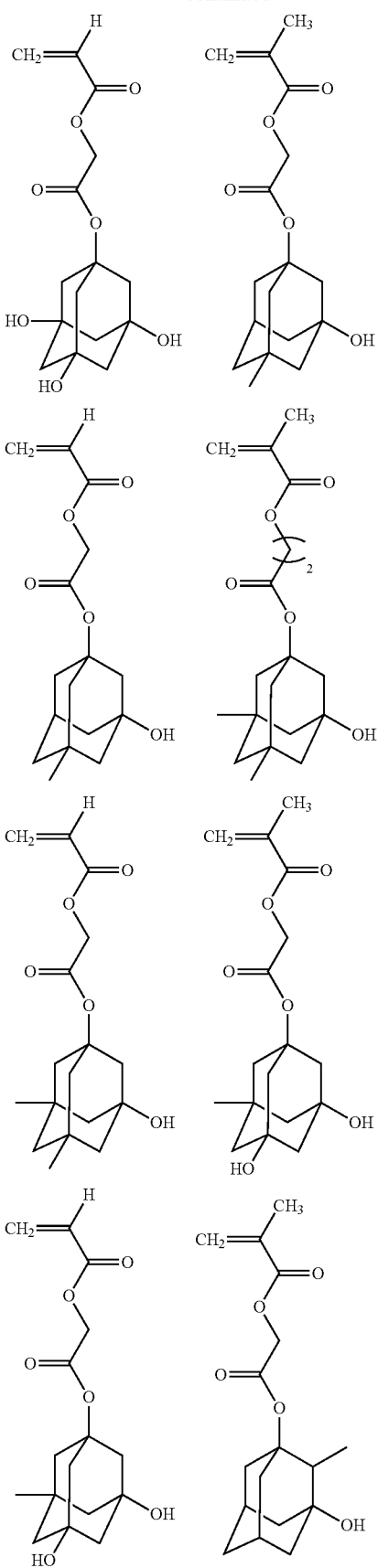
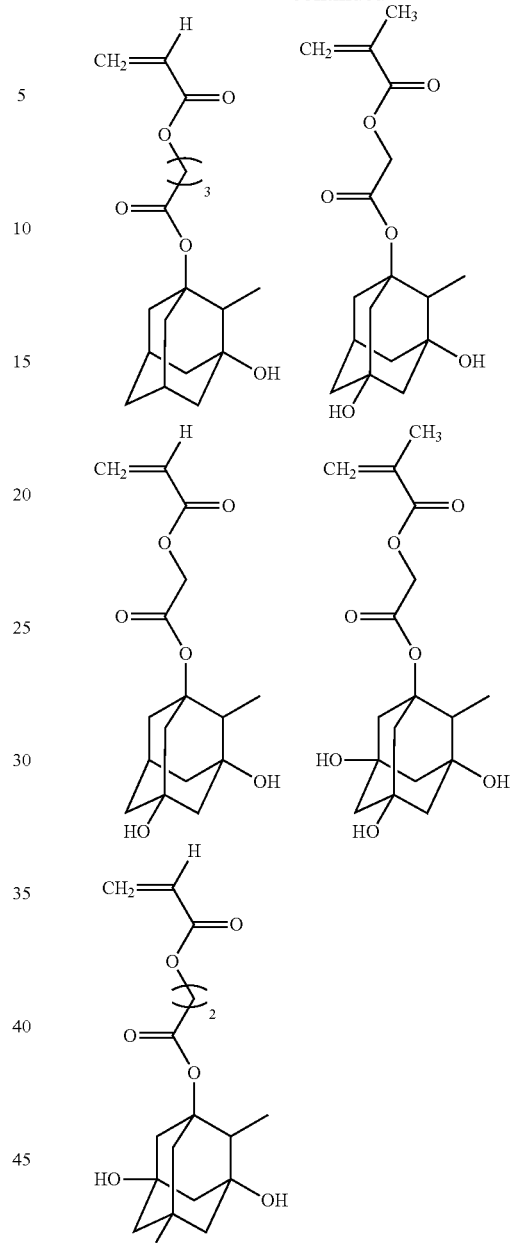

When RESIN (A) contains the structural unit derived from the monomer represented by the formula (a2-1), the content of the structural unit derived from the monomer represented by the formula (a2-1) is usually 3 to 40% by mole and preferably 5 to 35% by mole and more preferably 5 to 30% by mole based on total molar of all the structural units of RESIN (A).

Examples of the lactone ring of the monomer having no acid-labile group and having a lactone ring include a monocyclic lactone ring such as β-propiolactone ring, γ-butyrolactone ring and γ-valerolactone ring, and a condensed ring formed from a monocyclic lactone ring and the other ring. Among them, preferred are γ-butyrolactone ring and a condensed lactone ring formed from γ-butyrolactone ring and the other ring.

Preferable examples of the monomer having no acid-labile group and having a lactone ring include the monomers represented by the formulae (a3-1), (a3-2) and (a3-3):

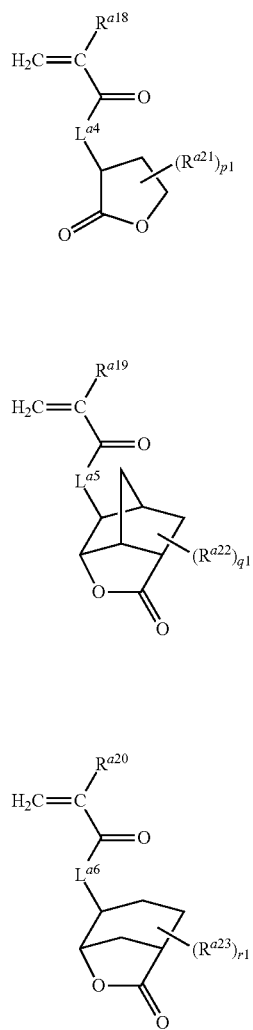

wherein $L^{a4}$, $L^{a5}$ and $L^{a6}$ independently represent *-O— or *-O—$(CH_2)_{k3}$—CO—O— in which * represents a binding position to —CO— and k3 represents an integer of 1 to 7, $R^{a18}$, $R^{a19}$ and $R^{a20}$ independently represent a hydrogen atom or a methyl group, $R^{a21}$ represents a C1-C4 aliphatic hydrocarbon group, $R^{a22}$ and $R^{a23}$ are independently in each occurrence a carboxyl group, a cyano group or a C1-C4 aliphatic hydrocarbon group, and p1 represents an integer of 0 to 5, q1 and r1 independently each represent an integer of 0 to 3.

It is preferred that $L^{a4}$, $L^{a5}$ and $L^{a6}$ each independently represent *-O— or *-O—$(CH_2)_{d1}$—CO—O— in which * represents a binding position to —CO— and d1 represents an integer of 1 to 4, and it is more preferred that $L^{a4}$, $L^{a5}$ and $L^{a6}$ are *-O—. $R^{a18}$, $R^{a19}$ and $R^{a20}$ are preferably methyl groups. $R^{a21}$ is preferably a methyl group. It is preferred that $R^{a22}$ and $R^{a23}$ are independently in each occurrence a carboxyl group, a cyano group or a methyl group. It is preferred that p1 is an integer of 0 to 2, and it is more preferred that p1 is 0 or 1. It is preferred that q1 and r1 independently each represent an integer of 0 to 2, and it is more preferred that q1 and r1 independently each represent 0 or 1.

Examples of the monomer represented by the formula (a3-1) include the followings.

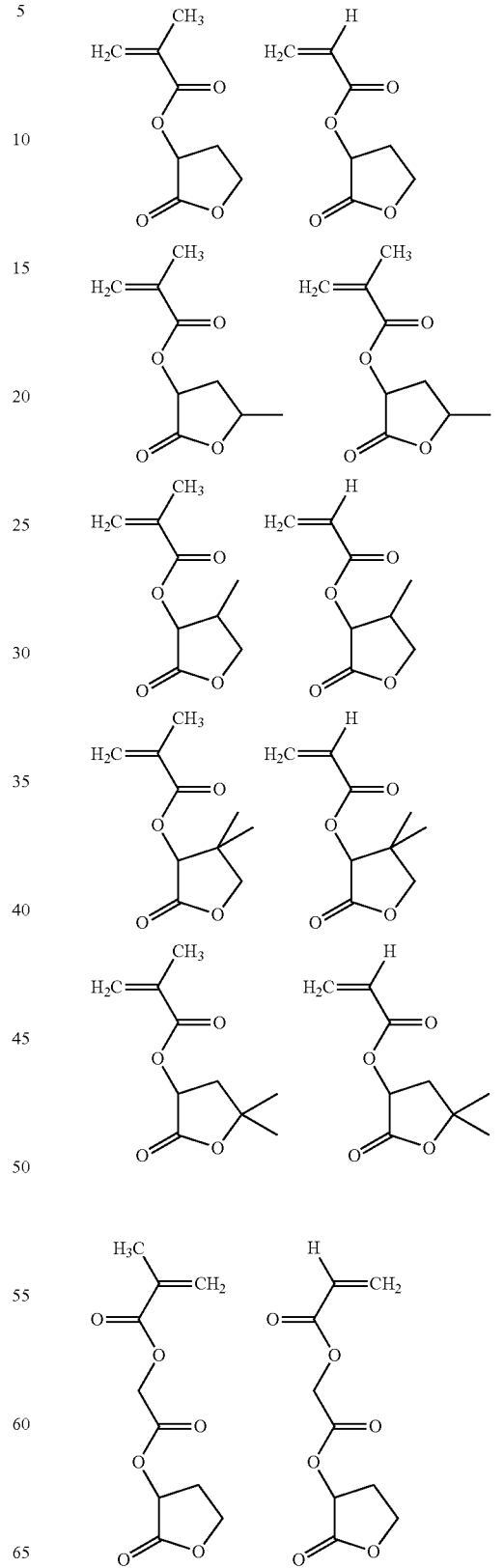

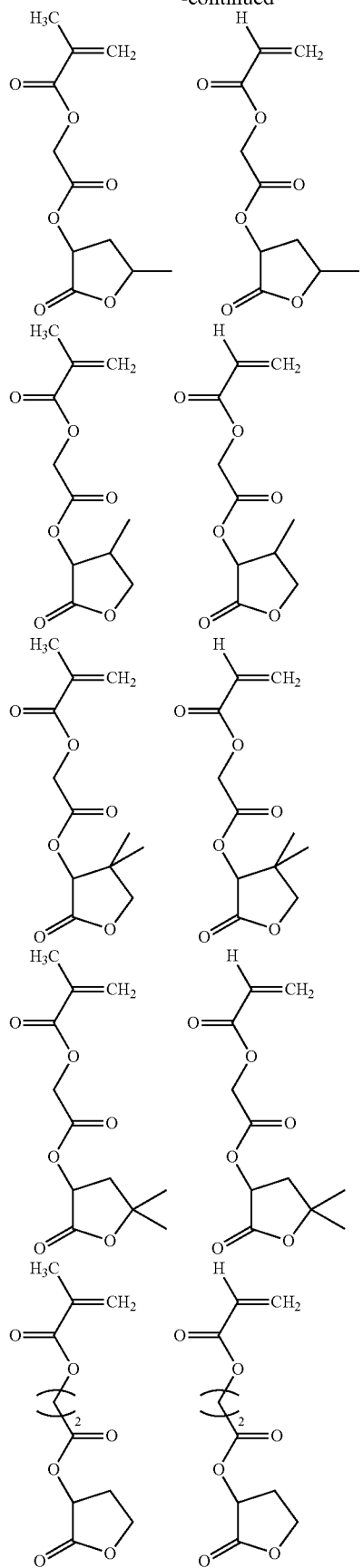
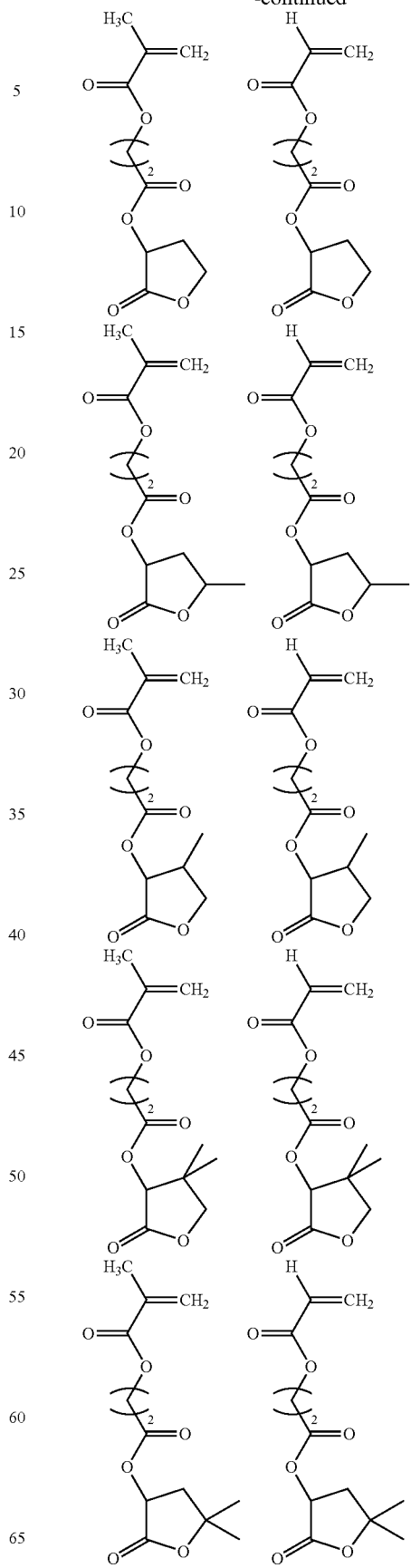

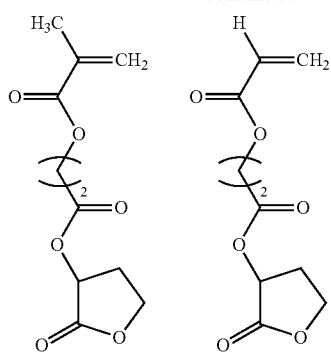
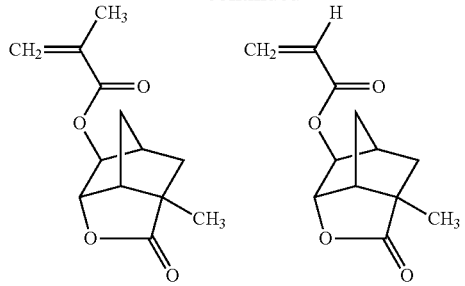
Examples of the monomer represented by the formula (a3-2) include the followings.
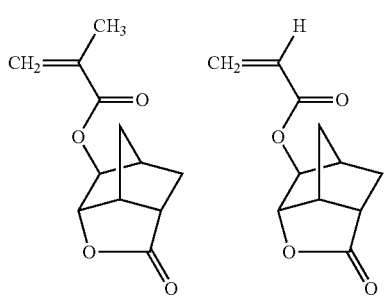
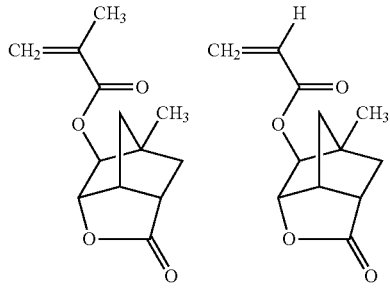
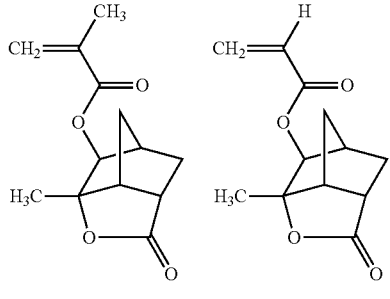
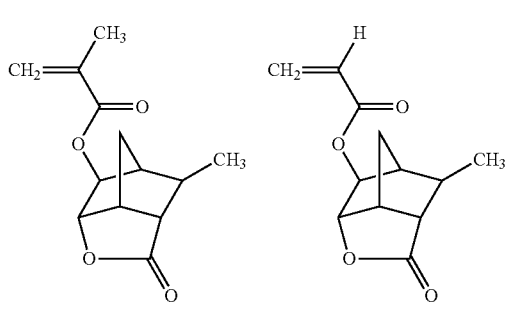

-continued
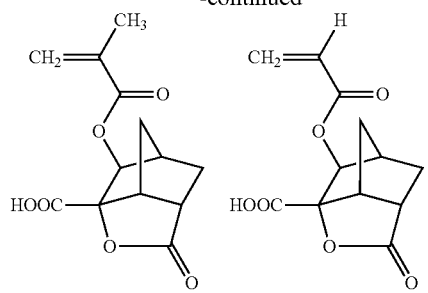
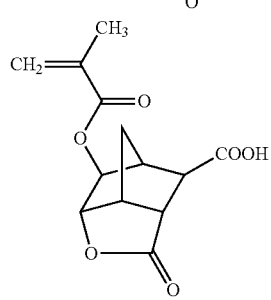
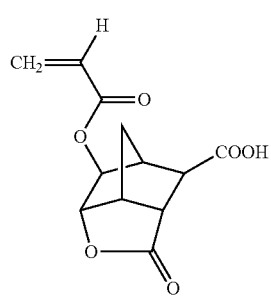
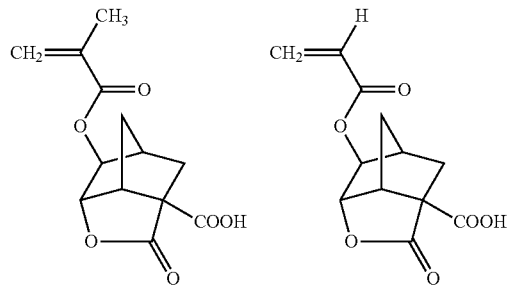
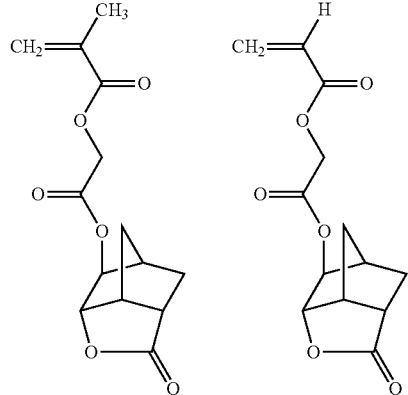
-continued
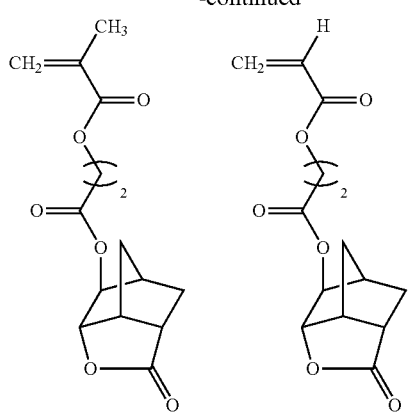
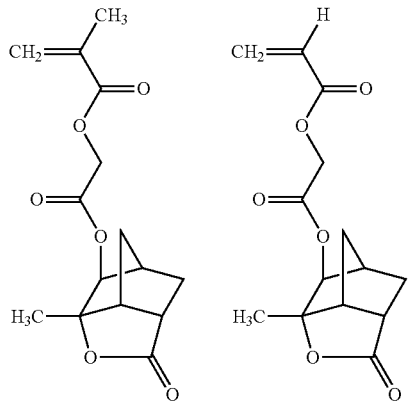
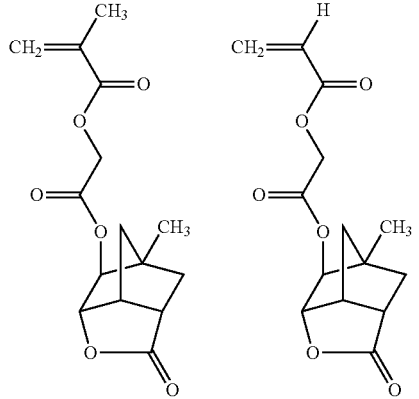
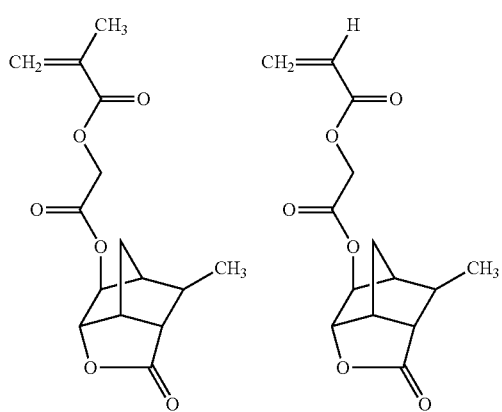

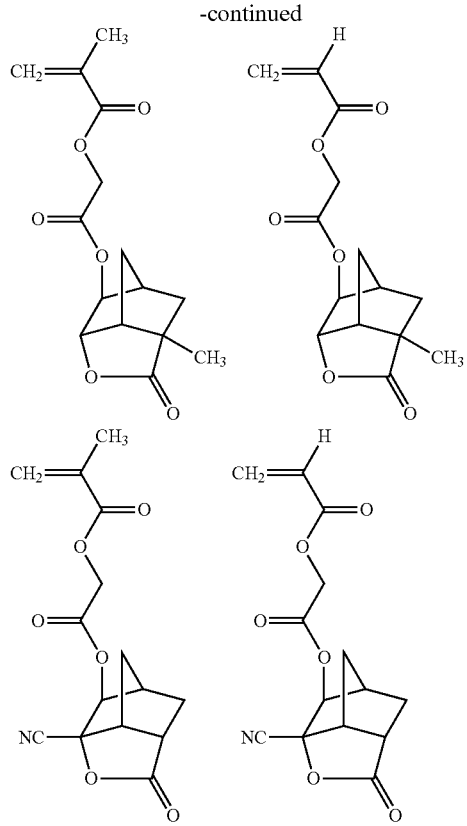
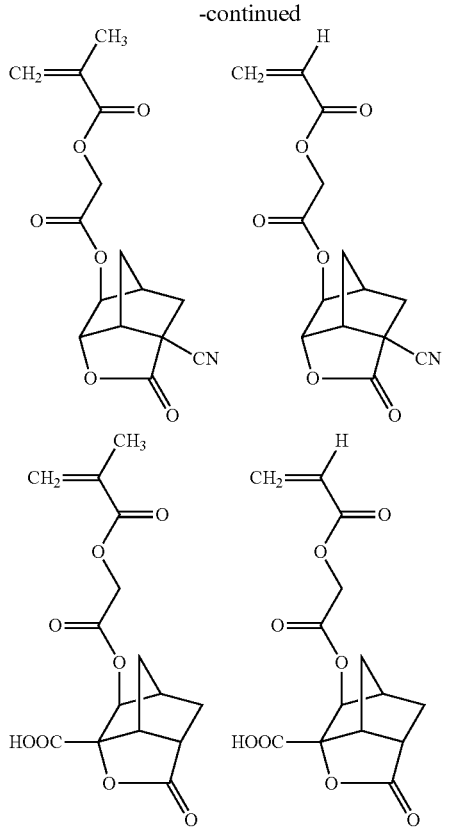
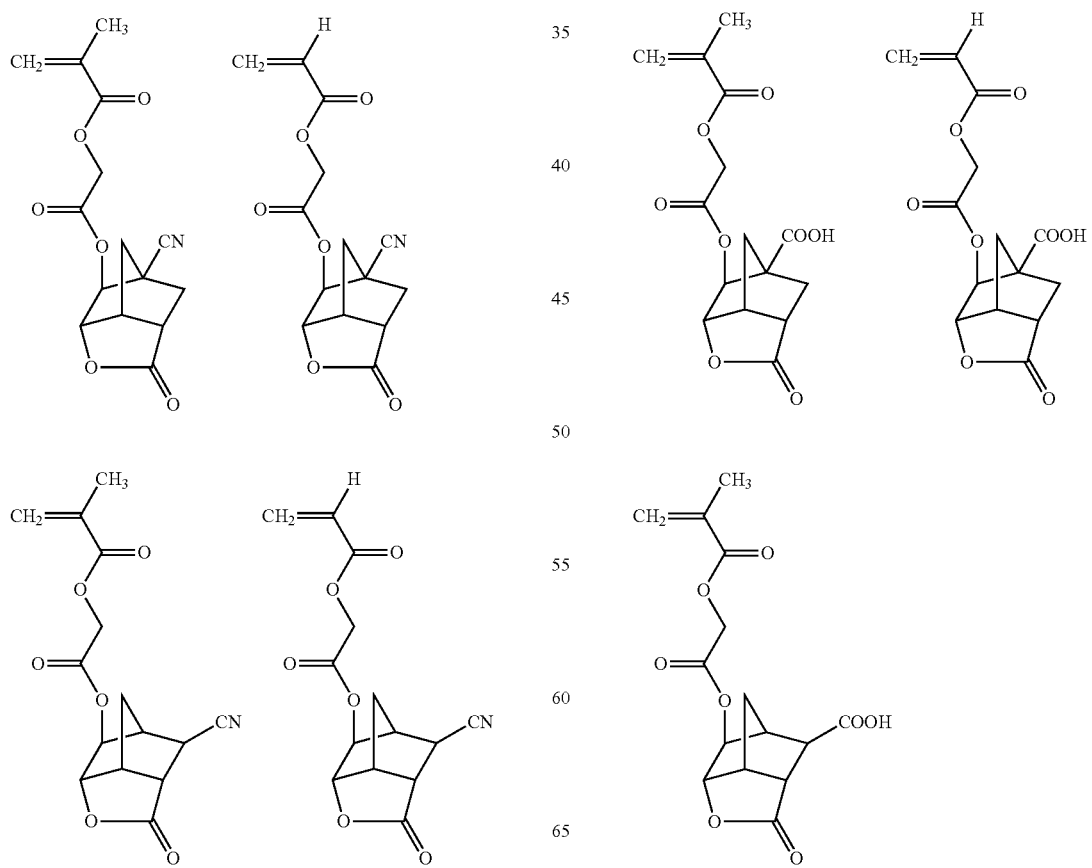

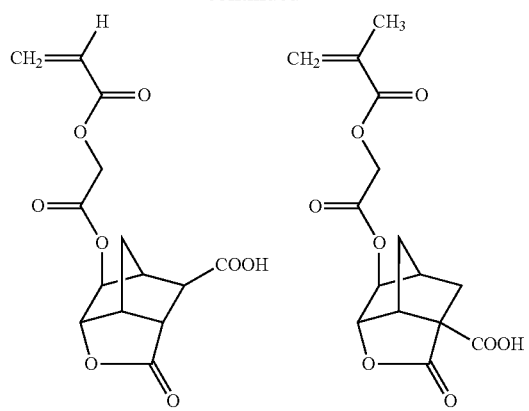
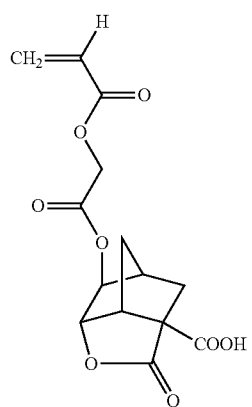
Examples of the monomer represented by the formula (a3-3) include the followings.
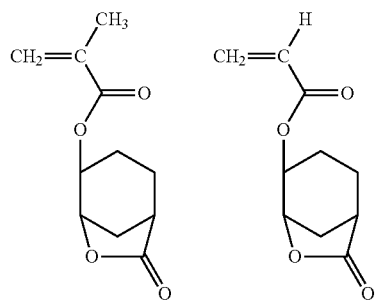
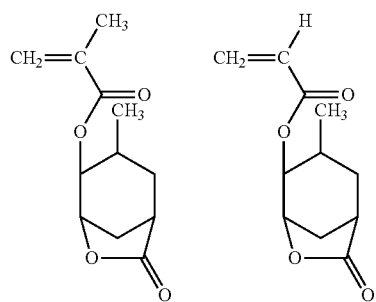
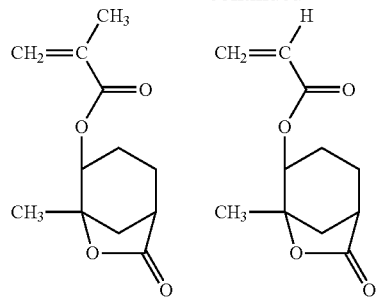
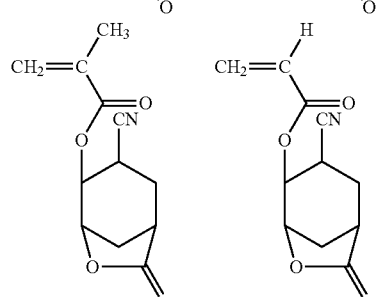
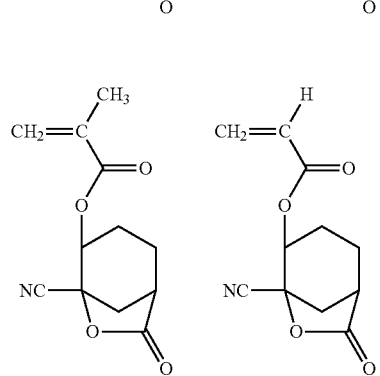
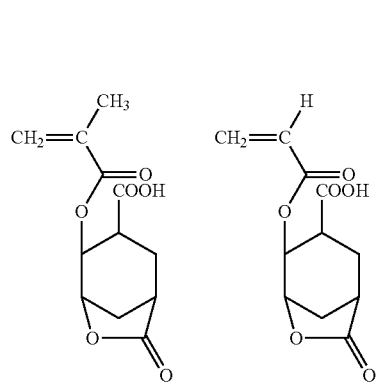
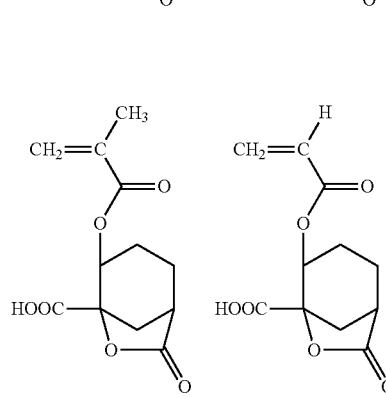

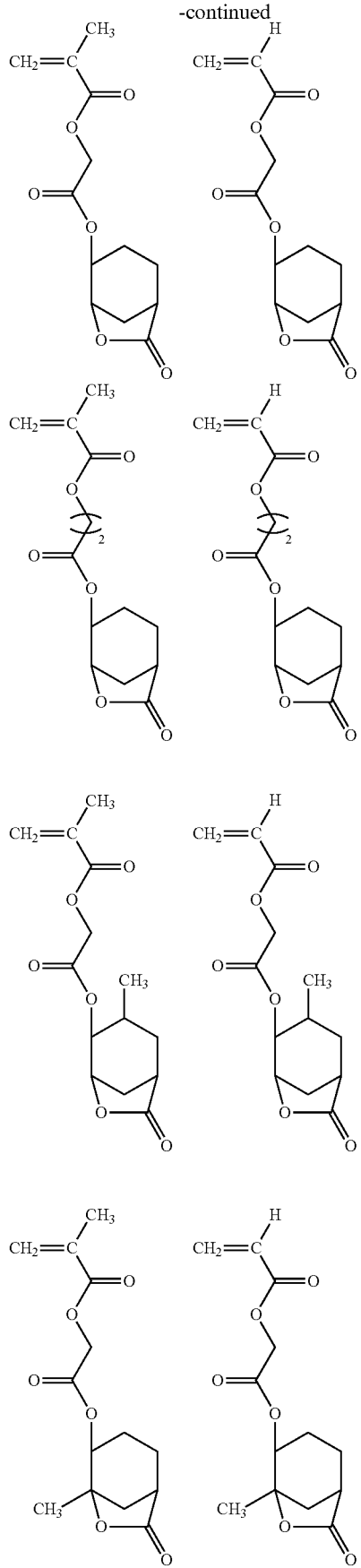
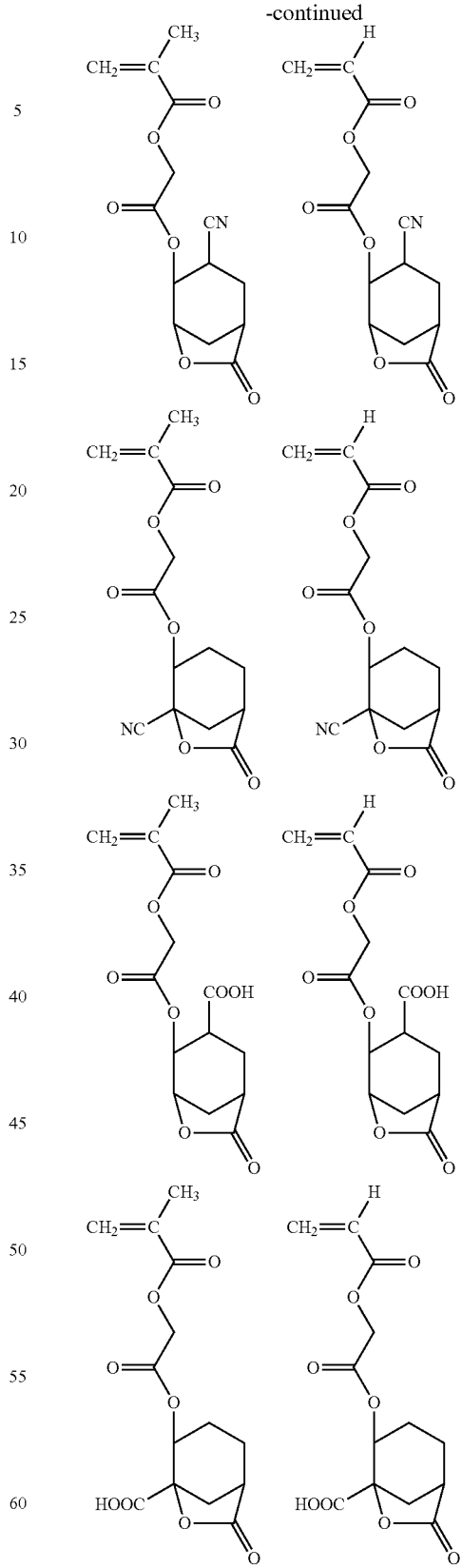
Among them, preferred are 5-oxo-4-oxatricyclo[4.2.1.0³,⁷]nonan-2-yl acrylate, 5-oxo-4-oxatricyclo[4.2.1.0³,⁷]nonan-2-yl methacrylate, tetrahydro-2-oxo-3-furyl acrylate, tetrahydro-2-oxo-3-furyl methacrylate, 2-(5-oxo-4-oxatricyclo[4.2.1.0$^{3,7}$]nonan-2-yloxy)-2-oxoethyl acrylate and 2-(5-oxo-4-oxatricyclo[4.2.1.0$^{3,7}$]nonan-2-yloxy)-2-oxoethyl methacrylate, and more preferred are 5-oxo-4-oxatricyclo[4.2.1.0$^{3,7}$]nonan-2-yl methacrylate, tetrahydro-2-oxo-3-furyl methacrylate and 2-(5-oxo-4-oxatricyclo[4.2.1.0$^{3,7}$]nonan-2-yloxy)-2-oxoethyl methacrylate.

When RESIN (A) contains the structural unit derived from the monomer having no acid-labile group and having a lactone ring, the content thereof is usually 5 to 50% by mole and preferably 10 to 45% by mole and more preferably 15 to 40% by mole based on total molar of all the structural units of RESIN (A).

RESIN (A) can contain a structural unit derived from a monomer having an acid labile group containing a lactone ring. Examples of the monomer having an acid labile group containing a lactone ring include the followings.

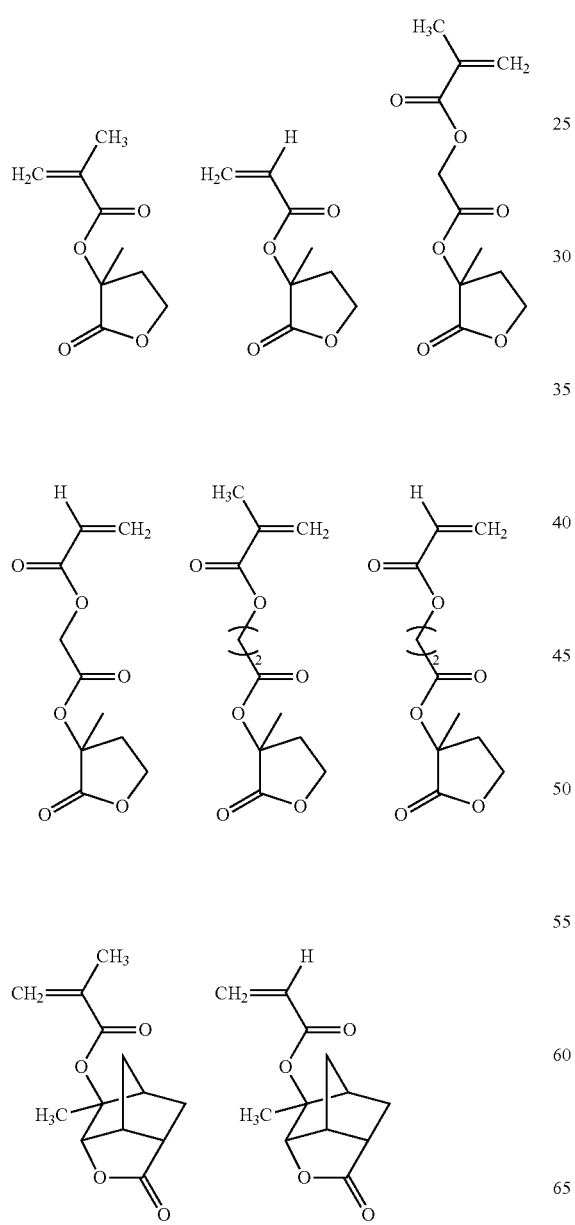

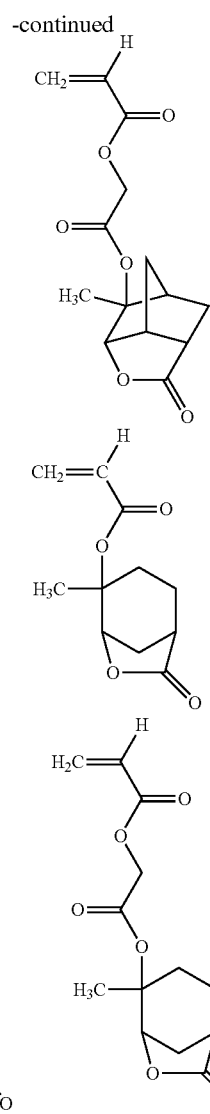

Examples of the other monomer having no acid-labile group include the monomers represented by the formulae (a-4-1), (a-4-2) and (a-4-3):

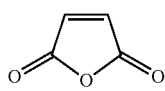
(a4-1)

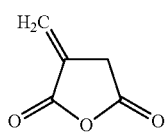
(a4-2)

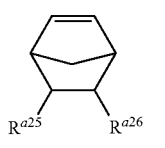
(a4-3)

wherein R$^{a25}$ and R$^{a26}$ independently represents a hydrogen atom, a C1-C3 aliphatic hydrocarbon group which can have one or more substituents, a carboxyl group, a cyano group or a —COOR$^{a27}$ group in which R$^{a27}$ represents a C1-C36 aliphatic hydrocarbon group or a C3-C36 saturated cyclic hydrocarbon group, and one or more —CH$_2$— in the C1-C36 aliphatic hydrocarbon group and the C3-C36 saturated cyclic hydrocarbon group can be replaced by —O— or —CO—, with the proviso that the carbon atom bonded to —O— of R$^{a27}$ of —COOR$^{a27}$ is not a tertiary carbon atom, or R$^{a25}$ and R$^{a26}$ are bonded together to form a carboxylic anhydride residue represented by —C(=O)OC(=O)—.

Examples of the substituent of the C1-C3 aliphatic hydrocarbon group include a hydroxyl group. Examples of the C1-C3 aliphatic hydrocarbon group which can have one or more substituents include a C1-C3 alkyl group such as a methyl group, an ethyl group and a propyl group, and a C1-C3 hydroxyalkyl group such a hydroxymethyl group and a 2-hydroxyethyl group. The C1-C36 aliphatic hydrocarbon group represented by R$^5$ is preferably a C1-C8 aliphatic hydrocarbon group and is more preferably a C1-C6 aliphatic hydrocarbon group. The C3-C36 saturated cyclic hydrocarbon group represented by R$^{25}$ is preferably a C4-C36 saturated cyclic hydrocarbon group, and is more preferably C4-C12 saturated cyclic hydrocarbon group. Examples of R$^{25}$ include a methyl group, an ethyl group, a propyl group, a 2-oxo-oxolan-3-yl group and a 2-oxo-oxolan-4-yl group.

Examples of the monomer represented by the formula (a-4-3) include 2-norbornene, 2-hydroxy-5-norbornene, 5-norbornene-2-carboxylic acid, methyl 5-norbornene-2-carboxylate, 2-hydroxyethyl 5-norbornene-2-carboxylate, 5-norbornene-2-methanol and 5-norbornene-2,3-dicarboxylic anhydride.

When RESIN (A) contains a structural unit derived from a monomer represented by the formula (a-4-1), (a-4-2) or (a-4-3), the content thereof is usually 2 to 40% by mole and preferably 3 to 30% by mole and more preferably 5 to 20% by mole based on total molar of all the structural units of RESIN (A).

RESIN(A) can contain a structural unit represented by the formula (a5-1):

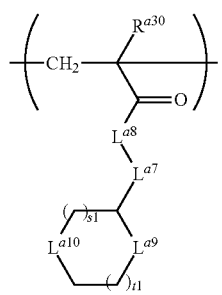

(a5-1)

wherein R$^{a30}$ represents a hydrogen atom, a halogen atom, a C1-C4 alkyl group or a C1-C4 perfluoroalkyl group, L$^{a7}$ represents a single bond or —(CH$_2$)$_{u1}$—CO-L$^{a11}$-, u1 represents an integer of 1 to 4, L$^{a8}$, L$^{a9}$, L$^{a10}$ and L$^{a11}$ independently represent an oxygen atom or a sulfur atom, s1 represents an integer of 1 to 3 and t1 represents an integer of 0 to 3.

Examples of the halogen atom include a fluorine atom. Examples of the C1-C4 alkyl group include a methyl group, an ethyl group, an n-propyl group, an isopropyl group, an n-butyl group and tert-butyl group, and a methyl group is preferable. Examples of the C1-C4 perfluoroalkyl group include a trifluoromethyl group, a pentafluoroethyl group, a heptafluoropropyl group and a nonafluorobutyl group, and a trifluoromethyl group is preferable. R$^{a30}$ is preferably a hydrogen atom, a C1-C4 alkyl group or a C1-C4 perfluoroalkyl group, and is more preferably a hydrogen atom, a methyl group or a trifluoromethyl group. L$^{a8}$, L$^{a9}$ and L$^{a11}$ are preferably oxygen atoms or a sulfur atom, and L$^{10}$ is preferably a sulfur atom.

In the formula (a5-1), s1 is preferably 1 and t1 is preferably 0, 1 or 2.

Examples of a monomer used for giving the structural unit (a5-1) include the followings:

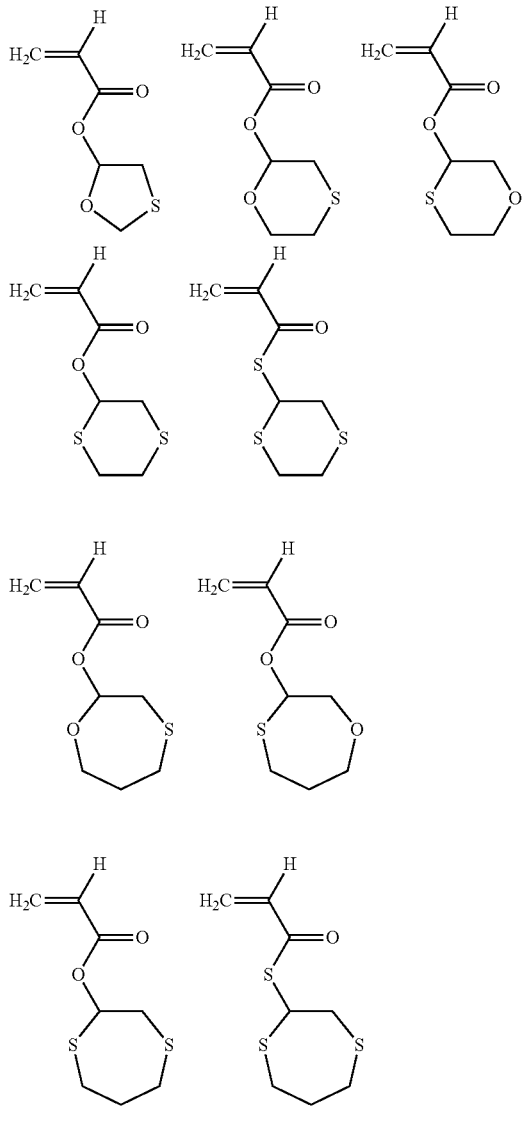

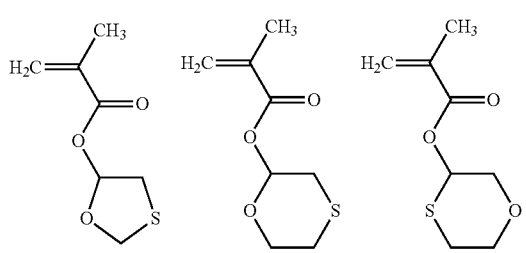

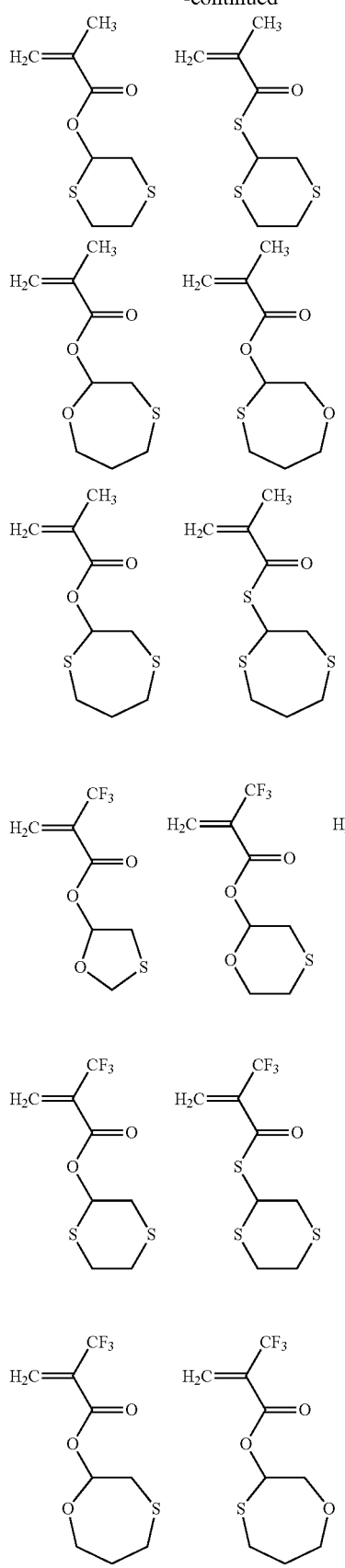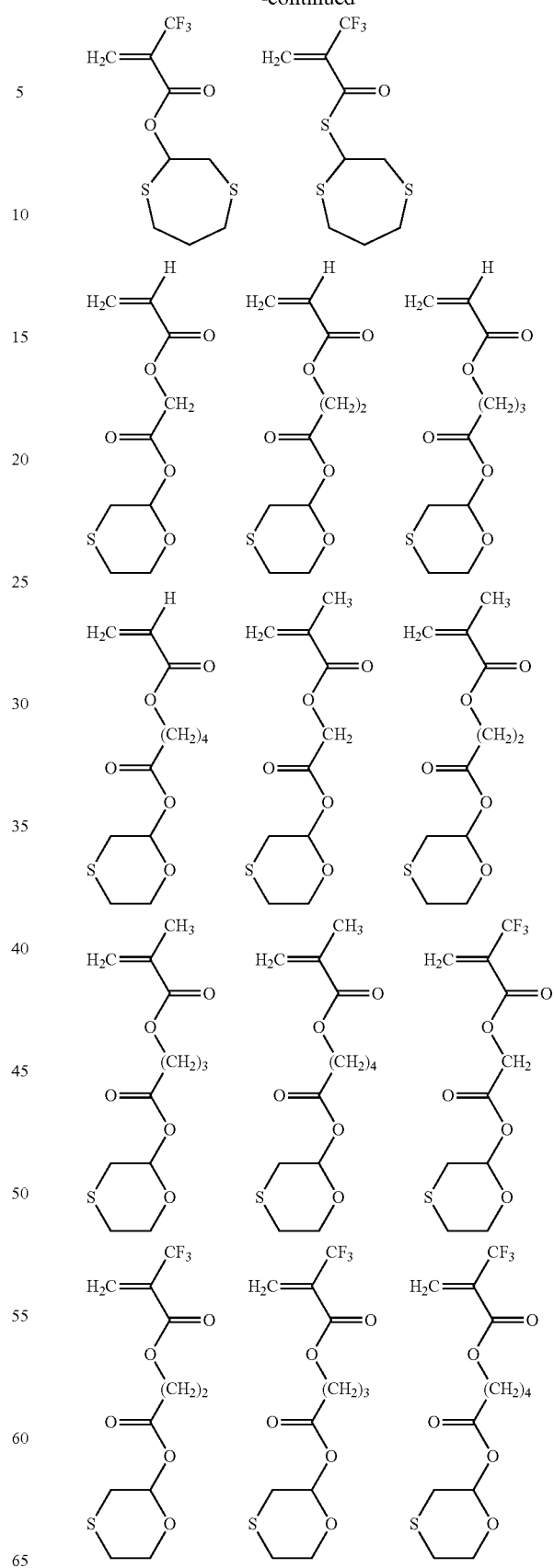

The content of the structural unit represented by the formula (a5-1) is usually 1 to 30% by mol and preferably 3 to 20% by mole based on total molar of all the structural units of RESIN (A).

Preferable RESIN (A) is a resin containing the structural units derived from the monomer having an acid-labile group, and the structural units derived from the monomer having one or more hydroxyl groups and/or the monomer having a lactone ring. The monomer having an acid-labile group is preferably the monomer represented by the formula (a1-1) or the monomer represented by the formula (a1-2), and is more preferably the monomer represented by the formula (a1-1). The monomer having one or more hydroxyl groups is preferably the monomer represented by the formula (a2-1), and the monomer having a lactone ring is preferably the monomer represented by the formula (a3-1) or (a3-2).

RESIN (A) can be produced according to known polymerization methods such as radical polymerization.

RESIN (A) usually has 2,500 or more of the weight-average molecular weight, and preferably 3,000 or more of the weight-average molecular weight. RESIN (A) usually has 50,000 or less of the weight-average molecular weight, and preferably has 30,000 or less of the weight-average molecular weight. The weight-average molecular weight can be measured with gel permeation chromatography.

The content of RESIN (A) is usually 80% by weight or more in the solid component. In this specification, "solid component" means components other than solvents in the photoresist composition. The content of the solid component can be analyzed with conventional means such as liquid chromatography and gas chromatography.

Next, the acid generator will be illustrated.

The acid generator is a substance which is decomposed to generate an acid by applying a radiation such as a light, an electron beam or the like on the substance itself or on a photoresist composition containing the substance. The acid generated from the acid generator acts on RESIN (A) resulting in cleavage of the acid-labile group existing in RESIN (A).

Examples of the acid generator include nonionic acid generators and ionic acid generators. Examples of the nonionic acid generator include organic halides, sulfonate esters such as 2-nitrobenzyl ester, aromatic sulfonate, oxime sulfonate, N-sulfonyloxyimide, sulfonyloxyketone and DNQ 4-sulfonate, and sulfones such as disulfone, ketosulfone and sulfonyldiazomethane. Examples of the ionic acid generator include onium salts such as a diazonium salt, a phosphonium salt, a sulfonium salt and an iodonium salt, and examples of the anion of the onium salt include sulfonic acid anion, sulfonylimide anion and sulfonylmethide anion. Other examples of the acid generator include acid generators described in JP 63-26653A, JP 55-164824 A, JP 62-69263A, JP 63-146038 A, JP 63-163452 A, JP 62-153853 A, JP 63-146029 A, U.S. Pat. No. 3,779,778, U.S. Pat. No. 3,849,137, DE Patent No. 3914407 and EP Patent No. 126,712.

A fluorine-containing acid generator is preferable.

Preferable examples of the acid generator include a salt represented by the formula (B1):

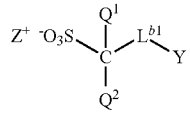

(B1)

wherein $Q^1$ and $Q^2$ each independently represent a fluorine atom or a C1-C6 perfluoroalkyl group, $L^{b1}$ represents a single bond or a C1-C17 divalent saturated hydrocarbon group in which one or more —CH$_2$— can be replaced by —O— or —CO—, Y represents a C1-C18 aliphatic hydrocarbon group which can have one or more substituents or a C3-C18 saturated cyclic hydrocarbon group which can have one or more substituents, and one or more —CH$_2$— in the aliphatic hydrocarbon group and the saturated cyclic hydrocarbon group can be replaced by —O—, —SO$_2$— or —CO—, and $Z^+$ represents an organic counter cation.

Examples of the C1-C6 perfluoroalkyl group include the same as described above, and a trifluoromethyl group is preferable. $Q^1$ and $Q^2$ independently preferably represent a fluorine atom or a trifluoromethyl group, and $Q^1$ and $Q^2$ are more preferably fluorine atoms.

Examples of the C1-C17 divalent saturated hydrocarbon group include a C1-C17 linear alkylene group such as a methylene group, an ethane-1,2-diyl group, a propane-1,3-diyl group, a propane-1,2-diyl group, a butane-1,4-diyl group, a butane-1,3-diyl group, a pentane-1,5-diyl group, a hexane-1,6-diyl group, a heptane-1,7-diyl group, an octane-1,8-diyl group, a nonane-1,9-diyl group, a decane-1,10-diyl group, a undecane-1,11-diyl group, a dodecane-1,12-diyl group, a tridecane-1,13-diyl group, a tetradecane-1,14-diyl group, a pentadecane-1,15-diyl group, a hexadecane-1,16-diyl group and a heptadecane-1,17-diyl group, a C1-C17 branched alkylene group such as a 1-methylpropane-1,3-diyl group, a2-methylpropane-1,3-diyl group, a2-methylpropane-1,2-diyl group, a 1-methylbutane-1,4-diyl group, and a 2-methylbutane-1,4-diyl group, a divalent saturated monocyclic hydrocarbon group such as a cycloalkanediyl group such as a cyclobutane-1,3-diyl group, a cyclopentane-1,3-diyl group, a cyclohexane-1,4-diyl group, and a cyclooctane-1,5-diyl group, a divalent saturated polycyclic hydrocarbon group such as a norbornane-1,4-diyl group, a norbornane-2,5-diyl group, an adamantane-1,5-diyl group and an adamantane-2,6-diyl group, and a group formed by combining two or more groups selected from the group consisting of the above-mentioned groups.

The C1-C17 divalent saturated hydrocarbon group can have one or more substituents, and examples of the substituent include a halogen atom, a hydroxyl group, a carboxyl group, a C6-C18 aromatic group, a C7-C21 aralkyl group such as a benzyl group, a phenethyl group, a phenylpropyl group, a trityl group, a naphthylmethyl group and a naphthylethyl group, a C2-C4 acyl group and a glycidyloxy group.

Examples of the C1-C17 saturated hydrocarbon group in which one or more —CH$_2$— are replaced by —O— or —CO— include *-CO—O-$L^{b2}$-, *-CO—O-$L^{b4}$-CO—O-$L^{b3}$-, *-$L^{b5}$-O—CO—, *-$L^{b7}$-O-$L^{b6}$-, *-CO—O-$L^{b8}$-O—, and *-CO—O-$L^{b10}$-O-$L^{b9}$-CO—O—, wherein $L^{b2}$ represents a single bond or a C1-C15 alkanediyl group, $L^{b3}$ represents a single bond or a C1-C12 alkanediyl group, $L^{b4}$ represents a single bond or a C1-C13 alkanediyl group, with proviso that total carbon number of $L^{b3}$ and $L^{b4}$ is 1 to 13, $L^{b5}$ represents a C1-C15 alkanediyl group, $L^{b6}$ represents a C1-C15 alkanediyl group, $L^{b7}$ represents a C1-C15 alkanediyl group, with proviso that total carbon number of $L^{b6}$ and $L^{b7}$ is 1 to 16, $L^{b8}$ represents a C1-C14 alkanediyl group, $L^{b9}$ represents a C1-C11 alkanediyl group, $L^{b10}$ represents a C1-C11 alkanediyl group, with proviso that total carbon number of $L^{b9}$ and $L^{b10}$ is 1 to 12, and * represents a binding position to —C($Q^1$)($Q^2$)-. Among them, preferred are *-CO—O-$L^{b2}$-, *-CO—O-$L^{b4}$-CO—O-$L^{b3}$-, *-$L^{b5}$-O—CO— and *-$L^{b7}$-O-$L^{b6}$-, and more preferred are *-CO—O-

$L^{b2}$- and *-CO—O-$L^{b4}$-CO—O-$L^{b3}$-, and much more preferred is *-CO—O-$L^{b2}$-, and especially preferred is *-CO—O-$L^{b2}$- in which $L^{b2}$ is a single bond or —CH$_2$—.

Examples of *-CO—O-$L^{b2}$- include *-CO—O— and *-CO—O—CH$_2$—. Examples of *-CO—O-$L^{b4}$-CO—O-$L^{b3}$- include *-CO—O—CH$_2$—CO—O—, *-CO—O—(CH$_2$)$_6$—CO—O—, *-CO—O—(CH$_2$)$_3$—CO—O—, *-CO—O—(CH$_2$)$_4$—CO—O—, *-CO—O—(CH$_2$)$_6$—CO—O—, *-CO—O—(CH$_2$)$_8$—CO—O—, *-CO—O—CH$_2$—CH(CH$_3$)—CO—O— and *-CO—O—CH$_2$—C(CH$_3$)$_2$—CO—O—. Examples of *-$L^{b5}$-O—OC— include *-CH$_2$—O—OC—, *-(CH$_2$)$_2$—O—CO—, *-(CH$_2$)$_3$—O—CO—, *-(CH$_2$)$_4$—O—CO—, *-(CH$_2$)$_6$—O—CO— and *-(CH$_2$)$_8$—O—CO—. Examples of *-$L^{b7}$-O-$L^{b6}$- include *-CH$_2$—O—CH$_2$—. Examples of *-CO—O-$L^{b8}$-O— include *-CO—O—CH$_2$—O—, *-CO—O—(CH$_2$)$_2$—O—, *-CO—O—(CH$_2$)$_3$—O—, *-CO—O—(CH$_2$)$_4$—O— and *-CO—O—(CH$_2$)$_6$—O—. Examples of *-CO—O-$L^{b10}$-O-$L^{b9}$-CO—O- include the followings.

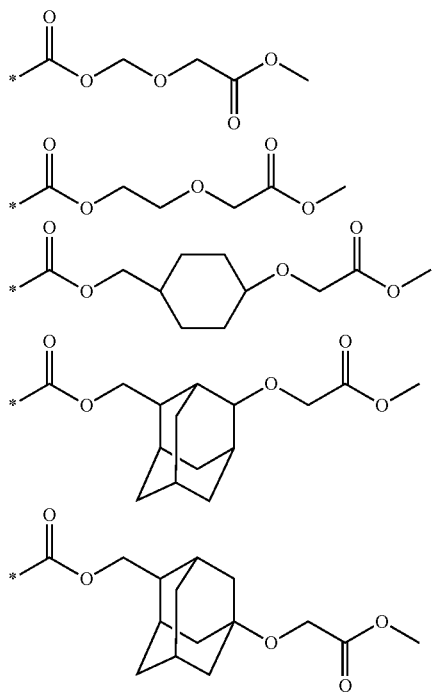

The saturated hydrocarbon group can have one or more substituents, and examples of the substituent include a halogen atom, a hydroxyl group, a carboxyl group, a 06-018 aromatic hydrocarbon group, a C7-C21 aralkyl group such as a benzyl group, a phenethyl group, a phenylpropyl group, a trityl group, a naphthylmethyl group and a naphthyethyl group, a C2-C4 acyl group and a glycidyloxy group.

Examples of the substituent in Y include a halogen atom, a hydroxyl group, an oxo group, a glycidyloxy group, a C2-C4 acyl group, a C1-C12 alkoxy group, a C2-C7 alkoxycarbonyl group, a C1-C12 aliphatic hydrocarbon group, a C1-C12 hydroxy-containing aliphatic hydrocarbon group, a C3-C16 saturated cyclic hydrocarbon group, a C6-C18 aromatic hydrocarbon group, a C7-C21 aralkyl group and —(CH$_2$)$_{j2}$—O—CO—R$^{b1}$— in which R$^{b1}$ represents a C1-C16 aliphatic hydrocarbon group, a C3-C16 saturated cyclic hydrocarbon group or a C6-C18 aromatic hydrocarbon group and j 2 represents an integer of 0 to 4. Examples of the halogen atom include a fluorine atom, a chlorine atom, a bromine atom and an iodine atom. Examples of the acyl group include an acetyl group and a propionyl group, and examples of the alkoxy group include a methoxy group, an ethoxy group, a propoxy group, an isopropoxy group and a butoxy group. Examples of the alkoxycarbonyl group include a methoxycarbonyl group, an ethoxycarbonyl group, a propoxycarbonyl group, an isopropoxycarbonyl group and a butoxycarbonyl group. Examples of the aliphatic hydrocarbon group include the same as described above. Examples of the hydroxyl-containing aliphatic hydrocarbon group include a hydroxymethyl group. Examples of the C3-C16 saturated cyclic hydrocarbon group include the same as described above, and examples of the aromatic hydrocarbon group include a phenyl group, a naphthyl group, an anthryl group, a p-methylphenyl group, a p-tert-butylphenyl group and a p-adamantylphenyl group. Examples of the aralkyl group include a benzyl group, a phenethyl group, a phenylpropyl group, a trityl group, a naphthylmethyl group and a naphthylethyl group.

Examples of the C1-C18 aliphatic hydrocarbon group represented by Y include a methyl group, an ethyl group, a propyl group, an isopropyl group, a butyl group, an isobutyl group, a sec-butyl group, a tert-butyl group, a pentyl group, a neopentyl group, a 1-methylbutyl group, a 2-methylbutyl group, a 1,2-dimethylpropyl group, a 1-ethylpropyl group, a hexyl group, a-1-methylpentyl group, a heptyl group, an octyl group, a 2-ethylhexyl group, a nonyl group, a decyl group, an undecyl group and a dodecyl group, and a C1-C6 alkyl group is preferable. Examples of the C3-C18 saturated cyclic hydrocarbon group represented by Y include the groups represented by the formulae (Y1) to (Y26).

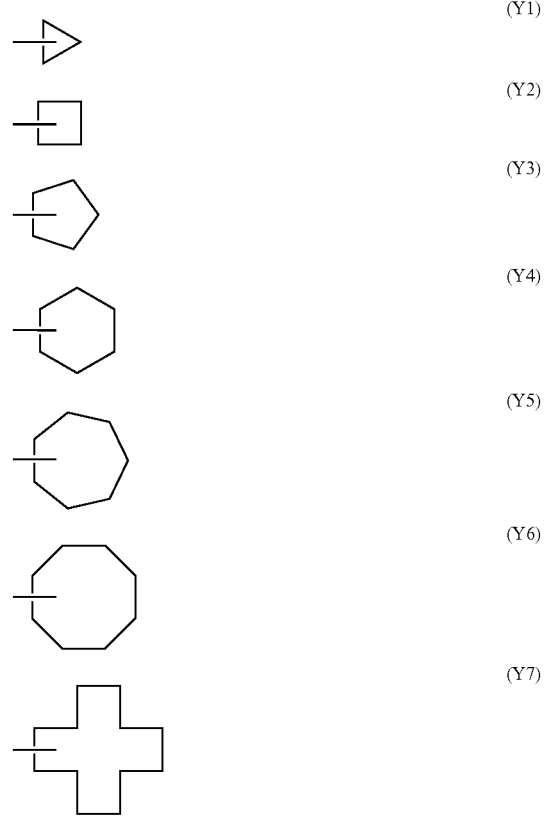

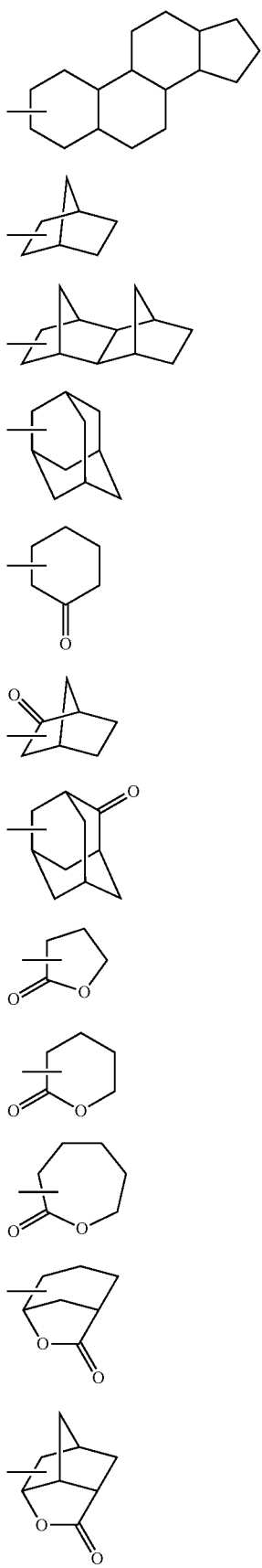
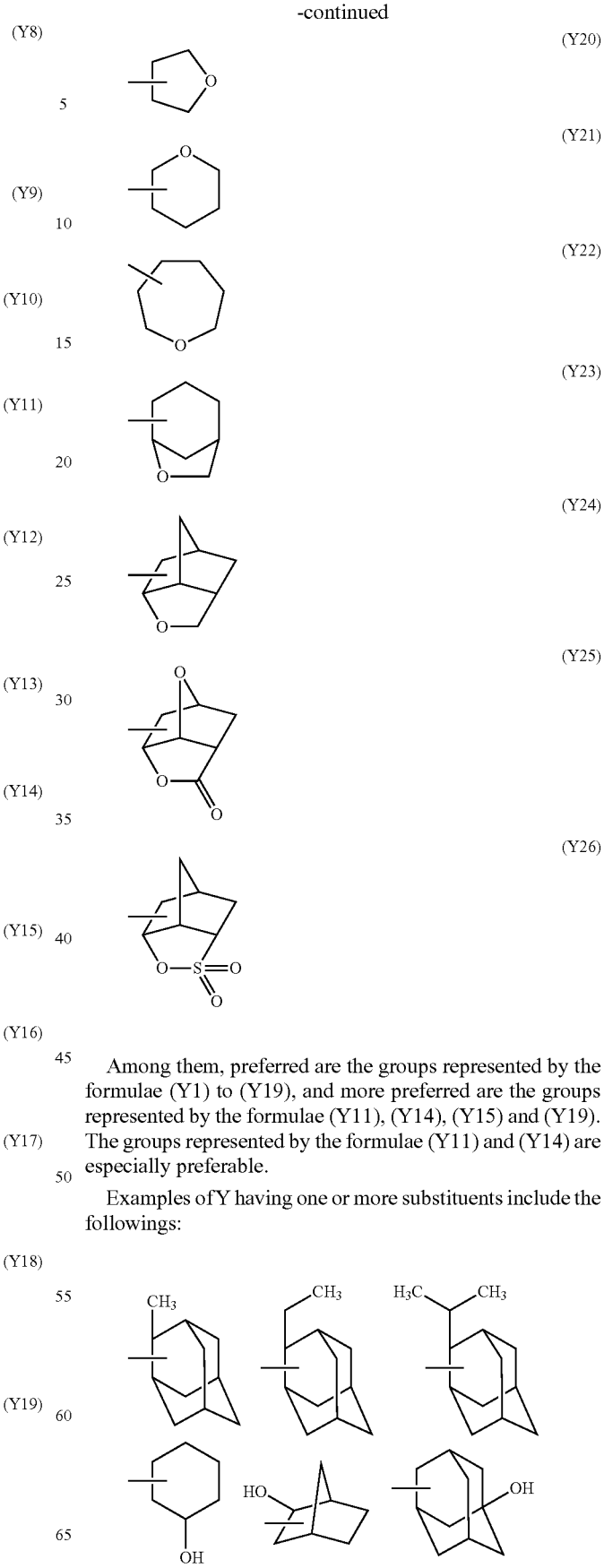
Among them, preferred are the groups represented by the formulae (Y1) to (Y19), and more preferred are the groups represented by the formulae (Y11), (Y14), (Y15) and (Y19). The groups represented by the formulae (Y11) and (Y14) are especially preferable.
Examples of Y having one or more substituents include the followings:

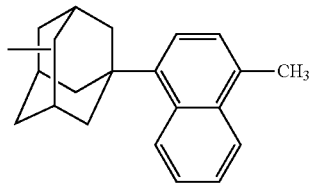
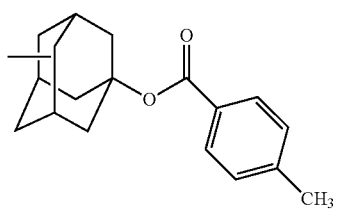

Y is preferably an adamantyl group which can have one or more substituents, and is more preferably an adamantyl group or an oxoadamantyl group.

Among the sulfonic acid anions of the salt represented by the formula (B1), preferred is a sulfonic acid anion in which $L^{b1}$ is *-CO—O-$L^{b2}$-, and more preferred are anions represented by the formulae (b1-1-1) to (b1-1-9).

(b1-1-1)
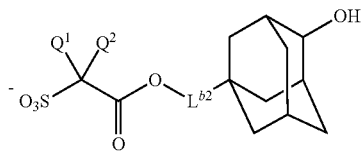

(b1-1-2)
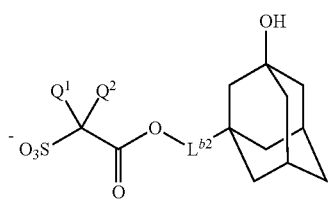

(b1-1-3)
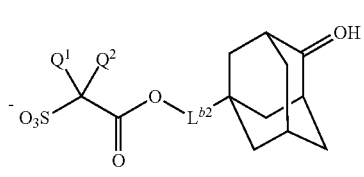

(b1-1-4)
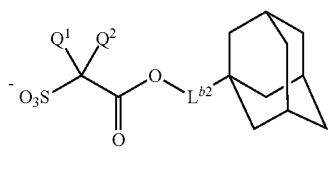

(b1-1-5)
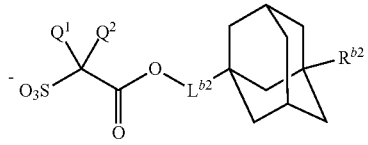

(b1-1-6)
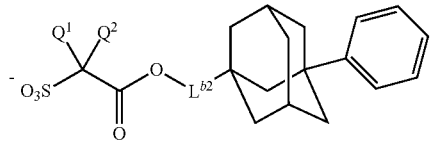

(b1-1-7)
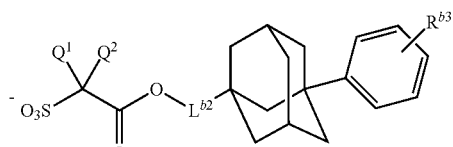

(b1-1-8)
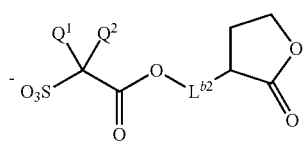

(b1-1-9)
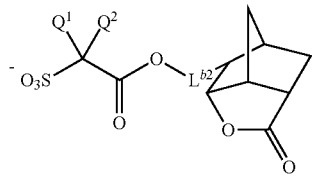

wherein $Q^1$, $Q^2$ and $L^{b2}$ are the same as defined above, and $R^{b2}$ and $R^{b3}$ each independently represent a C1-C4 aliphatic hydrocarbon group, preferably a methyl group.

Examples of the anion of the salt represented by the formula (B1) include the following anions:

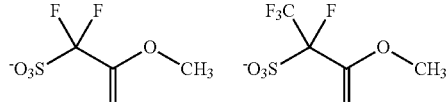
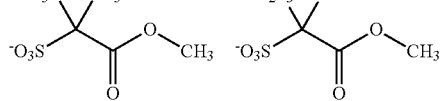
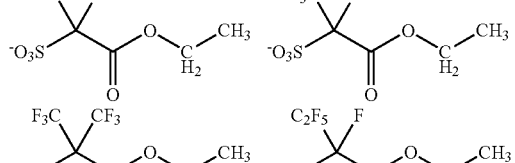
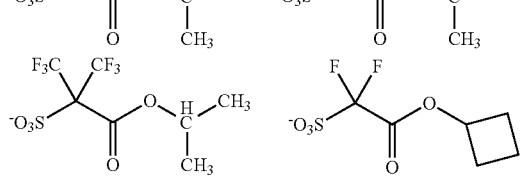

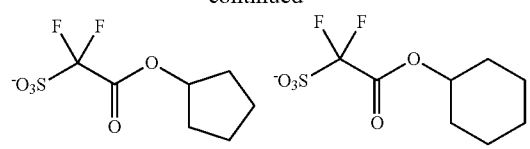
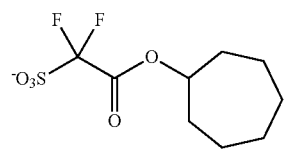
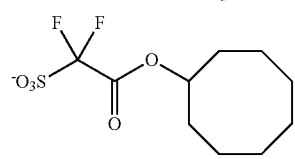
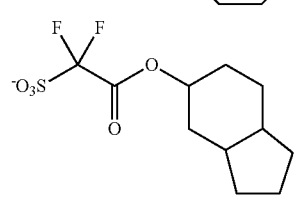
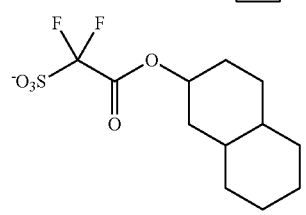
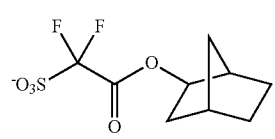
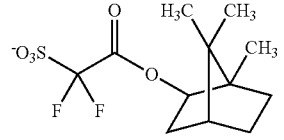
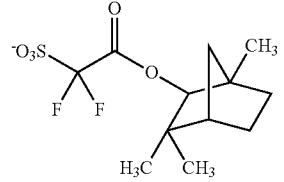
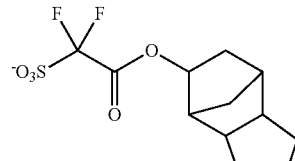
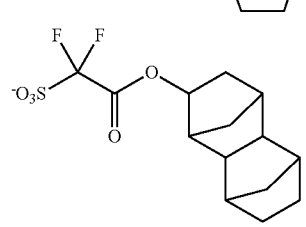
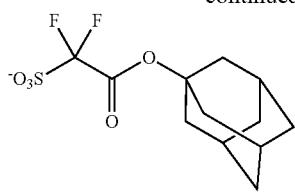
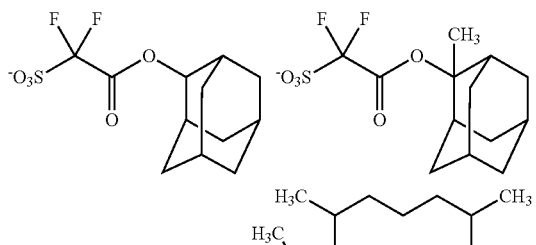
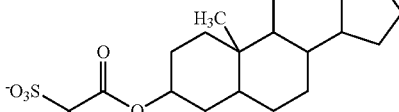
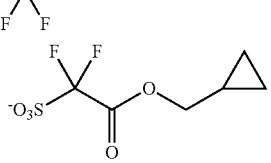
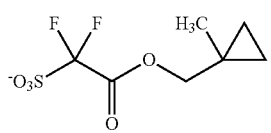
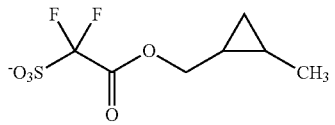
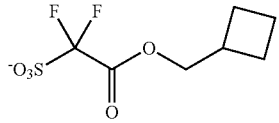
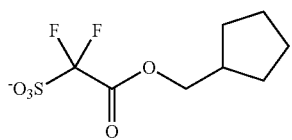
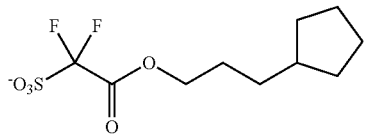
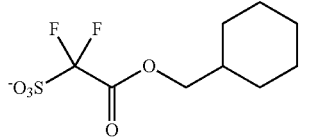
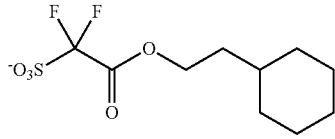

107
-continued
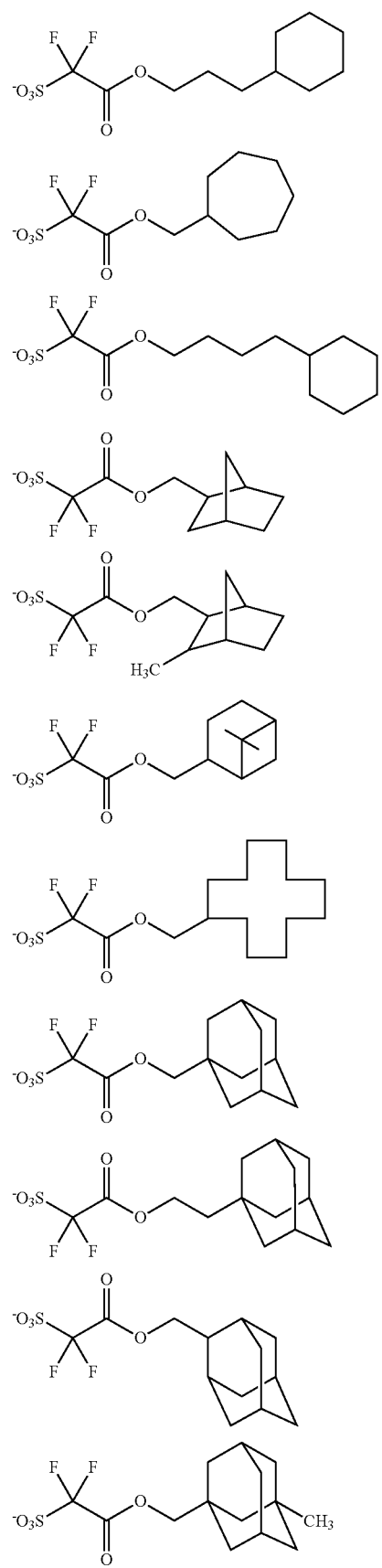
108
-continued
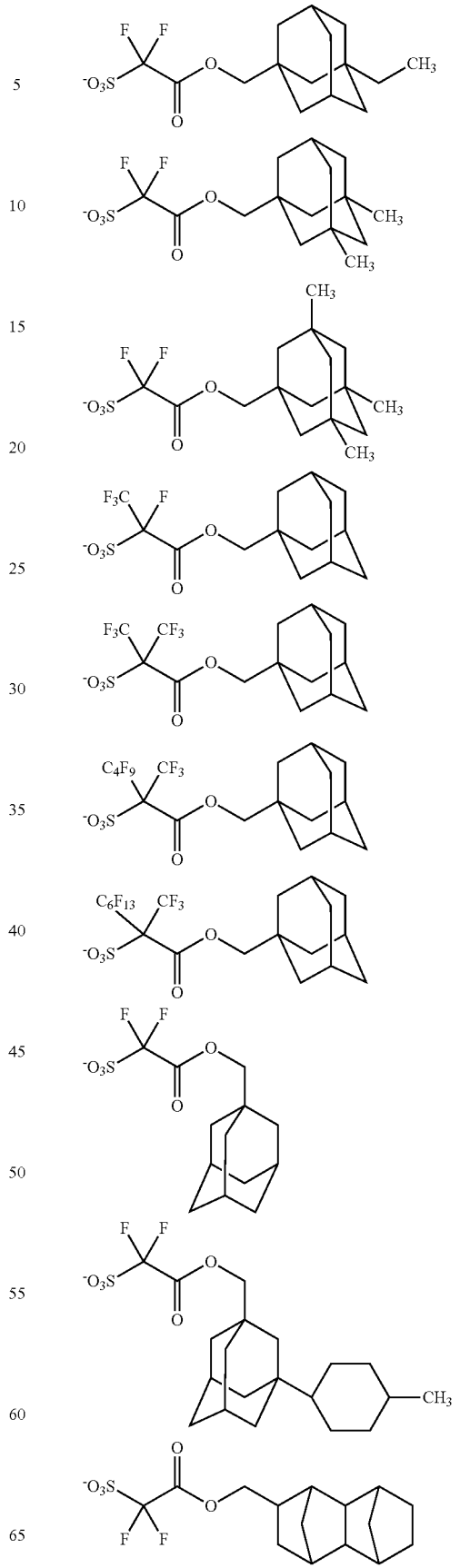

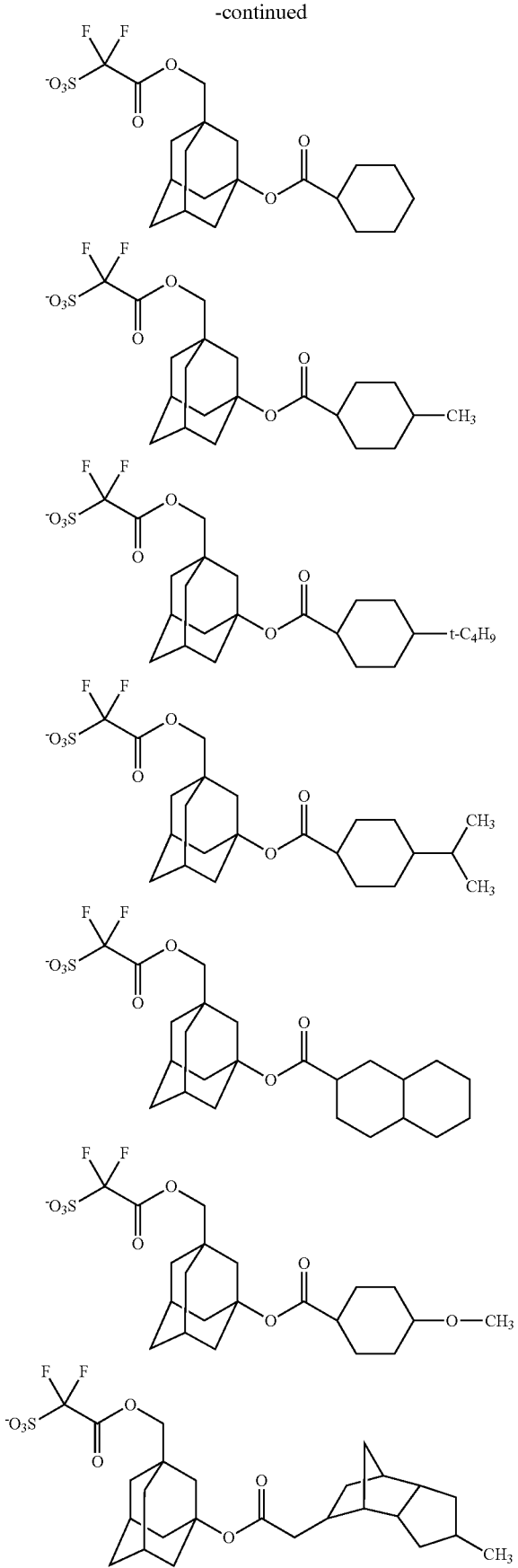
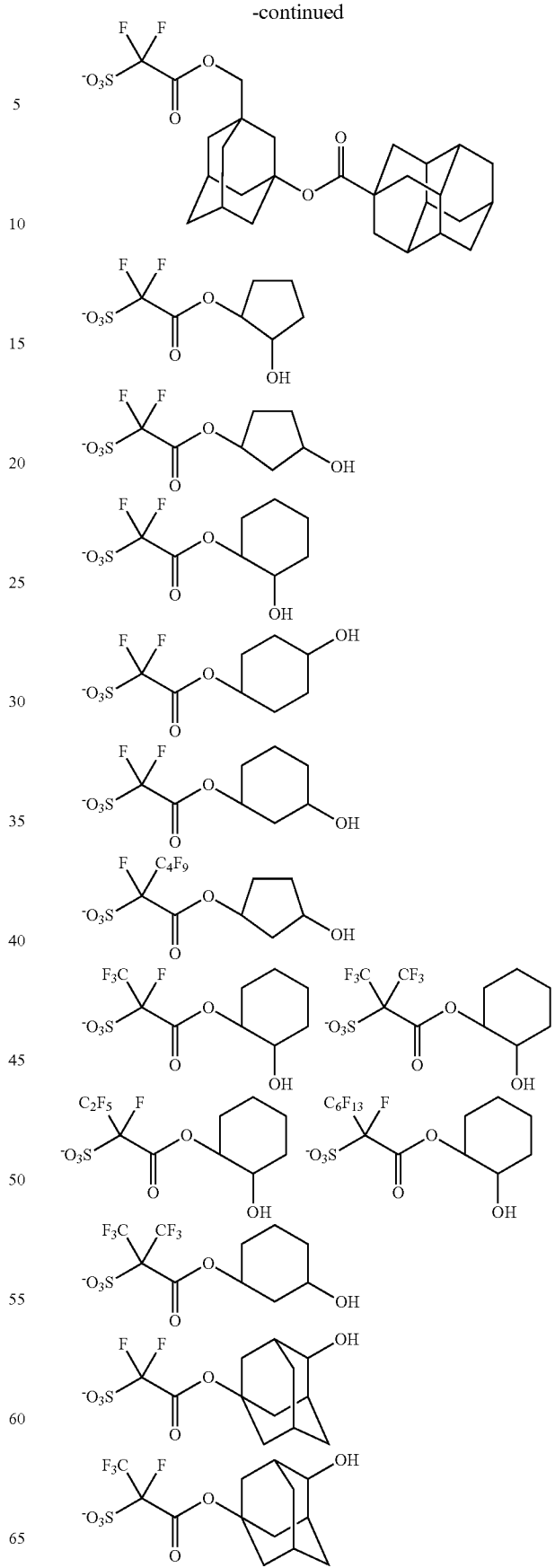

111
-continued
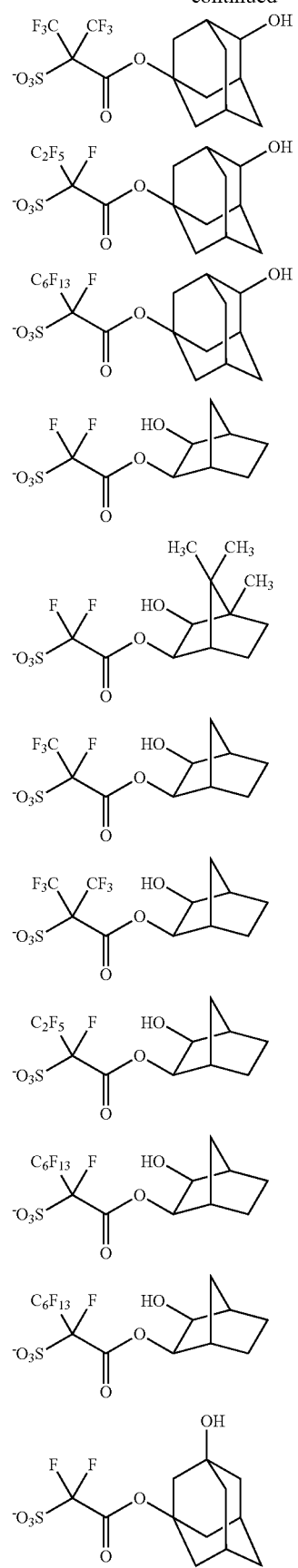
112
-continued
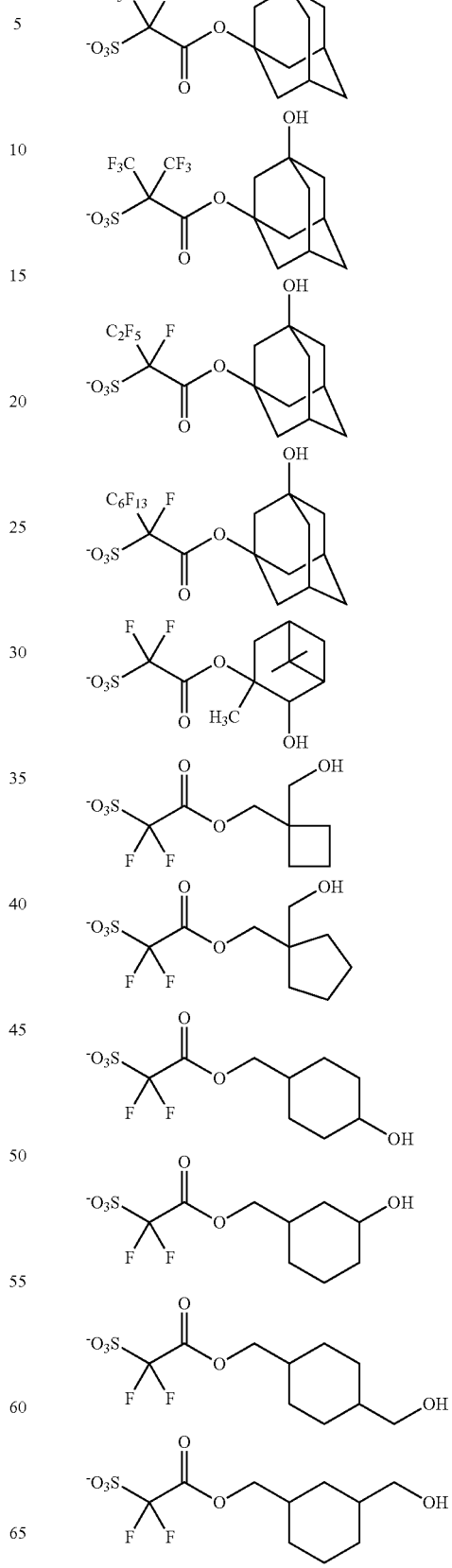

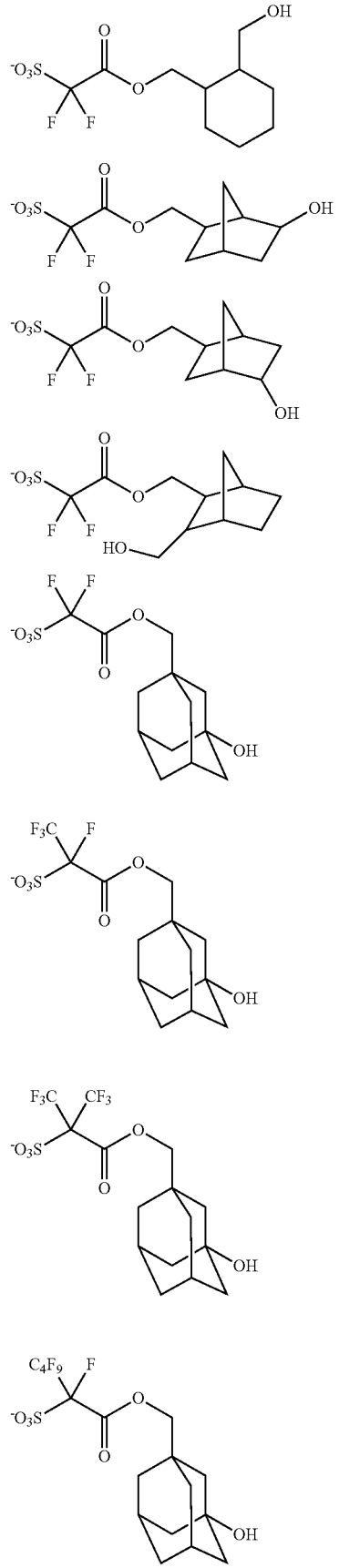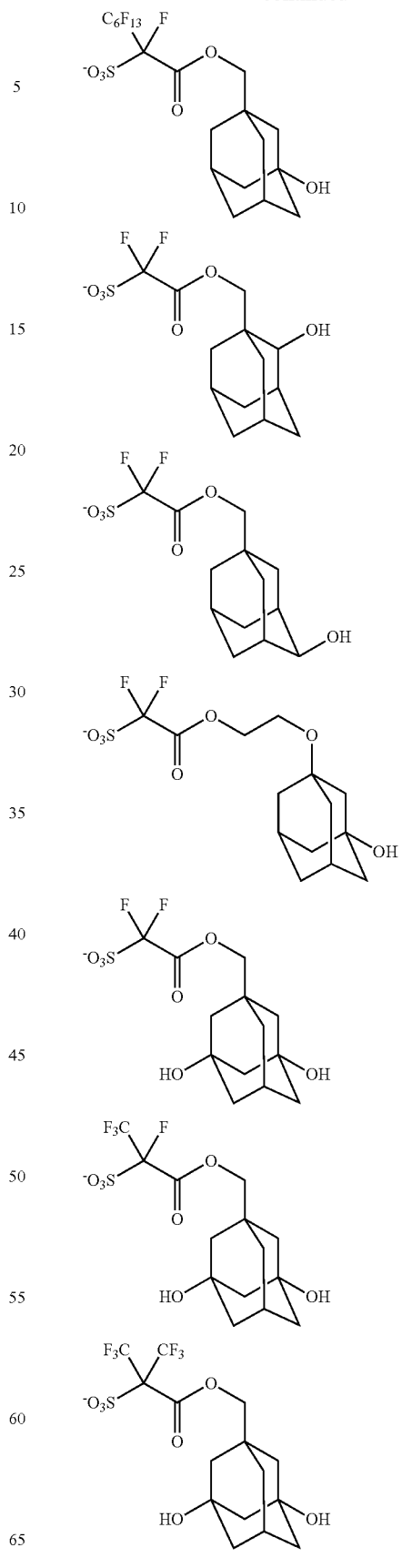

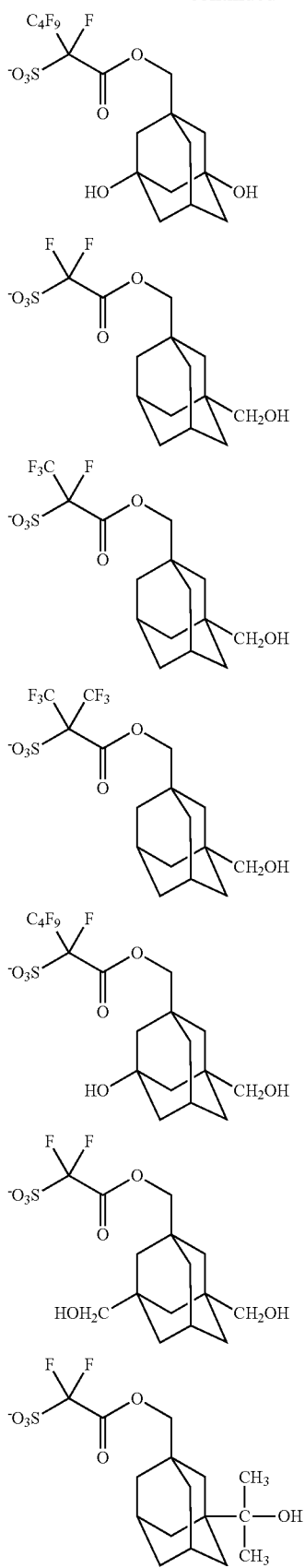
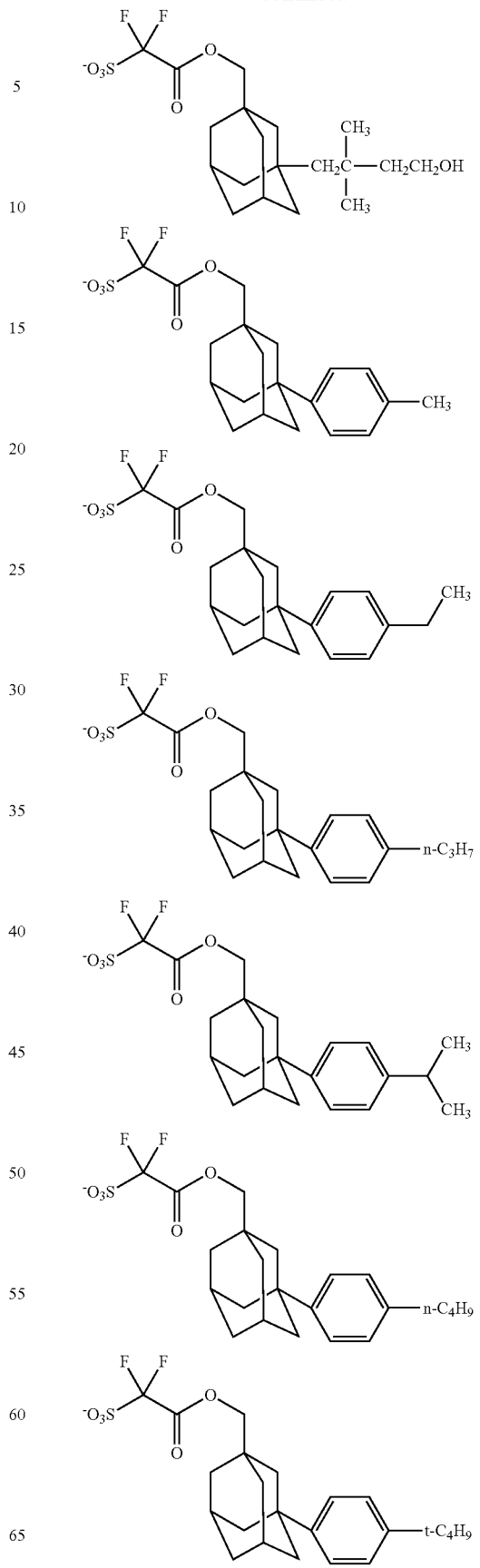

117
-continued
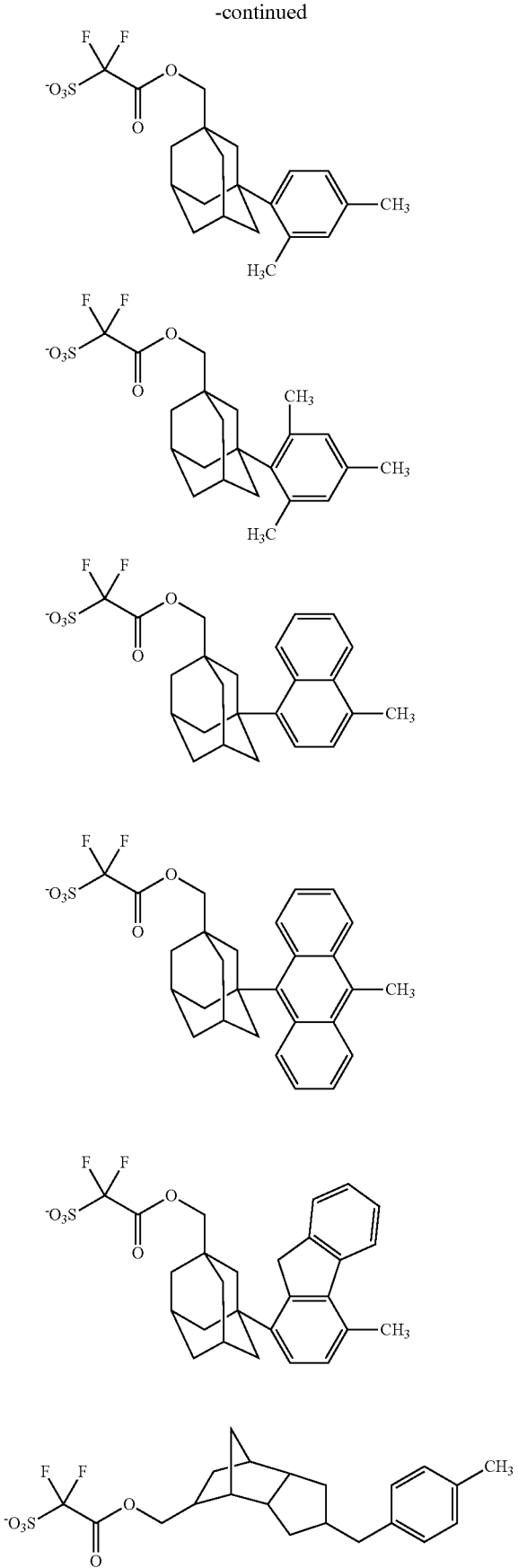
118
-continued
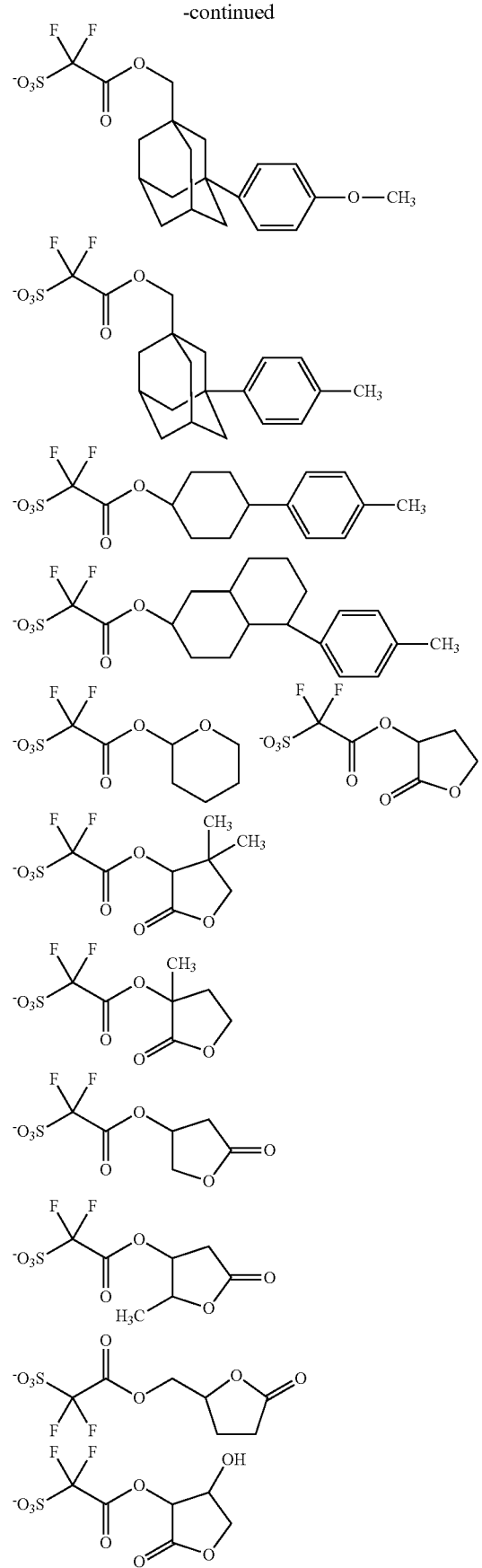

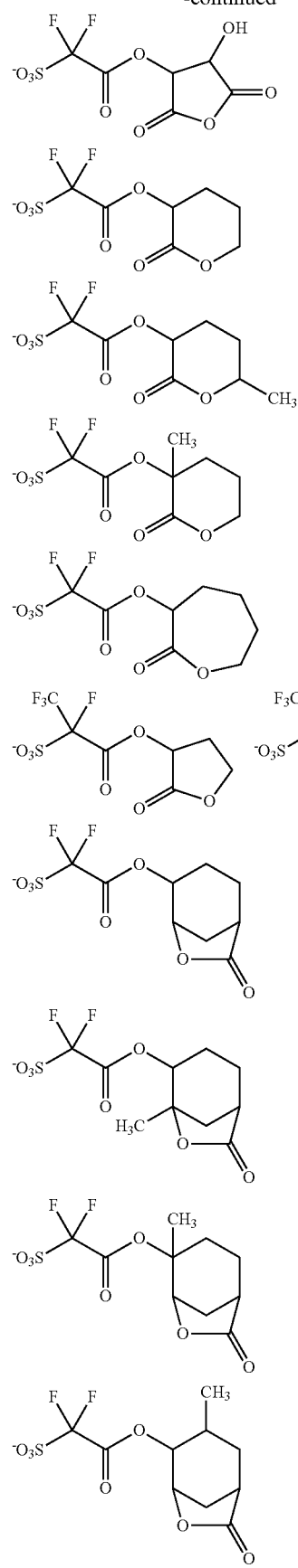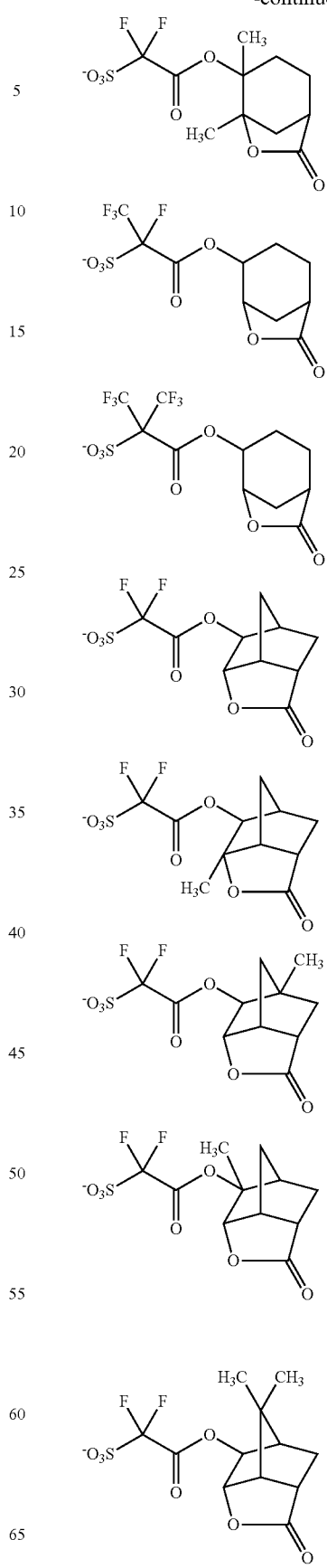

121
-continued
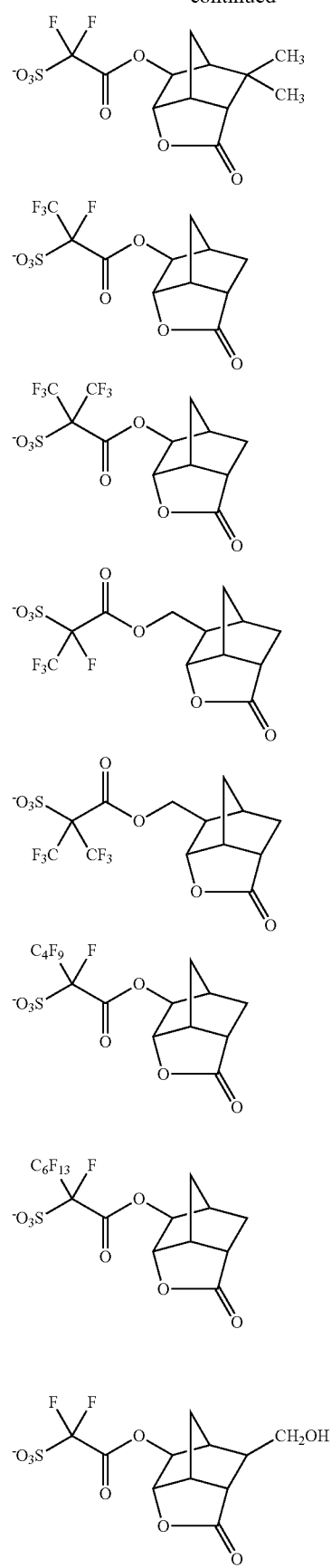
122
-continued
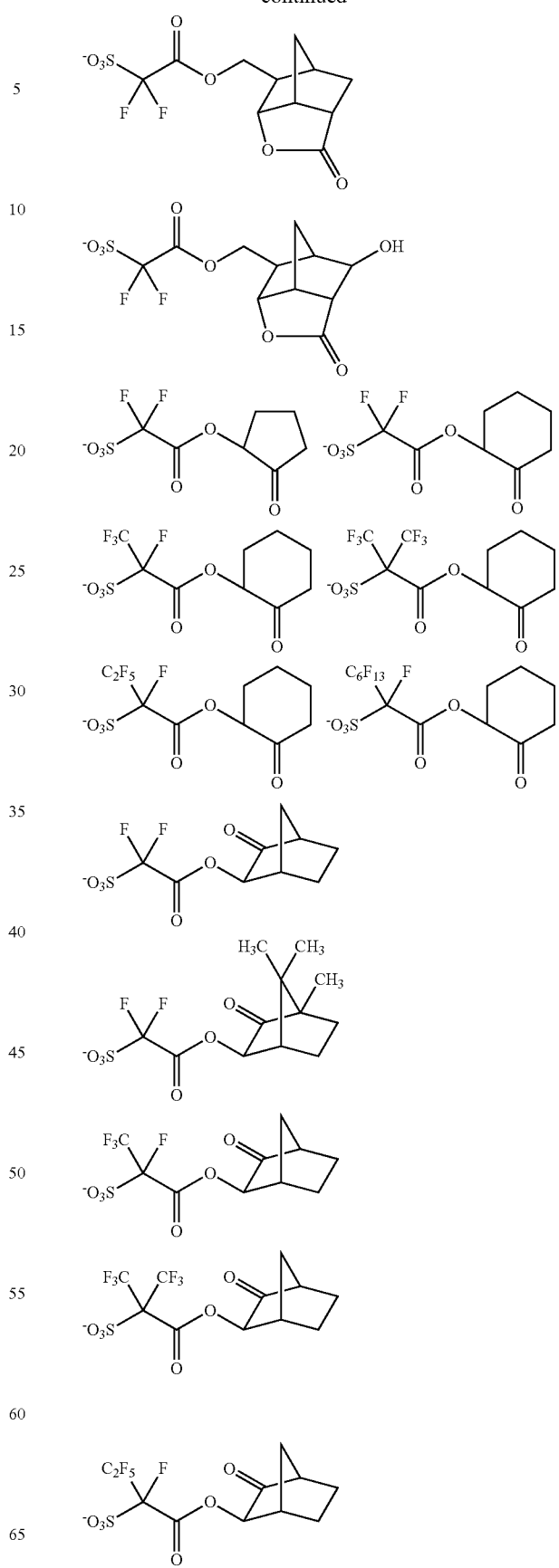

123 -continued
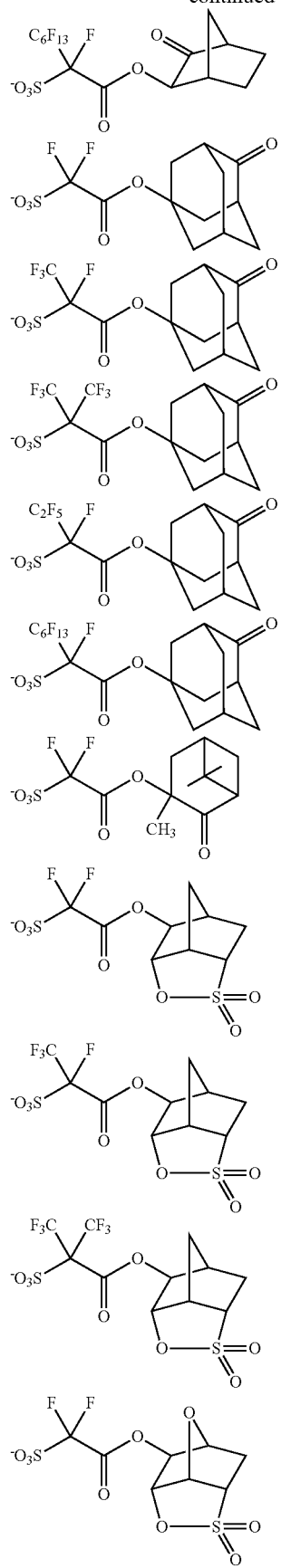
124 -continued
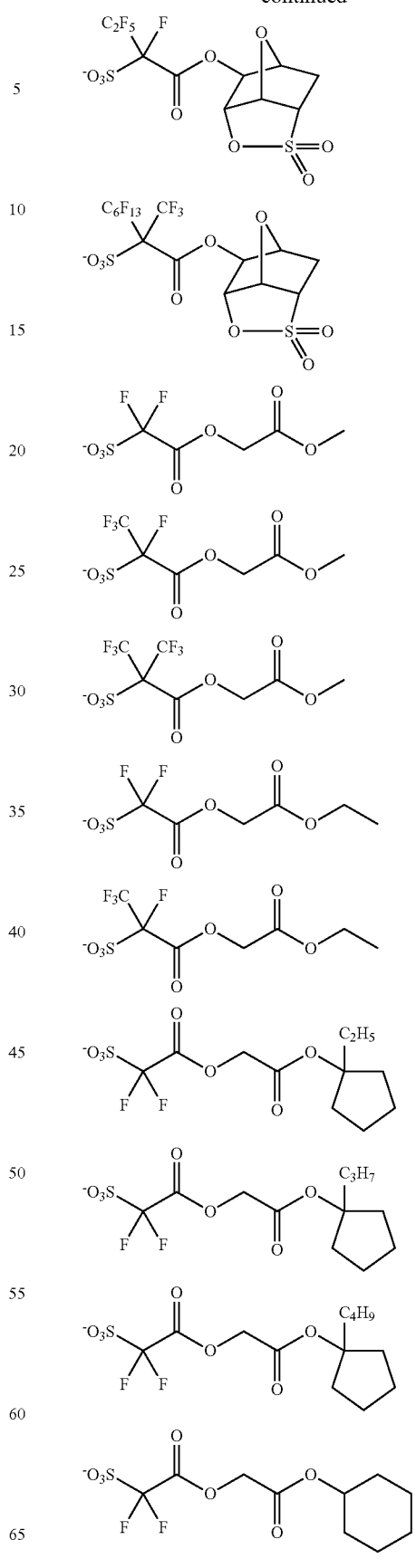

125
-continued
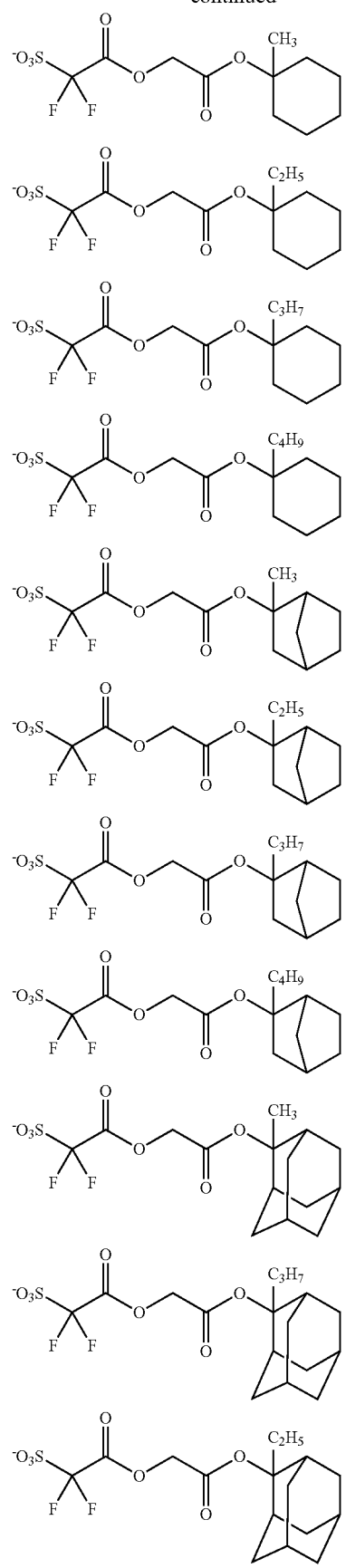
126
-continued
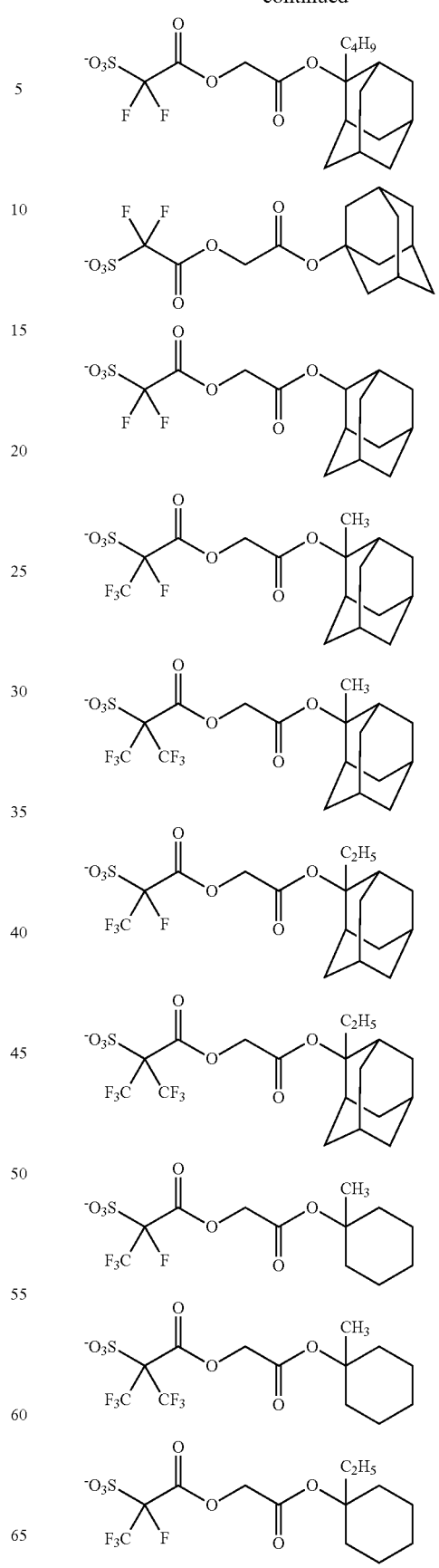

127
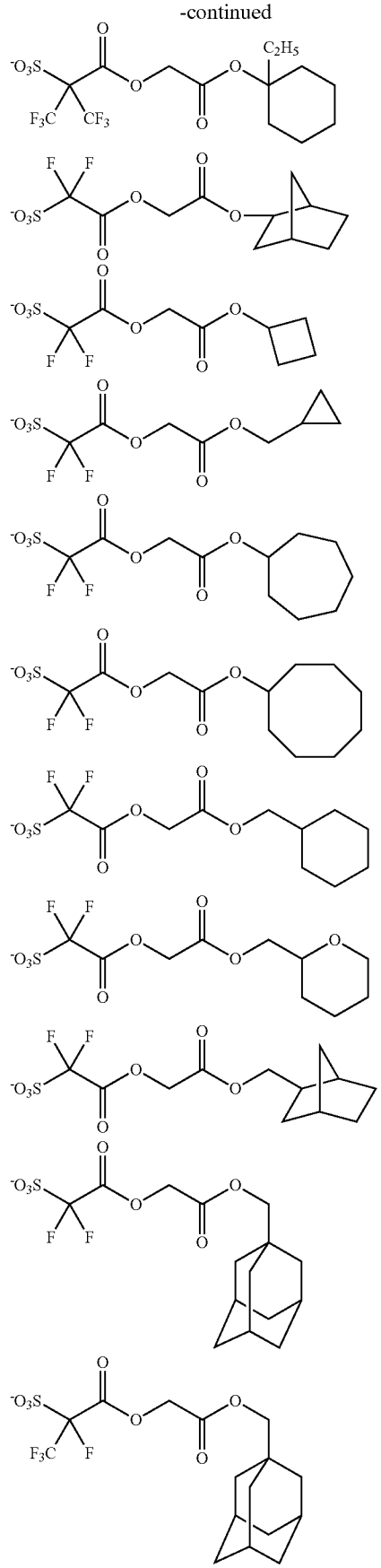
128
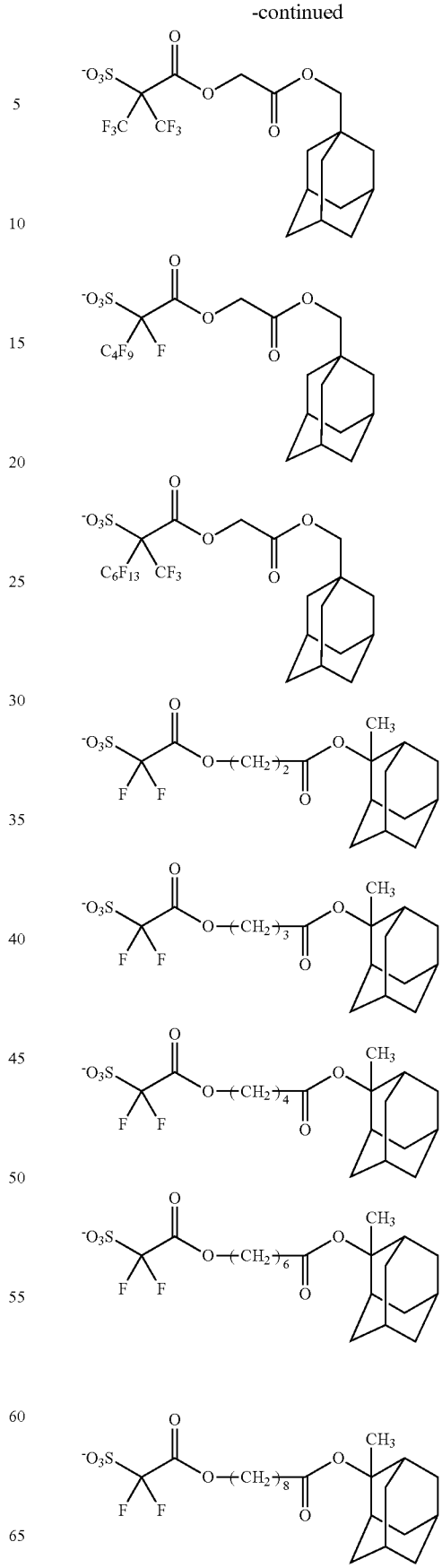

129
-continued
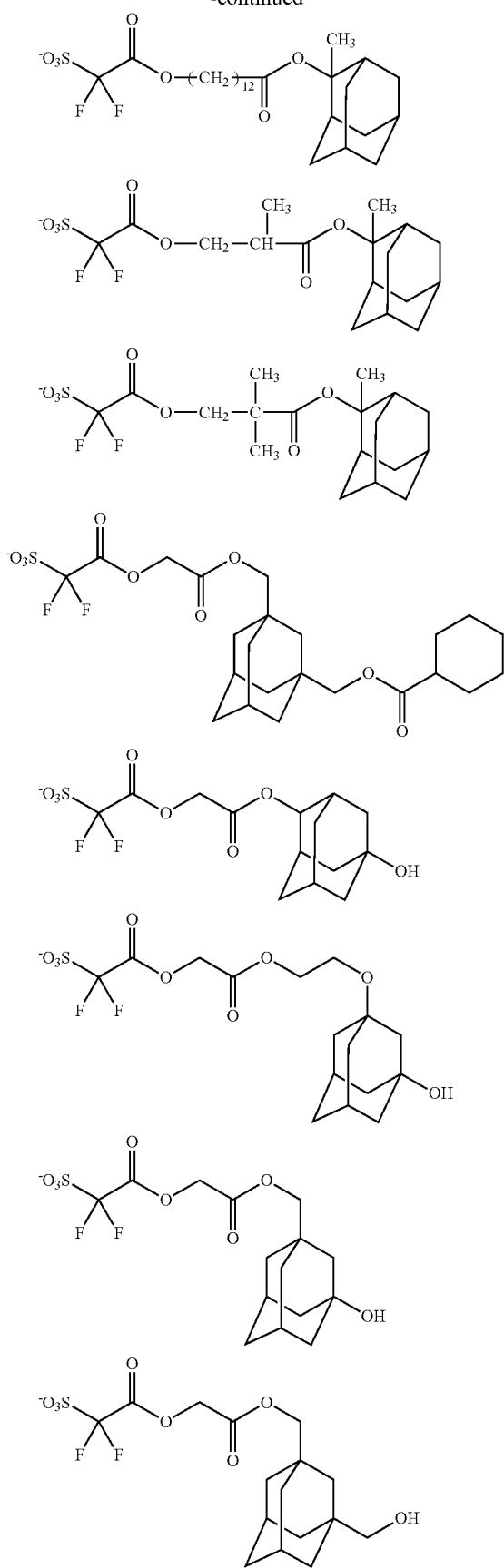
130
-continued
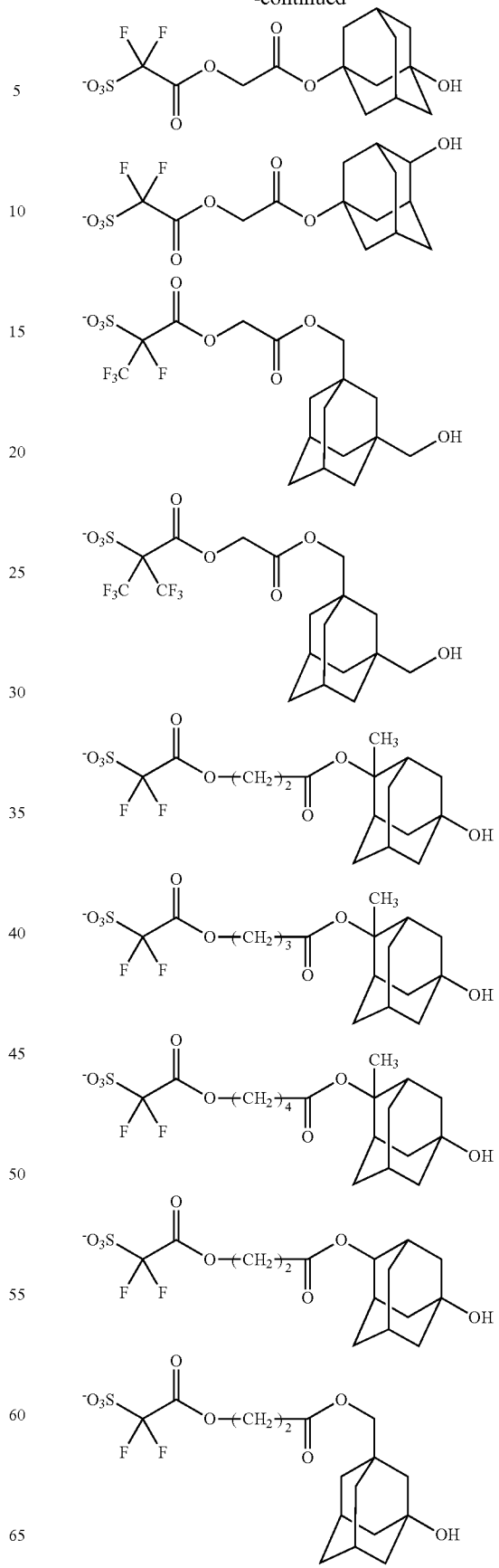

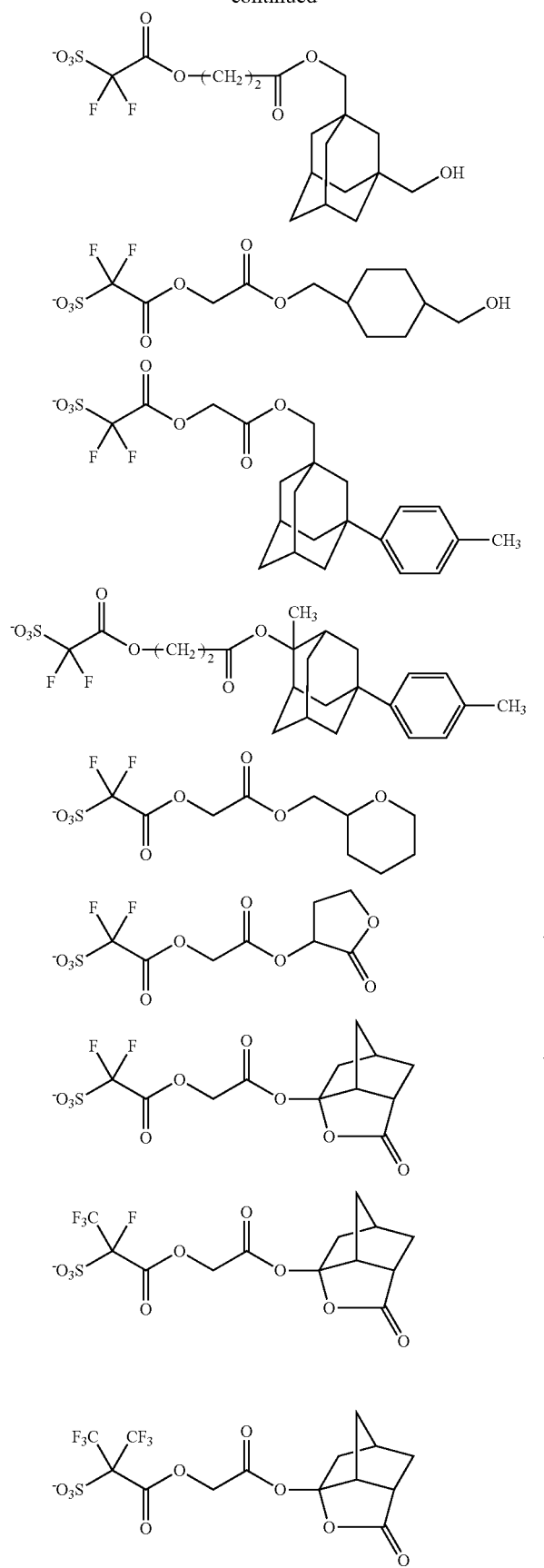
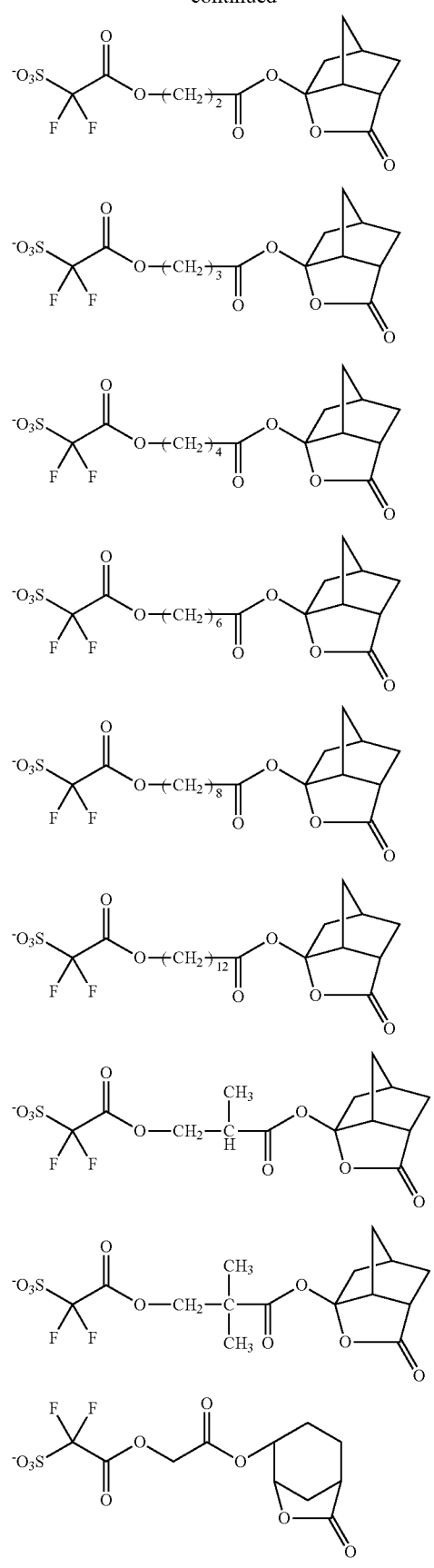

133
-continued
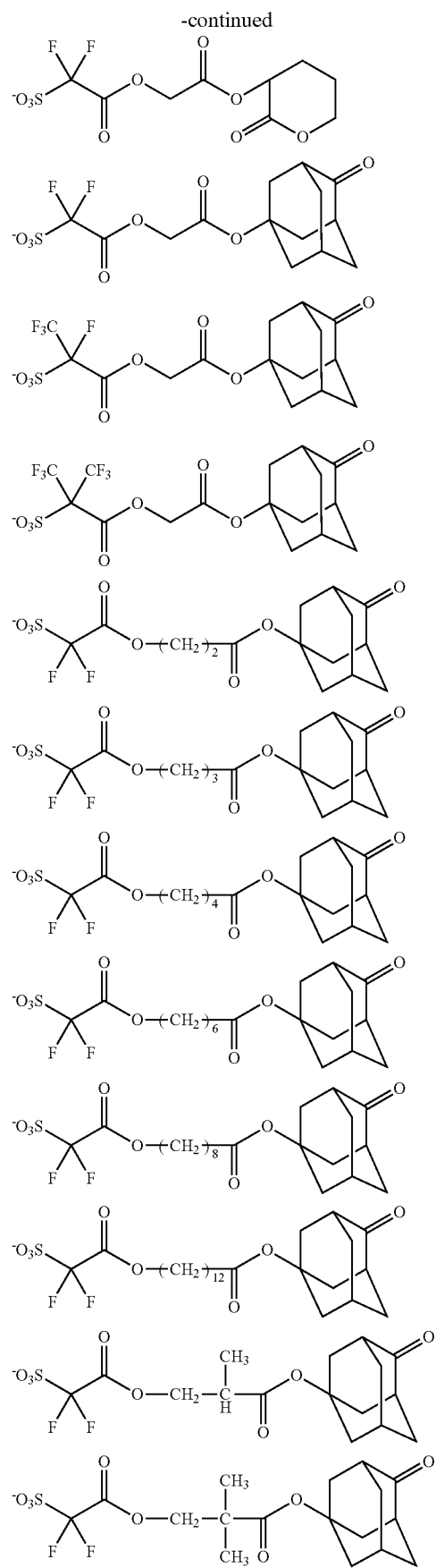
134
-continued
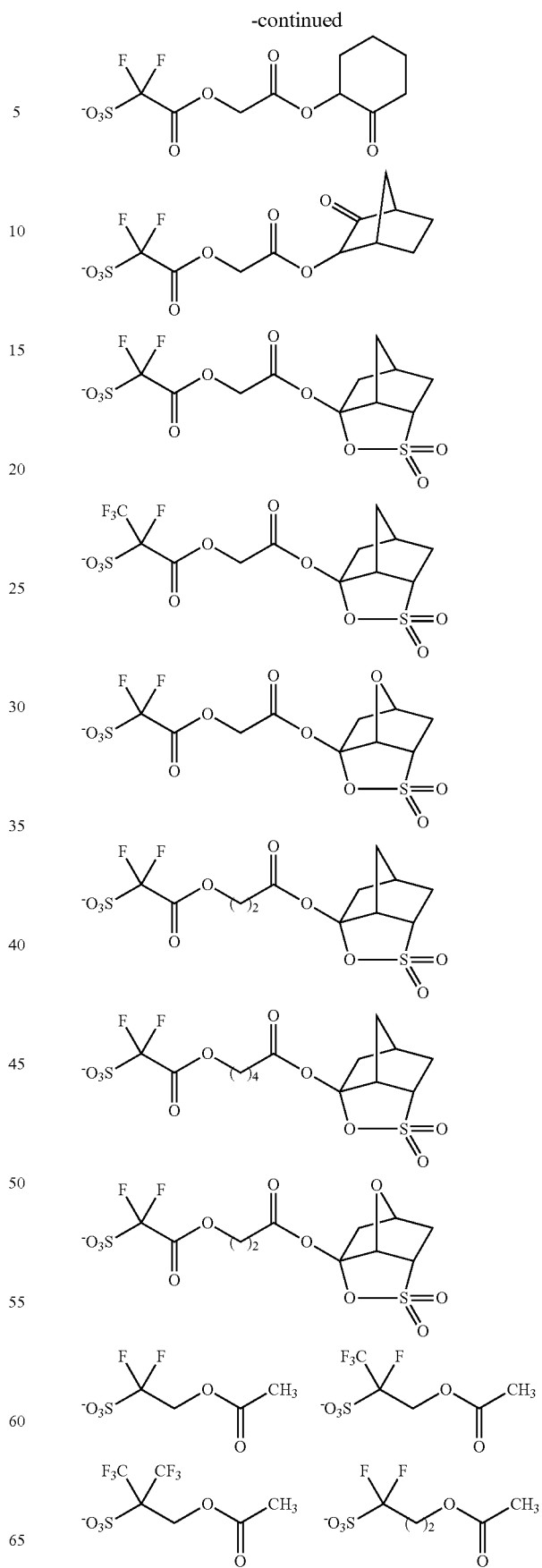

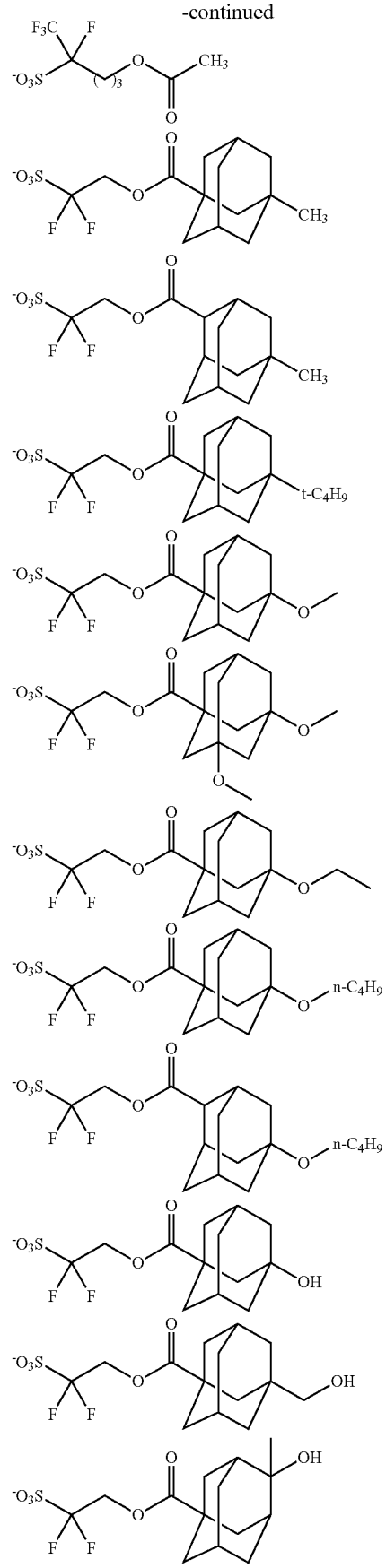
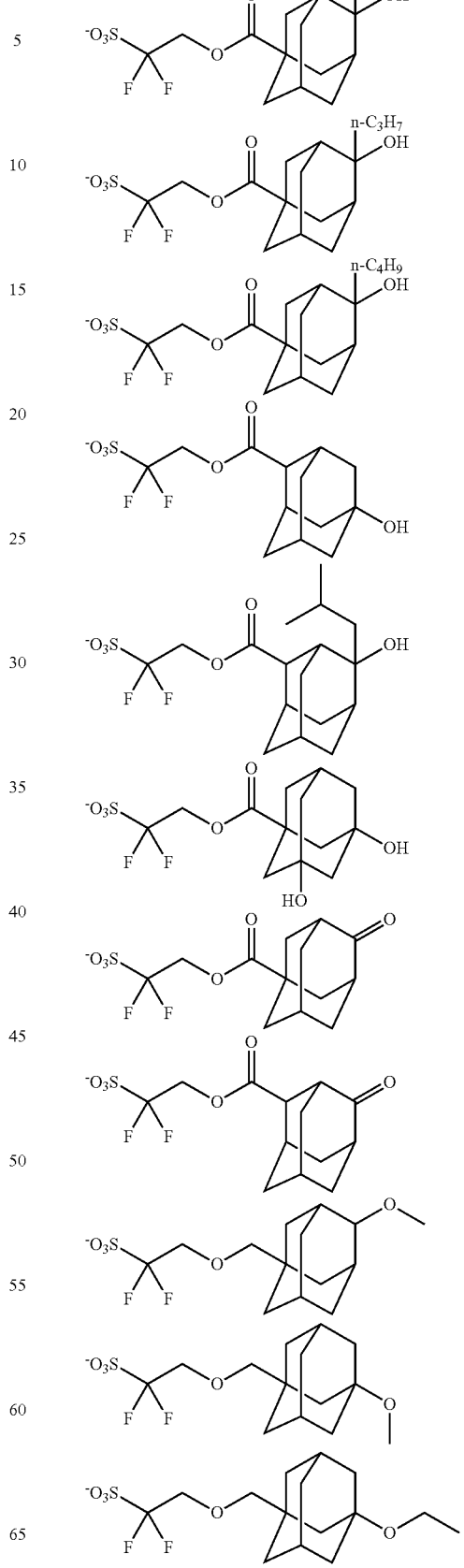

-continued
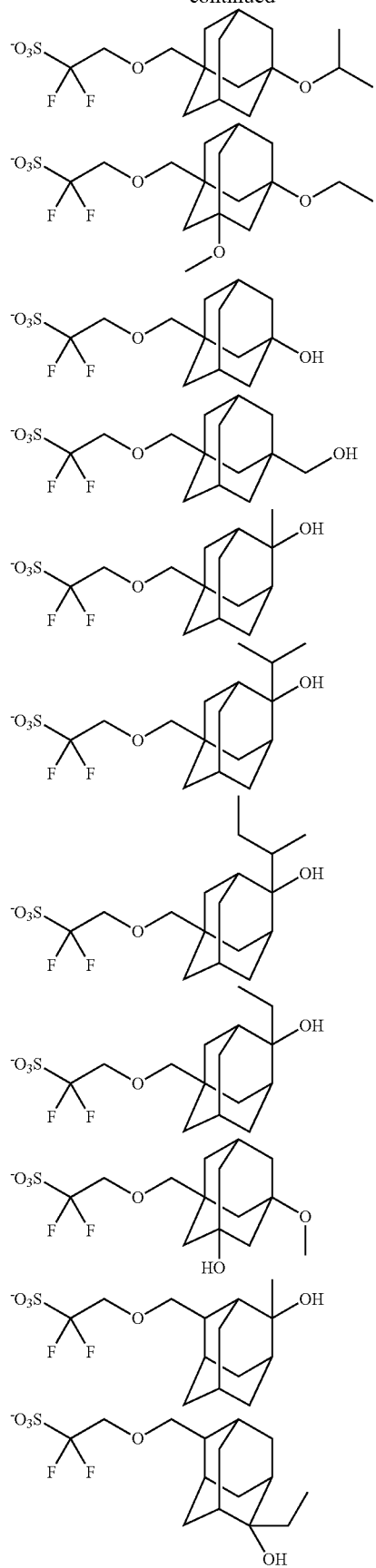
-continued
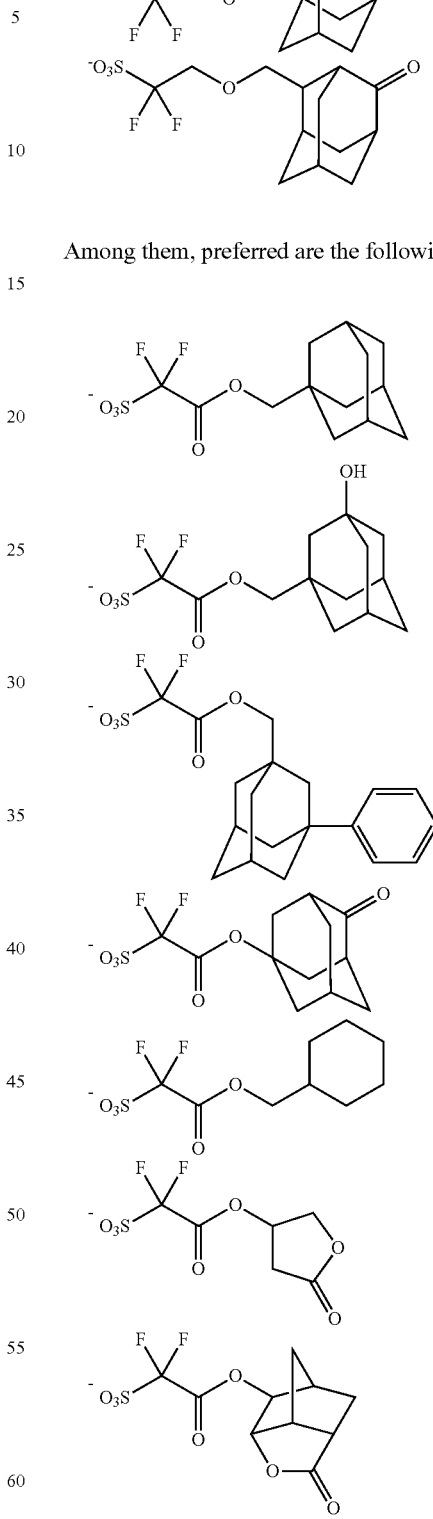
Among them, preferred are the following sulfonic anions.
Examples of the organic cation represented by Z⁺ in the salt represented by the formula (B1) include an onium cation such as a sulfonium cation, an iodonium cation, an ammonium cation, a benzothiazolium cation and a phosphonium cation, and a sulfonium cation and an iodonium cation are preferable, and an arylsulfonium cation is more preferable.

Preferable examples of the cation represented by $Z^+$ include the cations represented by the formulae (b2-1) to (b2-4):

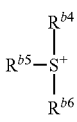
(b2-1)

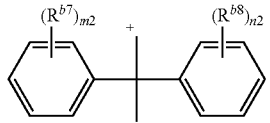
(b2-2)

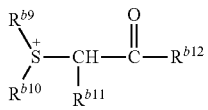
(b2-3)

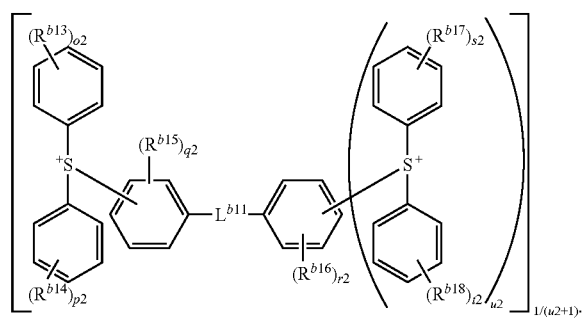
(b2-4)

wherein $R^{b4}$, $R^{b5}$ and $R^{b6}$ each independently represent a C1-C30 aliphatic hydrocarbon group which can have one or more substituents selected from the group consisting of a hydroxyl group, a C1-C12 alkoxy group and a C6-C18 aromatic hydrocarbon group, a C3-C36 saturated cyclic hydrocarbon group which can have one or more substituents selected from the group consisting of a halogen atom, a C2-C4 acyl group and a glycidyloxy group, or a C6-C18 aromatic hydrocarbon group which can have one or more substituents selected from the group consisting of a halogen atom, a hydroxyl group, a C1-C18 aliphatic hydrocarbon group, a C3-C36 saturated cyclic hydrocarbon group or a C1-C12 alkoxy group, $R^{b7}$ and $R^{b8}$ are independently in each occurrence a hydroxyl group, a C1-C12 aliphatic hydrocarbon group or a C1-C12 alkoxy group, m2 and n2 independently represents an integer of 0 to 5, $R^{b9}$ and $R^{b10}$ each independently represent a C1-C36 aliphatic hydrocarbon group or a C3-C36 saturated cyclic hydrocarbon group, or $R^{b9}$ and $R^{b10}$ are bonded to form a C2-C11 divalent acyclic hydrocarbon group which forms a ring together with the adjacent $S^+$, and one or more —$CH_2$— in the divalent acyclic hydrocarbon group may be replaced by —CO—, —O— or —S—, and $R^{b11}$ represents a hydrogen atom, a C1-C36 aliphatic hydrocarbon group, a C3-C36 saturated cyclic hydrocarbon group or a C6-C18 aromatic hydrocarbon group, $R^{b12}$ represents a C1-C12 aliphatic hydrocarbon group, a C3-C18 saturated cyclic hydrocarbon group or a C6-C18 aromatic hydrocarbon group and the aromatic hydrocarbon group can have one or more substituents selected from the group consisting of a C1-C12 aliphatic hydrocarbon group, a C1-C12 alkoxy group, a C3-C18 saturated cyclic hydrocarbon group and an C2-C13 acyloxy group, or $R^{b11}$ and $R^{b12}$ are bonded each other to form a C1-C10 divalent acyclic hydrocarbon group which forms a 2-oxocycloalkyl group together with the adjacent —CHCO—, and one or more —$CH_2$— in the divalent acyclic hydrocarbon group may be replaced by —CO—, —O— or —S—, and $R^{b13}$, $R^{b14}$, $R^{b15}$, $R^{b16}$, $R^{b17}$ and $R^{b18}$ each independently represent a hydroxyl group, a C1-C12 aliphatic hydrocarbon group or a C1-C12 alkoxy group, $L^{b11}$ represents —S— or —O— and o2, p2, s2 and t2 each independently represents an integer of 0 to 5, q2 and r2 each independently represents an integer of 0 to 4, and u2 represents 0 or 1.

The aliphatic hydrocarbon group represented by $R^{b9}$ to $R^{b11}$ has preferably 1 to 12 carbon atoms. The saturated cyclic hydrocarbon group represented by $R^{b9}$ to $R^{b11}$ has preferably 3 to 18 carbon atoms and more preferably 4 to 12 carbon atoms.

Examples of the aliphatic hydrocarbon group and the aromatic hydrocarbon group include the same as described above. Preferable examples of the aliphatic hydrocarbon group include a methyl group, an ethyl group, a propyl group, an isopropyl group, a butyl group, a sec-butyl group, a tert-butyl group, a pentyl group, a hexyl group, an octyl group and a 2-ethylhexyl group. Preferable examples of the saturated cyclic hydrocarbon group include a cyclopropyl group, a cyclobutyl group, a cyclopentyl group, a cyclohexyl group, a cycloheptyl group, a cyclodecyl group, a 2-alkyl-a-adamantyl group, a 1-(1-adamantyl)-1-alkyl group and an isobornyl group. Preferable examples of the aromatic group include a phenyl group, a 4-methylphenyl group, a 4-ethylphenyl group, a 4-tert-butylphenyl group, a 4-cyclohexylphenyl group, a 4-methoxyphenyl group, a biphenyl group and a naphthyl group. Examples of the aliphatic hydrocarbon group having an aromatic hydrocarbon group include a benzyl group. Examples of the alkoxy group include a methoxy group, an ethoxy group, a propoxy group, an isopropoxy group, a butoxy group, a sec-butoxy group, a tert-butoxy group, a pentyloxy group, a hexyloxy group, a heptyloxy group, an octyloxy group, a 2-ethylhexyloxy group, a nonyloxy group, a decyloxy group, an undecyloxy group and a dodecyloxy group.

Examples of the C3-C12 divalent acyclic hydrocarbon group formed by bonding $R^{b9}$ and $R^{b10}$ include a trimethylene group, a tetramethylene group and a pentamethylene group. Examples of the ring group formed together with the adjacent $S^+$ and the divalent acyclic hydrocarbon group include a thiolan-1-ium ring (tetrahydrothiophenium ring), a thian-1-ium ring and a 1,4-oxathian-4-ium ring. A C3-C7 divalent acyclic hydrocarbon group is preferable.

Examples of the C1-C10 divalent acyclic hydrocarbon group formed by bonding $R^{b11}$ and $R^{b12}$ include a methylene group, an ethylene group, a trimethylene group, a tetramethylene group and a pentamethylene group and examples of the ring group include the followings.

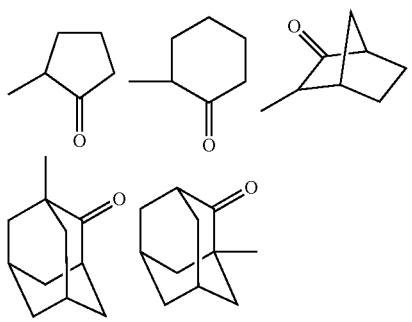

Among the above-mentioned cations, preferred is the cation represented by the formula (b2-1), and more preferred is the cation represented by the formula (b2-1-1), and especially preferred are a triphenylsulfonium cation and a tris(4-methylphenyl)sulfonium cation.

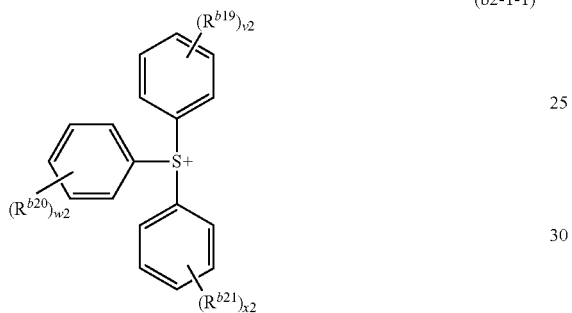

(b2-1-1)

wherein $R^{b19}$, $R^{b20}$ and $R^{b21}$ are independently in each occurrence a halogen atom, a hydroxyl group, a C1-C36 aliphatic hydrocarbon group, a C3-C36 saturated cyclic hydrocarbon group or a C1-C12 alkoxy group, and one or more hydrogen atoms in the aliphatic hydrocarbon group can be replaced by a hydroxyl group, a C1-C12 alkoxy group or a C6-C18 aromatic hydrocarbon group, one or more hydrogen atoms of the saturated cyclic hydrocarbon group can be replaced by a halogen atom, a C2-C4 acyl group or a glycidyloxy group, and v2, w2 and x2 independently each represent an integer of 0 to 5. The aliphatic hydrocarbon group preferably has 1 to 12-carbon atoms, and the saturated cyclic hydrocarbon group preferably has 4 to 36 carbon atoms, and it is preferred that v2, w2 and x2 independently each represent 0 or 1. It is preferred that $R^{b19}$, $R^{b20}$ and $R^{b21}$ are independently halogen atom (preferably a chlorine atom), a hydroxyl group, a C1-C12 alkyl group or a C1-C12 alkoxy group.

Examples of the cation represented by the formula (b2-1) include the followings.

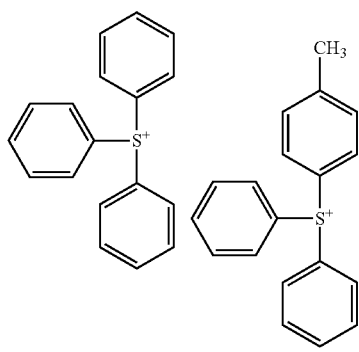

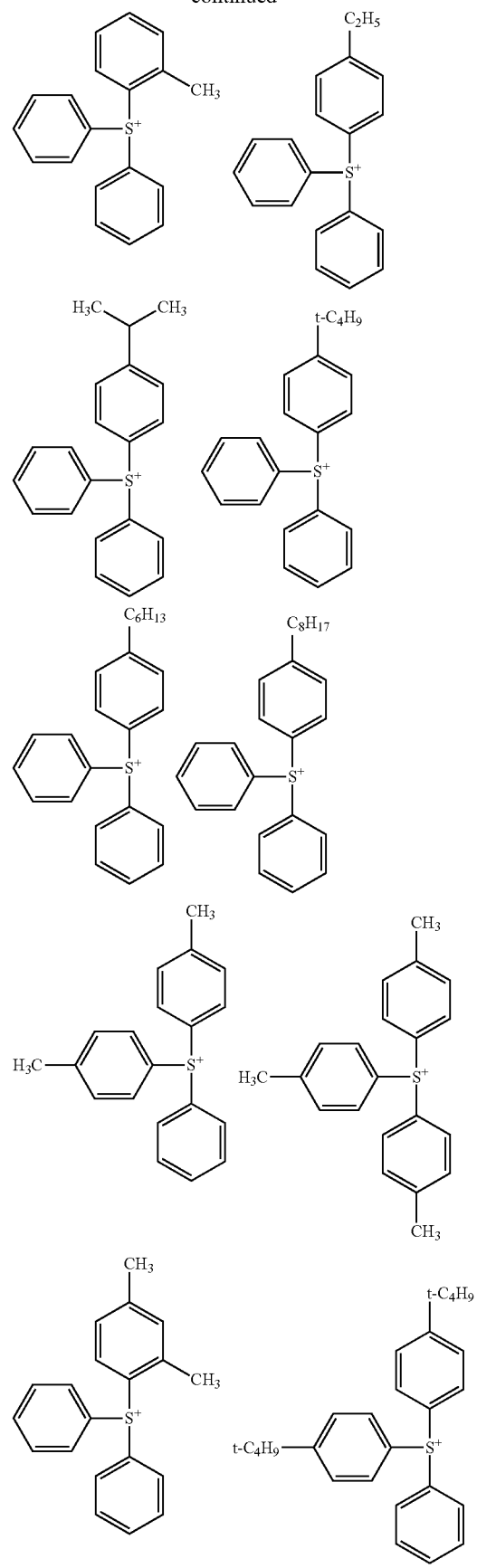

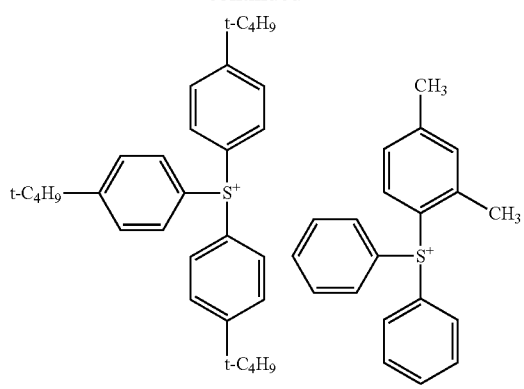
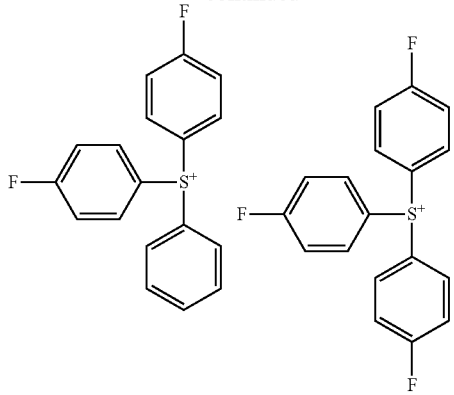 [SMILES: Fc1ccc([S+](c2ccccc2)c2ccc(F)cc2)cc1 ; Fc1ccc([S+](c2ccc(F)cc2)c2ccc(F)cc2)cc1]
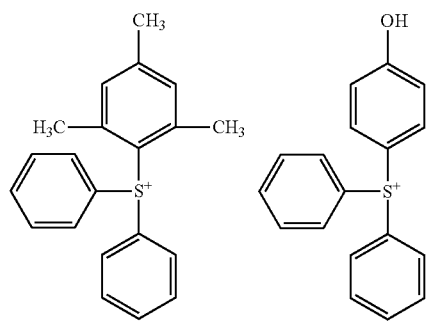
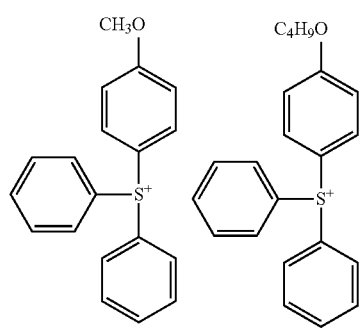
Examples of the cation represented by the formula (b2-2) include the followings.
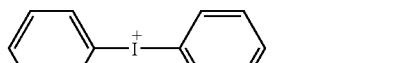
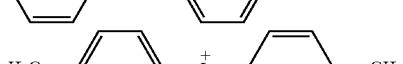
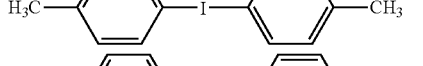
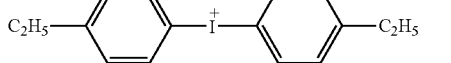
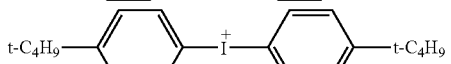
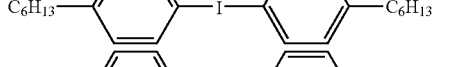
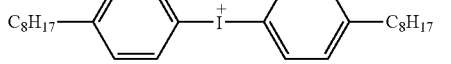
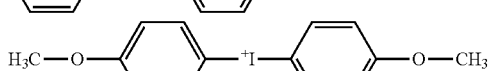
Examples of the cation represented by the formula (b2-3) include the followings.
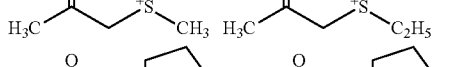
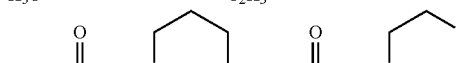
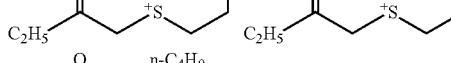
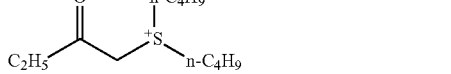

-continued
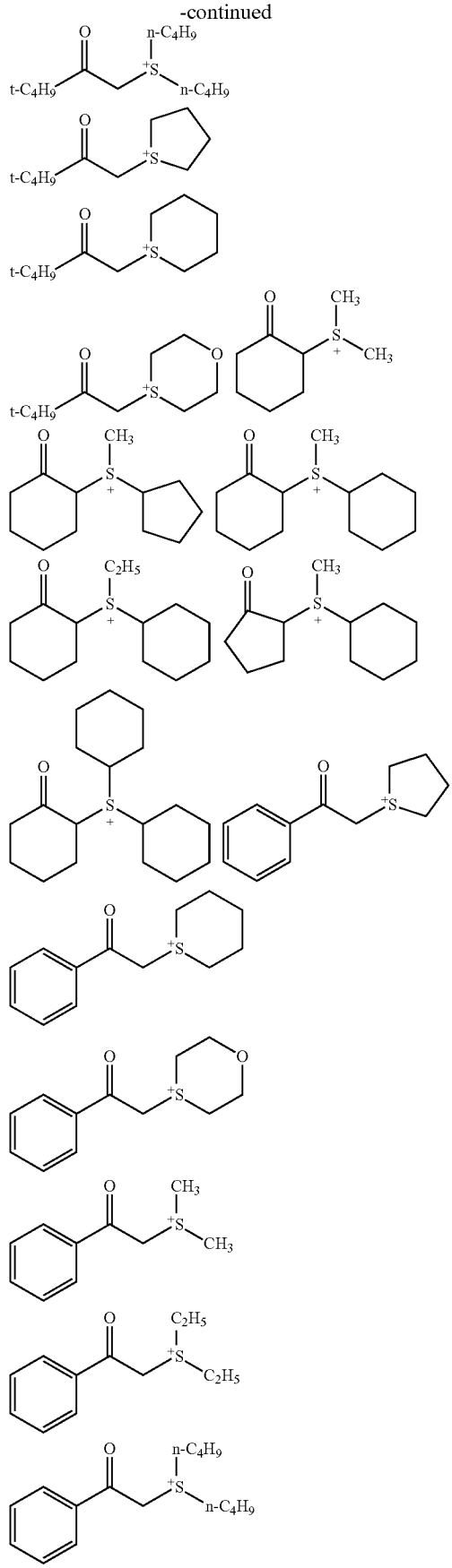
-continued
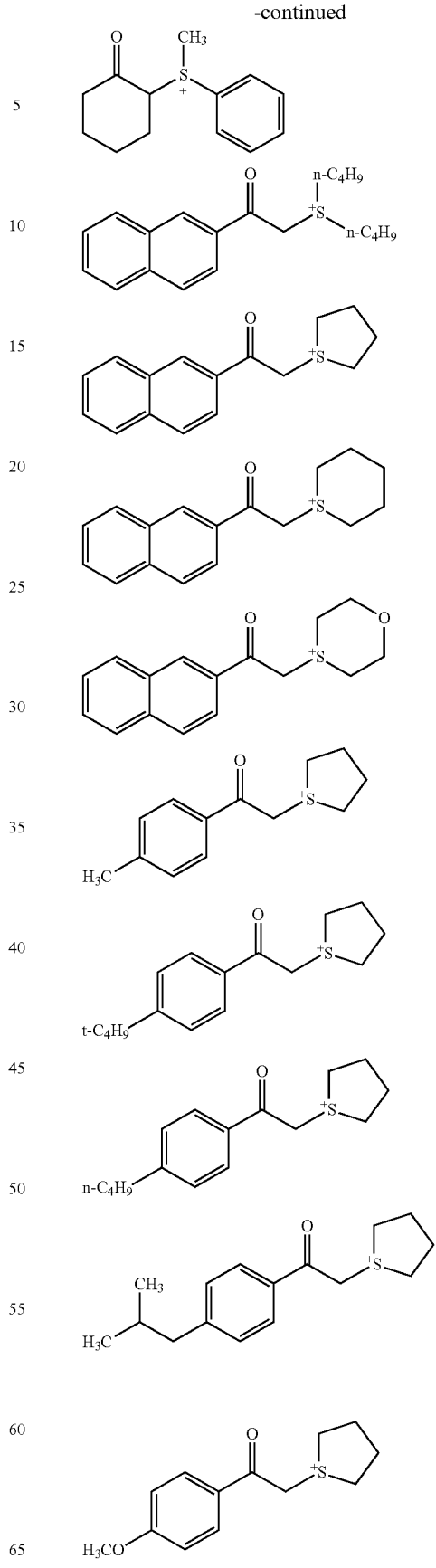

147
-continued
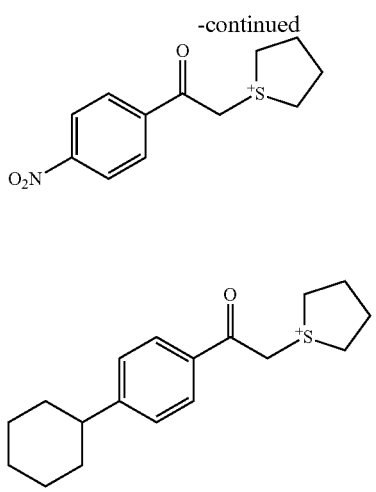
148
-continued
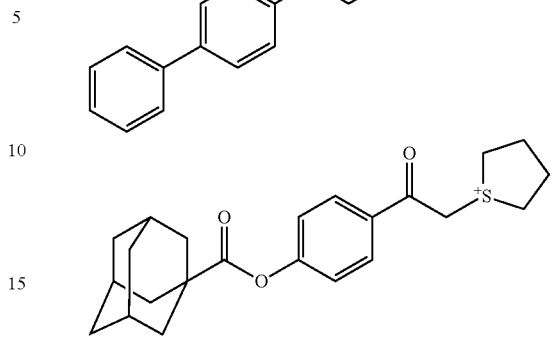
Examples of the cation represented by the formula (b2-4) include the followings.
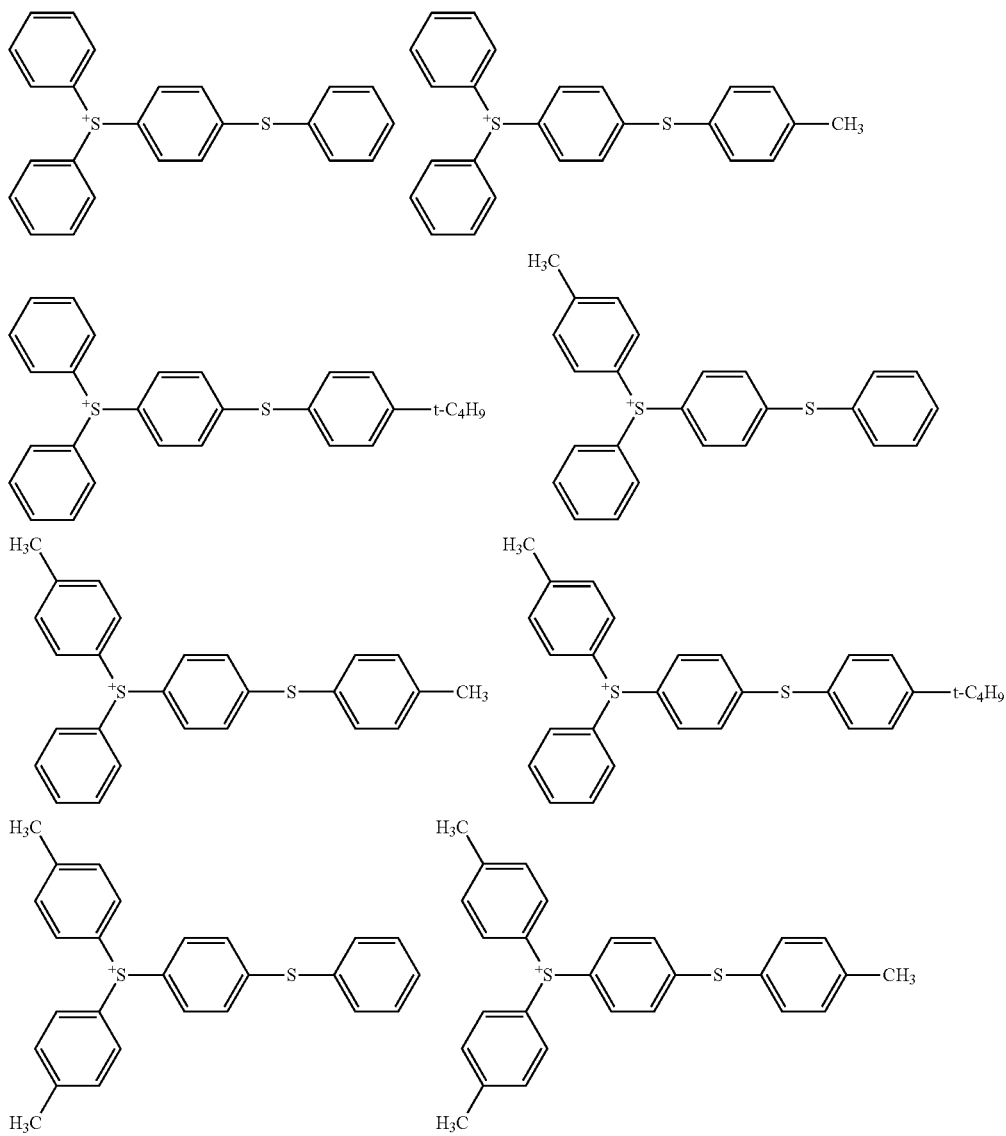

-continued
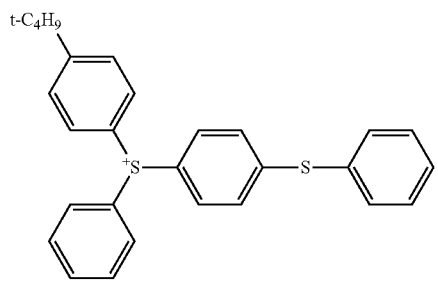
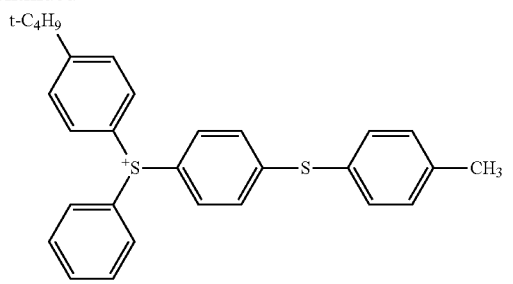
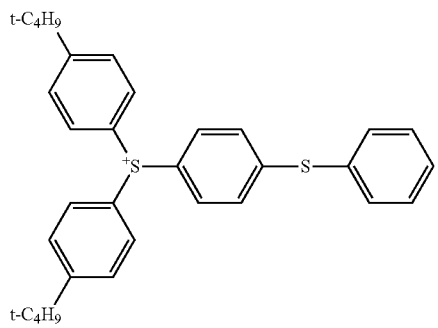
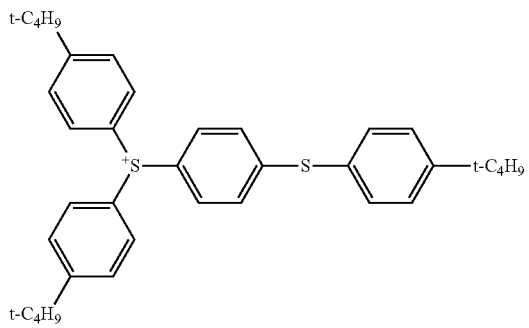
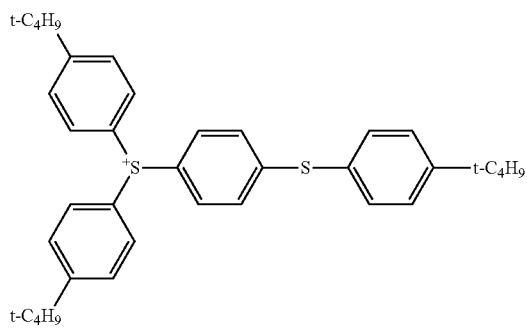
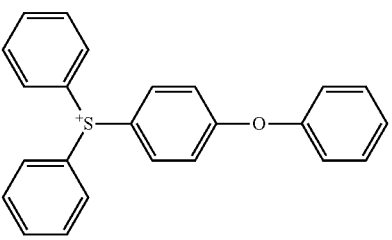
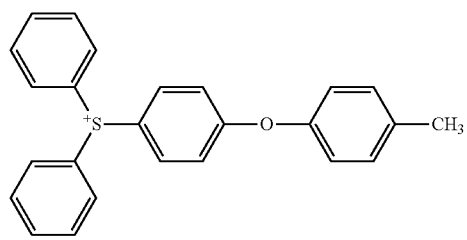
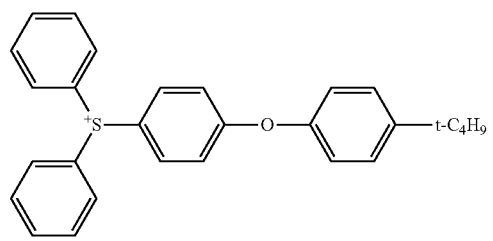
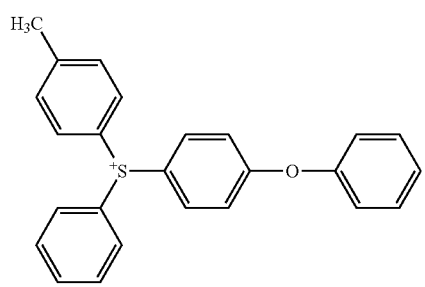
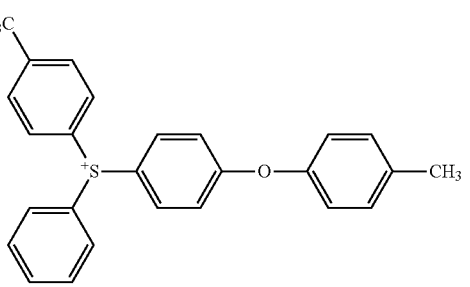

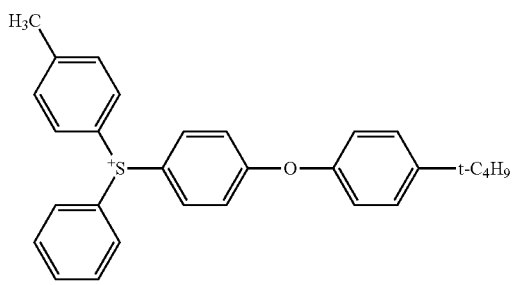
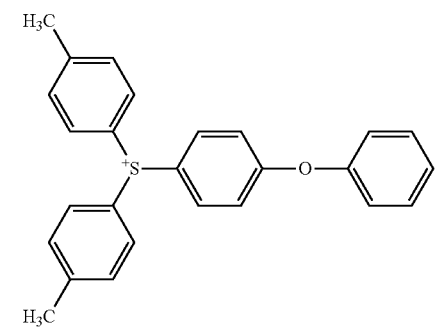
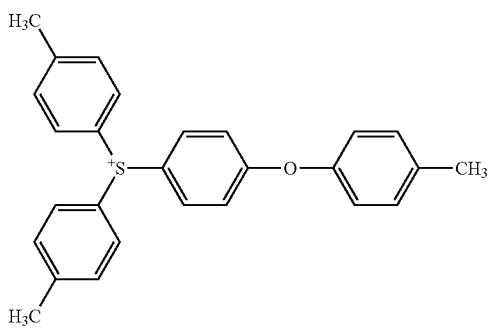
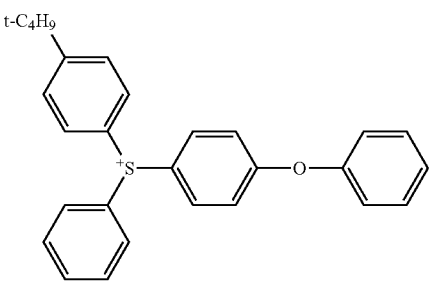
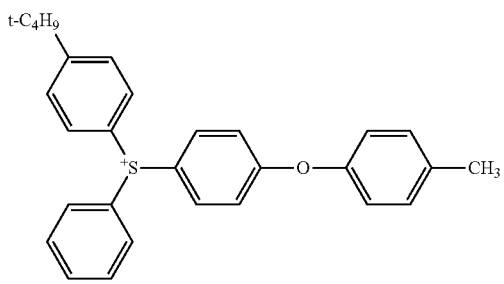
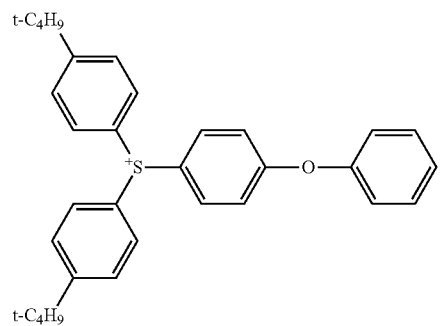
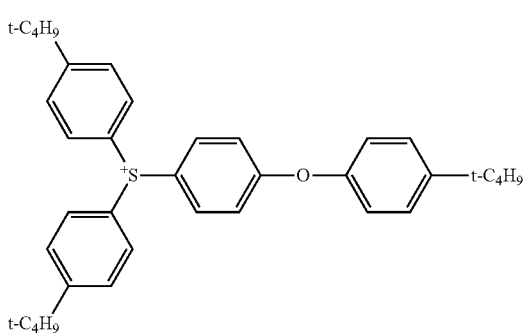
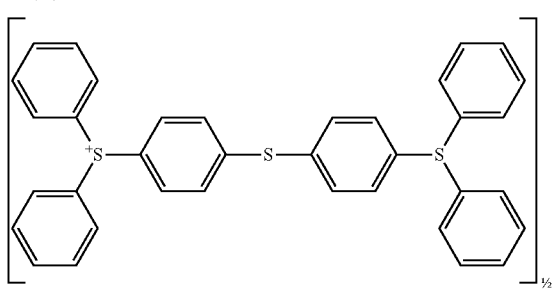

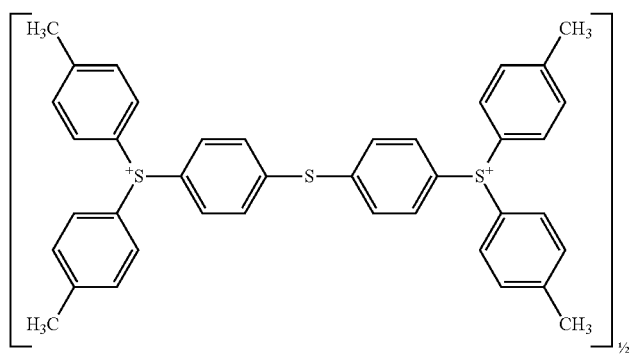
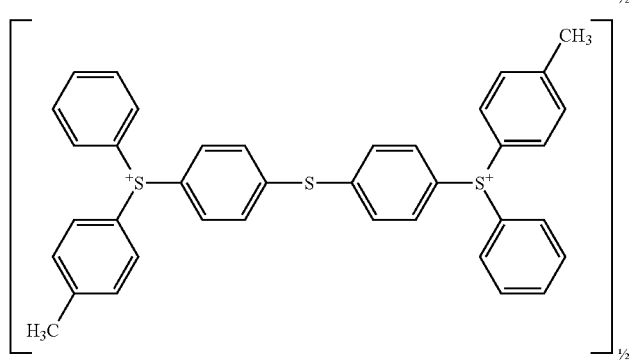
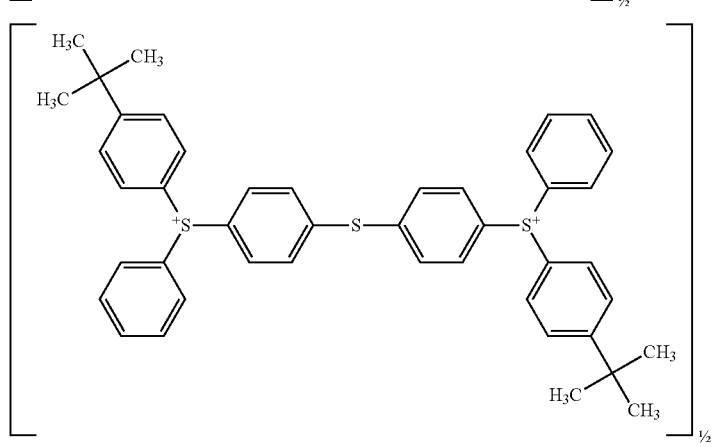
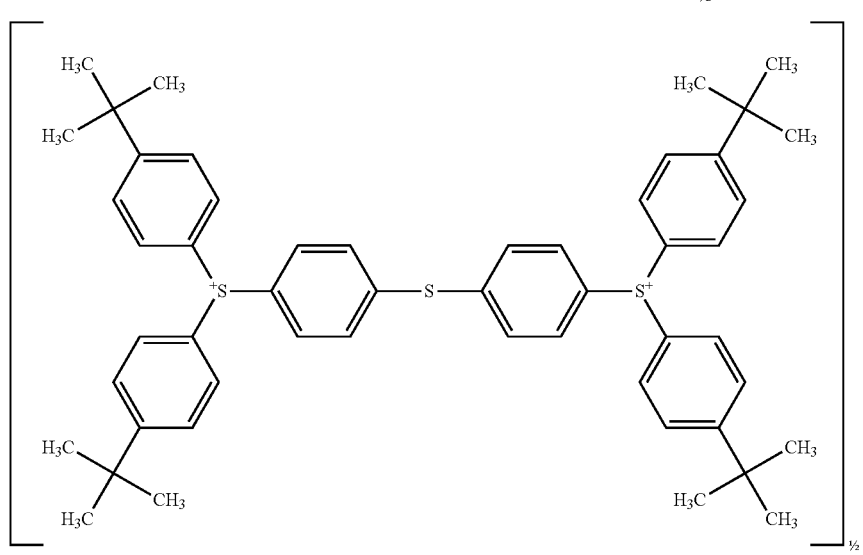

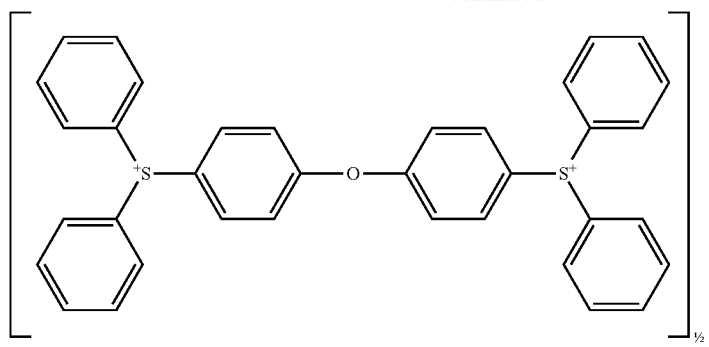
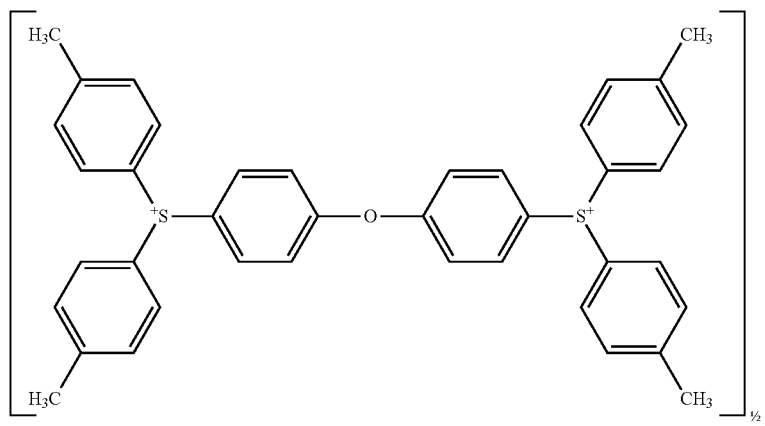
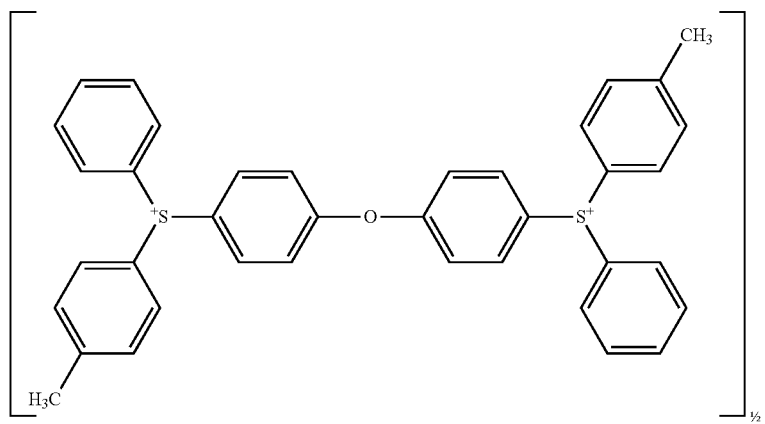
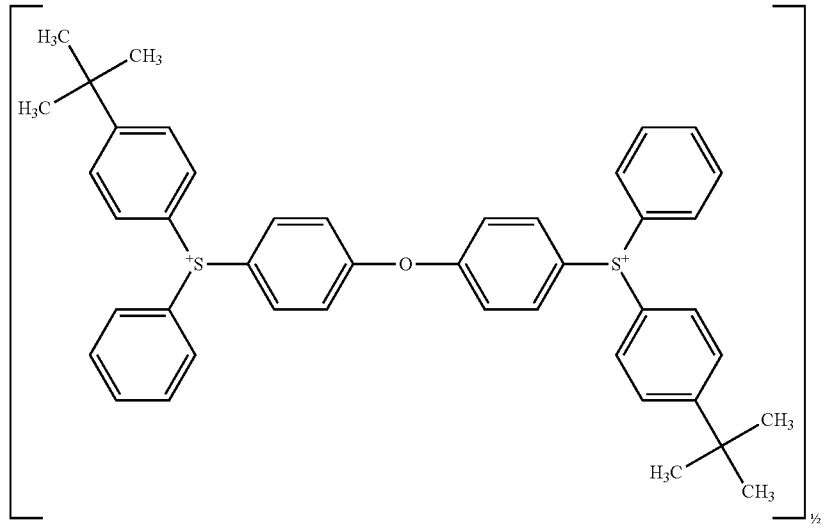

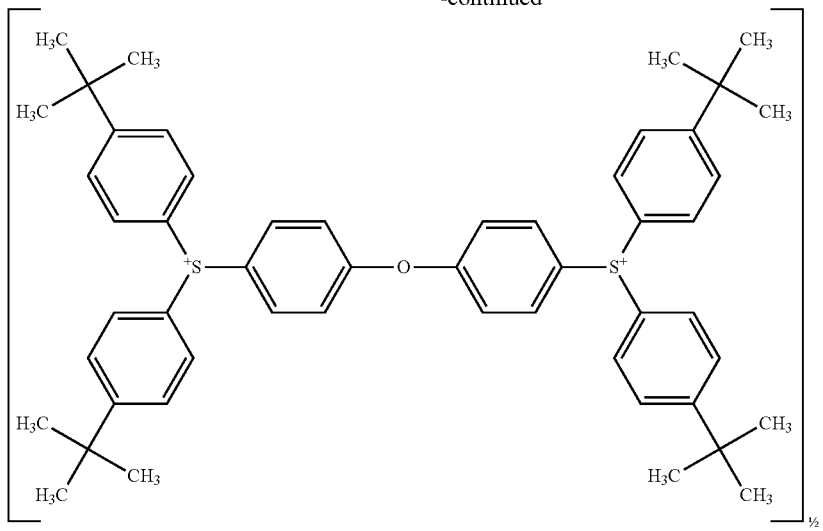
Examples of the salt represented by the formula (B1) include a salt wherein the anion is any one of the above-mentioned anions and the cation is any one of the above-mentioned cations. The salts represented by the formulae (B1-1) to (B1-17) are preferable, and the salts represented by the formulae (B1-1), (B1-2), (B1-6), (B1-11), (B1-12), (B1-13) and (B1-14) are more preferable.
(B1-1)
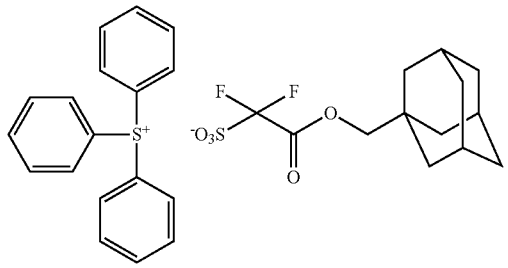
(B1-2)
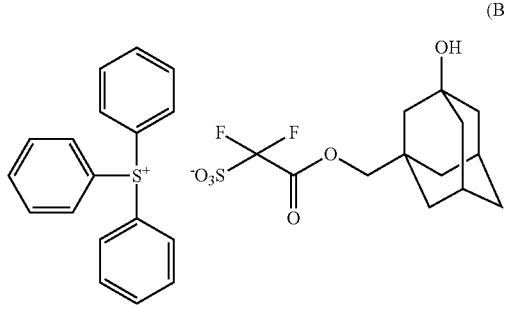
(B1-3)
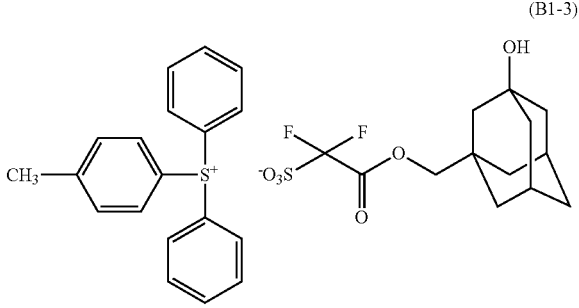
(B1-4)
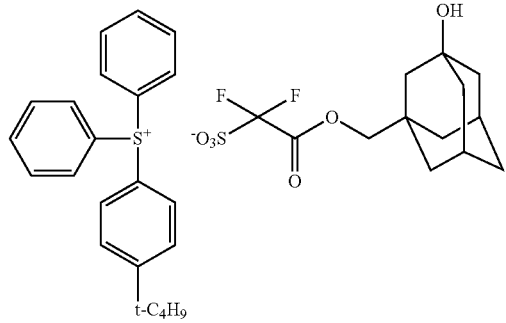
(B1-5)
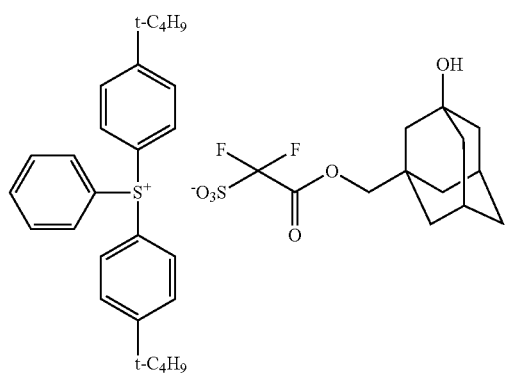

-continued
(B1-6)
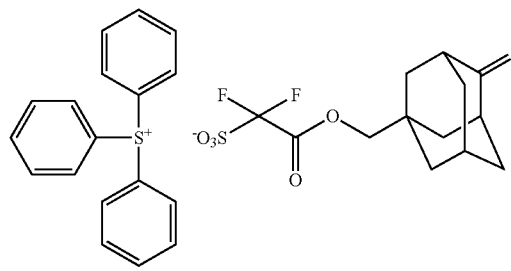
(B1-7)
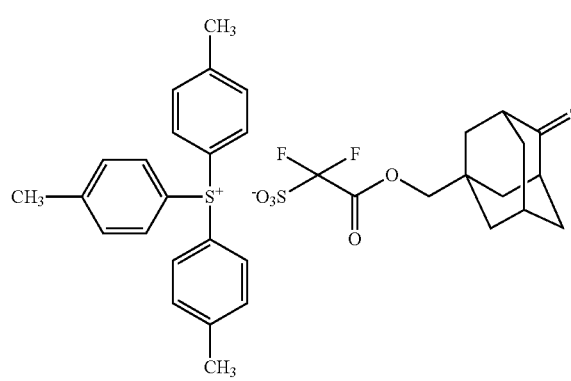
(B1-8)
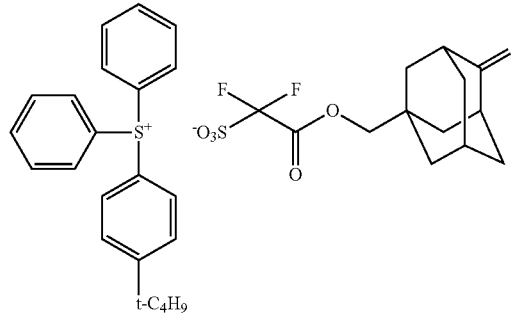
(B1-9)
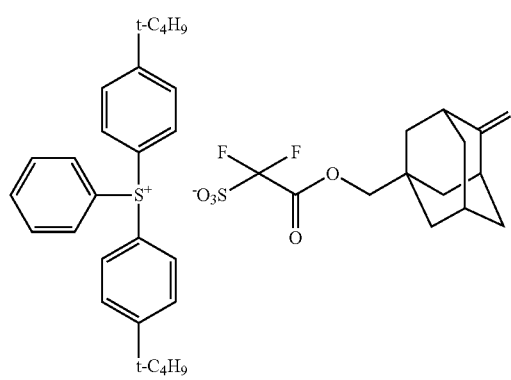
-continued
(B1-10)
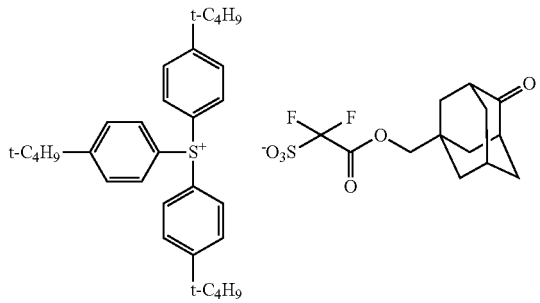
(B1-11)
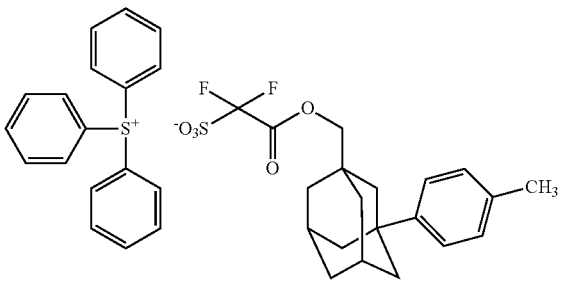
(B1-12)
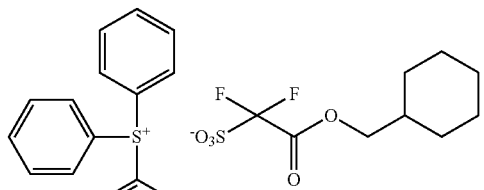
(B1-13)
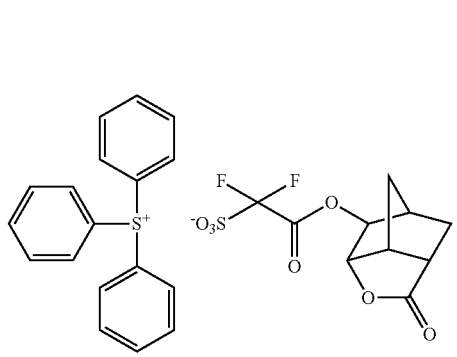
(B1-14)
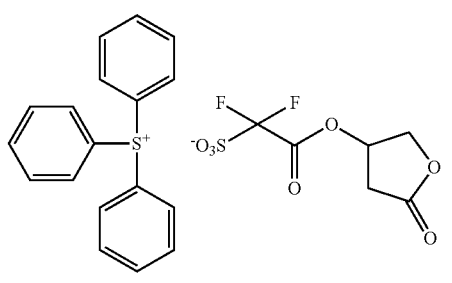

-continued (B1-15)
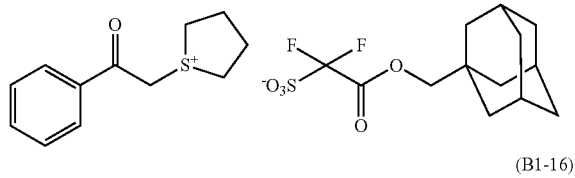

(B1-16)
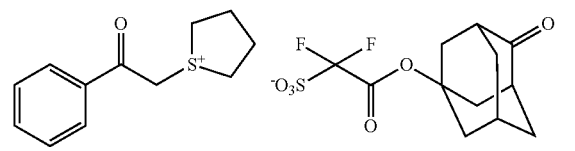

(B1-17)
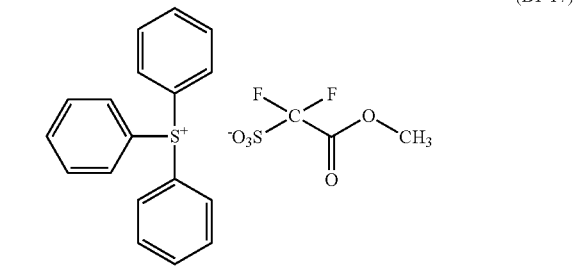

Two or more kinds of the acid generator can be used in combination.

The content of the acid generator in the photoresist composition is preferably 1 part by weight or more and more preferably 3 parts by weight or more per 100 parts by weight of RESIN (A). The content of the acid generator in the photoresist composition is preferably 30 parts by weight or less and more preferably 25 parts by weight or less per 100 parts by weight of RESIN (A).

The photoresist composition of the present invention preferably contains a basic compound.

When the basic compound is contained in the photoresist composition, the amount of the basic compound is usually 0.01 to 1 parts by weight per 100 parts by weight of solid component.

The basic compound is preferably a basic nitrogen-containing organic compound, and examples thereof include an amine compound such as an aliphatic amine and an aromatic amine and an ammonium salt. Examples of the aliphatic amine include a primary amine, a secondary amine and a tertiary amine. Examples of the aromatic amine include an aromatic amine in which aromatic ring has one or more amino groups such as aniline and a heteroaromatic amine such as pyridine. Preferable examples thereof include an aromatic amine represented by the formula (C2):

(C2)
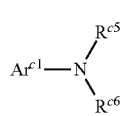

wherein $Ar^{c1}$ represents an aromatic hydrocarbon group, and $R^{c5}$ and $R^{c6}$ each independently represent a hydrogen atom, an aliphatic hydrocarbon group, a saturated cyclic hydrocarbon group or an aromatic hydrocarbon group, and the aliphatic hydrocarbon group, the saturated cyclic hydrocarbon group and the aromatic hydrocarbon group can have one or more substituents selected from the group consisting of a hydroxyl group, an amino group, an amino group having one or two C1-C4 alkyl groups and a C1-C6 alkoxy group.

The aliphatic hydrocarbon group is preferably an alkyl group and the saturated cyclic hydrocarbon group is preferably a cycloalkyl group. The aliphatic hydrocarbon group preferably has 1 to 6 carbon atoms. The saturated cyclic hydrocarbon group preferably has 5 to 10 carbon atoms. The aromatic hydrocarbon group preferably has 6 to 10 carbon atoms.

As the aromatic amine represented by the formula (C2), an amine represented by the formula (C2-1):

(C2-1)
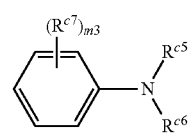

wherein $R^{c5}$ and $R^{c6}$ are the same as defined above, and $R^{c7}$ is independently in each occurrence an aliphatic hydrocarbon group, an alkoxy group, a saturated cyclic hydrocarbon group or an aromatic hydrocarbon group, and the aliphatic hydrocarbon group, the alkoxy group, the saturated cyclic hydrocarbon group and the aromatic hydrocarbon group can have one or more substituents selected from the group consisting of a hydroxyl group, an amino group, an amino group having one or two C1-C4 alkyl groups and a C1-C6 alkoxy group, and m3 represents an integer of 0 to 3, is preferable. The aliphatic hydrocarbon group is preferably an alkyl group and the saturated cyclic hydrocarbon group is preferably a cycloalkyl group. The aliphatic hydrocarbon group preferably has 1 to 6 carbon atoms. The saturated cyclic hydrocarbon group preferably has 5 to 10 carbon atoms. The aromatic hydrocarbon group preferably has 6 to 10 carbon atoms. The alkoxy group preferably has 1 to 6 carbon atoms.

Examples of the aromatic amine represented by the formula (C2) include 1-naphthylamine, 2-naphthylamine, aniline, diisopropylaniline, 2-methylaniline, 3-methylaniline, 4-methylaniline, 4-nitroaniline, N-methylaniline, N,N-dimethylaniline, and diphenylamine, and among them, preferred is diisopropylaniline and more preferred is 2,6-diisopropylaniline.

Other examples of the basic compound include amines represented by the formulae (C3) to (C11):

(C3)
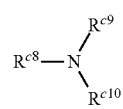

(C4)
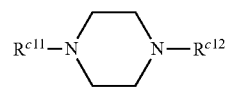

(C5)
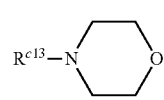

(C6)
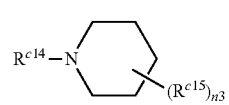

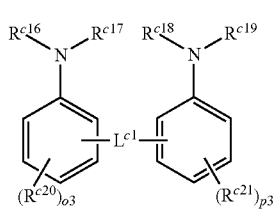 (C7)

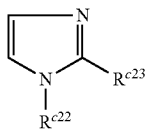 (C8)

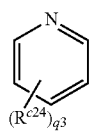 (C9)

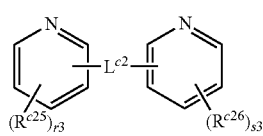 (C10)

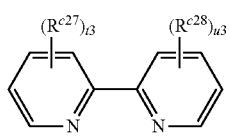 (C11)

wherein $R^{c8}$, $R^{c20}$, $R^{c21}$, and $R^{c23}$ to $R^{c28}$ each independently represent an aliphatic hydrocarbon group, an alkoxy group, a saturated cyclic hydrocarbon group or an aromatic hydrocarbon group, and the aliphatic hydrocarbon group, the alkoxy group, the saturated cyclic hydrocarbon group and the aromatic hydrocarbon group can have one or more substituents selected from the group consisting of a hydroxyl group, an amino group, an amino group having one or two C1-C4 alkyl groups and a C1-C6 alkoxy group, $R^{c9}$, $R^{c10}$, $R^{c11}$ to $R^{c14}$, $R^{c16}$ to $R^{c19}$, and $R^{c22}$ each independently represents a hydrogen atom, an aliphatic hydrocarbon group, a saturated cyclic hydrocarbon group or an aromatic hydrocarbon group, and the aliphatic hydrocarbon group, the saturated cyclic hydrocarbon group and the aromatic hydrocarbon group can have one or more substituents selected from the group consisting of a hydroxyl group, an amino group, an amino group having one or two C1-C4 alkyl groups and a C1-C6 alkoxy group, $R^{c15}$ is independently in each occurrence an aliphatic hydrocarbon group, a saturated cyclic hydrocarbon group or an alkanoyl group, $L^{c1}$ and $L^{c2}$ each independently represents a divalent aliphatic hydrocarbon group, —CO—, —C(=NH)—, —C(=NR$^{c3}$)—, —S—, —S—S— or a combination thereof and $R^{c3}$ represents a C1-C4 alkyl group, O3 to u3 each independently represents an integer of 0 to 3 and n3 represents an integer of 0 to 8.

The aliphatic hydrocarbon group has preferably 1 to 6 carbon atoms, and the saturated cyclic hydrocarbon group has preferably 3 to 6 carbon atoms, and the alkanoyl group has preferably 2 to 6 carbon atoms, and the divalent aliphatic hydrocarbon group has preferably 1 to 6 carbon atoms. The divalent aliphatic hydrocarbon group is preferably an alkylene group.

Examples of the amine represented by the formula (C3) include hexylamine, heptylamine, octylamine, nonylamine, decylamine, dibutylamine, dipentylamine, dihexylamine, diheptylamine, dioctylamine, dinonylamine, didecylamine, triethylamine, trimethylamine, tripropylamine, tributylamine, tripentylamine, trihexylamine, triheptylamine, trioctylamine, trinonylamine, tridecylamine, methyldibutylamine, methyldipentylamine, methyldihexylamine, methyldicyclohexylamine, methyldiheptylamine, methyldioctylamine, methyldinonylamine, methyldidecylamine, ethyldibutylamine, ethydipentylamine, ethyldihexylamine, ethydiheptylamine, ethyldioctylamine, ethyldinonylamine, ethyldidecylamine, dicyclohexylmethylamine, tris[2-(2-methoxyethoxy)ethyl]amine, triisopropanolamine, ethylenediamine, tetramethylenediamine, hexamethylenediamine, 4,4'-diamino-1,2-diphenylethane, 4,4'-diamino-3,3'-dimethyldiphenylmethane and 4,4'-diamino-3,3'-dimethyldiphenylmethane.

Examples of the amine represented by the formula (C4) include piperazine. Examples of the amine represented by the formula (C5) include morpholine. Examples of the amine represented by the formula (C6) include piperidine and hindered amine compounds having a piperidine skeleton as disclosed in JP 11-52575 A. Examples of the amine represented by the formula (C7) include 2,2'-methylenebisaniline. Examples of the amine represented by the formula (C8) include imidazole and 4-methylimidazole. Examples of the amine represented by the formula (C9) include pyridine and 4-methylpyridine. Examples of the amine represented by the formula (C10) include di-2-pyridyl ketone, 1,2-di(2-pyridyl)ethane, 1,2-di(4-pyridyl)ethane, 1,3-di(4-pyridyl)propane, 1,2-bis(2-pyridyl)ethene, 1,2-bis(4-pyridyl)ethene, 1,2-di(4-pyridyloxy)ethane, 4,4'-dipyridyl sulfide, 4,4'-dipyridyl disulfide, 2,2'-dipyridylamine and 2,2'-dipicolylamine. Examples of the amine represented by the formula (C11) include bipyridine.

The photoresist composition of the present invention usually contains one or more solvents. Examples of the solvent include a glycol ether ester such as ethyl cellosolve acetate, methyl cellosolve acetate and propylene glycol monomethyl ether acetate; a glycol ether such as propylene glycol monomethyl ether; an acyclic ester such as ethyl lactate, butyl acetate, amyl acetate and ethyl pyruvate; a ketone such as acetone, methyl isobutyl ketone, 2-heptanone and cyclohexanone; and a cyclic ester such as γ-butyrolactone.

The amount of the solvent is usually 90% by weight or more, preferably 92% by weight or more preferably 94% by weight or more based on total amount of the photoresist composition of the present invention. The amount of the solvent is usually 99.9% by weight or less and preferably 99% by weight or less based on total amount of the photoresist composition of the present invention.

The photoresist composition of the present invention can contain, if necessary, a small amount of various additives such as a sensitizer, a dissolution inhibitor, other polymers, a surfactant, a stabilizer and a dye as long as the effect of the present invention is not prevented.

The photoresist composition of the present invention is useful for a chemically amplified photoresist composition.

A photoresist pattern can be produced by the following steps (1) to (5):

(1) a step of applying the photoresist composition of the present invention on a substrate, (2) a step of forming a photoresist film by conducting drying, (3) a step of exposing the photoresist film to radiation,
(4) a step of baking the exposed photoresist film, and
(5) a step of developing the baked photoresist film with an alkaline developer, thereby forming a photoresist pattern.

The applying of the photoresist composition on a substrate is usually conducted using a conventional apparatus such as spin coater. The photoresist composition is preferably filtrated with filter having 0.2 μm of a pore size before applying. Examples of the substrate include a silicon wafer or a quartz wafer on which a sensor, a circuit, a transistor or the like is formed.

The formation of the photoresist film is usually conducted using a heating apparatus such as hot plate or a decompressor, and the heating temperature is usually 50 to 200° C., and the operation pressure is usually 1 to $1.0*10^5$ Pa.

The photoresist film obtained is exposed to radiation using an exposure system. The exposure is usually conducted through a mask having a pattern corresponding to the desired photoresist pattern. Examples of the exposure source include a light source radiating laser light in a UV-region such as a KrF excimer laser (wavelength: 248 nm), an ArF excimer laser (wavelength: 193 nm) and a $F_2$ laser (wavelength: 157 nm), and a light source radiating harmonic laser light in a far UV region or a vacuum UV region by wavelength conversion of laser light from a solid laser light source (such as YAG or semiconductor laser).

The temperature of baking of the exposed photoresist film is usually 50 to 200° C., and preferably 70 to 150° C.

The development of the baked photoresist film is usually carried out using a development apparatus. The alkaline developer used may be any one of various alkaline aqueous solution used in the art. Generally, an aqueous solution of tetramethylammonium hydroxide or (2-hydroxyethyl)trimethylammonium hydroxide (commonly known as "choline") is often used. After development, the photoresist pattern formed is preferably washed with ultrapure water, and the remained water on the photoresist pattern and the substrate is preferably removed.

The photoresist composition of the present invention is suitable for ArF excimer laser lithography, KrF excimer laser lithography, ArF immersion lithography, EUV lithography, EUV immersion lithography and EB lithography.

EXAMPLES

The present invention will be described more specifically by Examples, which are not construed to limit the scope of the present invention.

The "%" and "part(s)" used to represent the content of any component and the amount of any material used in the following examples and comparative examples are on a weight basis unless otherwise specifically noted. The weight-average molecular weight of any material used in the following examples is a value found by gel permeation chromatography [HLC-8120GPC Type, Column (Three Columns with guard column): TSKgel Multipore HXL-M, manufactured by TOSOH CORPORATION, Solvent: tetrahydrofuran, Flow rate: 1.0 mL/min., Detector: RI detector, Column temperature: 40° C., Injection volume: 100 μL] using standard polystyrene, manufactured by TOSOH CORPORATION, as a standard reference material. Structures of compounds were determined by NMR (EX-270 Type, manufactured by JEOL LTD.) and mass spectrometry (Liquid Chromatography: 1100 Type, manufactured by AGILENT TECHNOLOGIES LTD., Mass Spectrometry: LC/MSD Type or LC/MSD TOF Type, manufactured by AGILENT TECHNOLOGIES LTD.).

Synthesis Example 1

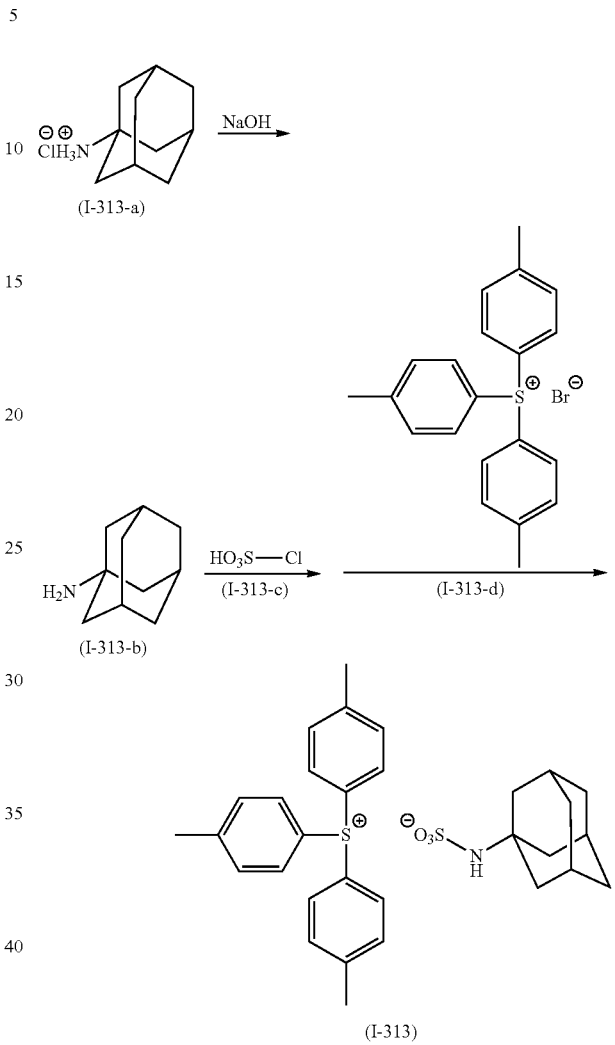

To a solution prepared by mixing 75.0 parts of a compound represented by the formula (I-313-a) which was available from Tokyo Industrial Chemistry, Co., Ltd. with 600 parts of chloroform, 240 parts of 10% aqueous sodium hydroxide solution was added, and the resultant mixture was stirred at room temperature for 1 hour. The obtained mixture was separated to an organic layer and an aqueous layer. The organic layer was dried over magnesium sulfate. After removing magnesium sulfate by filtration, 106 parts of triethylamine was added to the filtrate. The resultant mixture was cooled down to −10° C., and 51.2 parts of a compound represented by the formula (I-313-c) was added thereto. The mixture obtained was stirred at room temperature for 1 hour. To the reaction mixture obtained, a salt represented by the formula (I-313-d) was added, and the resultant mixture was stirred overnight. The reaction mixture obtained was mixed with 205 parts of ion-exchanged water to extract with chloroform. The organic layer obtained was concentrated under reduced pressure, and the solid obtained was recrystallized with a mixed solvent of acetonitrile and 2-methoxy-2-methylpropane to obtain 124.0 parts of a salt represented by the formula (I-313), which is called as Salt (I-313).

MS (ESI (+) Spectrum): $M^+$=305.1 ($C_{21}H_{21}S^+$=305.1)
MS (ESI (−) Spectrum): $M^-$=230.1 ($C_{10}H_{16}NO_3S^-$=230.1)

Synthesis Example 2

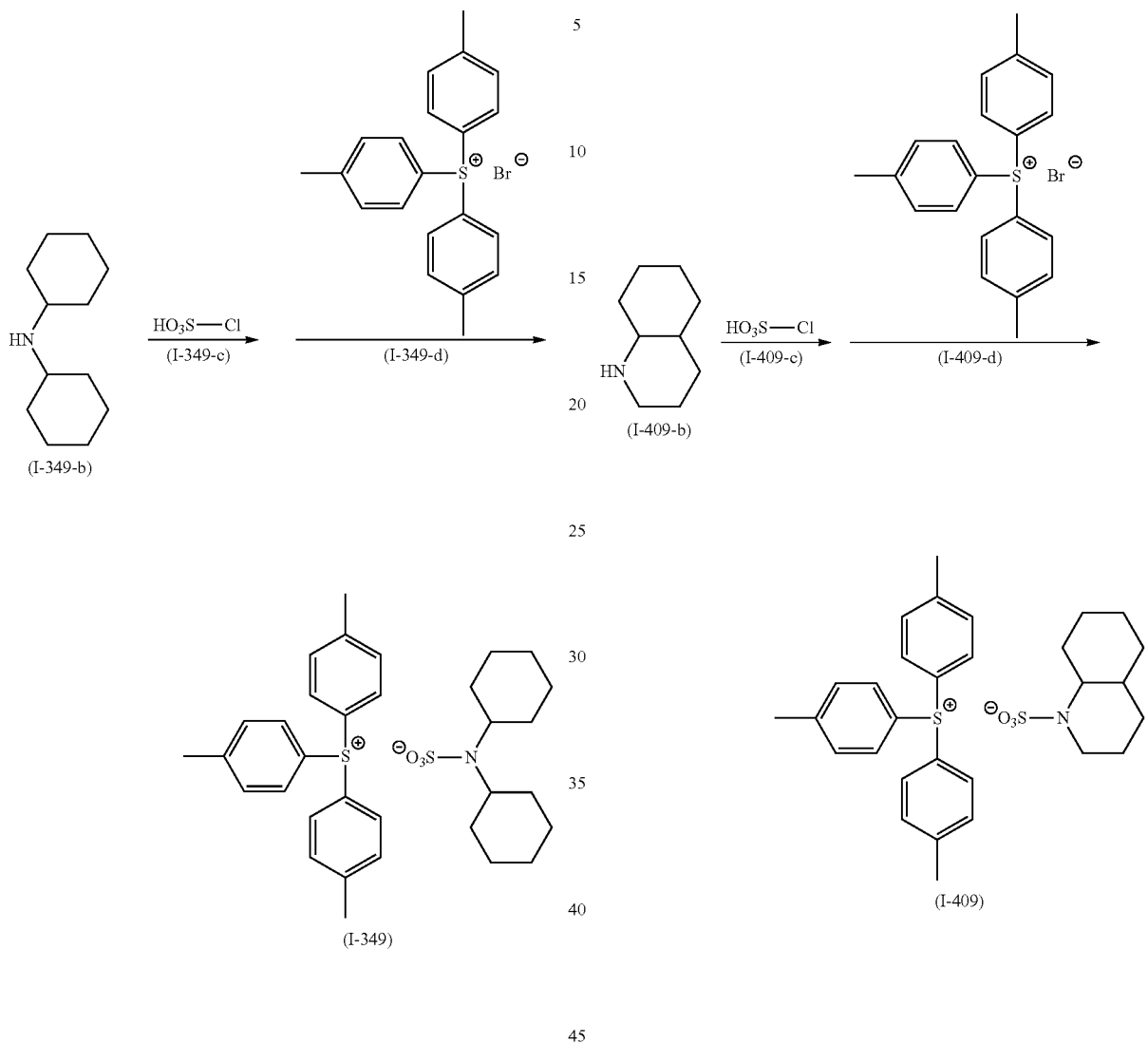

Synthesis Example 3

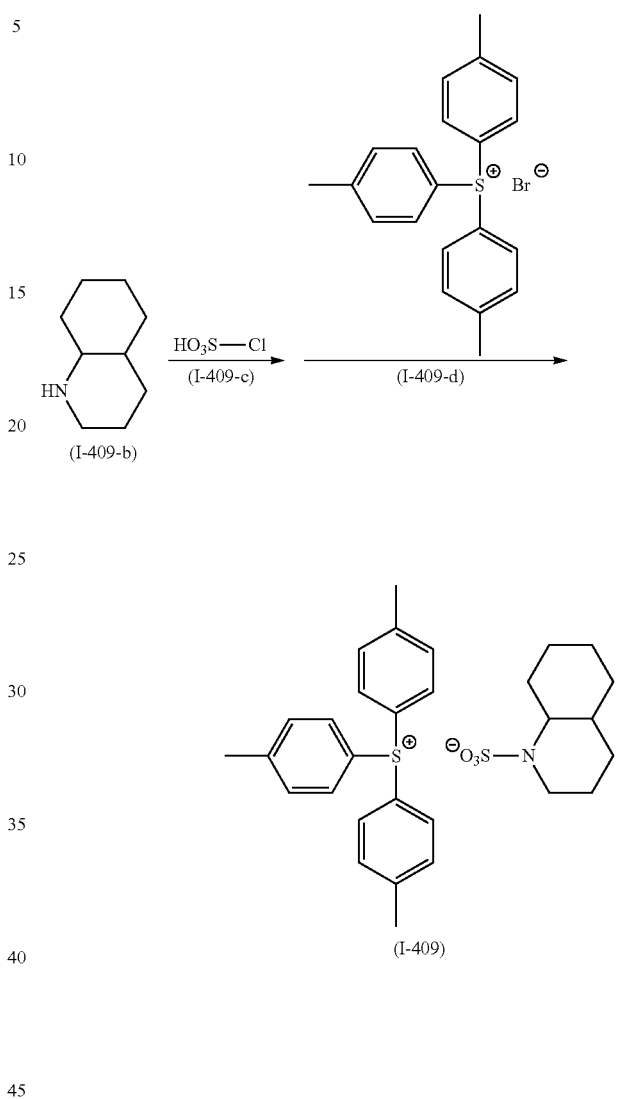

To a solution prepared by mixing 2.2 parts of a compound represented by the formula (I-349-b) which was available from Tokyo Industrial Chemistry, Co., Ltd. with 50 parts of chloroform, 2.8 parts of triethylamine was added. The resultant mixture was cooled down to $-10°$ C., and 1.6 parts of a compound represented by the formula (I-349-c) was added thereto. The mixture obtained was stirred at room temperature for 1 hour. To the reaction mixture obtained, 4.0 parts of a salt represented by the formula (I-349-d) was added, and the resultant mixture was stirred overnight. The reaction mixture obtained was mixed with 20 parts of ion-exchanged water to extract with chloroform. The organic layer obtained was concentrated under reduced pressure, and the solid obtained was recrystallized with a mixed solvent of acetonitrile and 2-methoxy-2-methylpropane to obtain 3.5 parts of a salt represented by the formula (I-349), which is called as Salt (I-349).

MS (ESI (+) Spectrum): $M^+$=305.1 ($C_{21}H_{21}S^+$=305.1)
MS (ESI (−) Spectrum): $M^-$=260.1 ($C_{12}H_{22}NO_3S^-$=260.1)

To a solution prepared by mixing 1.7 parts of a compound represented by the formula (I-409-b) which was available from Tokyo Industrial Chemistry, Co., Ltd. with 50 parts of chloroform, 2.8 parts of triethylamine was added. The resultant mixture was cooled down to $-10°$ C., and 1.6 parts of a compound represented by the formula (I-409-c) was added thereto. The mixture obtained was stirred at room temperature for 1 hour. To the reaction mixture obtained, 4.0 parts of a salt represented by the formula (I-409-d) was added, and the resultant mixture was stirred overnight. The reaction mixture obtained was mixed with 20 parts of ion-exchanged water to extract with chloroform. The organic layer obtained was concentrated under reduced pressure, and the solid obtained was mixed with a mixed solvent of acetonitrile and 2-methoxy-2-methylpropane followed by removing a supernatant solution by decantation. The residual layer was dried to obtain 5.4 parts of a salt represented by the formula (I-409), which is called as Salt (I-409).

MS (ESI (+) Spectrum): $M^+$=305.1 ($C_{21}H_{21}S^+$=305.1)
MS (ESI (−) Spectrum): $M^-$=218.1 ($C_9H_{16}NO_3S^-$=218.1)

Synthesis Example 4

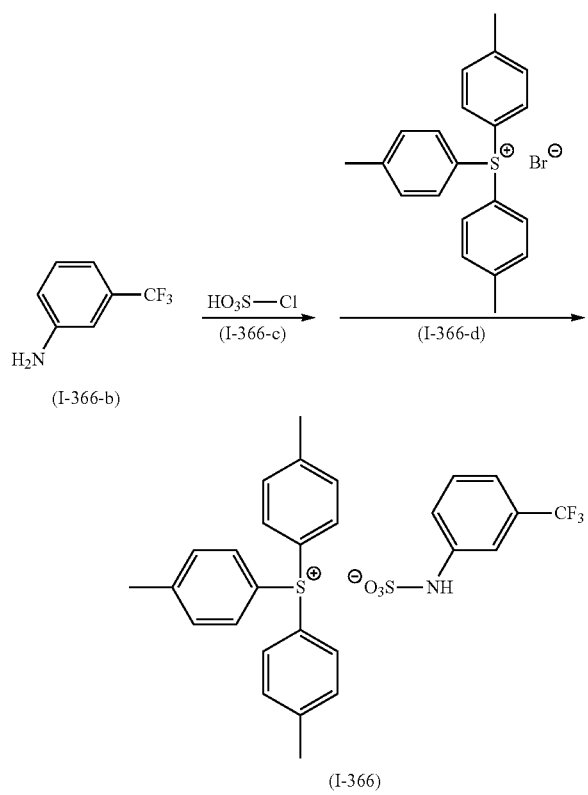

To a solution prepared by mixing 4.0 parts of a compound represented by the formula (I-366-b) which was available from Tokyo Industrial Chemistry, Co., Ltd. with 40 parts of chloroform, 6.6 parts of triethylamine was added. The resultant mixture was cooled down to −10° C., and 3.18 parts of a compound represented by the formula (I-366-c) was added thereto. The mixture obtained was stirred at room temperature for 1 hour. To the reaction mixture obtained, 7.0 parts of a salt represented by the formula (I-366-d) was added, and the resultant mixture was stirred overnight. The reaction mixture obtained was mixed with 13 parts of ion-exchanged water to extract with chloroform. The organic layer obtained was washed with ion-exchanged water and then, concentrated under reduced pressure. The residue obtained was mixed with a mixed solvent of acetonitrile and 2-methoxy-2-methylpropane followed by removing a supernatant solution by decantation. The residual layer was dried to obtain 7.1 parts of a salt represented by the formula (I-366), which is called as Salt (I-366).

MS (ESI (+) Spectrum): M$^+$=305.1 (C$_{21}$H$_{21}$S$^+$=305.1)
MS (ESI (−) Spectrum): M=240.0 (C$_7$H$_5$F$_3$NO$_3$S$^-$=240.0)

Synthesis Example 5

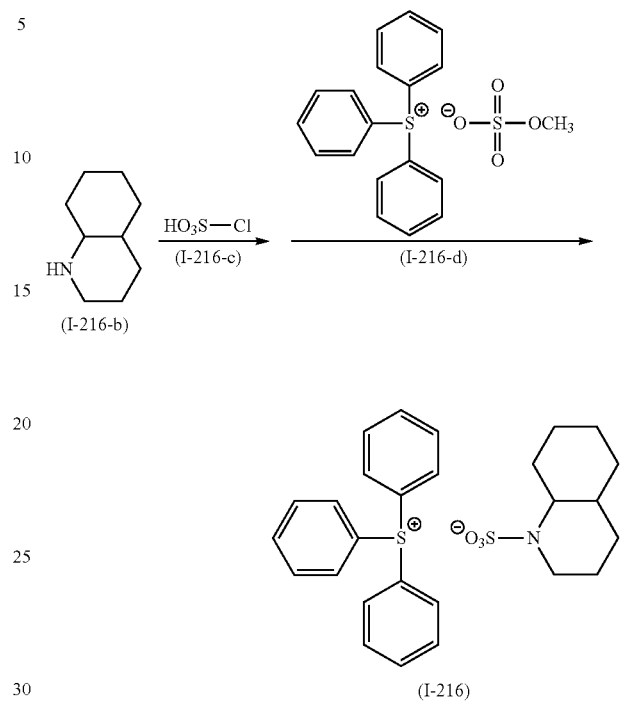

To a solution prepared by mixing 2.5 parts of a compound represented by the formula (I-216-b) which was available from Tokyo Industrial Chemistry, Co., Ltd. with 25 parts of chloroform, 4.8 parts of triethylamine was added. The resultant mixture was cooled down to −10° C., and 2.30 parts of a compound represented by the formula (I-216-c) was added thereto. The mixture obtained was stirred at room temperature for 1 hour. To the reaction mixture obtained, 5.0 parts of a salt represented by the formula (I-216-d) was added, and the resultant mixture was stirred overnight. The reaction mixture obtained was mixed with 13 parts of ion-exchanged water to extract with chloroform. The organic layer obtained was washed with ion-exchanged water and then, was concentrated under reduced pressure. The residue obtained was mixed with a mixed solvent of acetonitrile and 2-methoxy-2-methylpropane followed by removing a supernatant solution by decantation. The residual layer was dried to obtain 7.1 parts of a salt represented by the formula (I-216), which is called as Salt (I-216).

MS (ESI (+) Spectrum): M$^+$=263.1 (C$_{18}$H$_{15}$S$^+$=263.1)
MS (ESI (−) Spectrum): M$^-$=218.1 (C$_9$H$_{16}$NO$_3$S$^-$=218.1)

Synthesis Example 6

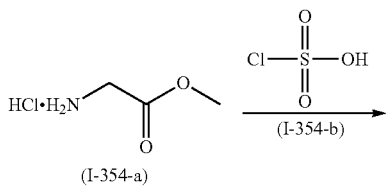

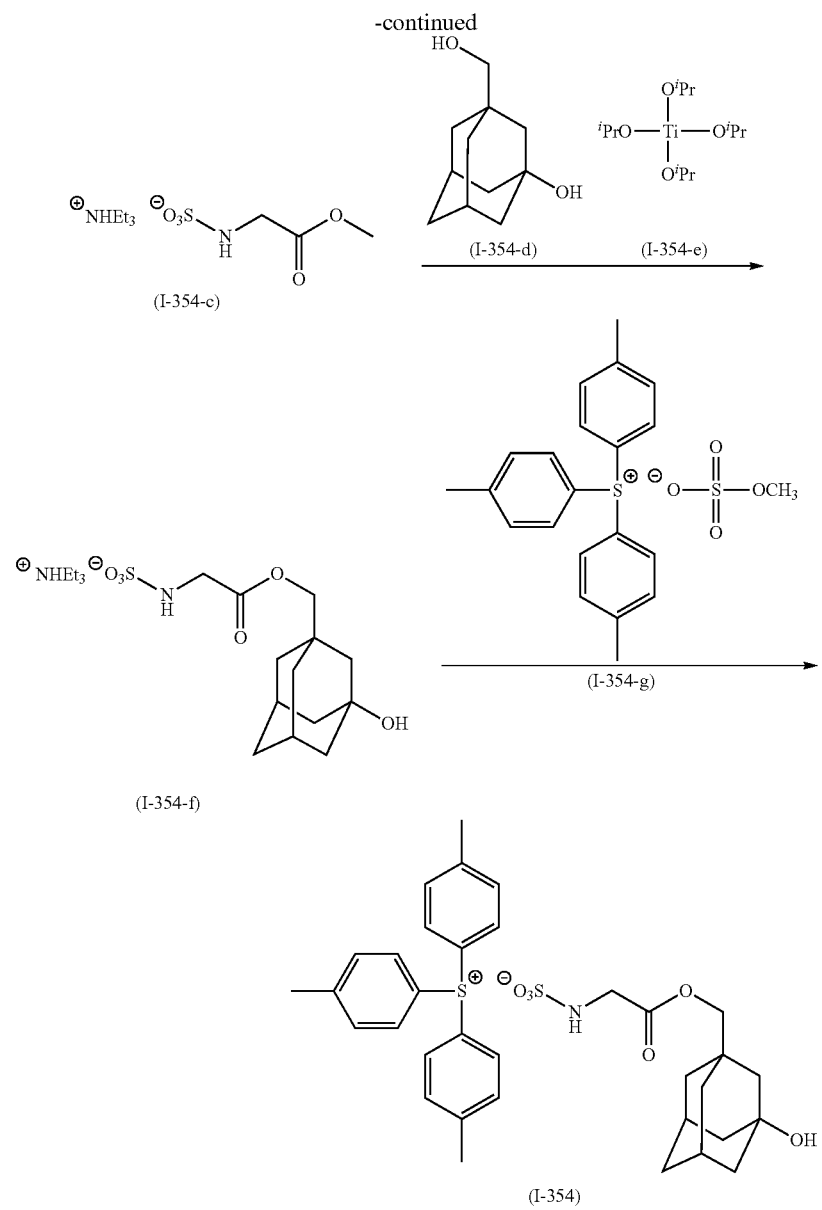

To a solution prepared by mixing 20.0 parts of a compound represented by the formula (I-354-a) which was available from Tokyo Industrial Chemistry, Co., Ltd. with 160 parts of chloroform, 19.0 parts of triethylamine was added. The resultant mixture was stirred overnight at room temperature. The mixture obtained was filtrated and, 41.6 parts of triethylamine was added to the filtrate obtained. The resultant mixture was cooled down to −10° C., and 20.0 parts of a compound represented by the formula (I-354-b) was added thereto. The mixture obtained was stirred for 2 hours. The reaction mixture obtained was filtrated and the filtrate obtained was concentrated to obtain 27.9 parts of a salt represented by the formula (I-354-c).

To a solution prepared by mixing 24.6 parts of the salt represented by the formula (I-354-c) with 160 parts of dichloroethane, 20.0 parts of a compound represented by the formula (I-354-d) and 1.36 parts of a compound represented by the formula (I-354-e) were added. The resultant mixture was stirred under reflux for 17 hours. The mixture obtained was concentrated and the residue obtained was purified with silica gel chromatography (chloroform/methanol=5/1) to obtain 10.1 parts of a salt represented by the formula (I-354-f).

To a solution prepared by mixing 5.25 parts of a salt represented by the formula (I-354-f) with 28 parts of chloroform, 4.0 parts of a salt represented by the formula (I-354-g) was added. The resultant mixture was stirred overnight. The reaction mixture obtained was mixed with 5.0 parts of ion-exchanged water to extract with chloroform. The organic layer obtained was washed with ion-exchanged water and then, was concentrated under reduced pressure. The residue obtained was mixed with a mixed solvent of acetonitrile and 2-methoxy-2-methylpropane followed by removing a supernatant solution by decantation. The residual layer was dried to obtain 5.2 parts of a salt represented by the formula (I-354), which is called as Salt (I-354).

MS (ESI (+) Spectrum): $M^+$=305.1 ($C_{21}H_{21}S^+$=305.1)
MS (ESI (−) Spectrum): $M^-$=318.1 ($C_{13}H_{20}NO_6S^-$=318.1)

Synthesis Example 7

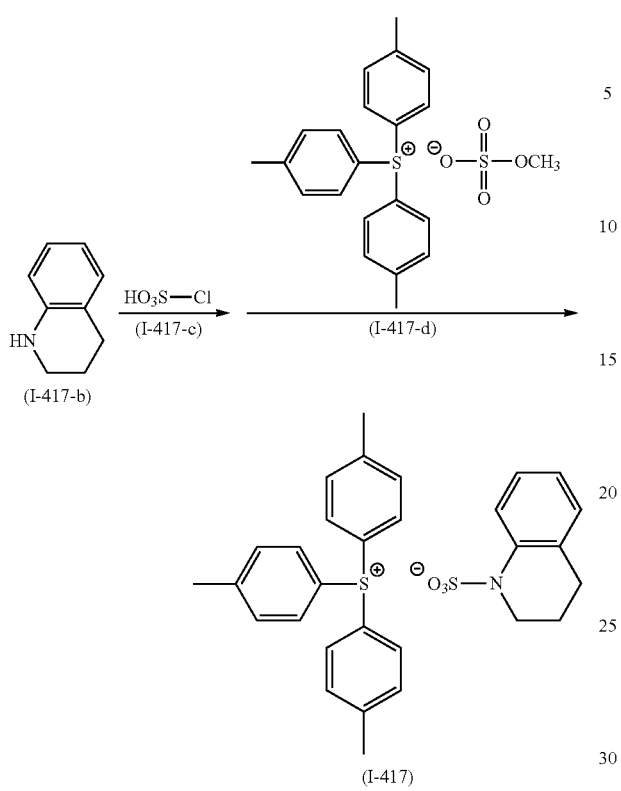

To a solution prepared by mixing 2.5 parts of a compound represented by the formula (I-417-b) which was available from Tokyo Industrial Chemistry, Co., Ltd. with 50 parts of chloroform, 2.5 parts of triethylamine was added. The resultant mixture was cooled down to −10° C., and 2.4 parts of a compound represented by the formula (I-417-c) was added thereto. The mixture obtained was stirred at room temperature for 1 hour. To the reaction mixture obtained, 5.0 parts of a salt represented by the formula (I-417-d) was added, and the resultant mixture was stirred overnight. The reaction mixture obtained was mixed with 17 parts of ion-exchanged water to extract with chloroform. The organic layer obtained was washed with ion-exchanged water and then, was concentrated under reduced pressure. The residue obtained was mixed with a mixed solvent of acetonitrile and 2-methoxy-2-methylpropane followed by removing a supernatant solution by decantation. The residual layer was dried to obtain 5.4 parts of a salt represented by the formula (I-417), which is called as Salt (I-417).

MS (ESI (+) Spectrum): M$^+$=305.1 (C$_{21}$H$_{21}$S$^+$=305.1)
MS (ESI (−) Spectrum): M$^-$=212.0 (C$_9$H$_{10}$NO$_3$S$^-$=212.0)

Synthesis Example 8

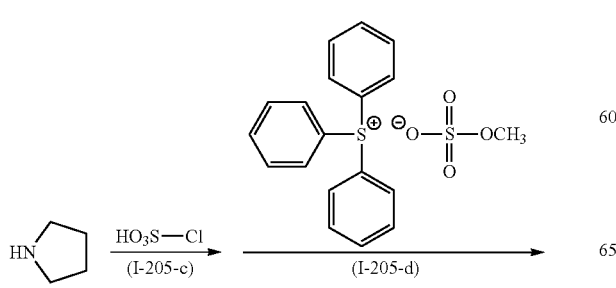

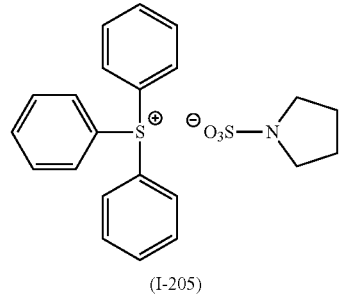

To a solution prepared by mixing 2.0 parts of a compound represented by the formula (I-205-b) which was available from Tokyo Industrial Chemistry, Co., Ltd. with 40 parts of chloroform, 3.7 parts of triethylamine was added. The resultant mixture was cooled down to −10° C., and 3.6 parts of a compound represented by the formula (I-205-c) was added thereto. The mixture obtained was stirred at room temperature for 1 hour. To the reaction mixture obtained, 8.0 parts of a salt represented by the formula (I-205-d) was added. The mixture obtained was stirred overnight. The reaction mixture obtained was mixed with 20 parts of ion-exchanged water to extract with chloroform. The organic layer obtained was washed with ion-exchanged water and then, was concentrated under reduced pressure. The residue obtained was mixed with a mixed solvent of acetonitrile and 2-methoxy-2-methylpropane followed by removing a supernatant solution by decantation. The residual layer was dried to obtain 5.1 parts of a salt represented by the formula (I-205), which is called as Salt (I-205).

MS (ESI (+) Spectrum): M$^+$=263.1 (C$_{18}$H$_{15}$S$^+$=263.1)
MS (ESI (−) Spectrum): M$^-$=150.0 (C$_4$H$_8$NO$_3$S$^-$=150.0)

Synthesis Example 9

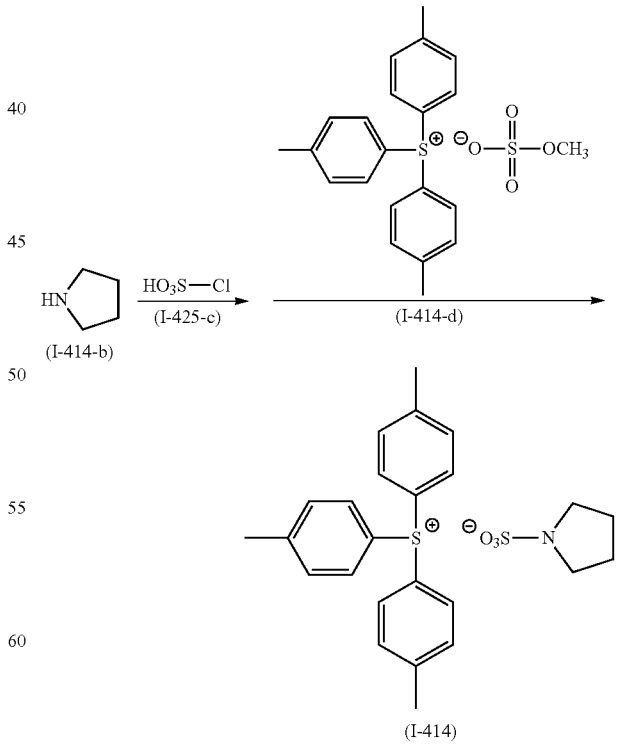

To a solution prepared by mixing 2.0 parts of a compound represented by the formula (I-414-b) which was available from Tokyo Industrial Chemistry, Co., Ltd. with 40 parts of chloroform, 3.7 parts of triethylamine was added. The resultant mixture was cooled down to −10° C., and 3.6 parts of a compound represented by the formula (I-414-c) was added thereto. The mixture obtained was stirred at room temperature for 1 hour. To the reaction mixture obtained, 8.0 parts of a salt represented by the formula (I-414-d) was added. The mixture obtained was stirred overnight. The reaction mixture obtained was mixed with 20 parts of ion-exchanged water to extract with chloroform. The organic layer obtained was washed with ion-exchanged water and then, was concentrated under reduced pressure. The residue obtained was mixed with a mixed solvent of acetonitrile and 2-methoxy-2-methylpropane followed by removing a supernatant solution by decantation. The residual layer was dried to obtain 3.1 parts of a salt represented by the formula (I-414), which is called as Salt (I-414).

MS (ESI (+) Spectrum): M$^+$=305.1 (C$_{21}$H$_{21}$S$^+$=305.1)
MS (ESI (−) Spectrum): (C$_4$H$_8$NO$_3$S$^-$=150.0)

Synthesis Example 10

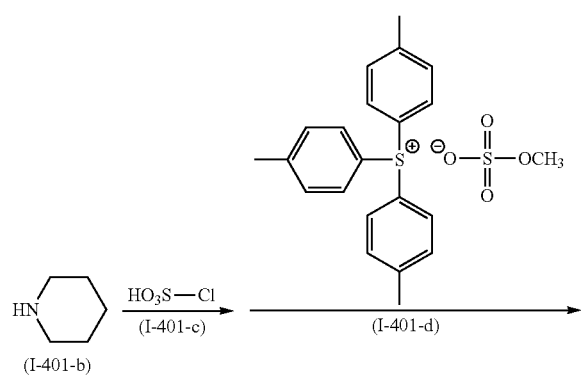

(I-401)

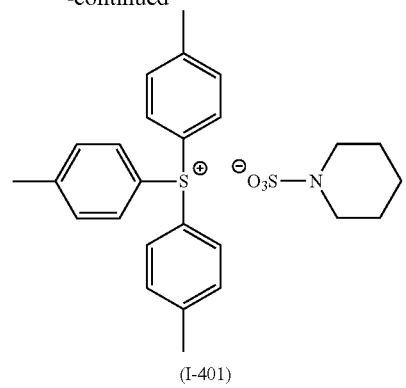

To a solution prepared by mixing 2.0 parts of a compound represented by the formula (I-401-b) which was available from Tokyo Industrial Chemistry, Co., Ltd. with 40 parts of chloroform, 2.3 parts of triethylamine was added. The resultant mixture was cooled down to −10° C., and 3.0 parts of a compound represented by the formula (I-401-c) was added thereto. The mixture obtained was stirred at room temperature for 1 hour. To the reaction mixture obtained, 8.0 parts of a salt represented by the formula (I-401-d) was added. The mixture obtained was stirred overnight. The reaction mixture obtained was mixed with 20 parts of ion-exchanged water to extract with chloroform. The organic layer obtained was washed with ion-exchanged water and then, was concentrated under reduced pressure. The residue obtained was mixed with a mixed solvent of acetonitrile and 2-methoxy-2-methylpropane followed by removing a supernatant solution by decantation. The residual layer was dried to obtain 10.6 parts of a salt represented by the formula (I-401), which is called as Salt (I-401).

MS (ESI (+) Spectrum): M$^+$=305.1 (C$_{21}$H$_{21}$S$^+$=305.1)
MS (ESI (−) Spectrum): (C$_5$H$_{10}$NO$_3$S$^-$=164.0)

Synthesis Example 11

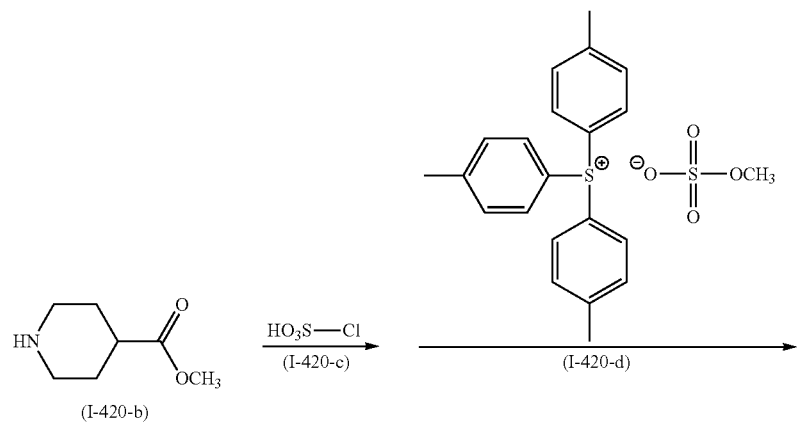

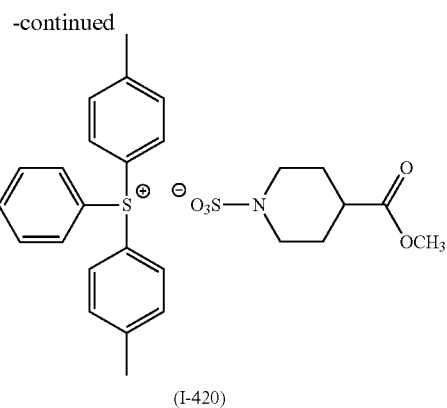

(I-420)

To a solution prepared by mixing 2.5 parts of a compound represented by the formula (I-420-b) which was available from Tokyo Industrial Chemistry, Co., Ltd. with 25 parts of chloroform, 2.3 parts of triethylamine was added. The resultant mixture was cooled down to −10° C., and 2.24 parts of a compound represented by the formula (I-420-c) was added thereto. The mixture obtained was stirred at room temperature for 1 hour. To the reaction mixture obtained, 5.0 parts of a salt represented by the formula (I-420-d) was added. The mixture obtained was stirred overnight. The reaction mixture obtained was mixed with 20 parts of ion-exchanged water to extract with chloroform. The organic layer obtained was washed with ion-exchanged water and then, was concentrated under reduced pressure. The residue obtained was mixed with a mixed solvent of acetonitrile and 2-methoxy-2-methylpropane followed by removing a supernatant solution by decantation. The residual layer was dried to obtain 5.4 parts of a salt represented by the formula (I-420), which is called as Salt (I-420).

MS (ESI (+) Spectrum): $M^+$=305.1 ($C_{21}H_{21}S^+$=305.1)
MS (ESI (−) Spectrum): $M^-$=222.0 ($C_7H_{12}NO_5S^-$=222.0)

Synthesis Example 12

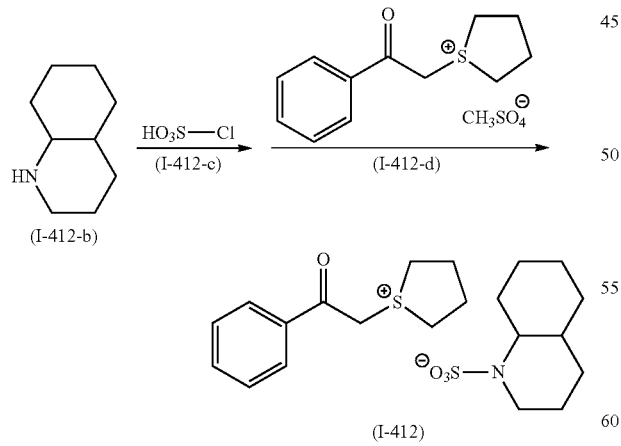

To a solution prepared by mixing 2.5 parts of a compound represented by the formula (I-412-b) which was available from Tokyo Industrial Chemistry, Co., Ltd. with 50 parts of chloroform, 4.8 parts of triethylamine was added. The resultant mixture was cooled down to −10° C., and 2.3 parts of a compound represented by the formula (1-412-c) was added thereto. The mixture obtained was stirred at room temperature for 1 hour. To the reaction mixture obtained, 5.0 parts of a salt represented by the formula (I-412-d) was added. The mixture obtained was stirred overnight. The reaction mixture obtained was mixed with 20 parts of ion-exchanged water to extract with chloroform. The organic layer obtained was concentrated under reduced pressure. The residue obtained was mixed with a mixed solvent of acetonitrile and 2-methoxy-2-methylpropane followed by conducting recrystallization. The solid obtained was dried to obtain 4.0 parts of a salt represented by the formula (I-412), which is called as Salt (I-412).

MS (ESI (+) Spectrum): $M^+$=207.1 ($C_{12}H_{15}OS^+$=207.1)
MS (ESI (−) Spectrum): $M^-$=218.1 ($C_9H_{16}NO_3S^-$=218.1)

Monomers used in the following Resin Synthetic Examples are following Monomer (M-1), Monomer (M-2), Monomer (M-3), Monomer (M-6), Monomer (M-10) and Monomer (M-11).

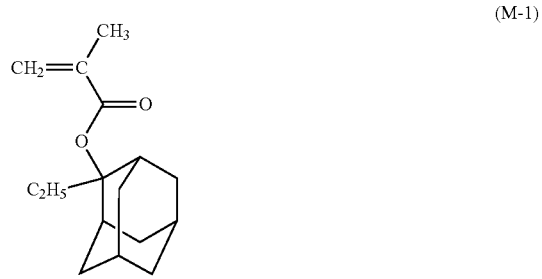

(M-1)

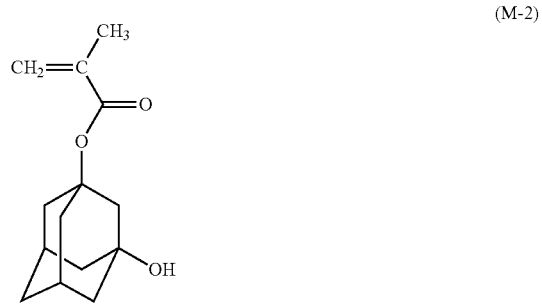

(M-2)

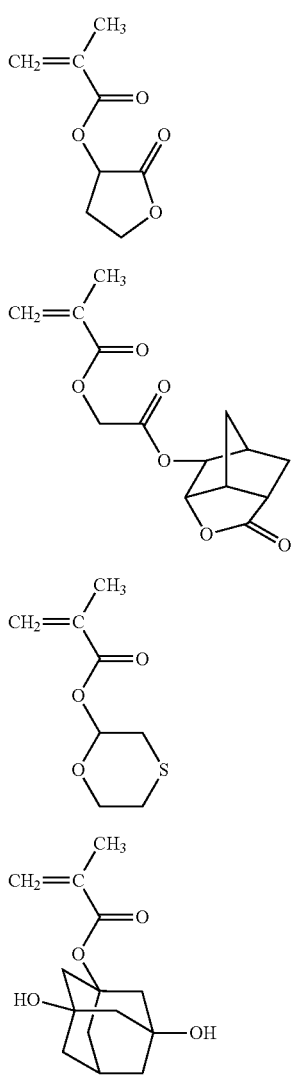
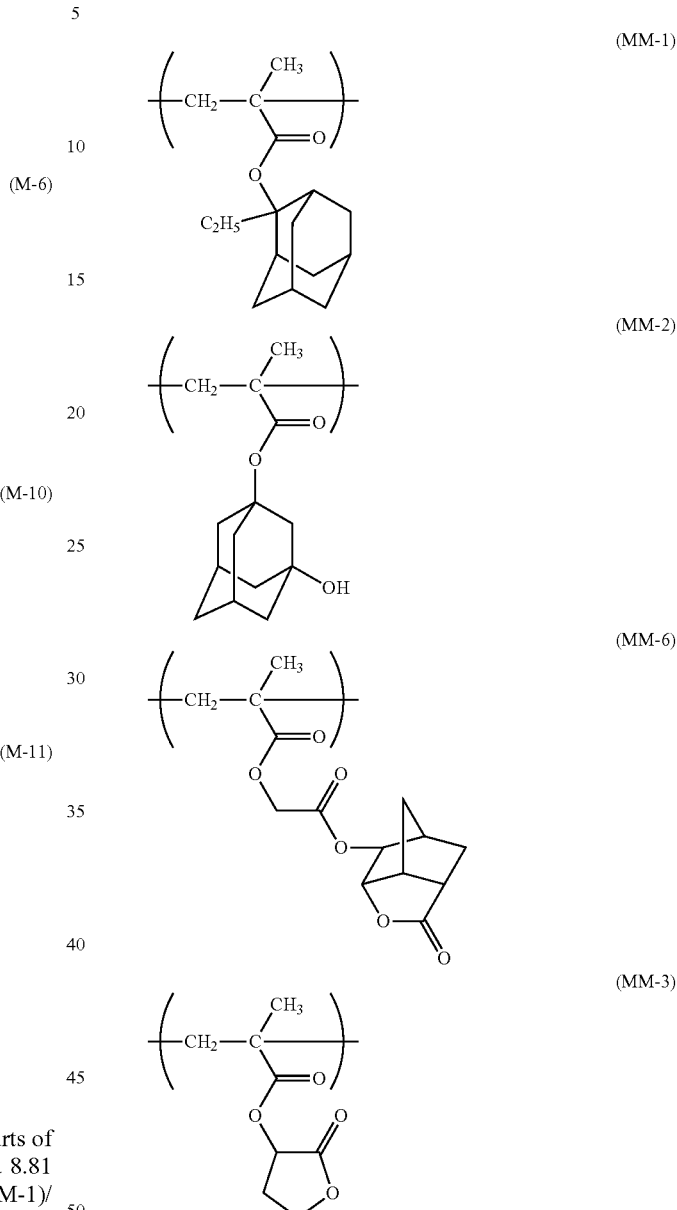

Resin Synthesis Example 1

Into a flask, 15.00 parts of Monomer (M-1), 4.89 parts of Monomer (M-2), 11.12 parts of Monomer (M-6) and 8.81 parts of Monomer (M-3) (molar ratio: Monomer (M-1)/Monomer (M-2)/Monomer (M-6)/Monomer (M-3)=35/12/23/30) were charged, and 1,4-dioxane of which amount was 1.5 times part based on total parts of all monomers was added thereto to prepare a solution. To the solution, 2,2'-azobisisobutyronitrile as an initiator in a ratio of 1 mol % based on all monomer molar amount and 2,2'-azobis(2,4-dimethylvaleronitrile) as an initiator in a ratio of 3 mol % based on all monomer molar amount were added, and the obtained mixture was heated at 77° C. for about 5 hours. The reaction mixture obtained was poured into a large amount of a mixture of methanol and water to cause precipitation. The precipitate was isolated and mixed with a large amount of a mixture of methanol and water followed by filtration. This operation wherein the precipitate was isolated and mixed with a large amount of a mixture of methanol and water followed by filtration was repeated three times for purification. As the result, a resin having a weight-average molecular weight of about $8.1 \times 10^3$ was obtained in a yield of 78%. This resin had the structural units represented by the followings. This resin is called as Resin A1.

Resin Synthesis Example 2

Into a flask equipped with a stirrer, a condenser and a thermometer, 18.00 parts of Monomer (M-1), 5.39 parts of Monomer (M-10), 3.85 parts of Monomer (M-11) and 12.66 parts of Monomer (M-3) were charged, and 1,4-dioxane of which amount was 1.5 times part based on total parts of all monomers was added thereto to prepare a solution. To the solution, 2,2'-azobisisobutyronitrile as an initiator in a ratio of 1 mol % based on all monomer molar amount and 2,2'-azobis(2,4-dimethylvaleronitrile) as an initiator in a ratio of 3 mol % based on all monomer molar amount were added, and the obtained mixture was heated at 75° C. for about 5 hours. The reaction mixture obtained was poured into a large amount of a mixture of methanol and water to cause precipitation. The precipitate was isolated and washed with methanol to obtain a resin having a weight-average molecular weight of about 7.9×10³ in a yield of 81%. This resin had the structural units represented by the followings. This resin is called as Resin A2.

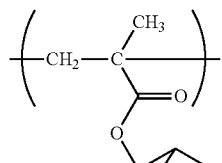
(MM-1)

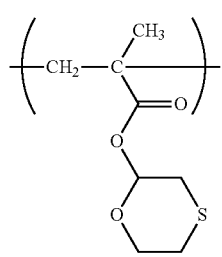
(MM-10)

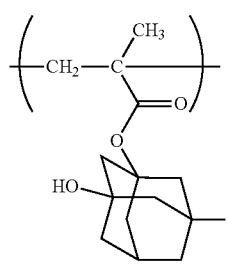
(MM-11)

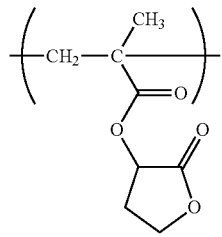
(MM-3)

Examples 1 to 2 and Comparative Example 1

<Resin>
Resin A1
<Acid Generator>
B1:

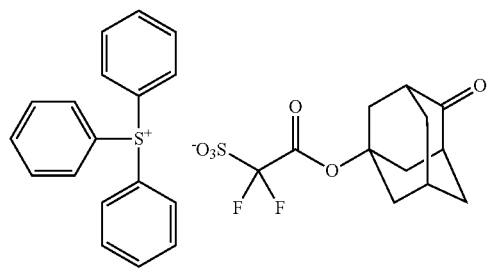

<Salt (IA)>
I-313: Salt (I-313)
<Quencher>
C1: 2,6-diisopropylaniline
<Solvent>
S1:

| | |
|---|---|
| Propylene glycol monomethyl ether acetate | 210.0 parts |
| Propylene glycol monomethyl ether | 20.0 parts |
| 2-heptanone | 20.0 parts |
| γ-butyrolactone | 3.5 parts |

The following components were mixed and dissolved to prepare photoresist compositions.
  Resin (kind and amount are described in Table 13)
  Acid generator (kind and amount are described in Table 13)
  SALT (I) (kind and amount are described in Table 13)
  Quencher (kind and amount are described in Table 13)
  Solvent S1

TABLE 13

| Ex. No. | Resin (kind/amount (part)) | Acid generator (kind/amount (part)) | SALT (IA) (kind/amount (part)) | Quencher (kind/amount (part)) |
|---|---|---|---|---|
| Ex. 1 | A1/10 | B1/0.50 | I-313/0.21 | — |
| Ex. 2 | A1/10 | B1/0.50 | I-313/0.10 | C1/0.034 |
| Comp. Ex. 1 | A1/10 | B1/0.50 | — | C1/0.068 |

Silicon wafers were each coated with "ARC-29", which is an organic anti-reflective coating composition available from Nissan Chemical Industries, Ltd., and then baked under the conditions: 205° C., 60 seconds, to form a 780 Å-thick organic anti-reflective coating. Each of the photoresist compositions prepared as above was spin-coated over the anti-reflective coating so that the thickness of the resulting film became 110 nm after drying. The silicon wafers thus coated with the respective photoresist compositions were each pre-baked on a direct hotplate at 100° C. for 60 seconds. Using an ArF excimer stepper for immersion exposure ("XT: 1900Gi" manufactured by ASML, NA=1.20, 3/4 Annular, X-Y deflection), each wafer thus formed with the respective resist film was subjected to line and space pattern exposure, with the exposure quantity being varied stepwise.

After the exposure, each wafer was subjected to post-exposure baking on a hotplate at 105° C. for 60 seconds and then to paddle development for 60 seconds with an aqueous solution of 2.38 wt % tetramethylammonium hydroxide.

Each of line and space patterns developed on the organic anti-reflective coating substrate after the development was observed with a scanning electron microscope, the results of which are shown in Table 14.

Effective Sensitivity (ES): It was expressed as the amount of exposure that the line pattern and the space pattern of 55 nm become 1:1 after exposure and development.

Line Width Roughness (LWR): The line widths of the line and space pattern at the exposure amount of ES were measured and the values of 3σ thereof were calculated based on the results of the measurement and shown in Table 14. The value of 3σ is one of index showing a variability of the line width and the smaller the value of 3σ is, the better LWR is. When the value of 3σ is 5.0 nm or less, LWR is good, and its evaluation is marked by "○", and when the value of 3σ is more than 5.0 nm, LWR is bad, and its evaluation is marked by "X". The smaller the value of 3σ is, the better LWR the photoresist pattern has, and the better pattern profile is.

Focus margin (DOE): The photoresist patterns were obtained at the exposure amount of ES, with the focal point distance being varied stepwise. Each of line and space patterns developed on the organic anti-reflective coating substrate after the development was observed and the focal point distances when the line and space patterns of which line width was within 55±2 nm (53 nm or more to 57 nm or less) and LWR was 6.0 or less were obtained were measured and the difference between the max value of the focal point distance and the minimum value of the focal point distance was calculated.

When the difference is more than 220 nm, DOF is good, and its evaluation is marked by "○", and when the difference is 220 nm or less, DOF is bad and its evaluation is marked by "X". The bigger the difference is, the better DOF the photoresist pattern shows, and the better pattern profile is.

TABLE 14

| Ex. No. | LWR | DOF |
|---|---|---|
| Ex. 1 | ○ | ○ |
| Ex. 2 | ○ | ○ |
| Comp. Ex. 1 | X | X |

Examples 3 to 13 and Comparative Examples 2 to 3

<Resin>
Resin A2
<Acid Generator>
B2:

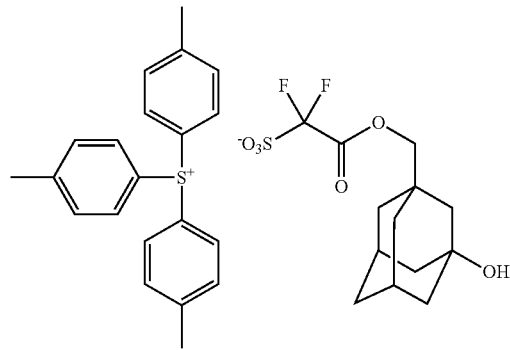

<Salt (IA)>

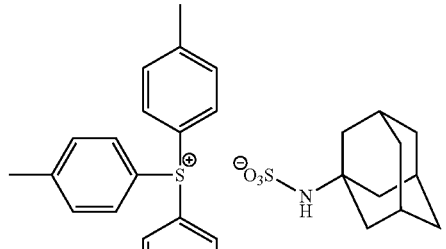

(I-313)

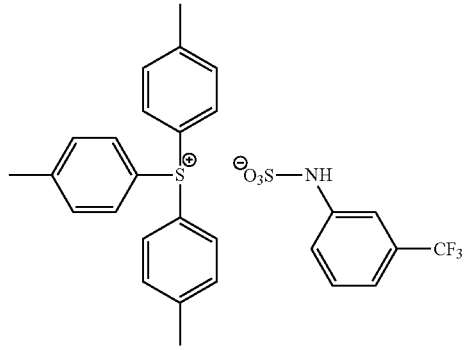

(I-366)

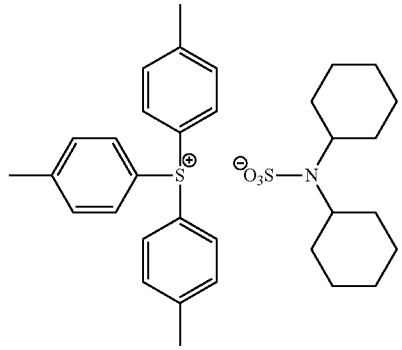

(I-349)

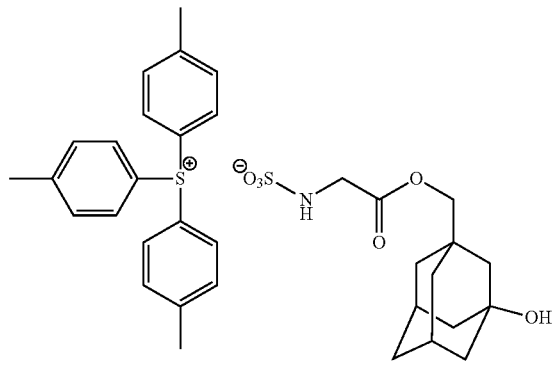

(I-354)

(I-417)
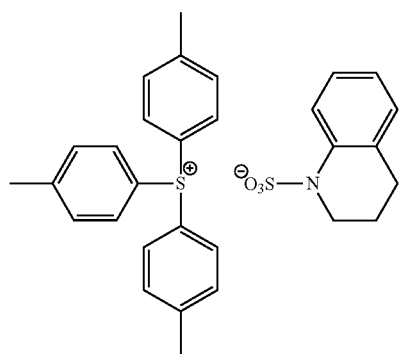
(I-216)
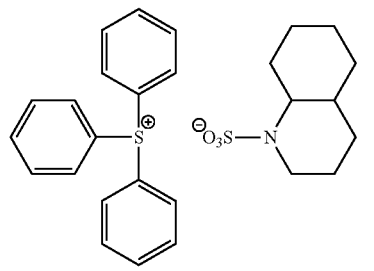
(I-409)
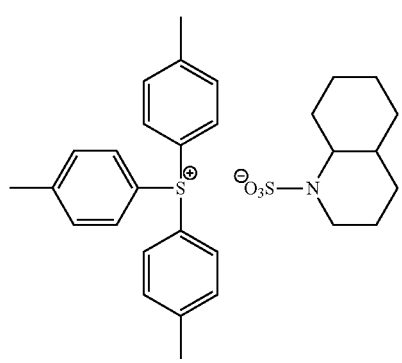
(I-205)
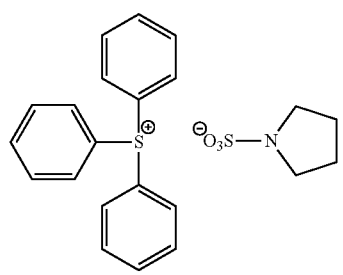
(I-414)
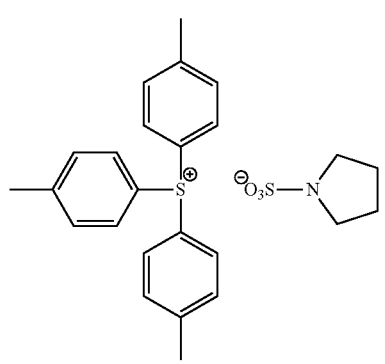
(I-401)
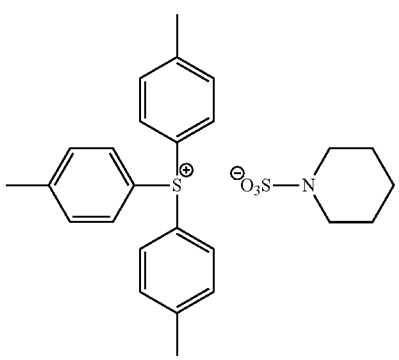
(I-420)
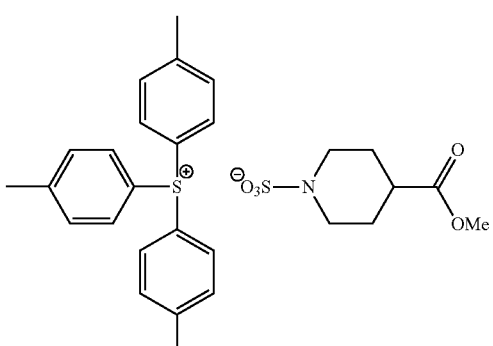
(i-412)
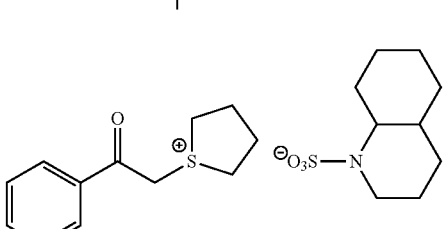
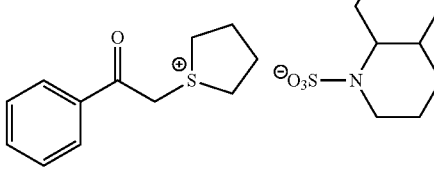
I-313: Salt (I-313)
I-366: Salt (I-366)
I-349: Salt (I-349)
I-354: Salt (I-354)
I-417: Salt (I-417)
I-216: Salt (I-216)
I-409: Salt (I-409)
I-205: Salt (I-205)
I-414: Salt (I-414)
I-401: Salt (I-401)
I-420: Salt (I-420)
I-412: Salt (I-412)
<Iodonium Salt>
II-1: bis(tert-butylphenyl)iodonium cyclamate
<Quencher>
C1: 2,6-diisopropylaniline
<Solvent>
S2:
| | |
|---|---|
| Propylene glycol monomethyl ether acetate | 220.0 parts |
| Propylene glycol monomethyl ether | 20.0 parts |
| 2-heptanone | 10.0 parts |
| γ-butyrolactone | 3.0 parts |

The following components were mixed and dissolved to prepare photoresist compositions.

Resin (kind and amount are described in Table 15)
Acid generator (kind and amount are described in Table 15)
SALT (I) (kind and amount are described in Table 15)
Iodonium salt (kind and amount are described in Table 15)
Quencher (kind and amount are described in Table 15)
Solvent S2

TABLE 15

| Ex. No. | Resin (kind/amount (part)) | Acid generator (kind/amount (part)) | SALT (IA) or Iodonium salt (kind/amount (part)) | Quencher salt (kind/amount (part)) |
|---|---|---|---|---|
| Ex. 3 | A2/10 | B2/0.85 | I-401/0.021 | — |
| Ex. 4 | A2/10 | B2/0.85 | I-366/0.025 | — |
| Ex. 5 | A2/10 | B2/0.85 | I-313/0.021 | — |
| Ex. 6 | A2/10 | B2/0.85 | I-349/0.02 | — |
| Ex. 7 | A2/10 | B2/0.85 | I-354/0.025 | — |
| Ex. 8 | A2/10 | B2/0.85 | I-409/0.030 | — |
| Ex. 9 | A2/10 | B2/0.85 | I-216/0.028 | — |
| Ex. 10 | A2/10 | B2/0.85 | I-417/0.020 | — |
| Ex. 11 | A2/10 | B2/0.85 | I-205/0.024 | — |
| Ex. 12 | A2/10 | B2/0.85 | I-414/0.026 | — |
| Ex. 13 | A2/10 | B2/0.85 | I-420/0.021 | — |
| Comp. Ex. 2 | A2/10 | B2/0.85 | — | C1/0.006 |
| Comp. Ex. 3 | A2/10 | B2/0.85 | II-1/0.027 | — |

Silicon wafers were each coated with "ARC29SR", which is an organic anti-reflective coating, composition available from Nissan Chemical Industries, Ltd., and then baked under the conditions: 205° C., 60 seconds, to form a 930 Å-thick organic anti-reflective coating. Each of the photoresist compositions prepared as above was spin-coated over the anti-reflective coating so that the thickness of the resulting film became 120 nm after drying. The silicon wafers thus coated with the respective photoresist compositions were each pre-baked on a direct hotplate at 100° C. for 60 seconds. Using an ArF excimer stepper for immersion exposure ("XT: 1900Gi" manufactured by ASML, NA=1.20, Quadrupole on axis ($\sigma_{out}/\sigma_{in}$=0.97/0.77), X-Y deflection), each wafer thus formed with the respective resist film was subjected to contact hole pattern exposure, with the exposure quantity being varied stepwise.

After the exposure, each wafer was subjected to post-exposure baking on a hotplate at 95° C. for 60 seconds and then to paddle development for 60 seconds with an aqueous solution of 2.38 wt % tetramethylammonium hydroxide.

Each of contact hole patterns developed on the organic anti-reflective coating substrate after the development was observed with a scanning electron microscope, the results of which are shown in Table 16.

Effective Sensitivity (ES): It was expressed as the amount of exposure that the hole pattern having a hole diameter of 140 nm was formed when an exposure was conducted using a mask having a pitch of 500 nm and a hole diameter of 160 nm.

Focus margin (DOF): The photoresist patterns were obtained at the exposure amount of ES, with the focal point distance being varied stepwise. Each of hole patterns developed on the organic anti-reflective coating substrate after the development was observed and the focal point distances when the hole patterns of which hole diameter was 135 nm or more and 140 nm or less were obtained were measured and the difference between the max value of the focal point distance and the minimum value of the focal point distance was calculated. When the difference is more than 135 nm, DOF is good, and its evaluation is marked by "○", and when the difference is 120 nm or more and less than 135 nm, DOF is bad and its evaluation is marked by "X", and when the difference is less than 120 nm, DOF is very bad and its evaluation is marked by "XX". The bigger the difference is, the better DOF the photoresist pattern shows, and the better pattern profile is.

TABLE 16

| Ex. No. | DOF |
|---|---|
| Ex. 3 | ○ |
| Ex. 4 | ○ |
| Ex. 5 | ○ |
| Ex. 6 | ○ |
| Ex. 7 | ○ |
| Ex. 8 | ○ |
| Ex. 9 | ○ |
| Ex. 10 | ○ |
| Ex. 11 | ○ |
| Ex. 12 | ○ |
| Ex. 13 | ○ |
| Comp. Ex. 2 | X X |
| Comp. Ex. 3 | X |

Example 14

A photoresist composition can be obtained according to the same manner as that in Example 8 except that Salt (I-412) is used in place of Salt (I-409), and a photoresist pattern can be formed using the photoresist composition.

The present photoresist composition provides a good resist pattern having a good pattern profile such as Line width roughness and Focus margin, and is especially suitable for ArF excimer laser lithography, EB lithography and EUV lithography.

What is claimed is:

1. A photoresist composition comprising a sulfonium salt having an anion represented by the formula (IA):

(IA)

wherein $R^1$ and $R^2$ independently represent a C1-C12 aliphatic hydrocarbon group, a C3-C20 saturated cyclic hydrocarbon group, a C6-C20 aromatic hydrocarbon group or a C7-C21 aralkyl group, and the aliphatic hydrocarbon group, the saturated cyclic hydrocarbon group, the aromatic hydrocarbon group and the aralkyl group can have one or more substituents selected from the group consisting of a hydroxyl group, a cyano group, a fluorine atom, a trifluoromethyl group and a nitro group, and one or more —$CH_2$— in the aliphatic hydrocarbon group can be replaced by —O— or —CO—, or $R^1$ and $R^2$ are bonded each other to form a C4-C20 nitrogen-containing ring together with the nitrogen atom to which they are bonded, an acrylic resin having an acid-labile group and being insoluble or poorly soluble in an aqueous alkali solution but becoming soluble in an aqueous alkali solution by the action of an acid, and an acid generator.

2. The photoresist composition according to claim 1, wherein the sulfonium salt having an anion represented by the formula (IA) has a cation represented by the formula (IB):

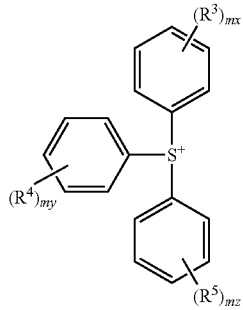

(IB)

wherein $R^3$, $R^4$ and $R^5$ are independently in each occurrence a hydroxyl group, a halogen atom, a C1-C12 alkoxy group, a C1-C30 aliphatic hydrocarbon group, a C3-C36 saturated cyclic hydrocarbon group or a C6-C18 aromatic hydrocarbon group, and one or more hydrogen atoms in the aliphatic hydrocarbon group can he replaced by a hydroxyl group, a C1-C12 alkoxy group or a C6-C18 aromatic hydrocarbon group, one or more hydrogen atoms of the saturated cyclic hydrocarbon group can be replaced by a halogen atom, a C2-C4 acyl group or a glycidyloxy group, one or more hydrogen atoms of the aromatic hydrocarbon group can be replaced by a halogen atom, a hydroxyl group, a C1-C36 aliphatic hydrocarbon group, a C3-C36 saturated cyclic hydrocarbon group or a C1-C12 alkoxy group, and mx, my and mz independently represent an integer of 0 to 5.

3. The photoresist composition according to claim 1, wherein $R^1$ represents a C1-C12 aliphatic hydrocarbon group, a C3-C20 saturated cyclic hydrocarbon group, a C6-C20 aromatic hydrocarbon group or a C7-C21 aralkyl group, and the aliphatic hydrocarbon group, the saturated cyclic hydrocarbon group, the aromatic hydrocarbon group and the aralkyl group can have one or more substituents selected from the group consisting of a hydroxyl group, a cyano group, a fluorine atom, a trifluoromethyl group and a nitro group, and one or more —$CH_2$—in the aliphatic hydrocarbon group can be replaced by —O— or —CO—, $R^2$ represents a C7-C20 saturated cyclic hydrocarbon group, a C6-C20 aromatic hydrocarbon group or a C7-C21 aralkyl group, and the aliphatic hydrocarbon group, the saturated cyclic hydrocarbon group, the aromatic hydrocarbon group and the aralkyl group can have one or more substituents selected from the group consisting of a hydroxyl group, a cyano group, a fluorine, atom, a trifluoromethyl group and a nitro group, and one or more —$CH_2$—in the aliphatic hydrocarbon group can be replaced by —O— or —CO—, or $R^1$ and $R^2$ are bonded each other to form a C4-C20 nitrogen-containing ring together with the nitrogen atom to which they are bonded.

4. A process for producing a photoresist pattern comprising the following steps (1) to (5):
(1) a step of applying the photoresist composition according to claim 1 on a substrate,
(2) a step of forming a photoresist film by conducting drying,
(3) a step of exposing the photoresist film to radiation,
(4) a step of baking the exposed photoresist film, and
(5) a step of developing the baked photoresist film with an alkaline developer, thereby forming a photoresist pattern.

5. A salt represented by the formula (I):

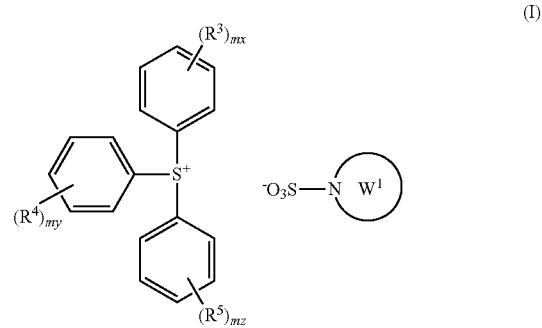

(I)

wherein $R^3$, $R^4$ and $R^5$ are independently in each occurrence a hydroxyl group, a halogen atom, a C1-C12 alkoxy group, a C1-C30 aliphatic hydrocarbon group, a C3-C36 saturated cyclic hydrocarbon group or a C6-C18 aromatic hydrocarbon group, and one or more hydrogen atoms in the aliphatic hydrocarbon group can be replaced by a hydroxyl group, a C1-C12 alkoxy group or a C6-C 18 aromatic hydrocarbon group, one or more hydrogen atoms of the saturated cyclic hydrocarbon group can be replaced by a halogen atom, a C2-C4 acyl group or a glycidyloxy group, one or more hydrogen atoms of the aromatic hydrocarbon group can be replaced by a halogen atom, a hydroxyl group, a C1-C36 aliphatic hydrocarbon group, a C3-C36 saturated cyclic hydrocarbon group or a C1-C12 alkoxy group, mx, my and mz independently represent an integer of 0 to 5, and $W^1$ represents a nitrogen-containing heteroring which can have one or more substituents.

* * * * *